US009062048B2

(12) United States Patent
Lanter et al.

(10) Patent No.: US 9,062,048 B2
(45) Date of Patent: Jun. 23, 2015

(54) CYCLOHEXYL-AZETIDINYL ANTAGONISTS OF CCR2

(71) Applicant: Janssen Pharmaceutica NV, Beerse (BE)

(72) Inventors: James C. Lanter, Audubon, PA (US); Thomas P. Markotan, Morgantown, PA (US); Nalin Subasinghe, Exton, PA (US); Zhihua Sui, Norristown, PA (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 13/947,340

(22) Filed: Jul. 22, 2013

(65) Prior Publication Data
US 2013/0310365 A1    Nov. 21, 2013

Related U.S. Application Data

(62) Division of application No. 13/161,572, filed on Jun. 16, 2011, now Pat. No. 8,518,969.

(60) Provisional application No. 61/355,663, filed on Jun. 17, 2010.

(51) Int. Cl.

| | |
|---|---|
| *A01N 43/42* | (2006.01) |
| *A61K 31/47* | (2006.01) |
| *C07D 215/00* | (2006.01) |
| *C07D 471/04* | (2006.01) |
| *A61K 31/4709* | (2006.01) |
| *A61K 31/4725* | (2006.01) |
| *A61K 31/502* | (2006.01) |
| *A61K 31/517* | (2006.01) |
| *A61K 31/5377* | (2006.01) |
| *A61K 31/541* | (2006.01) |
| *C07D 401/12* | (2006.01) |
| *C07D 401/14* | (2006.01) |
| *C07D 403/12* | (2006.01) |
| *C07D 403/14* | (2006.01) |
| *C07D 405/14* | (2006.01) |
| *C07D 413/14* | (2006.01) |
| *C07D 417/14* | (2006.01) |

(52) U.S. Cl.
CPC .......... *C07D 471/04* (2013.01); *A61K 31/4709* (2013.01); *A61K 31/4725* (2013.01); *A61K 31/502* (2013.01); *A61K 31/517* (2013.01); *A61K 31/5377* (2013.01); *A61K 31/541* (2013.01); *C07D 401/12* (2013.01); *C07D 401/14* (2013.01); *C07D 403/12* (2013.01); *C07D 403/14* (2013.01); *C07D 405/14* (2013.01); *C07D 413/14* (2013.01); *C07D 417/14* (2013.01)

(58) Field of Classification Search
USPC .......................................... 546/152; 514/311
See application file for complete search history.

(56) References Cited

U.S. PATENT DOCUMENTS

| | | | |
|---|---|---|---|
| 6,245,799 B1 | 6/2001 | Asselin et al. | |
| 6,255,315 B1 | 7/2001 | Patane et al. | |
| 8,269,015 B2 | 9/2012 | Zhang et al. | |
| 2003/0004151 A1 | 1/2003 | Cherney et al. | |
| 2006/0069123 A1 | 3/2006 | Xia et al. | |
| 2006/0135502 A1 | 6/2006 | Cherney et al. | |
| 2006/0252751 A1 | 11/2006 | Xue et al. | |
| 2010/0144695 A1 | 6/2010 | Zhang et al. | |
| 2010/0267668 A1 | 10/2010 | Zhang et al. | |
| 2010/0267689 A1 | 10/2010 | Zhang et al. | |

FOREIGN PATENT DOCUMENTS

| | | |
|---|---|---|
| EP | 1201239 | 5/2002 |
| WO | WO 98/57641 | 12/1998 |
| WO | WO 0134598 | 5/2001 |
| WO | WO 2004/050024 | 6/2004 |
| WO | WO 2005/060665 | 7/2005 |
| WO | WO 2006/073592 | 7/2006 |
| WO | WO 2007003965 | 1/2007 |
| WO | WO 2007/053498 | 5/2007 |
| WO | WO 2007/130712 | 11/2007 |
| WO | WO 2010/068663 | 6/2010 |

(Continued)

OTHER PUBLICATIONS

Barnes, et. Al. New Drugs for Asthma, 2004, Nature Reviews: Drug Discovery, vol. 3, p. 831-844.
Bryn, et al., "Hydrates and Solvates", Solid State Chemistry of Drugs, 2"" Edition, 1999, pp. 232-247, Chapter 10, Polymorphs.
Bundgaard, et al., "Design of Prodrugs: Bioreversible Derivatives for Various Functional Groups and Chemical Entities", Elsevier Science Publishers, 1985, pp. 1-4, Chapter 1.
Dawson, et al,"Targeting Monocyte Chemoattractant Protein-1 Signalling in Disease", Expert Opin. Ther. Targets, 2003, vol. 7(1), pp. 35-48.
Gdaniec, et al., "Conformation and Stereodynamics of N,N-Dinitroso-2,4,6,8-tetraaryl-3,7-diazabicyclo [3.3.1] nonanes", J. Org. Chem., 1997 vol. 62, pp. 5619-5622.
Han, et al.,"Targeted Prodrug Design to Optimize Drug Delivery", MPS PHARMSCI, 2000, vol. 2 (1) pp. 1-11.
Horuk, et al., Chemokine Receptor Antagonists: overcoming developmental hurdles, 2009, Nature Reviews: Drug Discovery, vol. 8, pp. 23-22.
Kang, CCR2 antagonism improves insulin resistance, lipid metabolism, and diabetic nephropathy in type 2 diabetic mice, 2010, Kidney Internation, vol. 78, p. 883-894.

(Continued)

*Primary Examiner* — Paul V Ward
(74) *Attorney, Agent, or Firm* — Mary A. Appollina

(57) ABSTRACT

The present invention comprises compounds of Formula I.

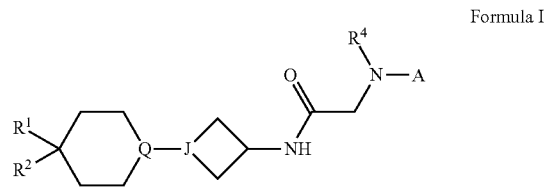

Formula I wherein: $R^1$, $R^2$, $R^4$, J, Q, and A are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula I.

11 Claims, No Drawings

(56) References Cited

FOREIGN PATENT DOCUMENTS

| WO | WO 2010/121011 | 10/2010 |
|----|----------------|---------|
| WO | WO 2010/121036 | 10/2010 |
| WO | WO 2010/121046 | 10/2010 |

OTHER PUBLICATIONS

Lanter, et al., "The discovery of Novel Cyclohexylamide CCR2 Antagonists", Bioorganic & Medicinal Chemistry Letters, Pergamon; 2011, vol. 21, No. 24, pp. 7496-7501.
Morissette, et al., "High-throughput crystallization: polymorphs, salts, co-crystals and solvates of pharmaceutical solids", Advanced Drug Delivery Reviews, 2004, pp. v-275-v-300, vol. 56.
Palmqvist, Chemokines and their receptors as potential targets for the treatment of asthma, 2007, British Journal of Pharmacology, vol. 151, p. 725-736'.
Rollins B J, Monocyte chemo attractant protein 1: a potential regulator of monocyte recruitment in inflammatory disease, Mol. Med. Today, 1996, 2:198.
Seebach, et al, "Safe One-Pot Carbon-Carbon Bond Formation with Lithiated Nitrosamines Including Denitrosation by Sequential Reduction with Lithium a Aluminium Hydride and Raney-Nickel", Synthesis, 1979, vol. 6, pp. 423-424.
Silva, A., et al., Mini Rev. Med. Chem 2005 vol. 5, pp. 893-914.
Tamura, Inhibition of CCR2 Amelolorates Insulin Resistance and Hepatic Steatosis in db/db Mice, 2008, Arterioscler Thromb Vasc Biol. p. 2195-2201.
Abdel-Magid, et al., "Reductive Amination of Aldehydes and Ketones with Sodium Triacetoxyborohydride. Studies on Direct and Indirect Reductive Amination Procedures", J. Org. Chem, 1996, vol. 61, pp. 3849-3862.
Banker et al., Prodrugs, Modern Pharmaceutics, Third Edition, Revised and Expanded, pp. 451 and 596, 1996.
Chan, et al., "1, 5-BIS (Trimethylsiloxy)-1,5-Dimethoxy-1-4-Pentadienes. Cyclopropance Synthesis Via Intramolecular Coupling", Tetrahedron Letters, 1982 vol. 23, No. 8, pp. 799-802.
Damasio, Alzheimer's Disease and related dementias, Cecil Textbook of Medicine, 20th Edition, vol. 2, pp. 1992-1996, 1996.
Golub, et al., "Molecular Classification of Cancer: Class Discovery and Class Prediction by Gene Expression Monitorin : J". Science, 1999, pp. 531-537, vol. 286.
Gura et al., Systems for identifying new drugs are often faulty, Science, 278:1041-1042, 1997.
Havlioglu et al., Slit Proteins potential endogenous modulators of inflammation, Neurovirology, 8, pp. 486-495, 2002.
Johnson et al., Relationships between drug activity in NCI preclinical in vitro and in vivo models and early clinical trials, British Journal of Cancer, 84(10):1424-1431, 2001.
Lala, et al., "role of nitric oxide in tumor progression: Lessions from experimental tumors", Cancer and Metastasis Reviews, 1998, pp. 91-106, 17(1).
Simone, Oncology: Introduction, Cecil Textbook of Medicine, 20th Edition, vol. 1, pp. 1004-1010, 1996.
Thornber, "Isosterism and Molecular Modification in Drug Design", Royal Society of Chemistry, 1979, pp. 563-580.
Ulrich, Chapter 4: Crystallization, Kirk-Othmer Encyclopedia of Chemical Technology, Aug. 2002.
Vippagunta, etal., "Crystalline Solids", Advanced Drug Delivery Reviews, 2001, pp. 3-26, vol. 48.
West, Solid Solutions, Solid State Chemistry and its applications, pp. 358 & 365, 1988.
Wolff, Some Consideration for prodrug design, Burger's Medicinal Chemistry and Drug Discovery, 5th Edition, vol. 1: Principles and Practice, pp. 975-977, 1995.
Das, B. et al. "A Highly Chemoselective Boc Protection of Amines using Sulfonic-Acid-Functionalized Silica as an Efficient Heterogeneous Recyclable Catalyst", Tetrahedron Lett. 2006, 47, 7551-7556.
Ingersoll, A. W. et. al., "Hippuric Acid", Organic Syntheses 1932, XII, vol. 12. pp. 40.
Lima et al., Bioisosterism: A Useful Strategy for Molecular Modification and Drug Design, Current Medicinal Chemistry, 2005, 12, pp. 23-49.
Xia M, Sui Z, "Recent Developments in CCR2 Antagonists", Expert Opin. Ther. Patents, 2009, 19(3), 295-303.
U.S. Appl. No. 12/760,832 Notice of Allowance, dated May 18, 2012.
U.S. Appl. No. 12/760,832 Office Action, dated Feb. 3, 2012.
U.S. Appl. No. 12/760,832 Office Action dated Dec. 20, 2011.
U.S. Appl. No. 12/160,855 Notice of Allowance, dated Aug. 3, 2012.
U.S. Appl. No. 12/160,855 Notice of Allowance dated Feb. 22, 2012.
U.S. Appl. No. 12/760,855 Office Action, dated Sep. 15, 2011.
U.S. Appl. No. 12/761,080 Notice of Abandonment dated Nov. 9, 2011.
U.S. Appl. No. 12/761,080 Notice of Allowance and Fees Due, dated Jul. 25, 2011.
U.S. Appl. No. 12/761,080 Office Action, dated Feb. 11, 2011.
U.S. Appl. No. 13/280,690 Notice of Allowance dated Jun. 27, 2012.
U.S. Appl. No. 13/280,690 Office Action, dated Mar. 26, 2012.
U.S. Appl. No. 13/280,690 Office Action dated Dec. 8, 2011.
International Search Report—PCT/US2011/039724, Jul. 12, 2009.
International Search Report, PCTJUS2010/031255, Oct. 18,2011.
International Search Report, PCTJUS2009/067307, Feb. 8, 2010.
International Search Report, PCTIUS2010/031265, Oct. 18, 20111.
International Search Report, PCTIUS2010/031212, Oct. 18, 2011.
International Search Report PCTIUS2011/039724 , Jul. 19, 2011.
International Search Report, PCTIUS2011/040610, Aug. 29, 2011.
U.S. Appl. No. 13/161,572, filed Jun. 16, 2011.
U.S. Appl. No. 12/761,080, filed Apr. 15, 2010.
U.S. Appl. No. 12/633,861, filed Dec. 9, 2009.
U.S. Appl. No. 12/760,832, filed Apr. 15, 2010.
U.S. Appl. No. 13/156,450, filed Jun. 9, 2011
U.S. Appl. No. 12/760,855, filed Apr. 15, 2010.

CYCLOHEXYL-AZETIDINYL ANTAGONISTS OF CCR2

CROSS-REFERENCE TO RELATED APPLICATIONS

This application is a divisional of U.S. Ser. No. 13/161,572 filed Jun. 16, 2011, which claims priority from U.S. Provisional Application Ser. No. 61/355,663 filed Jun. 17, 2010, the contents of each of which are hereby incorporated by reference in their entirety.

FIELD OF THE INVENTION

The invention is directed to substituted azetidine compounds, which are antagonists to the chemoattractant cytokine receptor 2 (CCR2), pharmaceutical compositions, and methods for use thereof. More particularly, the CCR2 antagonists are substituted cyclohexyl azetidinyl compounds useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today,* 1996, 2:198; and Dawson J, et al., Targeting monocyte chemoattractant protein-1 signaling in disease, *Expert Opin. Ther. Targets,* 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach.

Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e. to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation.

All documents cited herein are incorporated by reference.

SUMMARY OF THE INVENTION

The invention relates to the compounds of Formula I

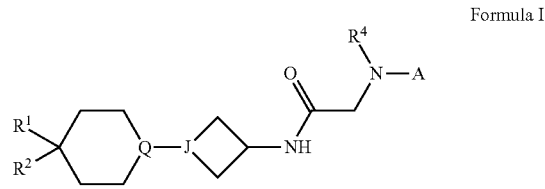

Formula I wherein:

A is

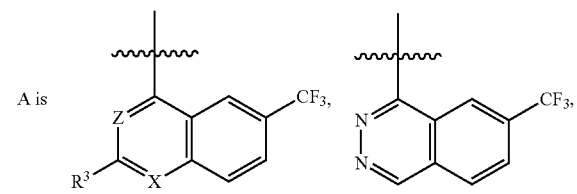

-continued

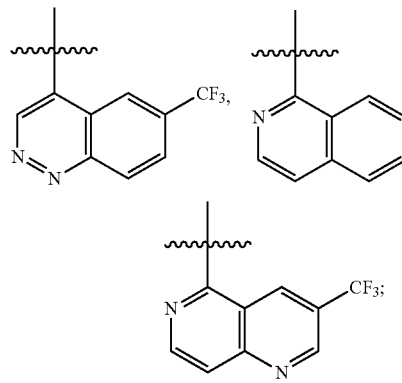

X is CH, or N;

Z is CH, or N, provided that X and Z are not both CH;

J is N or CH;

Q is C—$R^5$, provided that J is N, or Q is N, provided that J is CH;

$R^1$ is H, phenyl, heteroaryl, $CF_3$, —CH=$CH_2$, $CO_2C_{(1-4)}$ alkyl, NHBOC, $NHC_{(1-4)}$alkyl, $N(C_{(1-4)}$alkyl)$CO_2CH_2$Ph, $NR_bC(O)R_{bb}$, $NR_bSO_2R_{bb}$, $C(O)N(CH_3)OCH_3$, $C(O)NR_bC_{(1-4)}$alkyl, $C(O)NHCH_2Ph(OCH_3)_2$, —C(OH)$(CH_2CH$=$CH_2)_2$, 3,6-dihydropyran-2-yl, 2,5-dihydrofuran-2-yl, tetrahydropyranyl, cyclopentenyl, cyclopentanyl, cyclohexenyl, cyclohexanyl, tetrahydrofuran-2-yl, cycloheptanyl,

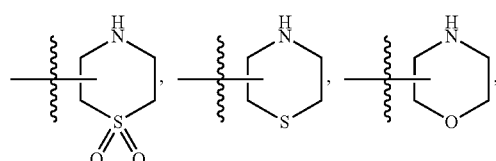

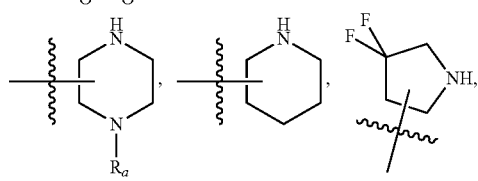

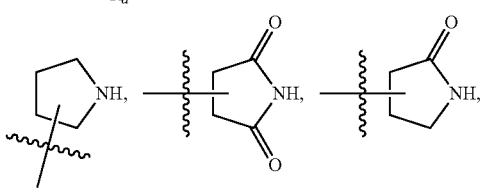

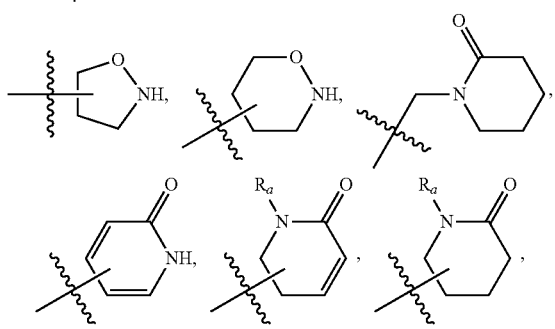

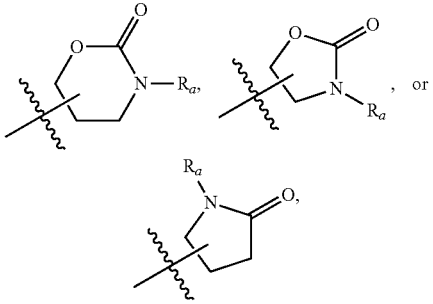

or unsubstituted or substituted $C_{(1-6)}$alkyl wherein said alkyl may be substituted with up to two substituents wherein one substituent (if present) is selected from the group consisting of OH, $C_{(2-4)}$alkenyl, $C_{(3-6)}$cycloalkyl, $NH_2$, NHBOC, $N(C_{(1-4)}$alkyl)$_2$, $NHSO_2R_b$, $NR_bC(O)R_{bb}$, $NHCO_2R_b$, $NHCONR_bR_{bb}$, $OC_{(1-2)}$alkyl, $OC(O)C_{(1-4)}$alkyl, $OC(O)NR_bR_{bb}$, $CO_2C_{(1-4)}$alkyl, $C(O)NR_bR_{bb}$, $C_{(2)}$alkylnyl, thiazolyl, oxazolyl, furyl, $CF_3$, $CF_2CF_2CF_3$, $CH_2NHCOC_{(1-3)}$alkyl, $N_3$, $SCH_3$, $S(O)CH_3$, $SO_2CH_3$, and —CN, and the second substituent on the $C_{(1-6)}$alkyl (if present) is OH, and wherein said phenyl or heteroaryl is optionally substituted with one substituent selected from the group consisting of: OH, —CN, $CH_2OH$, $OC_{(1-4)}$alkyl, $NH_2$, $NHC_{(1-4)}$alkyl, $OC_{(1-4)}$alkyl, $C(O)C_{(1-4)}$alkyl, $CO_2C_{(1-4)}$alkyl, $C(O)NHC_{(1-4)}$alkyl, $CO_2NHC_{(1-4)}$alkyl, $SC_{(1-4)}$alkyl, $SOC_{(1-4)}$alkyl, $SO_2C_{(1-4)}$alkyl, $SO_2NHC_{(1-4)}$alkyl, $NHSO_2C_{(1-4)}$alkyl, $NHCO_2C_{(1-4)}$alkyl, $NHC(O)C_{(1-4)}$alkyl, $NO_2$, and $C_{(1-4)}$alkyl;

$R^2$ is H, or OH;

or $R^1$ and $R^2$ may together form a carbonyl (i.e., $R^1$ and $R^2$ may be

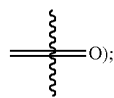

$R^3$ is H, $C_{(1-4)}$alkyl, —CN, $CHF_2$, or $CF_3$;

$R^4$ is H or $CH_3$;

$R^5$ is H or deuterium;

$R_a$ is H, or $CH_3$;

$R_b$ is H, $C_{(1-4)}$alkyl, or $CF_3$;

$R_{bb}$ is H, $C_{(1-4)}$alkyl, or $CF_3$;

and pharmaceutically acceptable salts thereof.

DETAILED DESCRIPTION OF THE INVENTION

The invention relates to the compounds of Formula I

Formula I

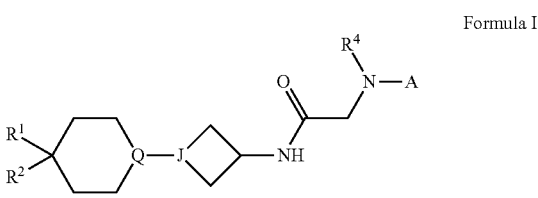

wherein the variables A, $R^1$, $R^2$, $R^4$, J, and Q are as defined above.

In another embodiment of the invention:
A is

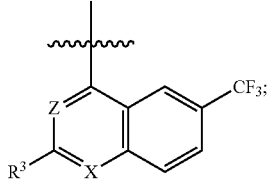

X is CH, or N;
Z is CH, or N, provided that X and Z are not both CH;
J is N;
Q is C—$R^5$;
$R^1$ is H, phenyl, heteroaryl, $CF_3$, —CH=$CH_2$, $CO_2C_{(1-4)}$alkyl, NHBOC, NHC$_{(1-4)}$alkyl, N($C_{(1-4)}$alkyl)$CO_2CH_2$Ph, NR$_b$C(O)R$_{bb}$, NR$_b$SO$_2$R$_{bb}$, C(O)N(CH$_3$)OCH$_3$, C(O)NR$_b$C$_{(1-4)}$alkyl, C(O)NHCH$_2$Ph(OCH$_3$)$_2$, —C(OH)(CH$_2$CH=CH$_2$)$_2$, 3,6-dihydropyran-2-yl, 2,5-dihydrofuran-2-yl, tetrahydropyranyl, cyclopentenyl, cyclopentanyl, cyclohexenyl, cyclohexanyl, tetrahydrofuranyl, cycloheptanyl,

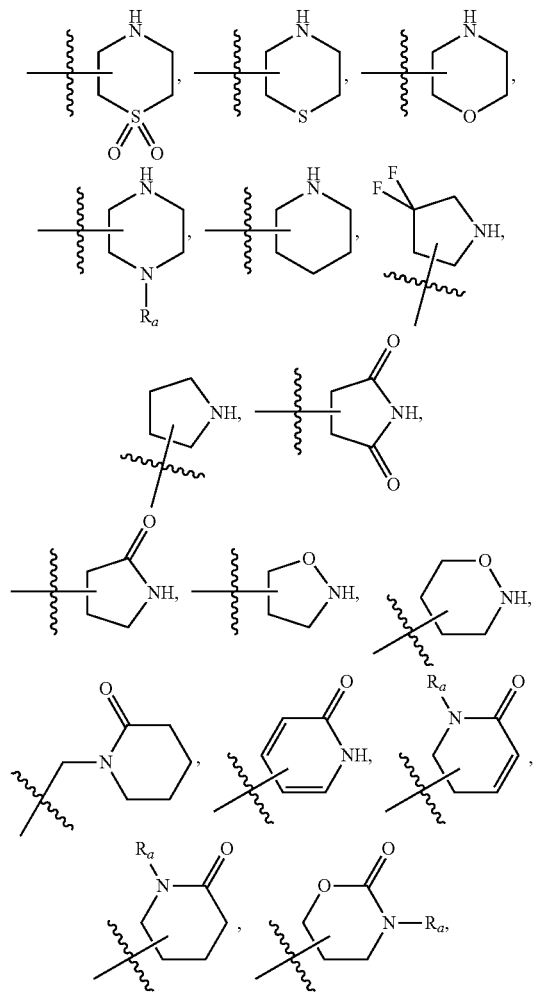

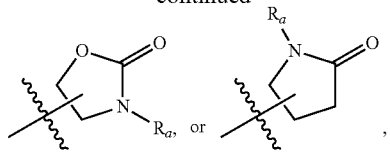

or unsubstituted or substituted $C_{(1-6)}$alkyl wherein said alkyl may be substituted with up to two substituents wherein one substituent (if present) is selected from the group consisting of OH, $C_{(2-4)}$alkenyl, $C_{(3-6)}$cycloalkyl, NH$_2$, NHBOC, N($C_{1-4}$alkyl)$_2$, NHSO$_2$R$_b$, NR$_b$C(O)R$_{bb}$, NHCO$_2$R$_b$, NHCONR$_b$R$_{bb}$, OC$_{(1-2)}$alkyl, OC(O)C$_{(1-4)}$alkyl, OC(O)NR$_b$R$_{bb}$, CO$_2$C$_{(1-4)}$alkyl, C(O)NR$_b$R$_{bb}$, C$_{(2)}$alkylnyl, thiazolyl, oxazolyl, furyl, CF$_3$, CF$_2$CF$_2$CF$_3$, CH$_2$NHCOC$_{(1-3)}$alkyl, N$_3$, SCH$_3$, S(O)CH$_3$, SO$_2$CH$_3$, and —CN, and the second substituent on the $C_{(1-6)}$alkyl (if present) is OH, and wherein said phenyl or heteroaryl is optionally substituted with one substituent selected from the group consisting of: OH, —CN, CH$_2$OH, OC$_{(1-4)}$alkyl, NH$_2$, NHC$_{(1-4)}$alkyl, OC$_{(1-4)}$alkyl, C(O)C$_{(1-4)}$alkyl, CO$_2$C$_{(1-4)}$alkyl, C(O)NHC$_{(1-4)}$alkyl, CO$_2$NHC$_{(1-4)}$alkyl, SC$_{(1-4)}$alkyl, SOC$_{(1-4)}$alkyl, SO$_2$C$_{(1-4)}$alkyl, SO$_2$NHC$_{(1-4)}$alkyl, NHSO$_2$C$_{(1-4)}$alkyl, NHCO$_2$C$_{(1-4)}$alkyl, NHC(O)C$_{(1-4)}$alkyl, NO$_2$, and C$_{(1-4)}$alkyl;
$R^2$ is H, or OH;
or $R^1$ and $R^2$ may together form a carbonyl (i.e., $R^1$ and $R^2$ may be

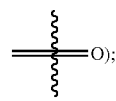

$R^3$ is H, $C_{(1-4)}$alkyl, —CN, CHF$_2$, or CF$_3$;
$R^4$ is H or CH$_3$;
$R^5$ is H or deuterium;
$R_a$ is H, or CH$_3$;
$R_b$ is H, $C_{(1-4)}$alkyl, or CF$_3$;
$R_{bb}$ is H, $C_{(1-4)}$alkyl, or CF$_3$;
and pharmaceutically acceptable salts thereof.
In another embodiment of the invention
A is

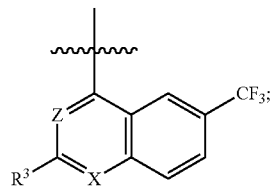

X is CH, or N;
Z is CH, or N, provided that X and Z are not both CH;
J is N;
Q is C—$R^5$;
$R^1$ is pyridyl, pyrimidyl, pyrazyl, pyranyl, furyl, isoxazolyl, oxazolyl, phenyl, thiazolyl, isothiazolyl, CF$_3$, —CH=CH$_2$, CO$_2$C$_{(1-4)}$alkyl, NHBOC, N(C$_{(1-4)}$alkyl)CO$_2$CH$_2$Ph, NR$_b$C(O)R$_{bb}$, C(O)N(CH$_3$)OCH$_3$, C(O)NHC$_{(1-4)}$alkyl, C(O)NHCH$_2$Ph(OCH$_3$)$_2$, —C(OH)(CH$_2$CH=CH$_2$)$_2$, 3,6-dihydropyran-2-yl, 2,5-dihydrofuran-2-yl, tetrahydropyranyl, cyclopentenyl, cyclopentanyl, cyclohexenyl, tetrahydrofuran-2-yl, cycloheptany

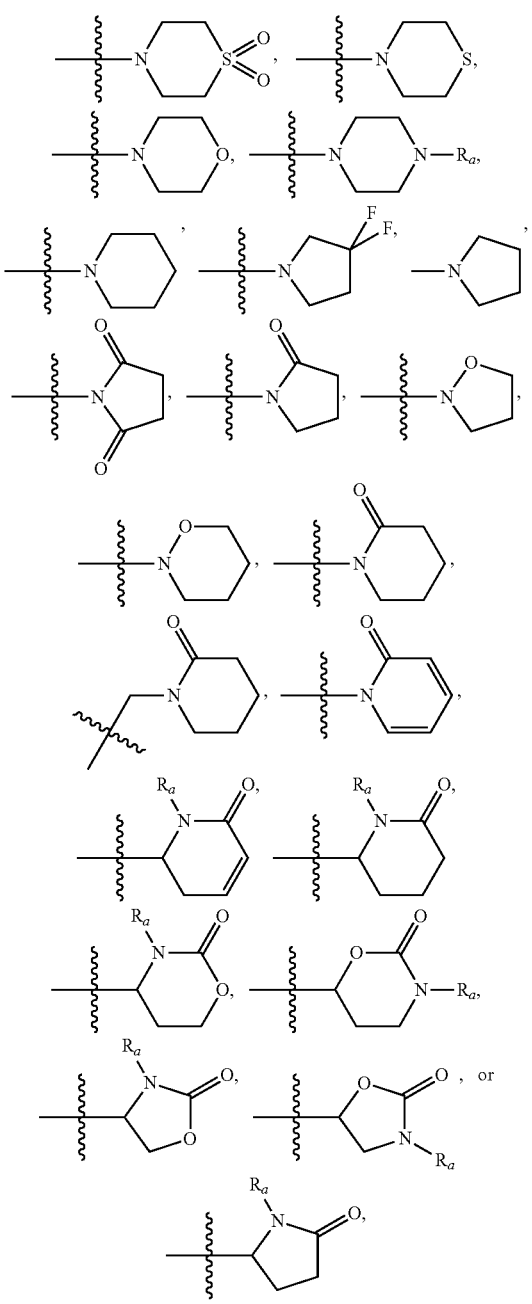

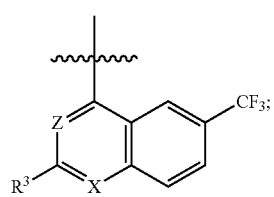

or unsubstituted or substituted $C_{(1-6)}$alkyl wherein said alkyl may be substituted with up to two substituents wherein one substituent (if present) is selected from the group consisting of OH, $C_{(3-6)}$cycloalkyl, $C_{(2-4)}$alkenyl, NHBOC, $N(C_{(1-4)}$alkyl$)_2$, $NHSO_2R_b$, $NR_bC(O)R_{bb}$, $NHCO_2R_b$, $NHCONR_b$ $R_{bb}$, $OC_{(1-2)}$alkyl, $OC(O)C_{(1-4)}$alkyl, $OC(O)NR_bR_{bb}$, $CO_2C_{(1-4)}$alkyl, $C(O)NR_bR_{bb}$, $C_{(2)}$alkylnyl, thiazolyl, oxazolyl, $CF_3$, $CF_2CF_2CF_3$, $CH_2NHCOC_{(1-3)}$alkyl, $N_3$, $SCH_3$ and $S(O)CH_3$, and the second substituent on the $C_{(1-6)}$ alkyl (if present) is OH; and wherein said pyridyl, pyrimidyl, pyrazyl, pyranyl, furyl, isoxazolyl, oxazolyl, phenyl, or thiazolyl is optionally substituted with one substituent selected from the group consisting of: OH, —CN, $CH_2OH$, $OC_{(1-4)}$ alkyl, $NH_2$, $NHC_{(1-4)}$alkyl, $OC_{(1-4)}$alkyl $C(O)C_{(1-4)}$alkyl, $CO_2C_{(1-4)}$alkyl, $C(O)NHC_{(1-4)}$alkyl, $CO_2NHC_{(1-4)}$alkyl, $SC_{(1-4)}$alkyl, $SOC_{(1-4)}$alkyl, $SO_2C_{(1-4)}$alkyl, $SO_2NHC_{(1-4)}$ alkyl, $NHSO_2C_{(1-4)}$alkyl, $NHCO_2C_{(1-4)}$alkyl, $NHC(O)C_{(1-4)}$ alkyl, and $C_{(1-4)}$alkyl;

$R^2$ is H, or OH; or $R^1$ and $R^2$ may be taken together and bonded to the same oxygen atom;

$R^3$ is H, $C_{(1-4)}$alkyl, —CN, $CHF_2$, or $CF_3$;

$R^4$ is H or $CH_3$;

$R^5$ is H or deuterium;

$R_a$ is H, or $CH_3$;

$R_b$ is H, $C_{(1-4)}$alkyl, or $CF_3$;

$R_{bb}$ is H, $C_{(1-4)}$alkyl, or $CF_3$;

and pharmaceutically acceptable salts thereof.

In another embodiment of the invention:

A is

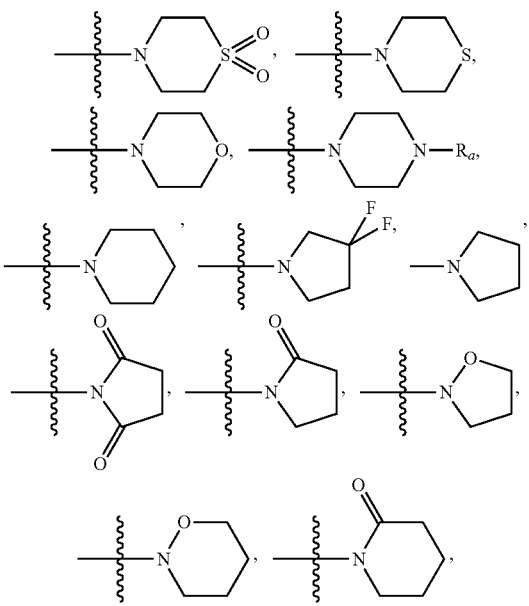

X is CH, or N;

Z is CH, or N, provided that X and Z are not both CH;

J is N;

Q is C—$R^5$;

$R^1$ is pyridyl, pyrimidyl, pyrazyl, oxazolyl, phenyl, thiazolyl, isothiazolyl, $CF_3$, —CH=$CH_2$, $CO_2C_{(1-4)}$alkyl, NHBOC, $N(C_{(1-4)}$alkyl$)CO_2CH_2Ph$, $NR_bC(O)R_{bb}$, $C(O)N(CH_3)$ $OCH_3$, $C(O)NHC_{(1-4)}$alkyl, $C(O)NHCH_2Ph(OCH_3)_2$, —$C(OH)(CH_2CH=CH_2)_2$, 3,6-dihydropyran-2-yl, 2,5-dihydrofuran-2-yl, tetrahydropyranyl, cyclopentenyl, cyclopentanyl, cyclohexenyl, tetrahydrofuran-2-yl, cycloheptanyl, -continued

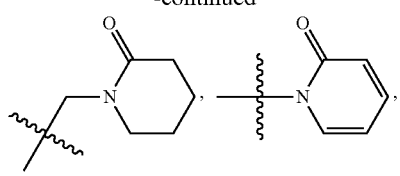

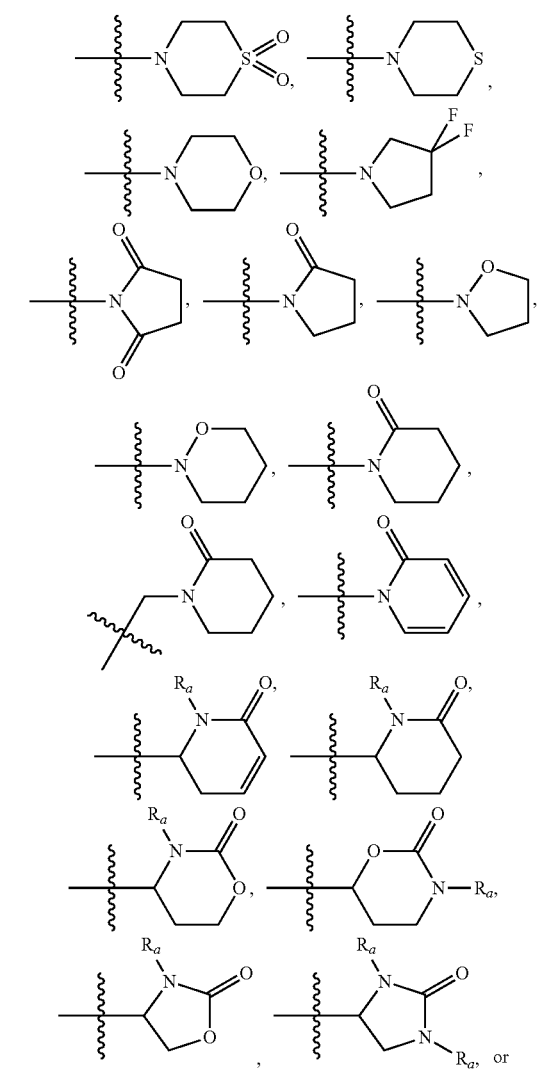

or unsubstituted or substituted $C_{(1-6)}$alkyl wherein said alkyl may be substituted with up to two substituents wherein one substituent (if present) is selected from the group consisting of OH, $C_{(3-6)}$cycloalkyl, $C_{(2-4)}$alkenyl, NHBOC, $N(C_{(1-4)}$alkyl$)_2$, $NHSO_2R_b$, $NR_bC(O)R_{bb}$, $NHCO_2R_b$, $NHCONR_b R_{bb}$, $OC_{(1-2)}$alkyl, $OC(O)C_{(1-4)}$alkyl, $OC(O)NR_bR_{bb}$, $CO_2C_{(1-4)}$alkyl, $C(O)NR_bR_{bb}$, $C_{(2)}$alkylnyl, thiazolyl, oxazolyl, $CF_3$, $CF_2CF_2CF_3$, $CH_2NHCOC_{(1-3)}$alkyl, $N_3$, $SCH_3$, $S(O)CH_3$ and $SO_2CH_3$, and the second substituent on the $C_{(1-6)}$alkyl (if present) is OH; and wherein said pyridyl, pyrimidyl, pyrazyl, oxazolyl, phenyl, or thiazolyl is optionally substituted with one substituent selected from the group consisting of: OH, —CN, $CH_2OH$, $OC_{(1-4)}$alkyl, $NH_2$, $NHC_{(1-4)}$alkyl, $OC_{(1-4)}$alkyl, $C(O)C_{(1-4)}$alkyl, $CO_2C_{(1-4)}$alkyl, $C(O)NHC_{(1-4)}$alkyl, $CO_2NHC_{(1-4)}$alkyl, $SC_{(1-4)}$alkyl, $SOC_{(1-4)}$alkyl, $SO_2C_{(1-4)}$alkyl, $SO_2NHC_{(1-4)}$alkyl, $NHSO_2 C_{(1-4)}$alkyl, $NHCO_2C_{(1-4)}$alkyl, $NHC(O)C_{(1-4)}$alkyl, and $C_{(1-4)}$alkyl;

$R^2$ is H, or OH; or $R^1$ and $R^2$ may be taken together and bonded to the same oxygen atom;

$R^3$ is H, $C_{(1-4)}$alkyl, —CN, $CHF_2$, or $CF_3$;

$R^4$ is H or $CH_3$;

$R^5$ is H or deuterium;

$R_a$ is H, or $CH_3$;

$R_b$ is H, $C_{(1-4)}$alkyl, or $CF_3$;

$R_{bb}$ is H, $C_{(1-4)}$alkyl, or $CF_3$;

and pharmaceutically acceptable salts thereof.

In another embodiment of the invention:

A is

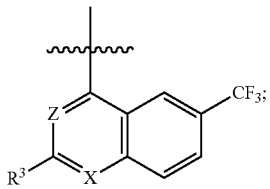

X is CH, or N;
Z is CH, or N, provided that X and Z are not both CH;
J is N;
Q is C—$R^5$;
$R^1$ is pyridyl, phenyl, thiazolyl, isothiazolyl, $CF_3$, —CH=$CH_2$, $CO_2C_{(1-4)}$alkyl, NHBOC, $N(C_{(1-3)}$alkyl) $CO_2CH_2Ph$, $NR_bC(O)R_{bb}$, $C(O)N(CH_3)OCH_3$, $C(O) NHC_{(1-4)}$alkyl, $C(O)NHCH_2Ph(OCH_3)_2$, —C(OH) $(CH_2CH=CH_2)_2$, 3,6-dihydropyran-2-yl, 2,5-dihydrofuran-2-yl, tetrahydropyranyl, cyclopentenyl, cyclopentanyl, tetrahydrofuran-2-yl, cycloheptanyl, -continued

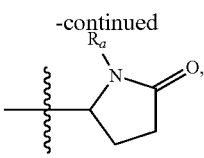

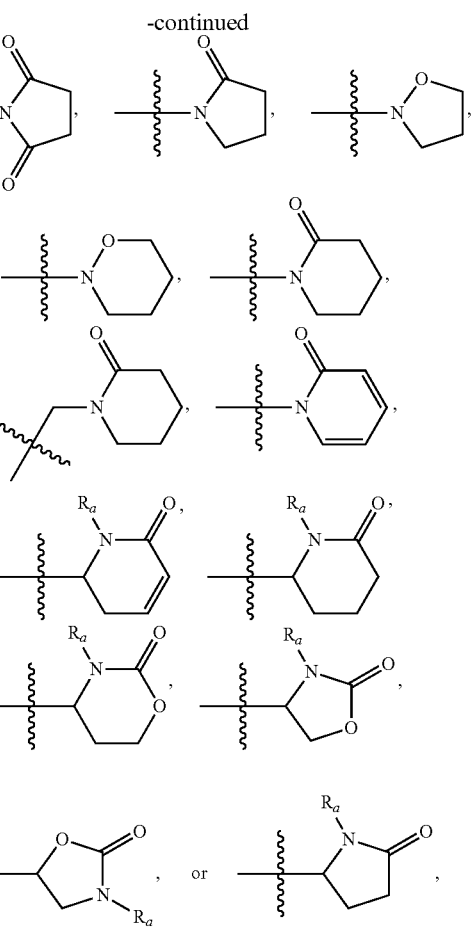

or unsubstituted or substituted $C_{(1-6)}$alkyl wherein said alkyl may be substituted with up to two substituents wherein one substituent (if present) is selected from the group consisting of OH, $C_{(3-5)}$cycloalkyl, $C_{(2)}$alkenyl, NHBOC, $N(C_{(1-4)}$alkyl$)_2$, $NHSO_2R_b$, $NR_bC(O)R_{bb}$, $NHCO_2R_b$, $NHCONR_b$ $R_{bb}$, $OC_{(1-4)}$alkyl, $OC(O)C_{(1-4)}$alkyl, $OC(O)NR_bR_{bb}$, $CO_2$ $C_{(1-4)}$alkyl, $C(O)NR_bR_{bb}$, $C_{(2)}$alkylnyl, cyclopentyl, thiazolyl, oxazolyl, $CF_3$, $CF_2CF_2CF_3$, $CH_2NHCOC_{(1-3)}$alkyl, $N_3$, $SCH_3$ and $S(O)CH_3$, and the second substituent on the $C_{(1-6)}$ alkyl (if present) is OH; and wherein said phenyl, pyridyl or thiazolyl is optionally substituted with one substituent selected from the group consisting of: OH, —CN, $CH_2OH$, $OCH_3$, $NH_2$, $NHCH_3$, and $C_{(1-4)}$alkyl;

$R^2$ is H, or OH;

or $R^1$ and $R^2$ may be taken together and bonded to the same oxygen atom;

$R^3$ is H, $C_{(1-4)}$alkyl, —CN, $CHF_2$, or $CF_3$;

$R^4$ is H or $CH_3$;

$R^5$ is H or deuterium;

$R_a$ is H, or $CH_3$;

$R_b$ is H, $C_{(1-4)}$alkyl, or $CF_3$;

$R_{bb}$ is H, $C_{(1-4)}$alkyl, or $CF_3$;

and pharmaceutically acceptable salts thereof.

In another embodiment of the invention:

A is

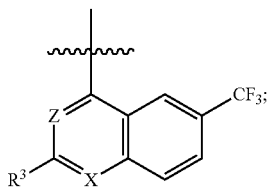

X is CH, or N;

Z is CH, or N, provided that X and Z are not both CH;

J is N;

Q is C—$R^5$;

$R^1$ is H, pyridyl, phenyl, thiazolyl, isothiazolyl, $CF_3$, —CH=$CH_2$, $CO_2CH_2CH_3$, NHBOC, $N(C_{(1-3)}$alkyl) $CO_2CH_2Ph$, $NR_bC(O)R_{bb}$, $C(O)N(CH_3)OCH_3$, $C(O)$ $NHCH_2CH_3$, $C(O)NHCH_2Ph(OCH_3)_2$, —C(OH)$(CH_2CH=CH_2)_2$, 3,6-dihydropyran-2-yl, 2,5-dihydrofuran-2-yl, tetrahydropyranyl, cyclopentenyl, cyclopentanyl, tetrahydrofuran-2-yl, cycloheptanyl,

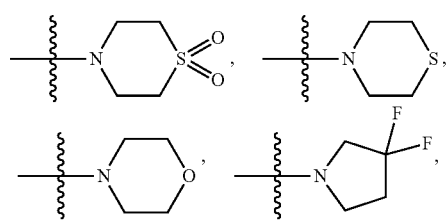

or unsubstituted or substituted $C_{(1-5)}$alkyl wherein said alkyl may be substituted with up to two substituents wherein one substituent (if present) is selected from the group consisting of OH, cyclopropyl, cyclopentyl, $C_{(2)}$alkenyl, NHBOC, $N(CH_3)_2$, $NHSO_2R_b$, $NR_bC(O)R_{bb}$, $NHCO_2R_b$, $NHCONR_b$ $R_{bb}$, $OC_{(1-2)}$alkyl, $OC(O)CH_3$, $OC(O)N(CH_3)_2$, $CO_2CH_2CH_3$, $C(O)N(CH_3)_2$, $C_{(2)}$alkylnyl, cyclopentyl, thiazolyl, $CF_3$, $CF_2CF_2CF_3$, $CH_2NHCOC_{(1-3)}$alkyl, $N_3$, $SCH_3$ and $S(O)CH_3$, and the second substituent on the $C_{(1-5)}$alkyl (if present) is OH; and wherein said phenyl is optionally substituted with one substituent selected from the group consisting of: OH, —CN, and $CH_2OH$; wherein said pyridyl is optionally substituted with one substituent selected from the group consisting of: $OCH_3$, OH, $NH_2$, $NHCH_3$, and $CH_3$; wherein said thiazolyl is optionally substituted with one substituent selected from the group consisting of isopropyl, and methyl;

$R^2$ is H, or OH;

or $R^1$ and $R^2$ may be taken together and bonded to the same oxygen atom;

$R^3$ is H, $CH_3$, —CN, $CH(CH_3)_2$, or $CF_3$;

$R^4$ is H or $CH_3$;

$R^5$ is H or deuterium;

$R_a$ is H, or $CH_3$;

$R_b$ is H, $C_{(1-4)}$alkyl, or $CF_3$;

$R_{bb}$ is H, $C_{(1-4)}$alkyl, or $CF_3$;

and pharmaceutically acceptable salts thereof.

In another embodiment, the invention is a compound of Formula I selected from any of the compounds disclosed in the Examples herein, and pharmaceutically acceptable salts thereof.

In another embodiment, the invention is a compound selected from the group consisting of
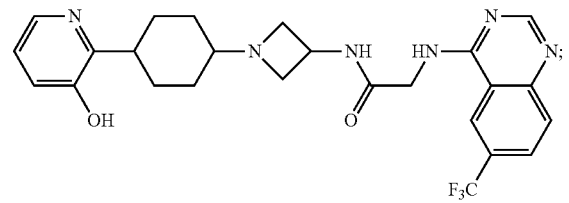
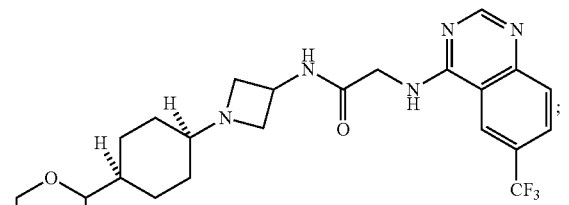
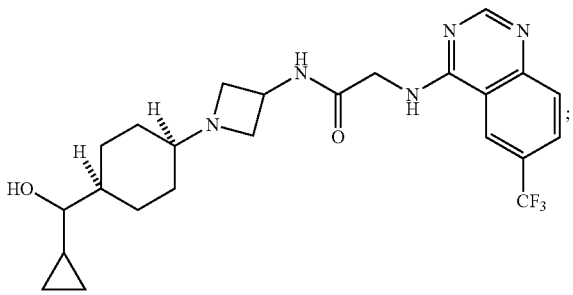
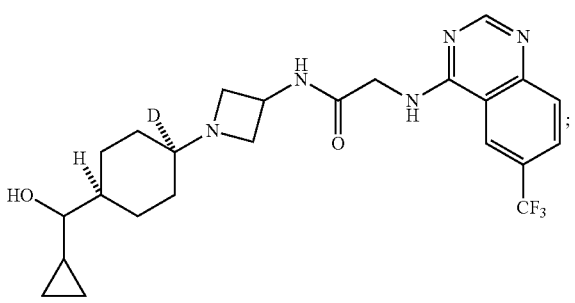
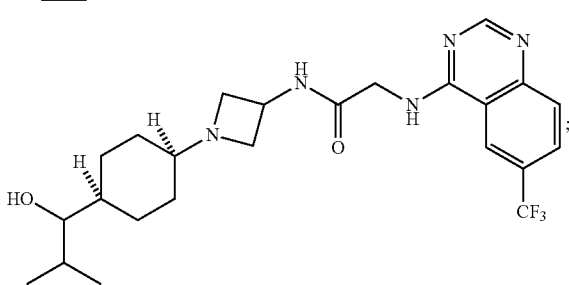
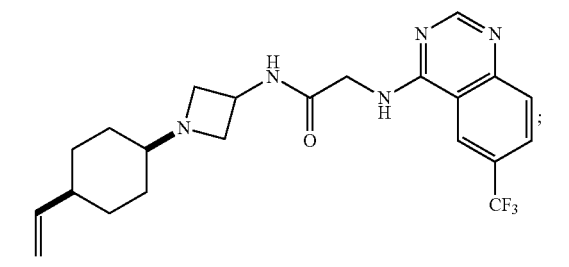
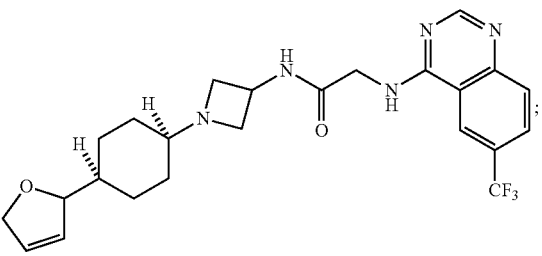
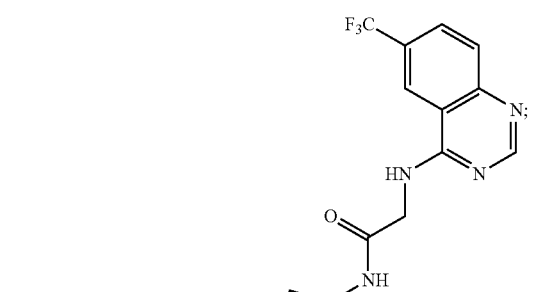
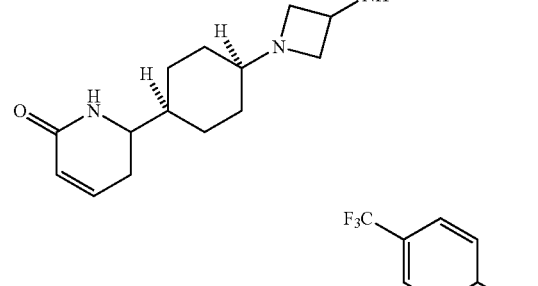
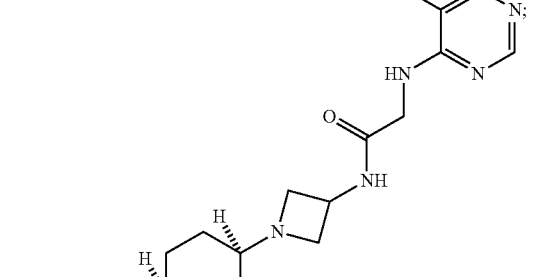
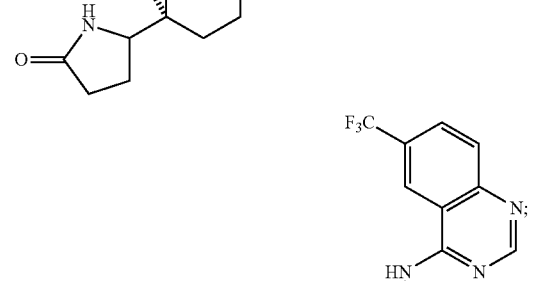
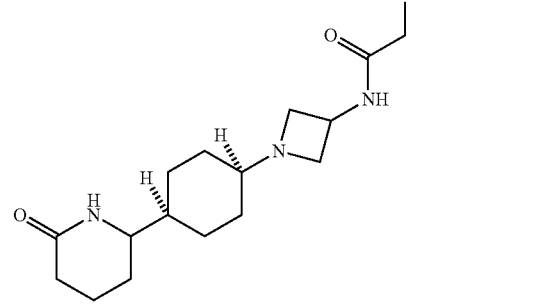

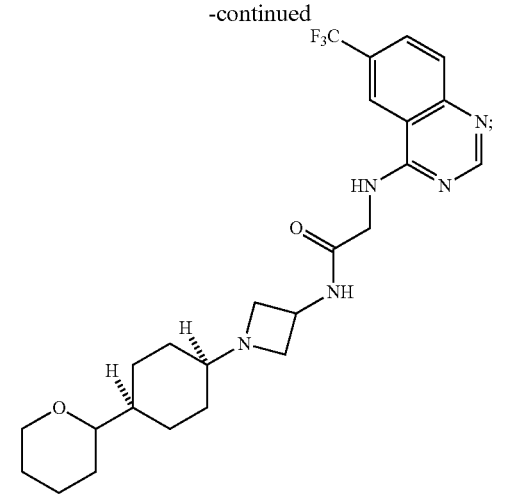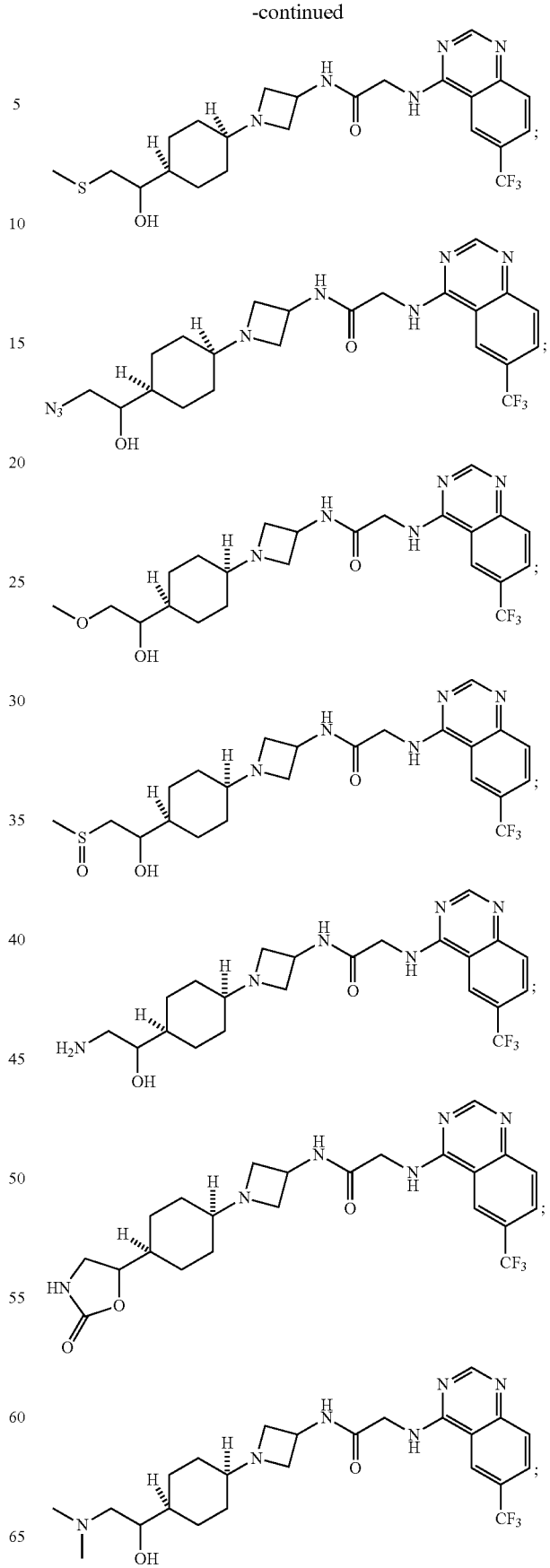

17
-continued
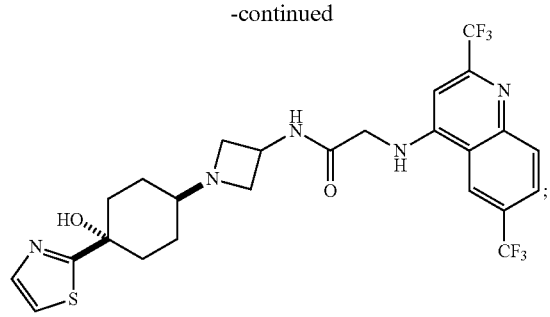
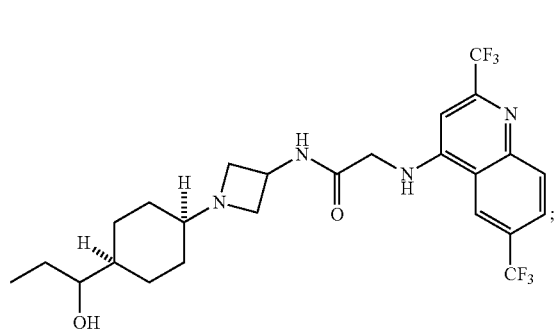
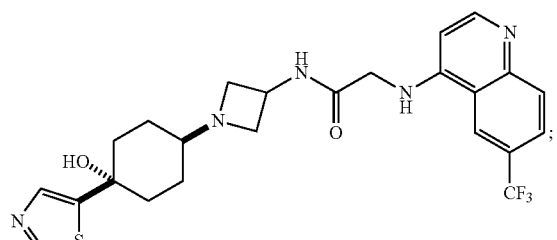
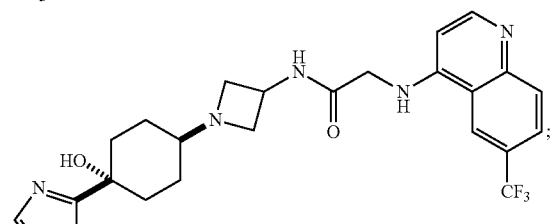
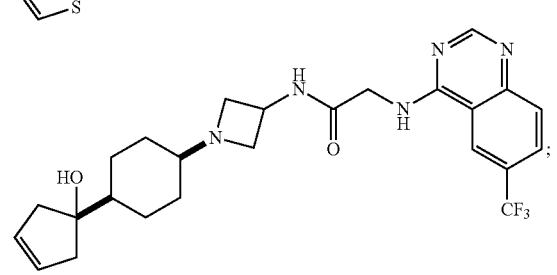
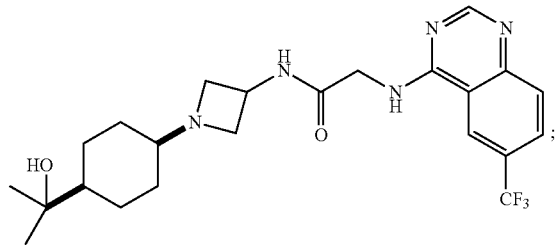
18
-continued
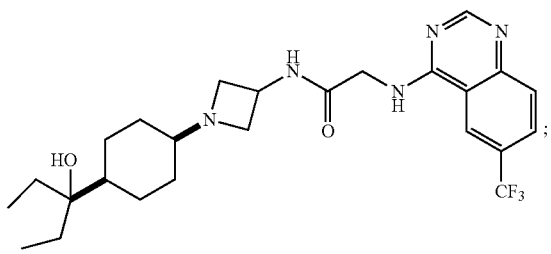
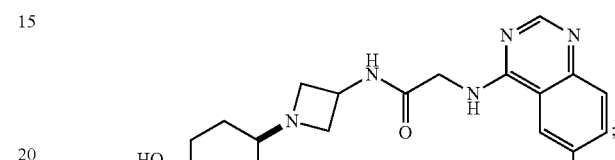
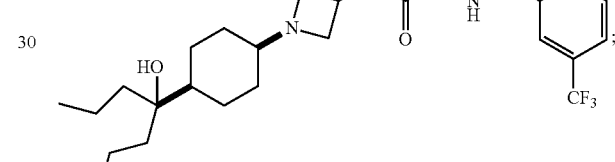
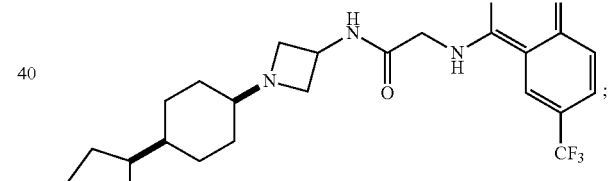
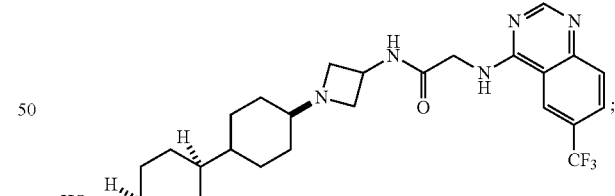
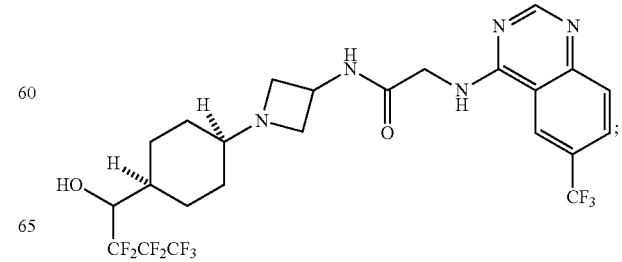

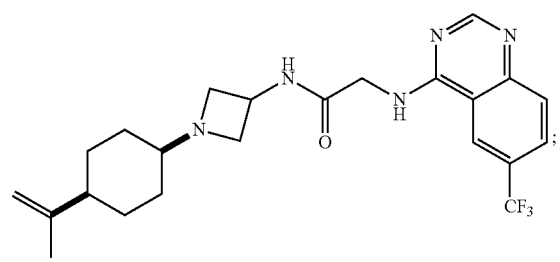
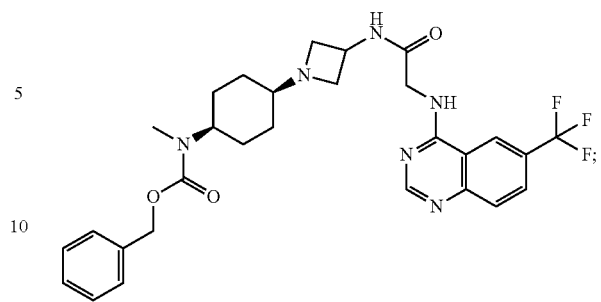
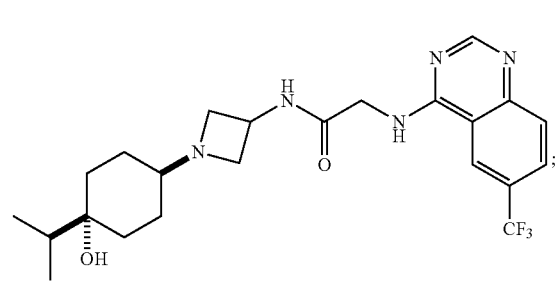
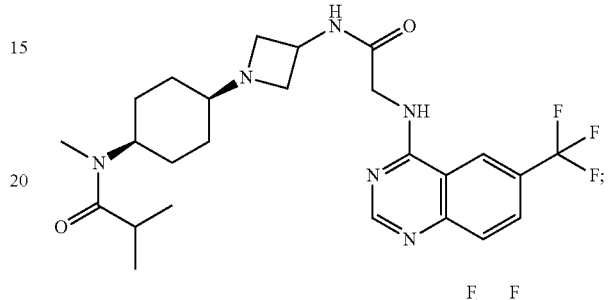
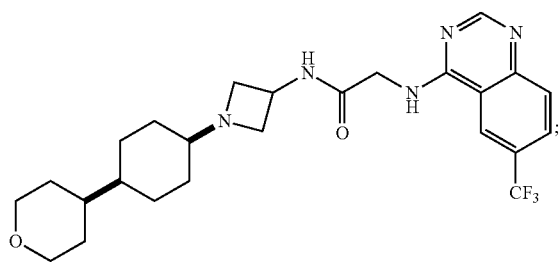
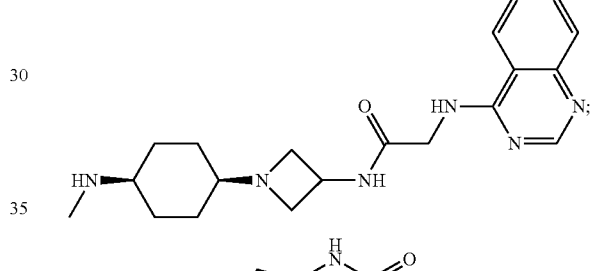
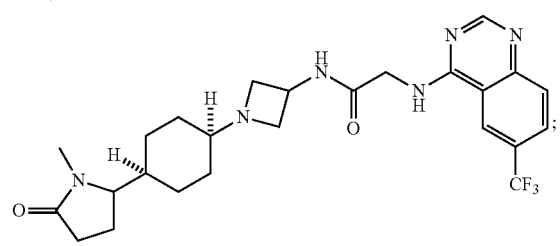
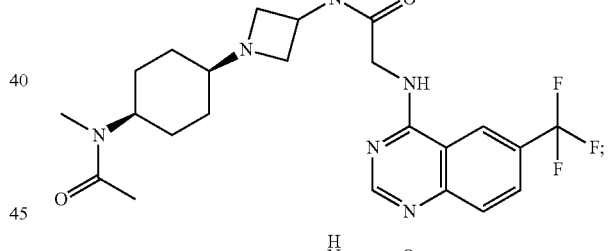
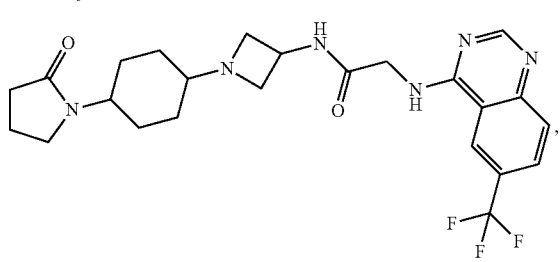
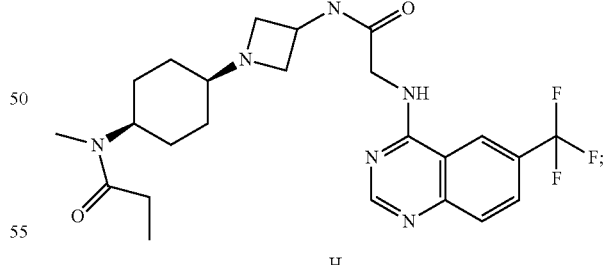
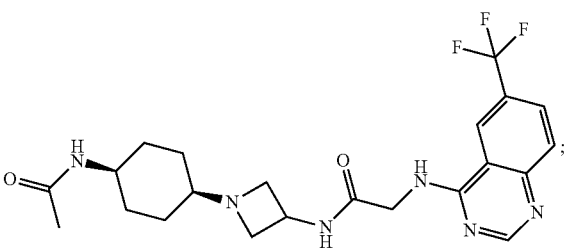
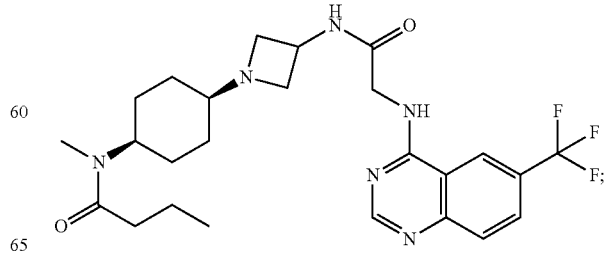

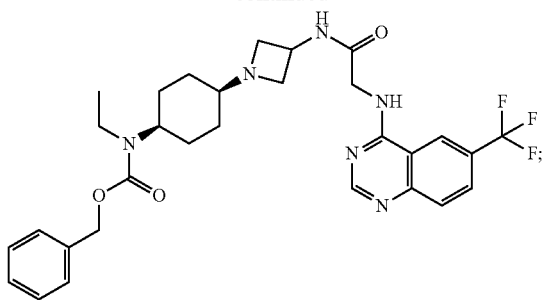
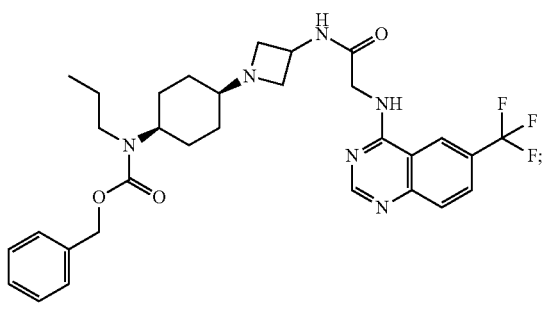
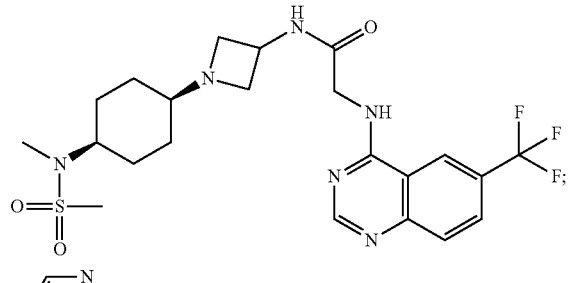
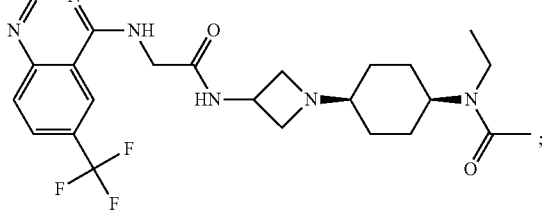
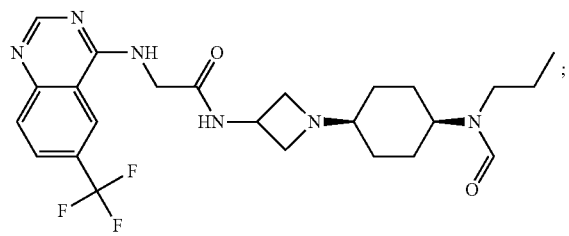
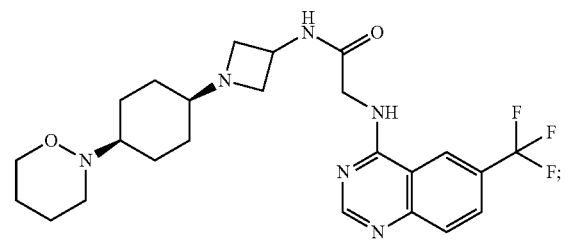
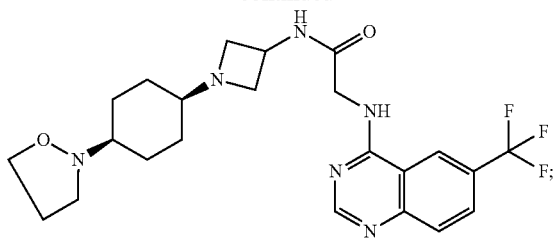
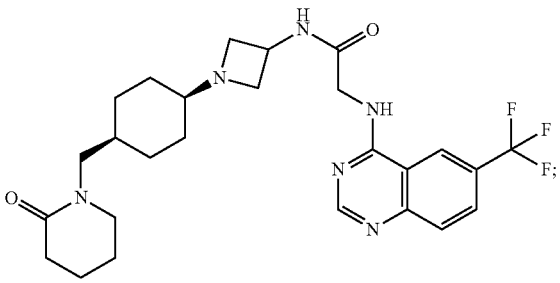
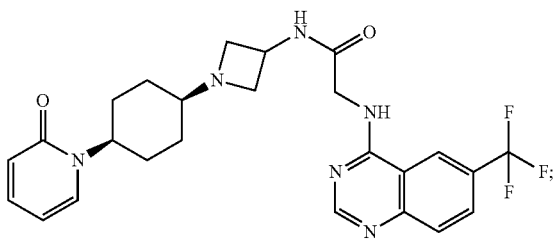
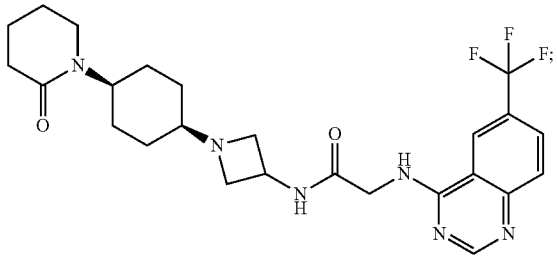
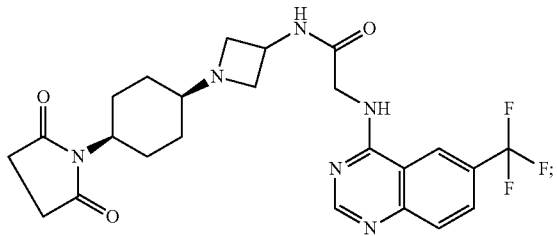
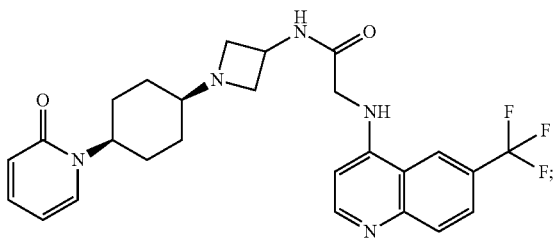

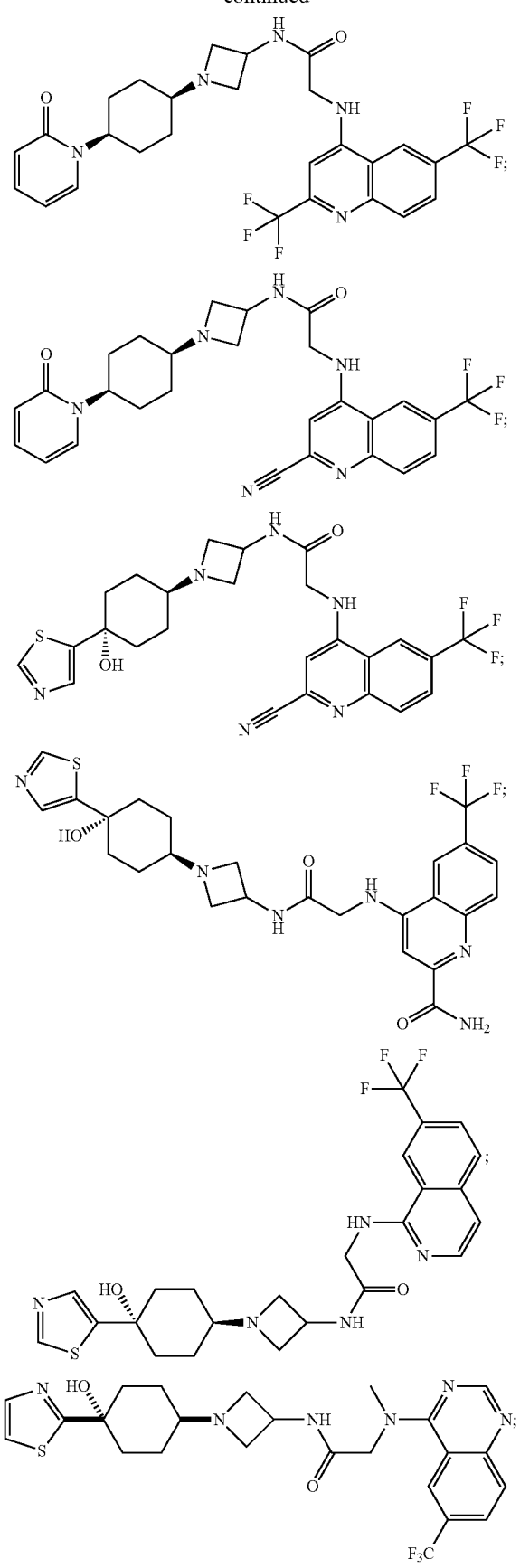
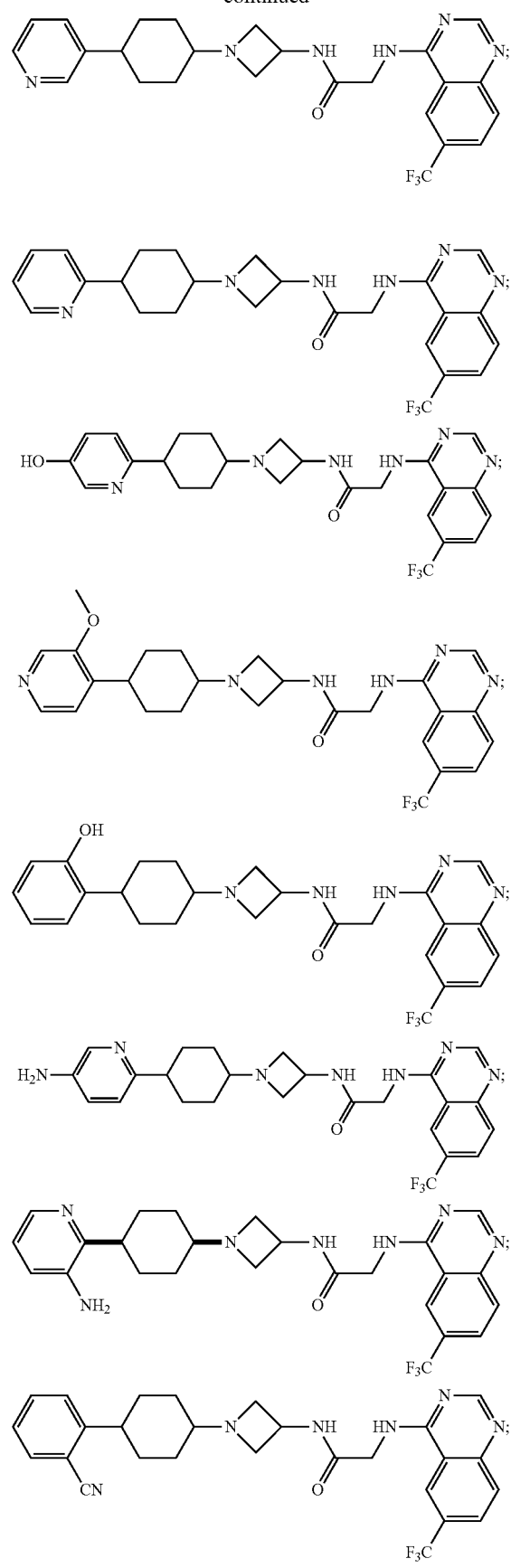

25
-continued
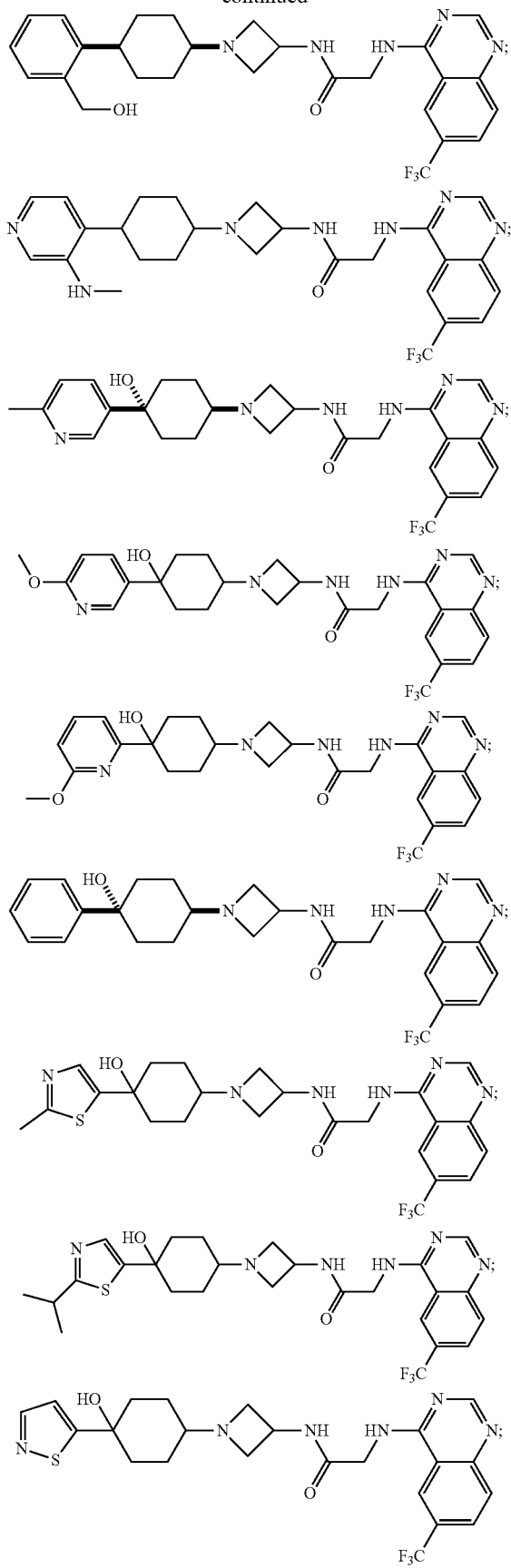
26
-continued
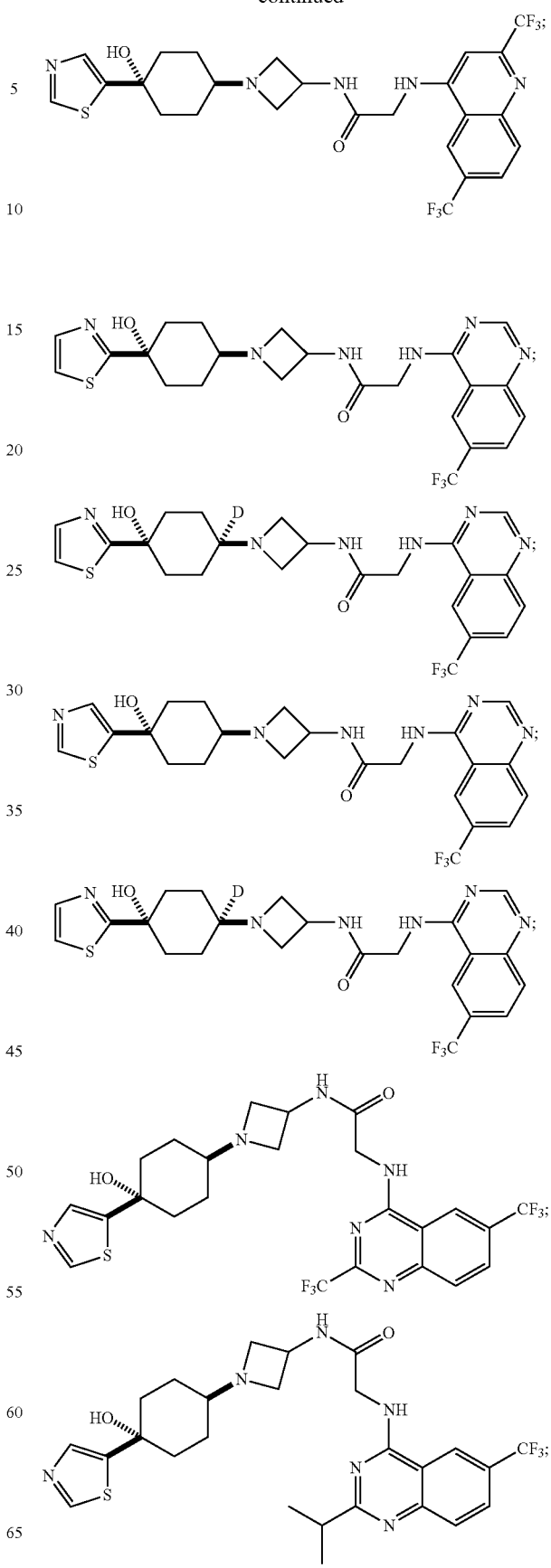

27
-continued
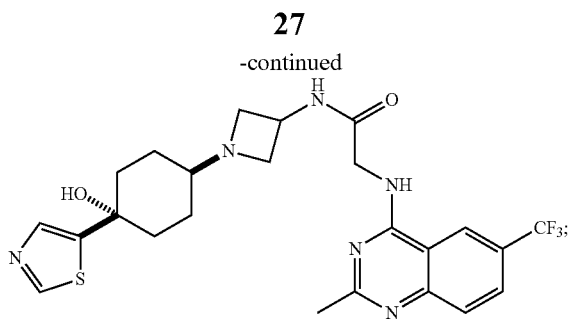
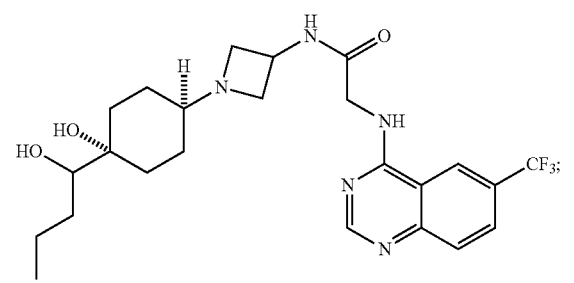
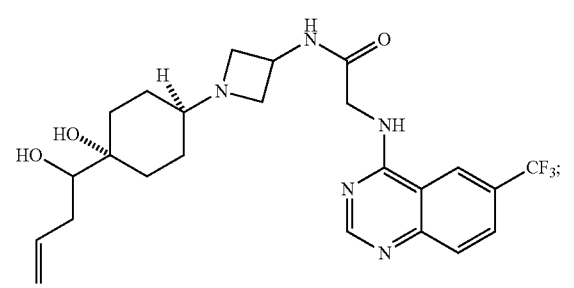
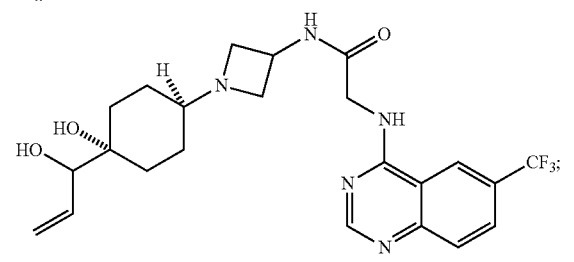
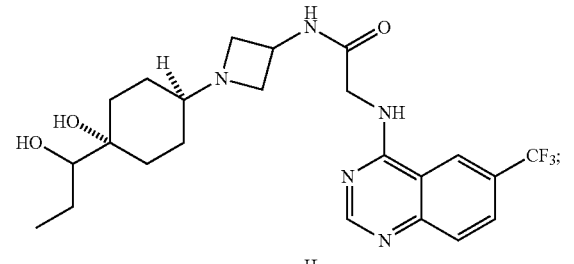
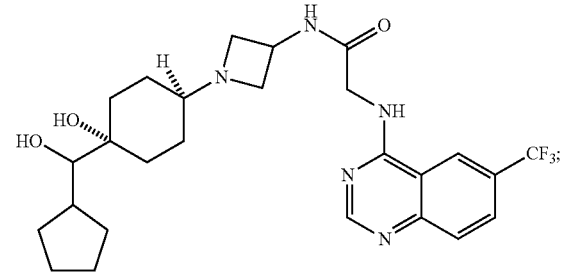
28
-continued
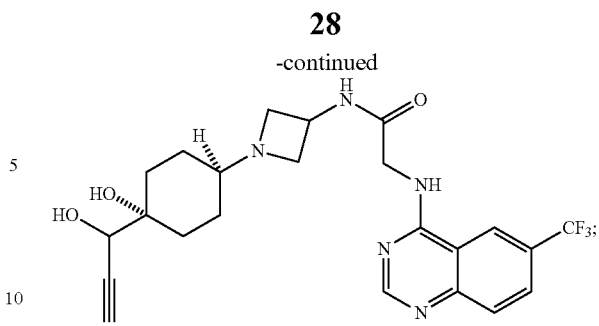
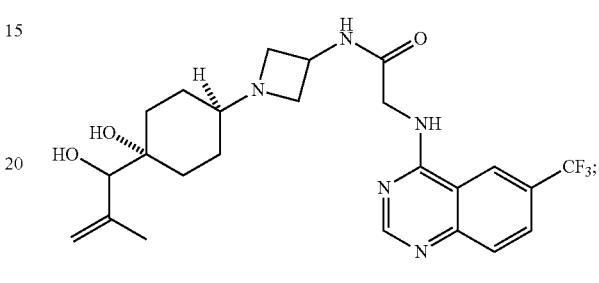
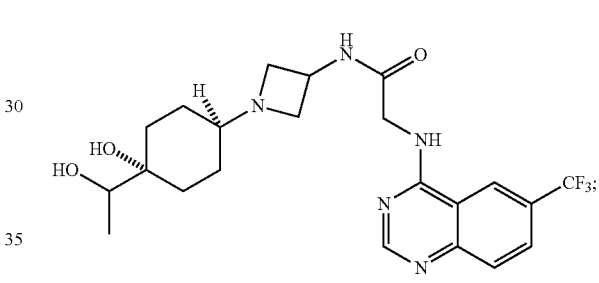
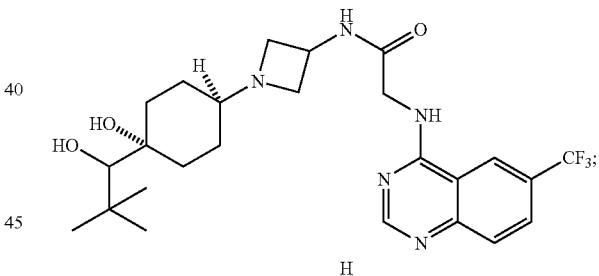
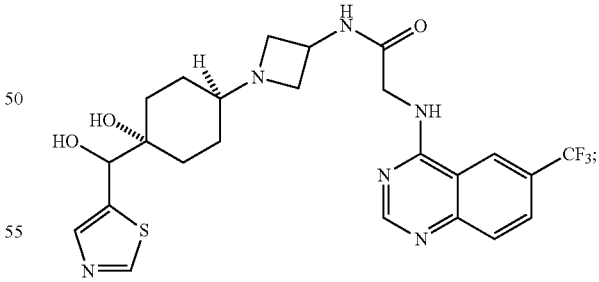
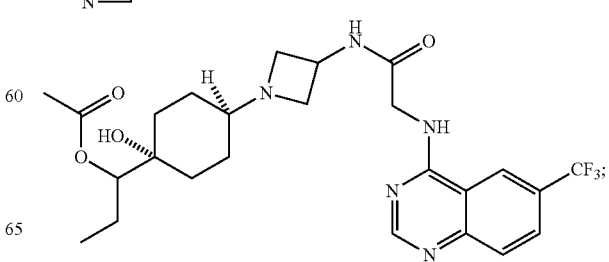

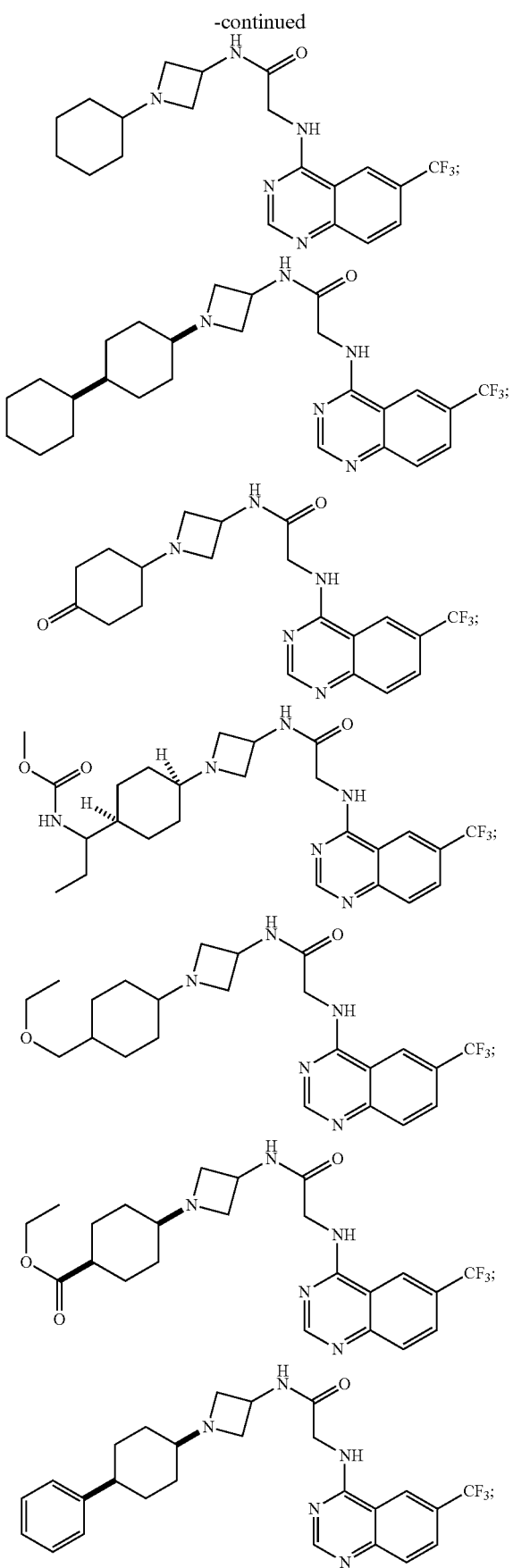

31
-continued
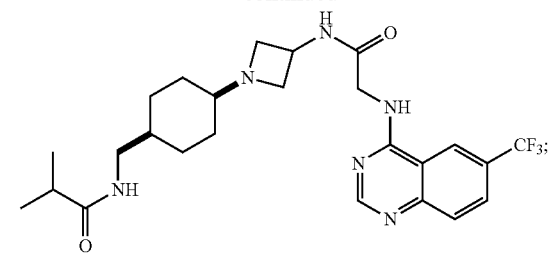
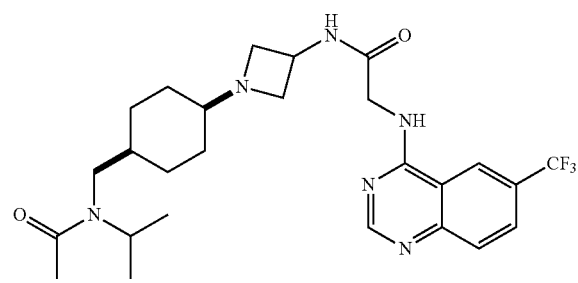
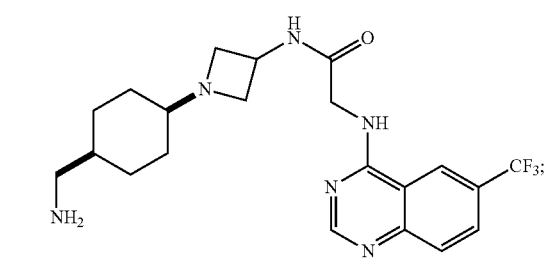
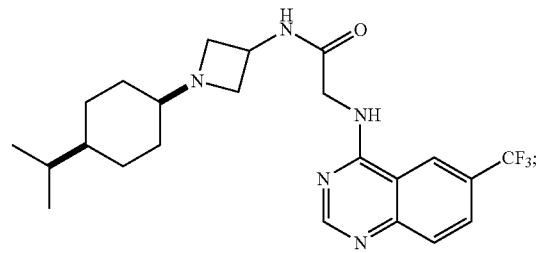
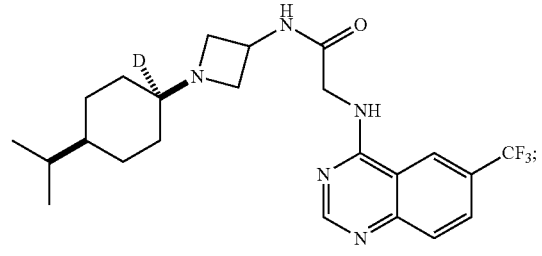
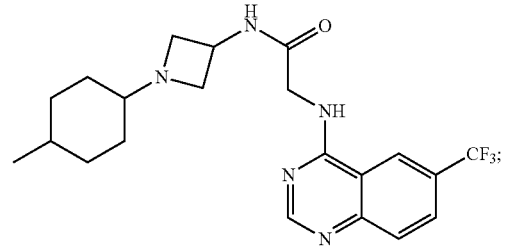
32
-continued
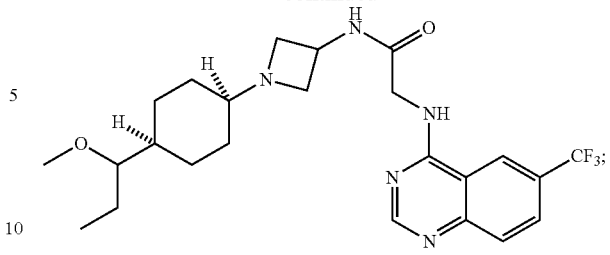
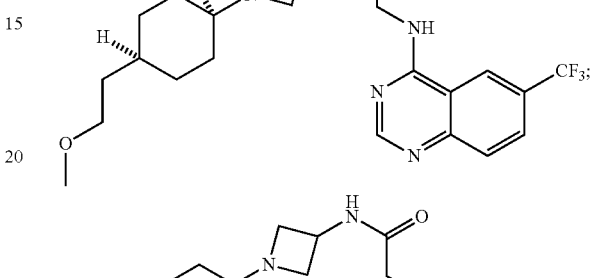
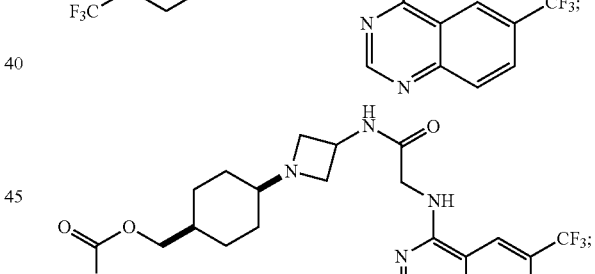
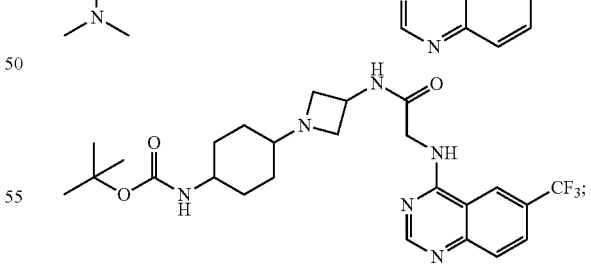
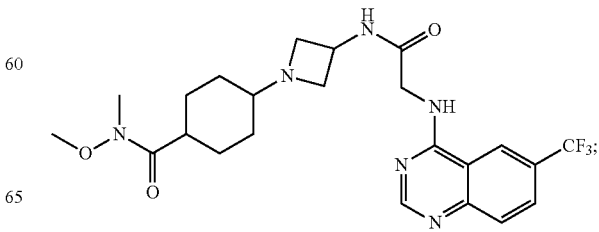

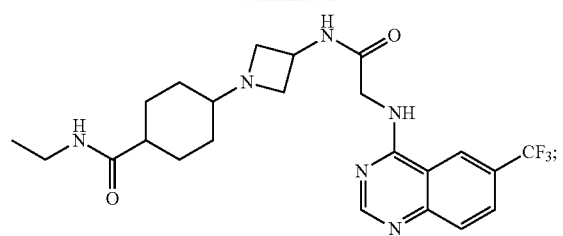
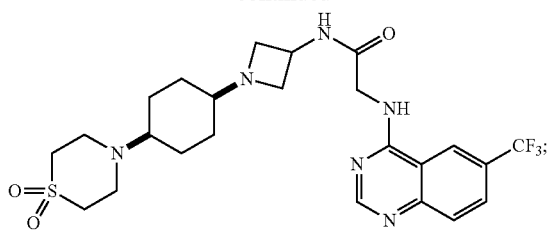
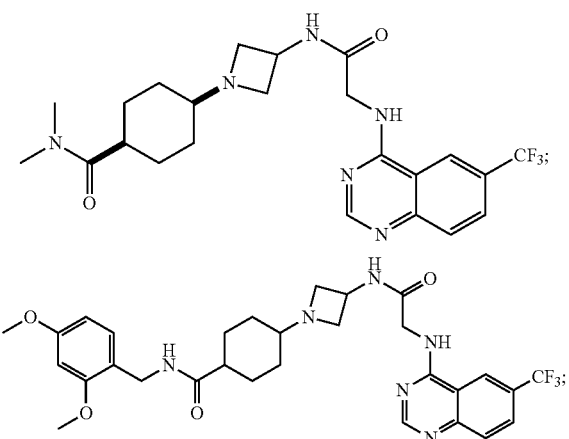
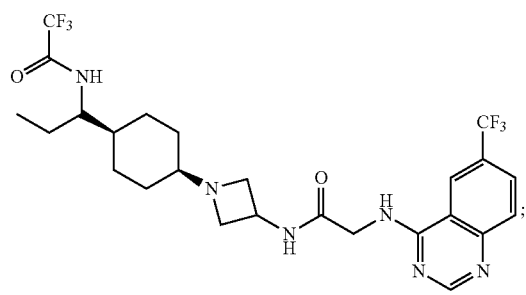
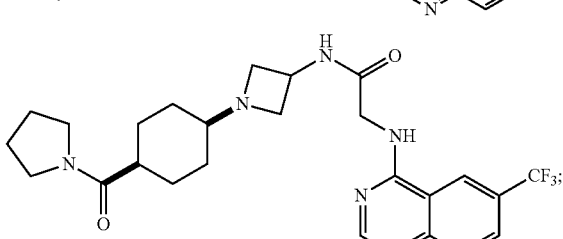
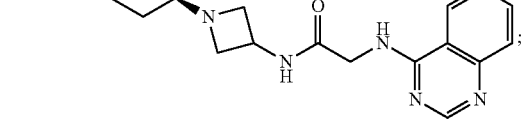
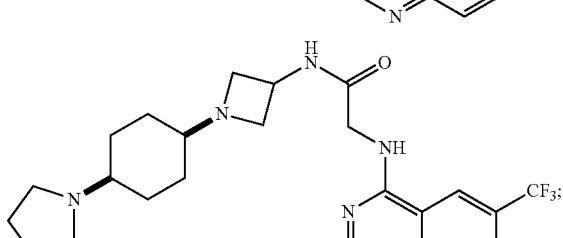
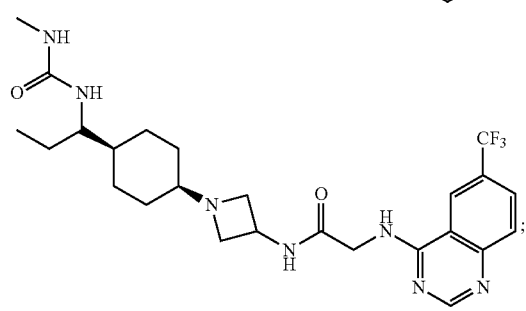
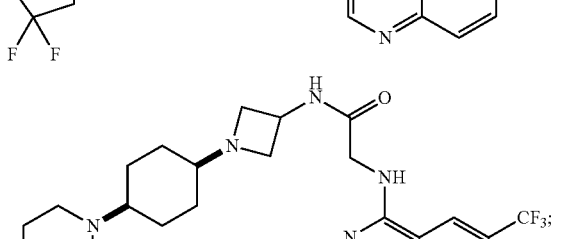
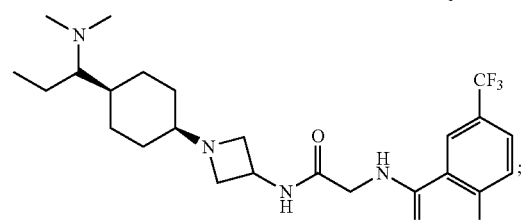
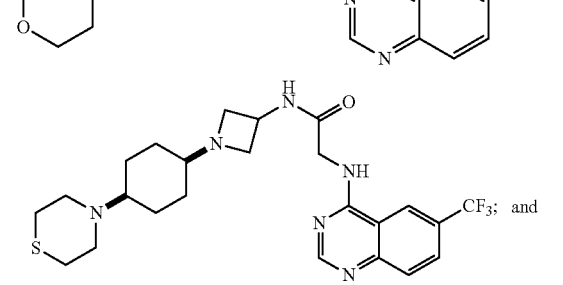
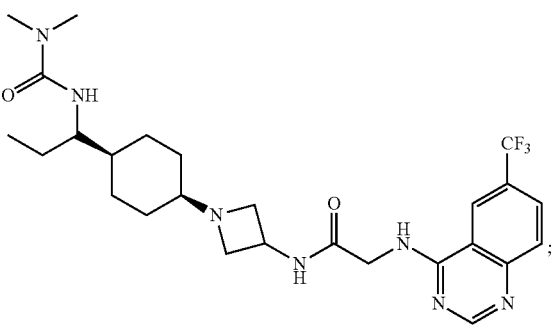

-continued
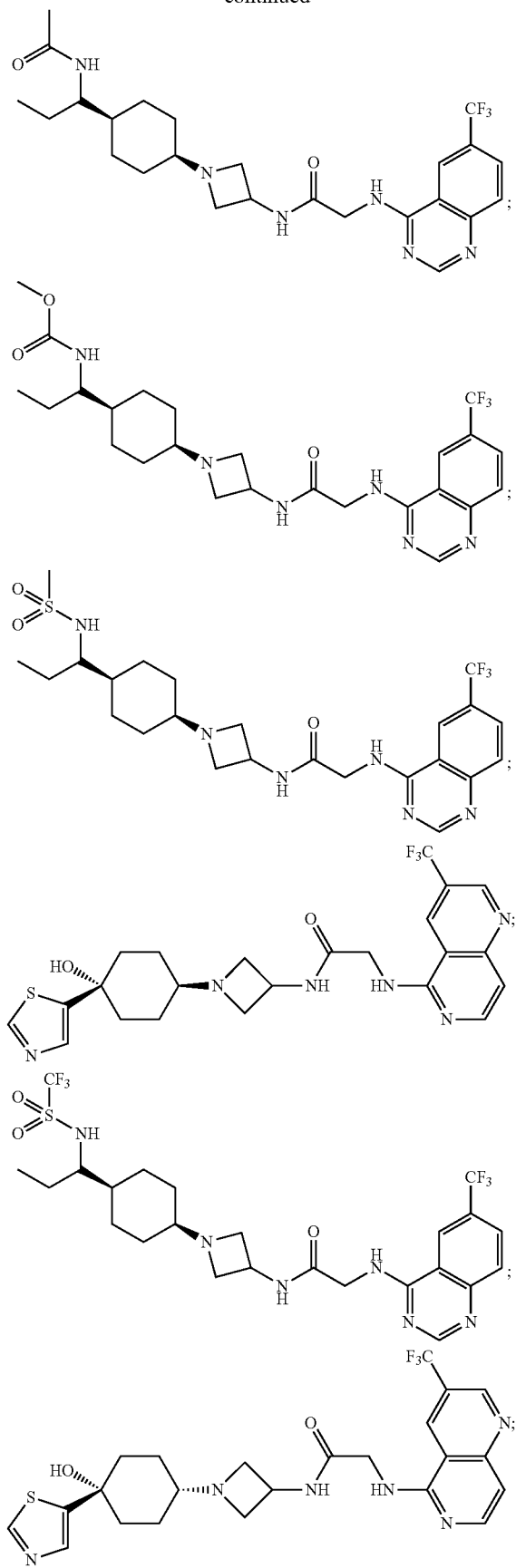
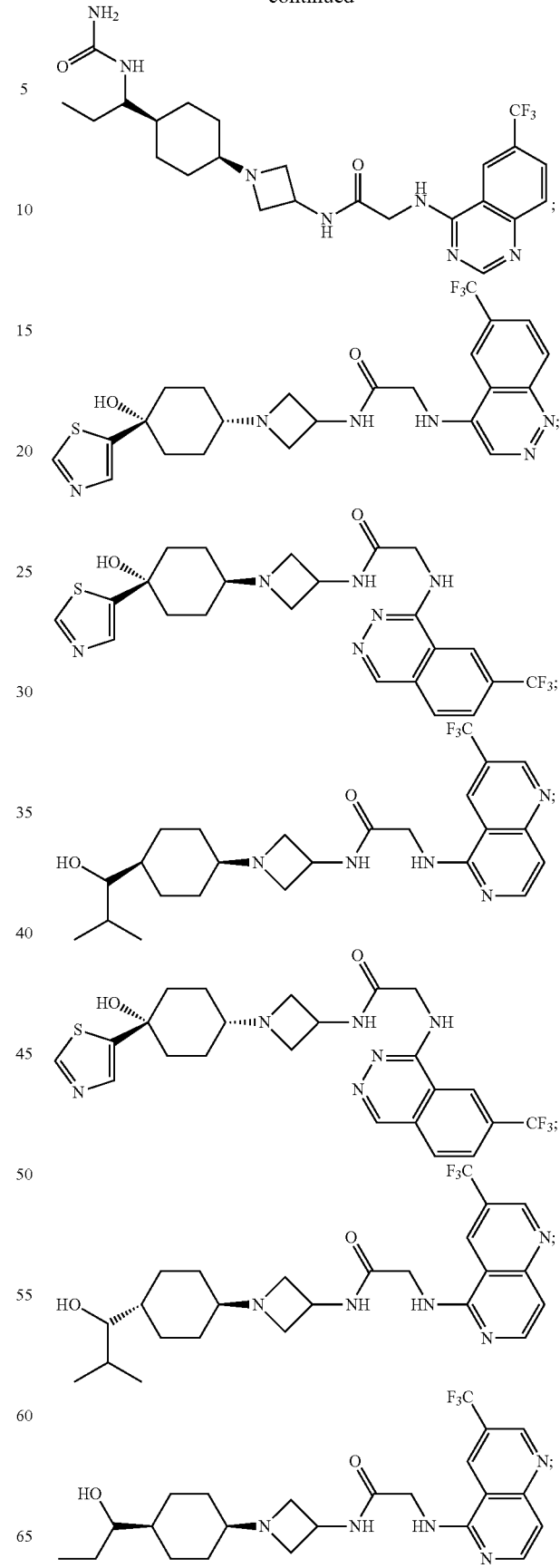

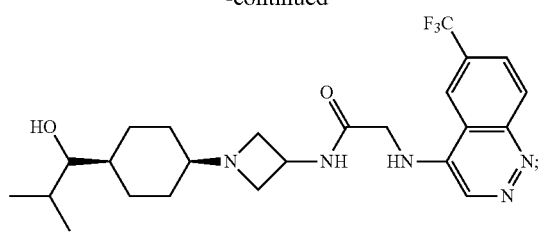
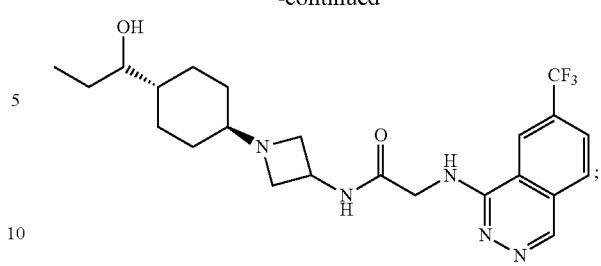
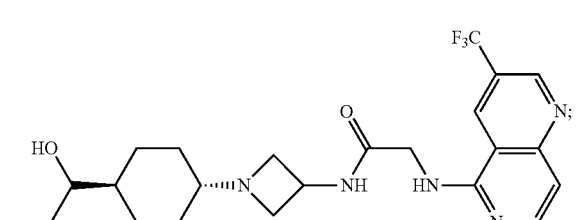
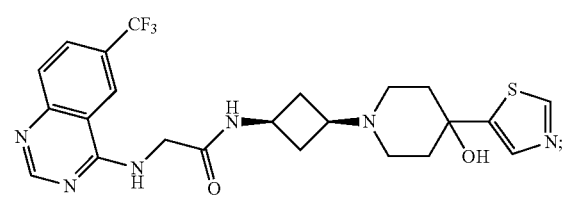
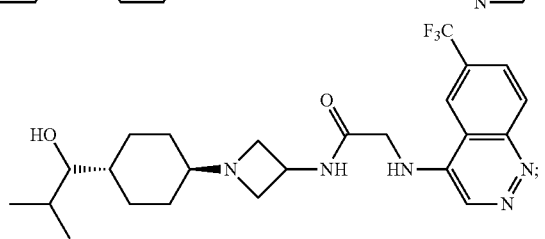
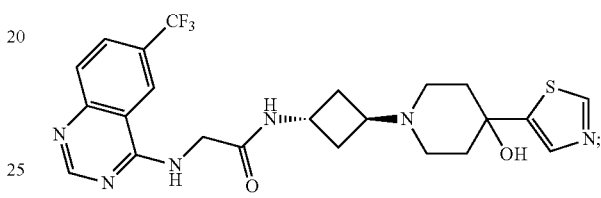
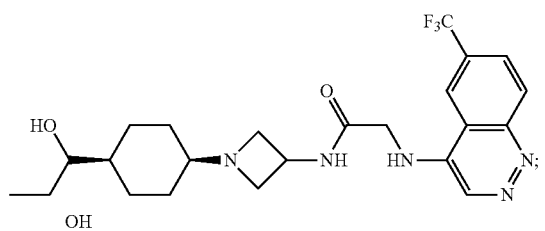
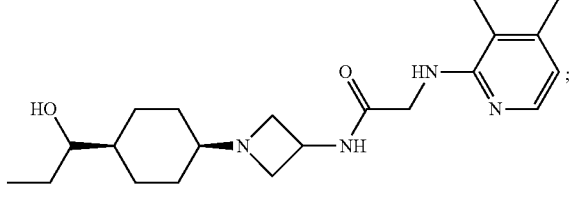
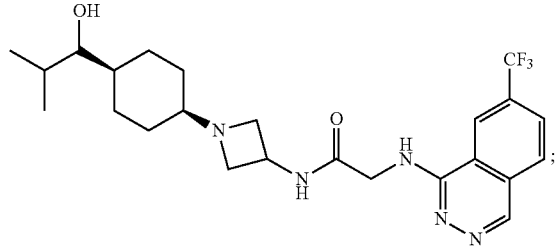
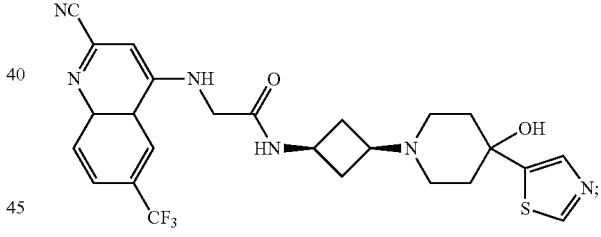
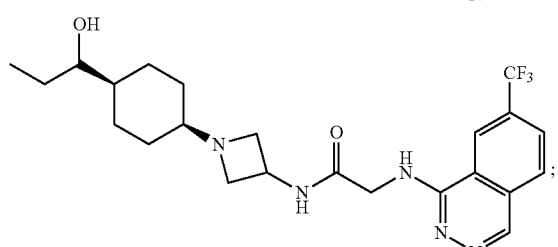
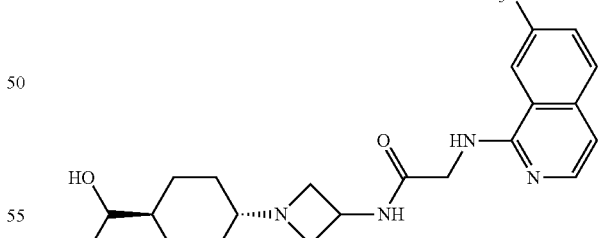
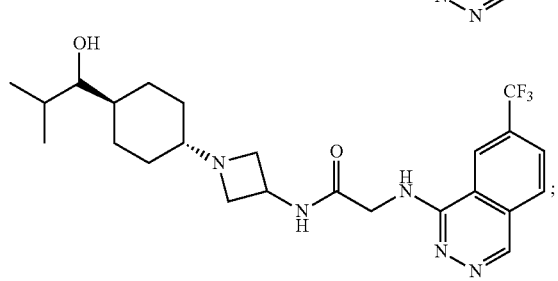
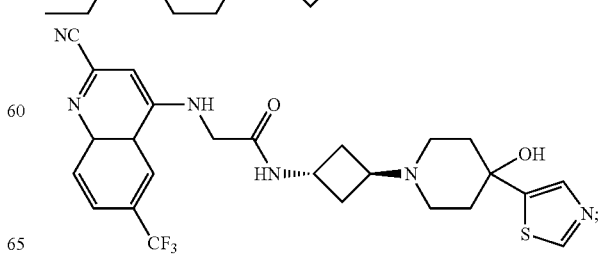

-continued

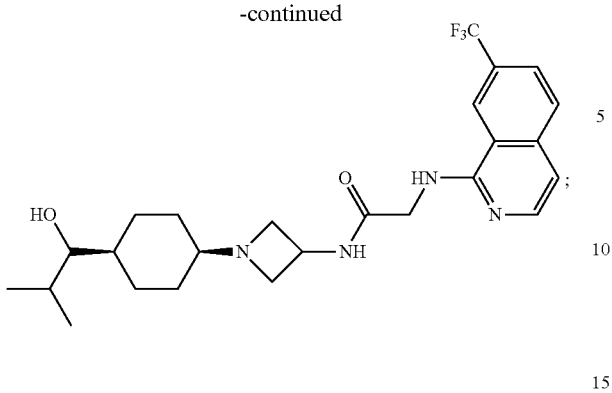

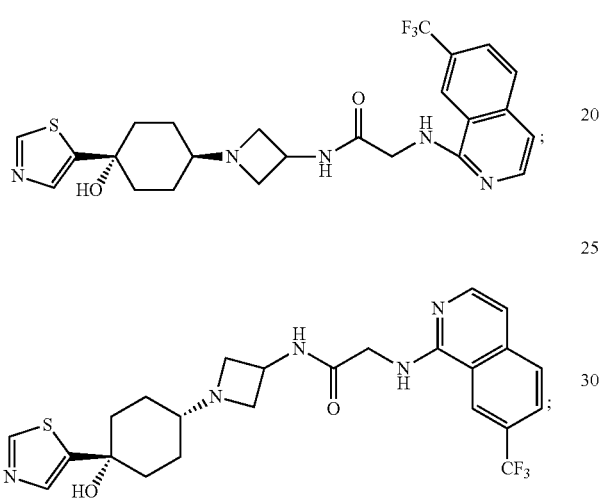

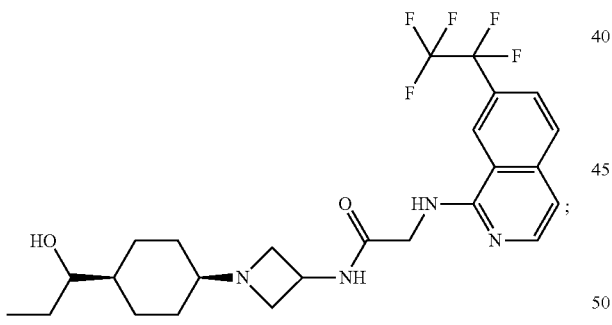

and pharmaceutically acceptable salts thereof.

In another embodiment, the invention relates to a pharmaceutical composition, comprising a compound of Formula I and a pharmaceutically acceptable carrier.

In another embodiment, the invention relates to a pharmaceutical composition made by mixing a compound of Formula I and a pharmaceutically acceptable carrier.

In another embodiment, the invention relates to a process for making a pharmaceutical composition comprising mixing a compound of Formula I and a pharmaceutically acceptable carrier.

In another embodiment, the invention relates to a process for the preparation of a compound of Formula I, comprising reacting a compound of Formula IV

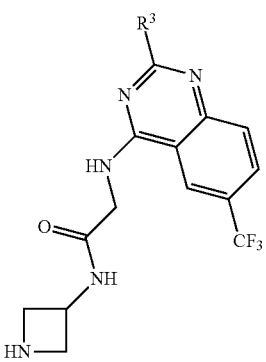

with a compound of Formula VI

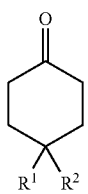

in the presence of a reducing agent to provide the compound of Formula I.

In another embodiment, the invention relates to a process for the preparation of a compound of Formula I, comprising reacting a compound of Formula IX

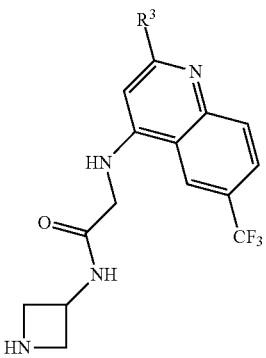

with a compound of Formula VI

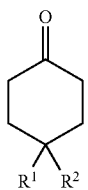

in the presence of a reducing agent to provide the compound of Formula I.

In another embodiment, the invention relates to a process for the preparation of a compound of Formula I, comprising reacting a compound of Formula XXXVIII

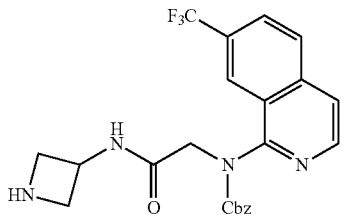 [SMILES: O=C(CN(C(=O)OCc1ccccc1)c1nccc2ccc(C(F)(F)F)cc12)NC1CNC1]

with a compound of Formula VI

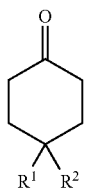

in the presence of a reducing agent to provide the compound of Formula I.

In another embodiment, the invention relates to a product made by the any of the above-described processes.

In another embodiment, the invention relates to a method for preventing, treating or ameliorating a CCR2 mediated syndrome, disorder or disease comprising administering to a subject in need thereof a therapeutically effective amount of a compound of Formula I.

In another embodiment, the invention relates to a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof an effective amount of a compound of Formula I.

In another embodiment, the invention relates to a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes and diabetic complications, diabetic nephropathy, diabetic retinopathy, diabetic retinitis, diabetic microangiopathy, overweight, obesity, obesity-associated insulin resistance, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I.

In another embodiment, the invention relates to a method of preventing, treating or ameliorating a syndrome, disorder or disease, wherein said syndrome, disorder or disease is selected from the group consisting of: type II diabetes and diabetic complications, diabetic nephropathy, diabetic retinopathy, diabetic retinitis, diabetic microangiopathy, obesity, asthma, and allergic asthma, comprising administering to a subject in need thereof a therapeutically effective amount of a compound of Formula I.

In another embodiment, the invention relates to a method of treating a disorder selected from the group consisting of type II diabetes, obesity and asthma comprising administering to a subject in need thereof a therapeutically effective amount of a compound of Formula I.

In another embodiment, the invention relates to a compound of Formula I, selected from any of the Examples 1-170, and pharmaceutically acceptable salts thereof.

In another embodiment, the invention relates to a compound of Formula I, which is the less polar isomer of any of Examples #1-170.

In another embodiment, the invention relates to a product made by the process of any of Examples from Example 1 to Example 170.

Definitions

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "heteroaromatic" or "heteroaryl" refers to 5- to 7-membered mono- or 8- to 10-membered bicyclic aromatic ring systems, containing from one to four heteroatoms selected from N, O, or S where the nitrogen and sulfur atoms can exist in any allowed oxidation state. Examples include, but are not limited to, benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

For use in medicines, the salts of the compounds of this invention refer to non-toxic "pharmaceutically acceptable salts." FDA approved pharmaceutically acceptable salt forms (Ref International J. Pharm. 1986, 33, 201-217; J. Pharm. Sci., 1977, January, 66(1), p1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium.

Abbreviations

Herein and throughout this application, the following abbreviations may be used.

BOC or Boc tert-butyloxycarbonyl
Bu butyl
D deuterium
DCC dicyclohexylcarbodiimide
DCE dichloroethane
DCM dicholomethane
DMF dimethylformamide
DMSO dimethylsulfoxide
EDCI 1-ethyl-3-(3'-dimethylaminopropyl)carbodiimide
Et ethyl
EtOAc ethyl acetate
DIPEA diisopropylethylamine
DMAP dimethylaminopyridine
HOBt hydroxybenzotriazole
IPA isopropyl alcohol
mCPBA meta-chloroperoxy benzoic acid
Me methyl
Ms mesylate
NMM N-methyl morpholine
NMP N-methylpyrrolidine
OAc acetate
PdCl$_2$(dppf) [1,1'-bis(diphenylphosphino)ferrocene]dichloropalladium(II)
Ph phenyl
iPr isopropyl
PyBrop bromo-tris-pyrrolidinophosphonium hexafluorophosphate
RT or rt room temperature
TEA triethylamine
TFA trifluoroacetic acid
THF tetrahydrofuran Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH$_3$, NH$_4$OH, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine or zinc.

Methods of Use

The present invention is directed to a method for preventing, treating or ameliorating a CCR2 mediated syndrome, disorder or disease comprising administering to a subject in need thereof an effective amount of a compound of Formula I or a form, composition or medicament thereof.

Examples of a CCR2 mediated syndrome, disorder or disease for which the compounds of Formula I are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodontis, gingivitis, gum disease, diastolic cardiomyopathies, cardiac infarction, myocarditis, chronic heart failure, angiostenosis, restenosis, reperfusion disorders, aortic abdominal aneurism, multiple sclerosis, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury.

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (~19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents micobial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples or Formula I for use as a medicament.

In another embodiment, the invention relates to the use of a compound as described in the Examples of Formula I for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

General Reaction Scheme

Representative compounds of the present invention are synthesized in accordance with the general synthetic methods described below. Compounds of Formula I are prepared by methods known to those who are skilled in the art. The following reaction schemes and examples are only meant to represent examples of the invention and are in no way meant to be a limit of the invention.

Compounds of Formula I where X and Z are both nitrogen may be prepared according to the processes outlined in Scheme 1.

Scheme 1

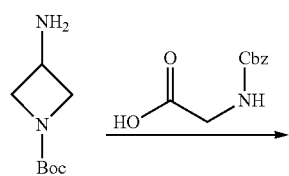

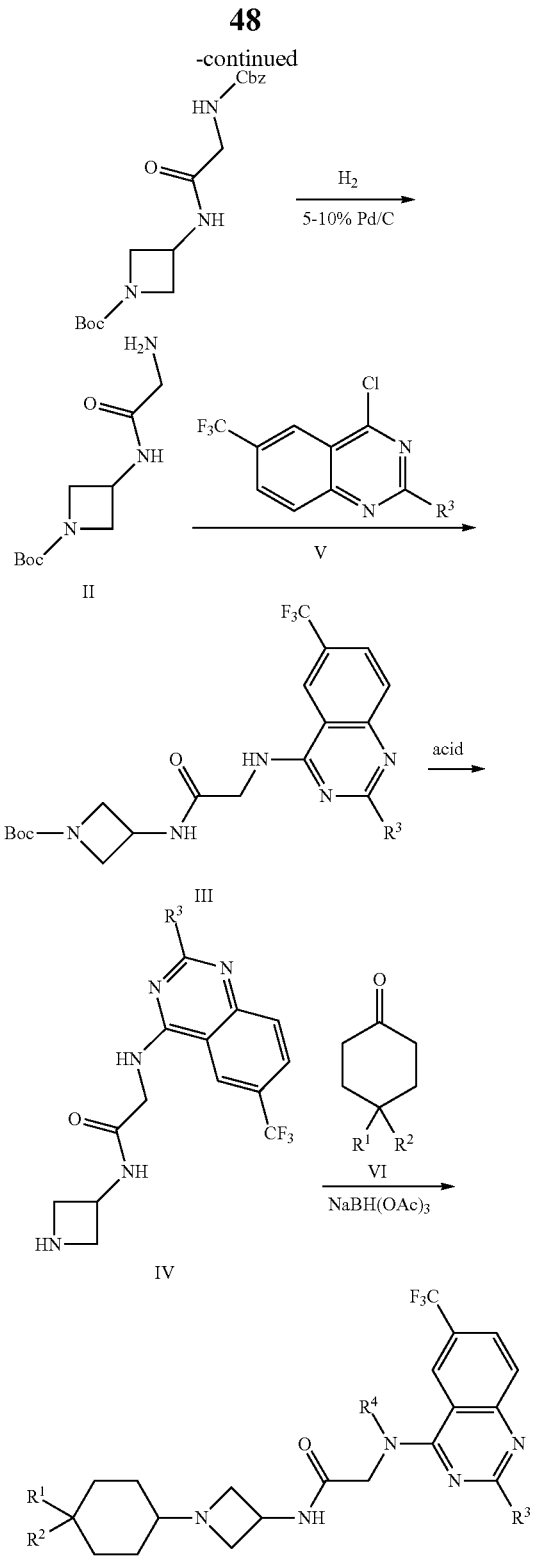

Commercially available 2-(((benzyloxy)carbonyl)amino) acetic acid is reacted with commercially available tert-butyl 3-aminoazetidine-1-carboxylate in the presence of a peptide coupling reagent such as EDCI, DIC, PyBrOP, PyBOP in an organic solvent such as dichloromethane, THF or dioxane to afford a substituted azetidine. The substituted azetidine is treated with hydrogen gas under pressure from 5 to 50 psi catalyzed by 5-10% Pd/C, in an organic solvent such as methanol, at a temperature in the range of about 25° C. to about 50° C., to yield the corresponding amine II. Amine II is reacted with chloroquinazoline V in the presence of an organic base such as TEA or DIEA in an organic solvent such as isopropanol at reflux temperature to yield azetidine III. Azetidine III is treated with an acid such as 1N HCl, 1N H$_2$SO$_4$ or trifluoroacetic acid in an organic solvent such as diethyl ether, THF, dichloromethane or dioxane, at a temperature in the range of about 0° C. to about 25° C. to yield amine salt IV. Amine salt IV is reacted with a suitably substituted ketone VI, in the presence of a reducing reagent such as NaBH$_4$, NaBH$_3$CN or NaBH(OAc)$_3$, in the presence of an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding compound of Formula I wherein X and Z are both nitrogen.

Compounds of Formula I where X is nitrogen, and Z is C—H may be prepared according to the processes outlined in Scheme 2.

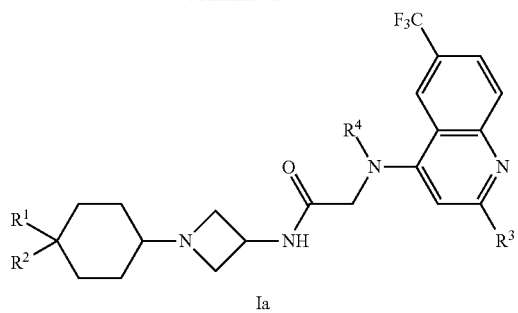

Ia

Commercially available quinolinol VII is treated with PyBroP in the presence of an organic base such as DIEA or TEA in dioxane at a temperature range from 40 to 60° C. for two hours, treated with azetidine II, and the mixture stirred overnight at ambient temperature to afford azetidine VIII. Azetidine VIII is treated with an acid such as 1N HCl, 1N H$_2$SO$_4$ or trifluoroacetic acid in an organic solvent such as diethyl ether, THF, dichloromethane or dioxane, at a temperature in the range of about 0° C. to about 25° C. to yield amine salt IX. Amine salt IX is reacted with a suitably substituted ketone VI, in the presence of a reducing reagent such as NaBH$_4$, NaBH$_3$CN or NaBH(OAc)$_3$, in the presence of an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding compound of Formula I wherein X is nitrogen, and Z is C—H (i.e., the compound of Formula Ia.

Alternatively, compounds of Formula I where X is nitrogen, and Z is C—H may be prepared according to the processes outlined in Scheme 3.

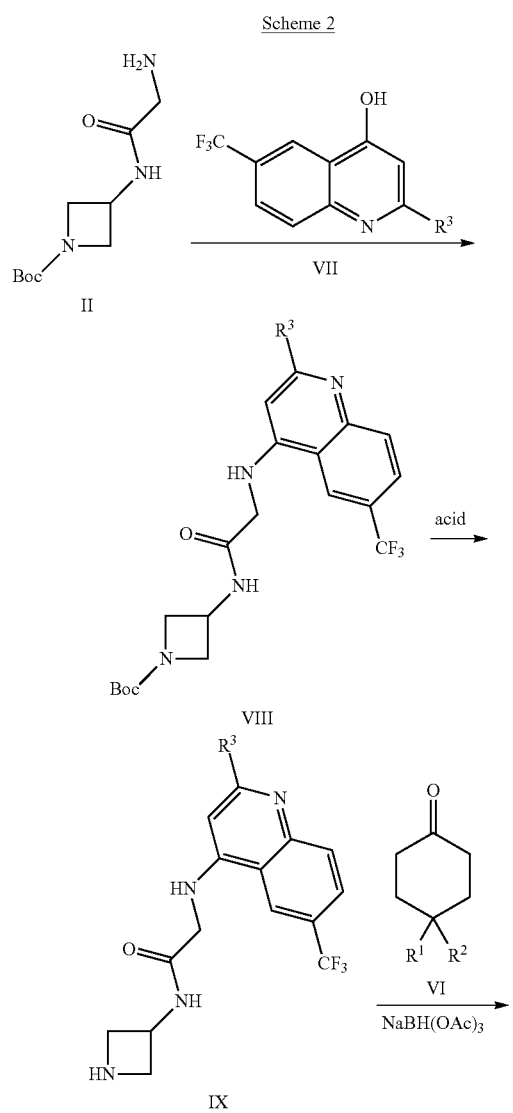

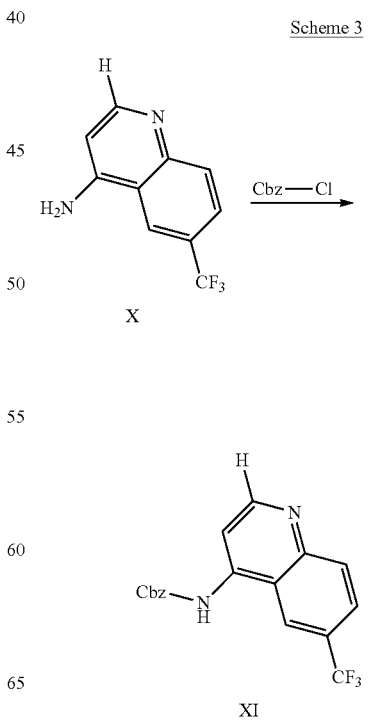

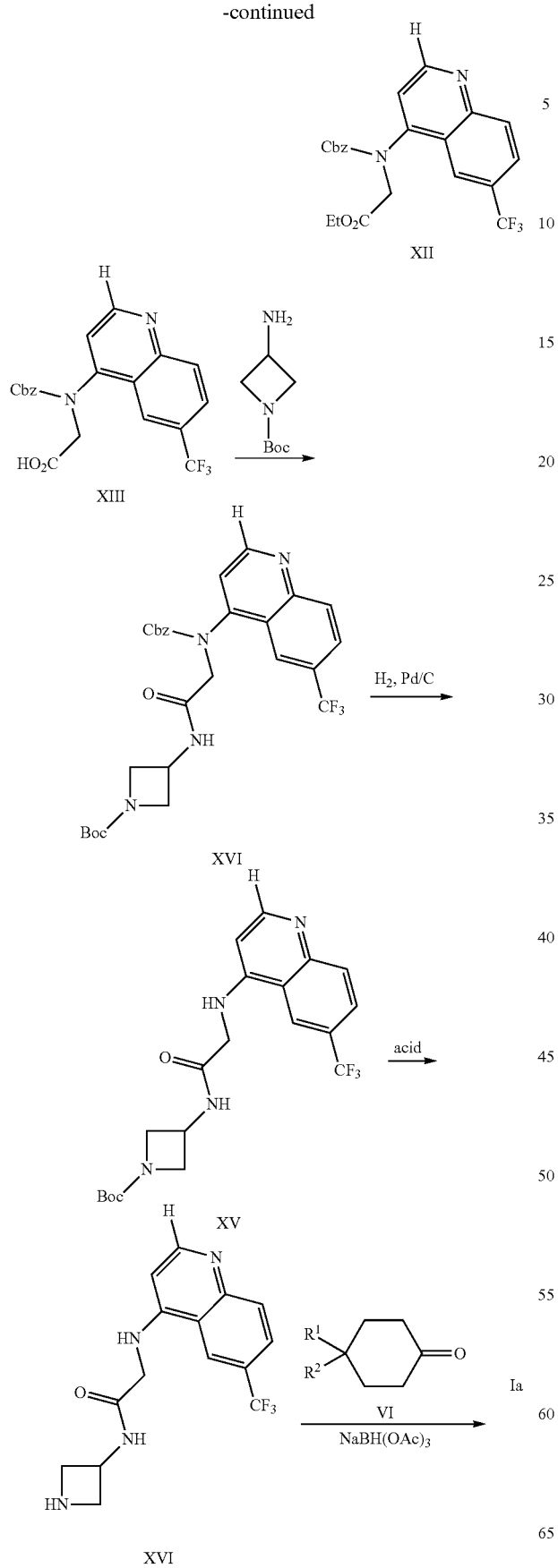

Commercially available 6-(trifluoromethyl)quinolin-4-amine X is reacted under Schotten-Bauman conditions using benzylchloroformate in a biphasic mixture of aqueous sodium bicarbonate and an organic solvent like ethyl acetate at or around ambient temperature to afford carbamate XI. Reaction of XI with methylbromoacetate in the presence of a base such as $Na_2CO_3$, $K_2CO_3$ or $Cs_2CO_3$ in an organic solvent such as DMF, NMP or DMSO affords compound XII. Compound XII is hydrolyzed by treatment with NaOH, KOH or LiOH in a mixture of an organic solvent such as THF or methanol with water at or around ambient temperature to yield acid 13. Acid 13 is coupled with tert-butyl 3-aminoazetidine-1-carboxylate in the presence of a peptide coupling reagent such as EDCI, DIC, PyBrOP, PyBOP in an organic solvent such as dichloromethane, THF or dioxane to afford azetidine XIV. Azetidine XIV is treated with hydrogen gas under pressure from 5 to 50 psi catalyzed by 5-10% Pd/C, in an organic solvent such as methanol, at a temperature in the range of about 25° C. to about 50° C., to yield the corresponding azetidine XV. Azetidine XV is treated with an acid such as 1N HCl, 1N $H_2SO_4$ or trifluoroacetic acid in an organic solvent such as diethyl ether, THF, dichloromethane or dioxane, at a temperature in the range of about 0° C. to about 25° C., to yield amine salt XVI. Amine salt XVI is reacted with ketone VI, in the presence of a reducing reagent such as $NaBH_4$, $NaBH_3CN$ or $NaBH(OAc)_3$, in the presence of an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding compound of Formula Ia.

Alternatively, compounds of Formula I where X is C—H and Z is nitrogen may be prepared according to the processes outlined in Scheme 4.

Scheme 4

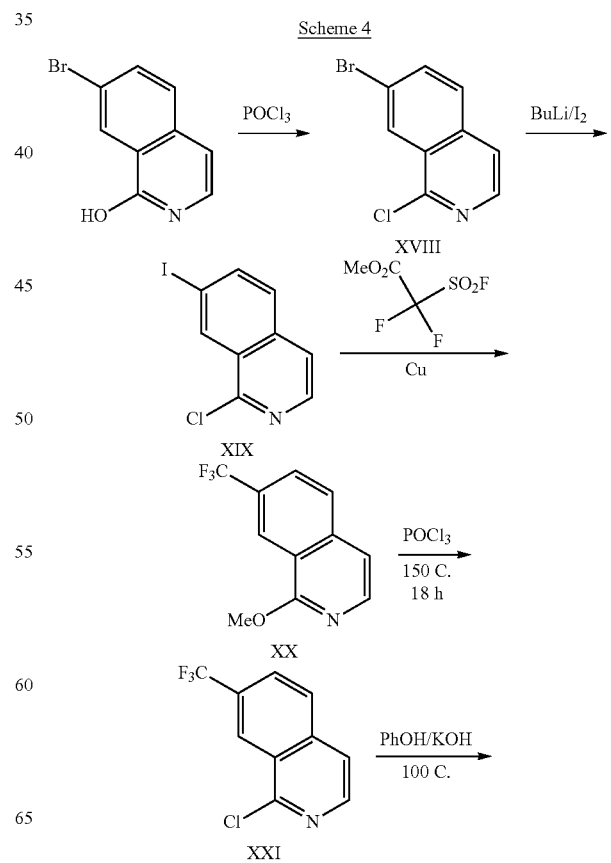

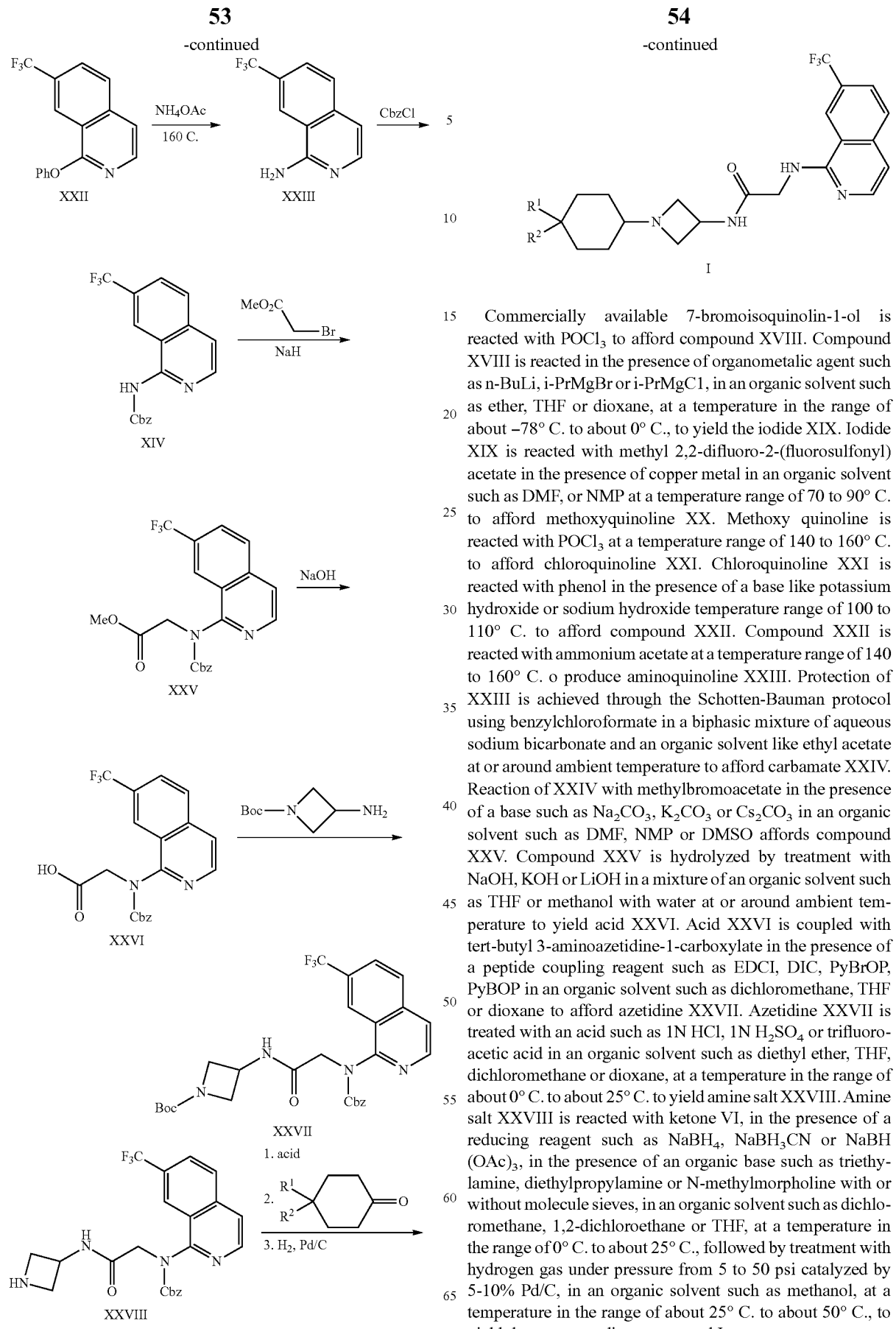

Commercially available 7-bromoisoquinolin-1-ol is reacted with POCl₃ to afford compound XVIII. Compound XVIII is reacted in the presence of organometalic agent such as n-BuLi, i-PrMgBr or i-PrMgCl, in an organic solvent such as ether, THF or dioxane, at a temperature in the range of about −78° C. to about 0° C., to yield the iodide XIX. Iodide XIX is reacted with methyl 2,2-difluoro-2-(fluorosulfonyl) acetate in the presence of copper metal in an organic solvent such as DMF, or NMP at a temperature range of 70 to 90° C. to afford methoxyquinoline XX. Methoxy quinoline is reacted with POCl₃ at a temperature range of 140 to 160° C. to afford chloroquinoline XXI. Chloroquinoline XXI is reacted with phenol in the presence of a base like potassium hydroxide or sodium hydroxide temperature range of 100 to 110° C. to afford compound XXII. Compound XXII is reacted with ammonium acetate at a temperature range of 140 to 160° C. o produce aminoquinoline XXIII. Protection of XXIII is achieved through the Schotten-Bauman protocol using benzylchloroformate in a biphasic mixture of aqueous sodium bicarbonate and an organic solvent like ethyl acetate at or around ambient temperature to afford carbamate XXIV. Reaction of XXIV with methylbromoacetate in the presence of a base such as Na₂CO₃, K₂CO₃ or Cs₂CO₃ in an organic solvent such as DMF, NMP or DMSO affords compound XXV. Compound XXV is hydrolyzed by treatment with NaOH, KOH or LiOH in a mixture of an organic solvent such as THF or methanol with water at or around ambient temperature to yield acid XXVI. Acid XXVI is coupled with tert-butyl 3-aminoazetidine-1-carboxylate in the presence of a peptide coupling reagent such as EDCI, DIC, PyBrOP, PyBOP in an organic solvent such as dichloromethane, THF or dioxane to afford azetidine XXVII. Azetidine XXVII is treated with an acid such as 1N HCl, 1N H₂SO₄ or trifluoroacetic acid in an organic solvent such as diethyl ether, THF, dichloromethane or dioxane, at a temperature in the range of about 0° C. to about 25° C. to yield amine salt XXVIII. Amine salt XXVIII is reacted with ketone VI, in the presence of a reducing reagent such as NaBH₄, NaBH₃CN or NaBH(OAc)₃, in the presence of an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., followed by treatment with hydrogen gas under pressure from 5 to 50 psi catalyzed by 5-10% Pd/C, in an organic solvent such as methanol, at a temperature in the range of about 25° C. to about 50° C., to yield the corresponding compound I.

Compounds of Formula I may be derived from Quinazoline 5. Preparation of 5 is outlined in Scheme 5.

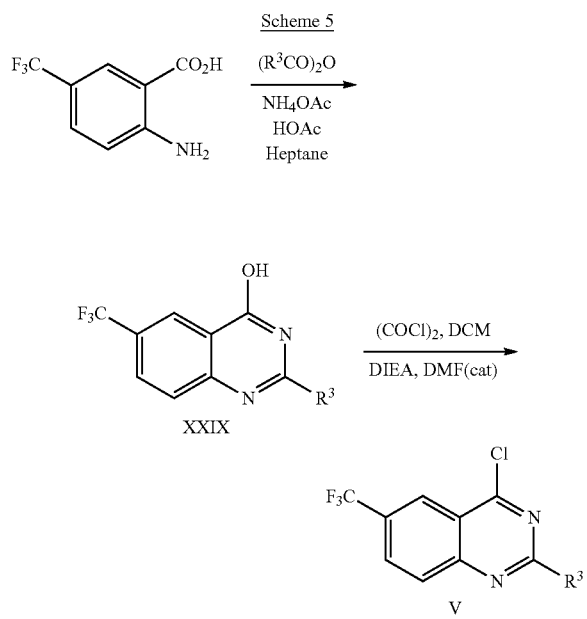

Scheme 5

Commercially available 2-amino-5-(trifluoromethyl)benzoic acid is reacted with the appropriate anyhydride in the presence of ammonium acetate and acetic acid in an organic solvent such as hexane, heptanes or octane at a temperature from ambient to 60° C. to afford compound XXIX. Compound XXIX is reacted with oxalyl chloride in the presence of an organic base like diisopropylethylamine or triethyl amine in an organic solvent like dichloromethane or dichloroethane with DMF as a promoter to afford compound V.

Compounds of Formula I may be derived from ketone VI. Preparation of VI is outlined in Scheme 6.

Scheme 6

Commercially available aryl halide or aryl alkane $R^1Lv^*$ (where $R^1$ is as defined in Formula I, and $Lv^*$ is H or a halogen) is reacted with commercially available 1,4-dioxaspiro[4.5]decan-8-one in the presence of organometalic agent such as n-BuLi, i-PrMgBr or i-PrMgCl, in an organic solvent such as ether, THF or dioxane, at a temperature in the range of about −78° C. to about 0° C., to yield the corresponding ketal XXX. Ketal XXX is treated with an acid such as 1N HCl or 1N $H_2SO_4$ in an organic solvent such as acetone, acetonitrile or THF, at a temperature in the range of about 0° C. to about 25° C., to yield the corresponding ketone VI.

Alternatively compound VI may be prepared according to the processes outlined in Scheme Scheme 7.

Scheme 7

Ketal XXX is treated with a dehydrating agent such as Burgess' reagent, in an organic solvent such as ether, THF or dioxane, at a temperature in the range of about 0° C. to about 25° C., to yield the corresponding alkene XXXI. Alkene XXXI is treated with hydrogen gas under pressure from 5 to 50 psi catalyzed by 5-10% Pd/C, in an organic solvent such as methanol, at a temperature in the range of about 25° C. to about 50° C., to yield the corresponding alkane XXXII. Alkane XXXII is treated with 1N HCl or 1N $H_2SO_4$, in an organic solvent such as acetone, acetonitrile or THF, at a temperature in the range of about 0° C. to about 25° C., to yield the corresponding ketone VI.

Alternatively compound XXXI may be prepared according to the processes outlined in Scheme 8.

Scheme 8

Commercially available aryl boronic acid, (wherein $R^1$ is as defined in Formula I) is reacted with vinyl triflate XXXIII prepared according to the procedure of Pearson, W. et. al., *J. Org. Chem.* 2004, 69, 9109-9122, in the presence of a catalyst such as $Pd(Ph_3P)_4$, $PdCl_2(Ph_3P)_2$ or $PdCl_2(dppf)$ and a base such as 2N $Na_2CO_3$ or $K_2CO_3$, in an organic solvent such as toluene, dioxane or THF, at a temperature in the range of about 80° C. to about 120° C., to yield the corresponding alkene XXXIV.

Alternatively, commercially available aryl or heteroaryl halide R¹Lv* is reacted with vinyl boronic ester XXXV prepared according to Birch, A. M. et. al., PCT Int. Appl. 2006, WO 2006064189, in the presence of a catalyst such as Pd(Ph₃P)₄, PdCl₂(Ph₃P)₂ or PdCl₂(dppf) and a base such as 2N Na₂CO₃ or K₂CO₃, in an organic solvent such as toluene, dioxane or THF, at a temperature in the range of about 80° C. to about 120° C., to yield the corresponding alkene XXXI.

Alternatively compound VI may be prepared according to the processes outlined in Scheme Scheme 9.

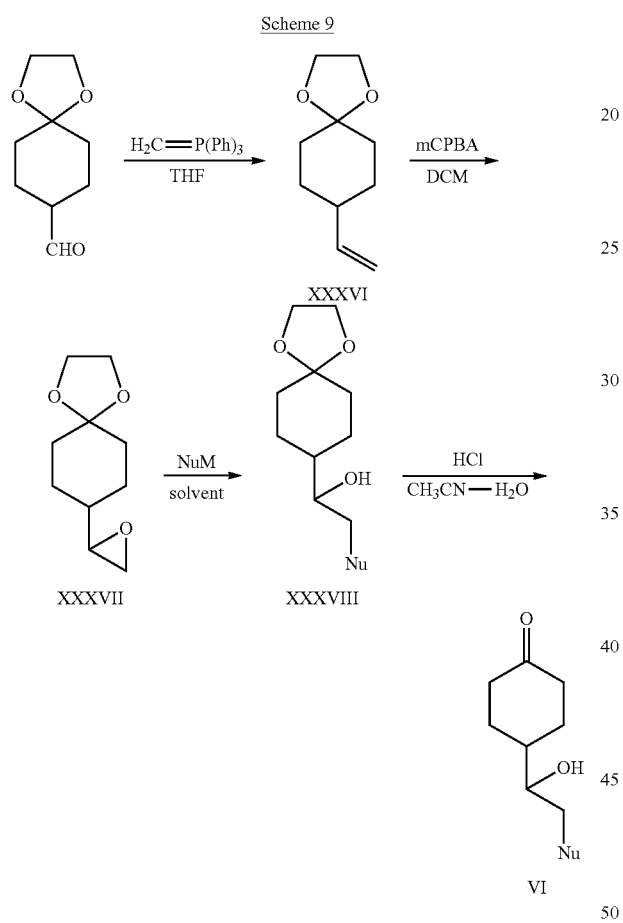

where M is a metal, such as Na⁺, and Nu is a nucleophile, such as —SCH₃

1,4-dioxaspiro[4.5]decane-8-carbaldehyde, prepared as described in Pearson, et al. in *J. Org. Chem.* 1997, 62(16), 5284-5292, is reacted with a Wittig reagent in an aprotic organic solvent such as THF, dioxane or ether at ambient temperature to afford alkene XXXVI. Alkene XXXVI is epoxidized through the action of mCPBA in an organic solvent such as dichloromethane to afford epoxide XXXVII. Epoxide XXXVII is opened by a variety of nucleophiles including NaOMe, NaSMe and NaN₃ in an organic solvent such as methanol, DMF or DMSO to produce carbinol XXXVIII. Carbinol XXXVIII is treated with 1N HCl or 1N H₂SO₄, in an organic solvent such as acetone, acetonitrile or THF, at a temperature in the range of about 0° C. to about 25° C., to yield the corresponding ketone VI.

Alternatively compound VI may be prepared according to the processes outlined in Scheme Scheme 10.

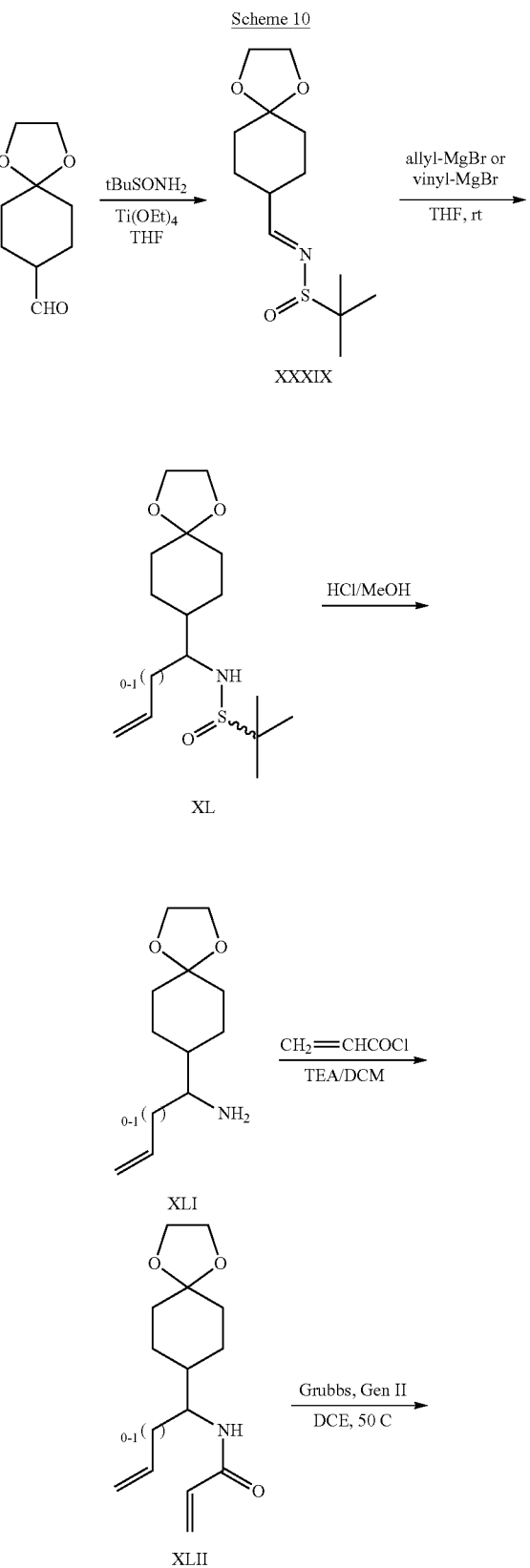

59

-continued

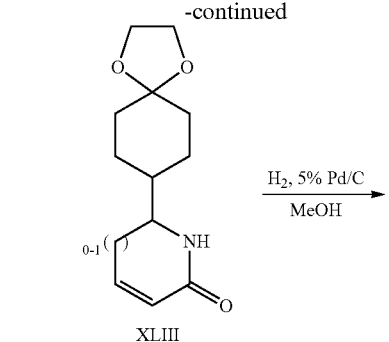

XLIII

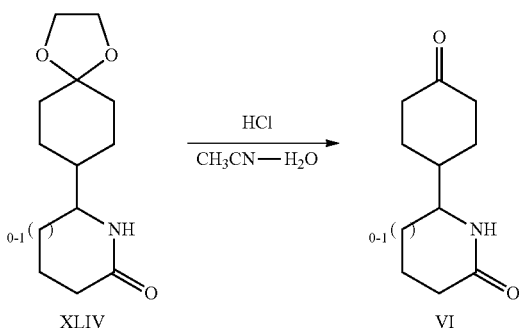

XLIV → VI 1,4-dioxaspiro[4.5]decane-8-carbaldehyde, prepared as described in Pearson, et al. in *J. Org. Chem.* 1997, 62(16), 5284-5292, is reacted with tert-butanesulfiamide in an aprotic organic solvent such as THF, dichloromethane or ether at ambient temperature in the presence of a dehydrating Lewis Acid such as $Ti(OEt)_4$, $Ti(OiPr)_4$ or anhydrous copper (II) sulfate to afford sulfinimine XXXIX. Sulfinimine XXXIX is reacted with a vinyl or allyl Grignard reagent in an aprotic organic solvent such as THF or ether at a temperature between −20° C. and ambient to afford sulfinamide XL. Sulfinamide XL is deprotected by treatment with a dilute methanolic hydrochloric acid solution at a temperature in the range of about 0° C. to about 25° C. to yield the corresponding amine hydrochloride salt XLI. Amine XLI is acylated with acryloyl chloride in the presence of a base such as triethylamine in an aprotic organic solvent such as dichloromethane, THF or ether at a temperature between −10° C. and 0° C. to afford amide XLII. Amide XLII is treated with a ring closing metathesis catalyst in an organic solvent such as dichloromethane, dichloroethane or benzene at a temperature range between 40° C. and 60° C. to afford unsaturated lactam XLIII. Unsaturated lactam XLIII is treated with hydrogen gas under pressure from 14 to 50 psi catalyzed by 5-10% Pd/C, in an organic solvent such as methanol, at a temperature in the range of about 25° C. to about 50° C., to yield the corresponding saturated lactam XLIV. Lactam XLIV is treated with 1N HCl or 1N $H_2SO_4$, in an organic solvent such as acetone, acetonitrile or THF, at a temperature in the range of about 0° C. to about 25° C., to yield the corresponding ketone VI.

60

Alternatively compound VI may be prepared according to the processes outlined in Scheme Scheme 11.

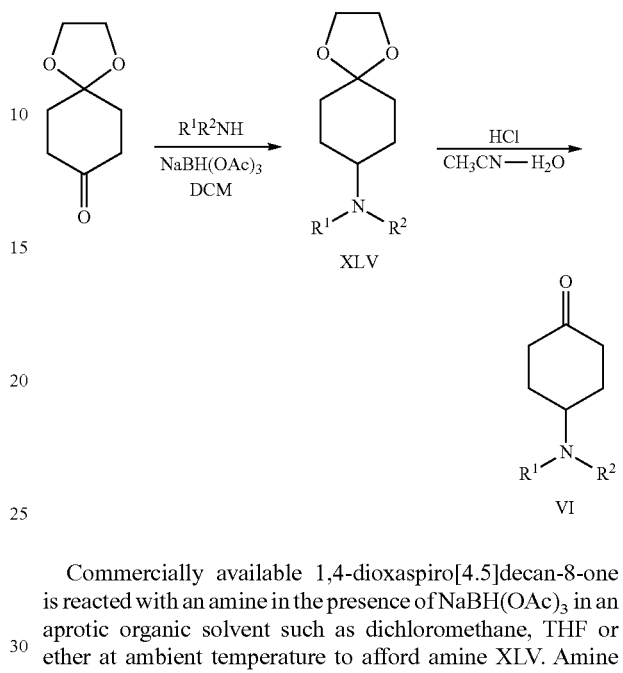

Commercially available 1,4-dioxaspiro[4.5]decan-8-one is reacted with an amine in the presence of $NaBH(OAc)_3$ in an aprotic organic solvent such as dichloromethane, THF or ether at ambient temperature to afford amine XLV. Amine XLV is treated with 1N HCl or 1N $H_2SO_4$, in an organic solvent such as acetone, acetonitrile or THF, at a temperature in the range of about 0° C. to about 25° C., to yield the corresponding ketone VI.

Alternatively compound VI may be prepared according to the processes outlined in Scheme Scheme 12.

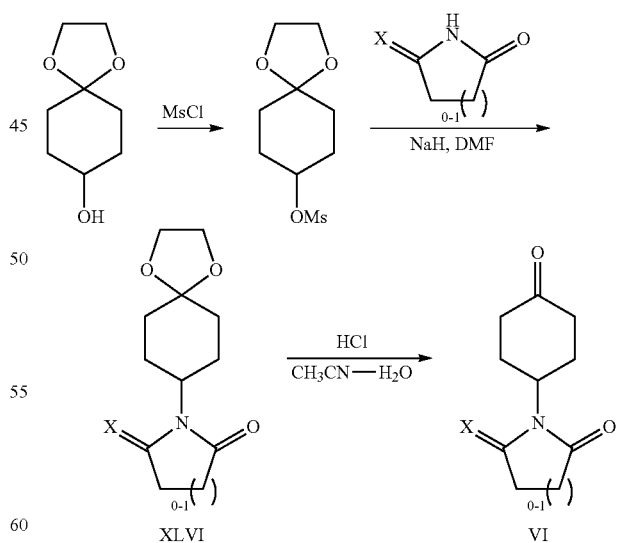

1,4-dioxaspiro[4.5]decan-8-yl methanesulfonate is generated from the corresponding alcohol, using mesyl chloride and an appropriate base, such as NEt3. Reaction with a lactam or imide in the presence of a base such as NaH or KH in an aprotic organic solvent such as THF or ether at a temperature between 0° C. and ambient affords compound XLVI. Compound XLVI is treated with 1N HCl or 1N H₂SO₄, in an organic solvent such as acetone, acetonitrile or THF, at a temperature in the range of about 0° C. to about 25° C., to yield the corresponding ketone VI.

Alternatively compound VI may be prepared according to the processes outlined in Scheme 13.

Scheme 13

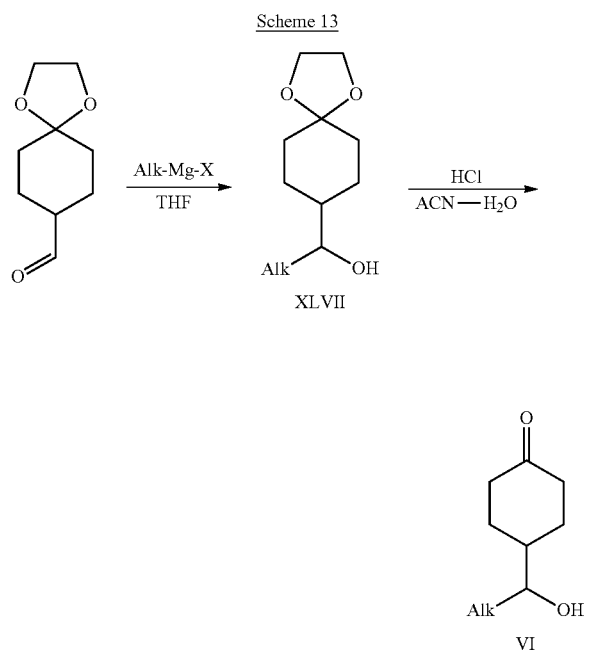

where Alk is an optionally substituted alkyl 1,4-dioxaspiro[4.5]decane-8-carbaldehyde (prepared as described in Pearson, et al. in *J. Org. Chem.* 1997, 62(16), 5284-5292) is reacted with a Grignard reagent in an aprotic organic solvent such as THF or ether at a temperature between −78° C. and −10° C. to afford carbinol XLVII. Carbinol XLVII is treated with 1N HCl or 1N H₂SO₄, in an organic solvent such as acetone, acetonitrile or THF, at a temperature in the range of about 0° C. to about 25° C., to yield the corresponding ketone VI.

Alternatively compound VI may be prepared according to the processes outlined in Scheme 14.

Scheme 14

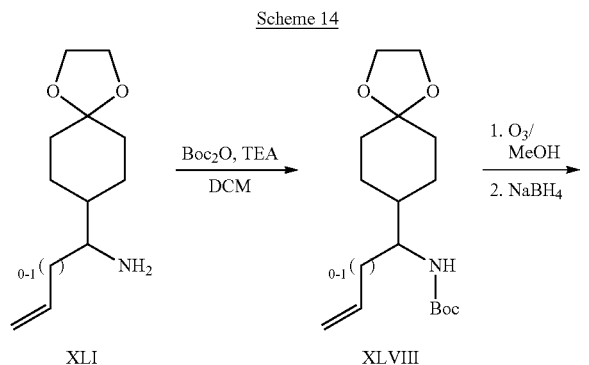

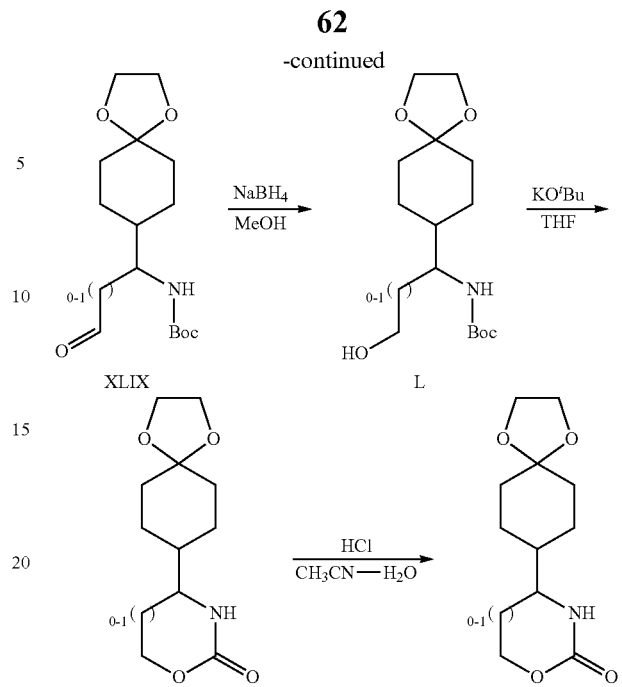

Amine XLI is reacted with Boc-Anhydride in the presence of a base such as triethylamine, diisopropylethylamine or pyridine in an organic solvent such as dichloromethane, dichloroethane or THF to afford carbamate XLVIII. Carbamate XLVIII can reacted with ozone in methyl at a temperature of −78° C. for 30 to 90 minutes followed by quenching with sodium borohydride or dimethyl sulfide to yield aldehyde XLIX. Aldehyde XLIX is reduced by sodium borohydride in an organic solvent such as methanol, ethanol or THF to produce alcohol L. Alcohol L is cyclized into carbamate LI by reaction with a base such as NaO$^t$Bu or NaO$^t$Bu in an organic solvent such as THF, dioxane or DME at room temperature. Carbamate LI is treated with 1N HCl or 1N H₂SO₄, in an organic solvent such as acetone, acetonitrile or THF, at a temperature in the range of about 0° C. to about 25° C., to yield the corresponding ketone VI.

EXAMPLES

Example 1

N-(1-(4-(3-hydroxypyridin-2-yl)cyclohexyl)azetidin-3-yl)-2-((6-(trifluoromethyl)quinazolin-4-yl)amino)acetamide Step A: 2-(1,4-Dioxa-spiro[4.5]dec-7-en-8-yl)-pyridin-3-ol

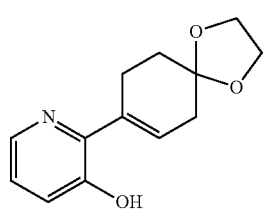 [SMILES: Oc1cccnc1C1=CCC2(CC1)OCCO2]

8-(4,4,5,5-Tetramethyl-[1,3,2]dioxaborolan-2-yl)-1,4-dioxa-spiro[4.5]dec-7-ene (prepared as described in PCT Int. Appl. WO2006064189, 0.292 g, 1.10 mmol), 2-iodo-3-hydroxypyridine (Aldrich, 0.177 g, 0.801 mmol), and tetrakis(triphenylphosphino)palladium(0) (Aldrich, 0.048 g, 0.042 mmol) were dissolved in 1,4-dioxane (9 mL), treated with 2M aqueous $Na_2CO_3$ (2.0 mL, 4.0 mmol), bubbled with argon for a few minutes, and heated to 100° C. under reflux condenser for 24 h. After cooling to ambient temperature, the reaction was diluted with water (30 mL), extracted thrice with dichloromethane, aqueous layer acidified to ca. pH 7, extracted twice more with dichloromethane, and the combined organic layers washed with brine, dried over $Na_2SO_4$, filtered, and concentrated in vacuo to give an orange oil. This was purified by thin layer chromatography on silica gel (EtOAc) to give the title compound as a yellow solid.

$^1$H NMR (400 MHz, CHLOROFORM-d) δ 8.16 (dd, J=4.5, 1.3 Hz, 1 H), 7.22 (dd, J=8.1, 1.3 Hz, 0 H), 7.07 (dd, J=8.2, 4.7 Hz, 1 H), 5.95-6.09 (m, 2 H), 4.03 (s, 4 H), 2.73 (dddd, J=6.4, 4.4, 2.2, 2.0 Hz, 2 H), 2.49 (d, J=2.8 Hz, 2 H), 1.96 (t, J=6.6 Hz, 2 H). ESI-MS (m/z): Calcd. For $C_{13}H_{15}NO_3$: 233. found: 234 (M+H).

Step B:
2-(1,4-Dioxa-spiro[4.5]dec-8-yl)-pyridin-3-ol

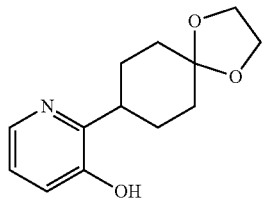 [SMILES: Oc1cccnc1C1CCC2(CC1)OCCO2]

A solution of 2-(1,4-dioxa-spiro[4.5]dec-7-en-8-yl)-pyridin-3-ol (1.3 g, 5.573 mmol) in methanol (60 mL) added to palladium (II) hydroxide (330 mg, 0.62 mmol) in a Parr bottle under argon. The reaction mixture was degassed with argon, evacuated and backfilled with hydrogen then shaken under 50 psi the gas at ambient temperature for 24 hours. After depressurizing and bubbling with argon, the reaction mixture was filtered through Celite 521, washing the filter with MeOH, and filtrate evaporated in vacuo giving a white solid.

$^1$H NMR (400 MHz, ACETONITRILE-$d_3$) δ 8.05 (dd, J=4.7, 1.4 Hz, 1 H), 7.19 (dd, J=8.1, 1.5 Hz, 1 H), 7.06 (dd, J=8.1, 4.5 Hz, 1 H), 3.86-3.99 (m, 4 H), 3.12 (tt, J=11.7, 3.7 Hz, 1 H), 1.72-1.94 (m, 6 H), 1.60-1.72 (m, 2 H). ESI-MS (m/z): Calcd. For $C_{13}H_{17}NO_3$: 235. found: 236 (M+H).

Step C: 4-(3-Hydroxy-pyridin-2-yl)-cyclohexanone

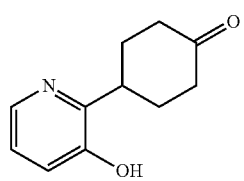 [SMILES: O=C1CCC(c2ncccc2O)CC1]

2-(1,4-dioxa-spiro[4.5]dec-8-yl)-pyridin-3-ol (1.30 g, 5.52 mmol) as prepared in the previous step was treated with 1N HCl (~16 mL) in acetonitrile (100 mL) at room tempera- ture for 4 hours. The reaction was neutralized with saturated $NaHCO_3$ solution and the solvent was removed. The residue was partitioned between ethyl acetate and water. The organic layer was washed with brine, dried over anhydrous $Na_2SO_4$, filtered and concentrated to give a yellow solid, which was purified by silica gel column on a CombiFlash® system using hexanes and ethyl acetate (from 10% ethyl acetate to 100% ethyl acetate) to afford the title compound as a pale yellow solid.

$^1$H NMR (400 MHz, ACETONITRILE-$d_3$) δ 7.94 (dd, J=4.7, 1.4 Hz, 1 H), 7.28 (br. s., 1 H), 7.07 (dd, J=8.1, 1.5 Hz, 1 H), 6.96 (dd, J=8.1, 4.5 Hz, 1 H), 3.46 (tt, J=11.2, 3.7 Hz, 1 H), 2.34-2.52 (m, 2 H), 2.22-2.34 (m, 2 H), 1.99-2.07 (m, 2 H), 1.88-1.99 (m, 2 H). ESI-MS (m/z): Calcd. For $C_{11}H_{13}NO_2$: 191. found: 192 (M+H).

Step D: tert-butyl 3-(2-(((benzyloxy)carbonyl)amino)acetamido)azetidine-1-carboxylate

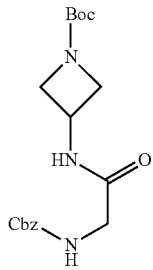

A mixture of commercially available 2-(((benzyloxy)carbonyl)amino)acetic acid (6.70 g, 32.0 mmol) and EDCI (8.42 g, 43.9 mmol) was stirred in anhydrous DCM for 15 minutes and then added to a solution of commercially available tert-butyl 3-aminoazetidine-1-carboxylate (5.02 g, 29.1 mmol) and HOBt (4.45 g, 29.0 mmol, mono hydrate). The reaction mixture was stirred at room temperature overnight and then concentrated in vacuo. The residue was dissolved in ethyl acetate, washed with saturated ammonium chloride solution, 1 N NaOH solution, brine and the organic layer dried over $Na_2SO_4$. After concentration in vacuo, the residue was purified by flash chromatography (silica gel, 0%-5% MeOH/EtOAc) to give a white solid after drying under high vacuum.

$^1$H NMR(CHLOROFORM-d) δ: 7.35 (s, 5H), 5.64-6.02 (m, 1H), 5.12 (s, 2H), 4.43-4.71 (m, 1H), 4.11-4.29 (m, 2H), 3.88 (d, J=5.1 Hz, 2H), 3.56-3.82 (m, 2H), 1.43 (s, 9H).

Step E: tert-butyl 3-(2-aminoacetamido)azetidine-1-carboxylate

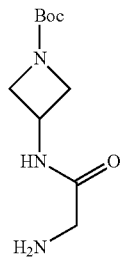

To a flask containing tert-butyl 3-(2-(((benzyloxy)carbonyl)amino)acetamido)azetidine-1-carboxylate (9.26 g, 25.5 mmol) and a stirbar, was added 10% Pd/C (1.356 g, 1.27 mmol). The flask was evacuated and back filled with argon. Methanol (100 mL) was carefully added via syringe and the flask was evacuated with stirring. It was then back filled with hydrogen and stirred 2 days under a hydrogen balloon. After evacuation with stirring and back filling with argon, the catalyst was removed by filtration over Celite 521 and concentrated in vacuo to afford the product.

$^1$H NMR (400 MHz, CHLOROFORM-d) δ=7.72-8.06 (m, 1 H), 4.53-4.75 (m, 1 H), 4.14-4.35 (m, 2 H), 3.65-3.87 (m, 2 H), 3.41 (s, 2 H), 2.08 (br. s., 2 H), 1.45 (s, 9 H), ESI-MS (m/z): Calcd. For $C_{10}H_{19}N_3O_3$: 229.28. found: 230 (M+H).

Step F: tert-butyl 3-(2((6-(trifluoromethyl)quinazolin-4-yl)amino)acetamido)azetidine-1-carboxylate

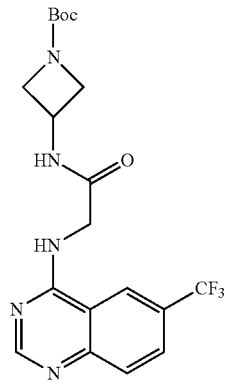

A mixture of tert-butyl 3-(2-aminoacetamido)azetidine-1-carboxylate (1.073 g, 4.682 mmol) as prepared in the previous step and commercially available 4-chloro-6-(trifluoromethyl)quinazoline (990 mg, 4.256 mmol) were stirred in anhydrous iPrOH and triethylamine at 90° C. under argon for 1 hour. The reaction mixture was concentrated in vacuo and the residue purified by flash chromatography (silica gel, 0%-5% MeOH/EtOAc) to give a yellow solid after drying under high vacuum.

$^1$H NMR (400 MHz, CHLOROFORM-d) δ ppm 1.46 (s, 10 H) 3.85 (dd, J=9.54, 5.14 Hz, 2 H) 4.27-4.36 (m, 4 H) 4.63-4.76 (m, 1 H) 7.21 (d, J=7.34 Hz, 1 H) 7.79-7.88 (m, 2 H) 7.90 (t, J=5.26 Hz, 1 H) 8.17 (s, 1 H) 8.66 (s, 1 H) Calcd. For $C_{19}H_{22}F_3N_5O_3$: 425.41. found: 426 (M+H).

Step G: N-(azetidin-3-yl)-2-(6-(trifluoromethyl)quinazolin-4-yl)amino)acetamide TFA salt

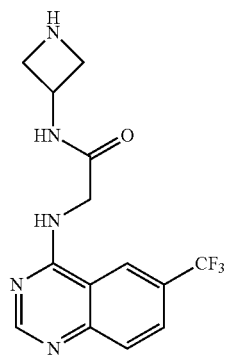 [SMILES: O=C(CNc1ncnc2ccc(C(F)(F)F)cc12)NC1CNC1]

3-[2-(3-Trifluoromethyl-benzoylamino)-acetylamino]-azetidine-1-carboxylic acid tert-butyl ester (8.35 g, 19.6 mmol) as prepared in the previous step was dissolved in DCM (250 mL) and treated with TFA (17 mL, 229 mmol) at room temperature. The reaction was stirred overnight at room temperature. The solvent was removed in vacuo and the residue first triturated with ether, decanting the supernatant, and dried on the high vacuum to give the title compound as a TFA salt containing extra TFA (colorless foam). The amount of TFA varied from run to run and was determined by integration of the $^{19}$F NMR signals of the aryl $CF_3$ and the $CF_3$ from TFA.

$^1$H NMR (400 MHz, DMSO-d6) δ ppm 3.96 (br. s., 2 H) 4.11 (t, J=9.05 Hz, 2 H) 4.19 (d, J=5.62 Hz, 2 H) 4.66 (sxt, J=7.73 Hz, 1 H) 6.99-7.51 (m, 9 H) 7.92 (d, J=8.80 Hz, 1 H) 8.11 (dd, J=8.80, 1.71 Hz, 1 H) 8.64 (s, 1 H) 8.85 (d, J=3.42 Hz, 2 H) 8.90-9.16 (m, 2 H) 9.44 (br. s., 1 H)], ESI-MS (m/z): Calcd. For $C_{14}H_{14}F_3N_5O$: 325.29. found: 326 (M+H).

Step H: N-(1-(4-(3-hydroxypyridin-2-yl)cyclohexyl)azetidin-3-yl)-2-((6-(trifluoromethyl)quinazolin-4-yl)amino)acetamide

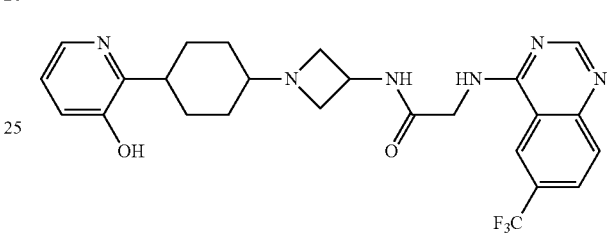

To a suspension of 4-(3-hydroxy-pyridin-2-yl)-cyclohexanone (as prepared in step C, 1 eq.) and N-(azetidin-3-yl)-246-(trifluoromethyl)quinazolin-4-yl)amino)acetamide (as prepared in the previous step, tris TFA salt, 1 eq.) in DCM was added TEA (3 eq.). After stirring at room temperature 30 minutes, $NaBH(OAc)_3$ (3 eq) was added and the mixture was stirred overnight. The reaction was quenched with saturated sodium bicarbonate solution and partially concentrated. Extraction with ethyl acetate followed by concentration of the organic layer in vacuo yielded a residue which was purified by flash chromatography (silica gel, 0-20% 7 N $NH_3$-MeOH/Ethyl acetate) to afford the product as a solid, mixture of isomers.

ESI-MS (m/z): Calcd. For $C_{25}H_{27}F_3N_6O_2$: 500.52. found: 501 (M+H).

Example 2

N-(1-((1S,4s)-4-(−3,6-dihydro-2H-pyran-2-yl)cyclohexyl)azetidin-3-yl)-2-((6-(trifluoromethyl)quinazolin-4-yl)amino)acetamide and N-(1-((1S,4r)-4-(3,6-dihydro-2H-pyran-2-yl)cyclohexyl)azetidin-3-yl)-2((6-(trifluoromethyl)quinazolin-4-yl)amino)acetamide Step A:
1-(1,4-dioxaspiro[4.5]decan-8-yl)but-3-en-1-ol

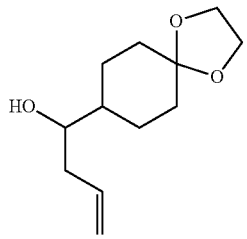

To a solution of 1,4-dioxaspiro[4.5]decane-8-carbaldehyde (627 mg, 3.68 mmol, prepared as described in Pearson, et al. in *J. Org. Chem.* 1997, 62(16), 5284-5292) cooled to −78° C. under argon was added a allylmagnesium bromide (5 mL, 5 mmol, 1 M in THF) dropwise. After the complete addition, the reaction mixture was allowed to reach room temperature overnight. It was then re-cooled to −78° C. and quenched with saturated NaHCO₃ solution and warmed to room temperature. After extraction with ether, the organic layer was concentrated in vacuo and the residue purified by flash chromatography (silica gel, 0-100% ether/hexanes) to afford the product.

Step B: 1 8-(1-(allyloxy)but-3-en-1-yl)-1,4-dioxaspiro[4.5]decane

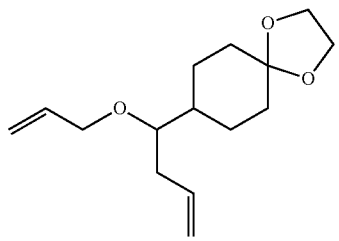 [SMILES: C=CCOC(CC=C)C1CCC2(CC1)OCCO2]

A solution of 1-(1,4-dioxaspiro[4.5]decan-8-yl)but-3-en-1-ol (436 mg, 2.05 mmol), prepared in the previous step, was added to a suspension of sodium hydride (104 mg, 4.12 mmol, 95%) dropwise at 0° C. under argon. After the complete addition, the reaction mixture was allowed to reach room temperature and stirred 1 hour. Allyl bromide (0.35 mL, 4.05 mmol) was added dropwise and the mixture stirred overnight at room temperature. It was poured onto ice cooled saturated NaHCO₃ solution. After extraction with ether, the organic layer was concentrated in vacuo and the residue purified by flash chromatography (silica gel, DCM) to afford the product.

Step C: 8-(3,6-dihydro-2H-pyran-2-yl)-1,4-dioxaspiro[4.5]decane

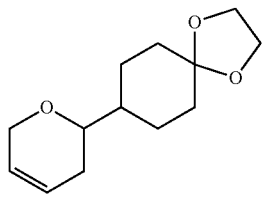 [SMILES: C1=CCC(C2CCC3(CC2)OCCO3)OC1]

A solution of 8-(1-(allyloxy)but-3-en-1-yl)-1,4-dioxaspiro[4.5]decane (454 mg, 1.80 mmol), prepared in the previous step, and the Grubbs Generation II catalyst (76 mg, 0.09 mmol) in DCM was degassed and heated to 40° C. under argon for 4 hours. After extraction with saturated NaHCO₃ solution, the organic layer was concentrated in vacuo and the residue purified by flash chromatography (silica gel, ether) to afford the product.

Step D:
4-(3,6-dihydro-2H-pyran-2-yl)cyclohexanone

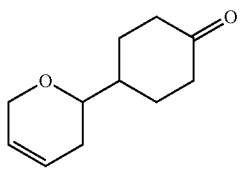 [SMILES: O=C1CCC(C2CC=CCO2)CC1]

A solution of 8-(3,6-dihydro-2H-pyran-2-yl)-1,4-dioxaspiro[4.5]decane (195 mg, 0.869 mmol), prepared in the previous step, was deprotected as described in example 1, step C to afford the product.

Step E: N-(1-((1S,4s)-4-(3,6-dihydro-2H-pyran-2-yl)cyclohexyl)azetidin-3-yl)-2-((6-(trifluoromethyl)quinazolin-4-yl)amino)acetamide and N-(1-((1S,4r)-4-(3,6-dihydro-2H-pyran-2-yl)cyclohexyl)azetidin-3-yl)-2-((6-(trifluoromethyl)quinazolin-4-yl)amino)acetamide

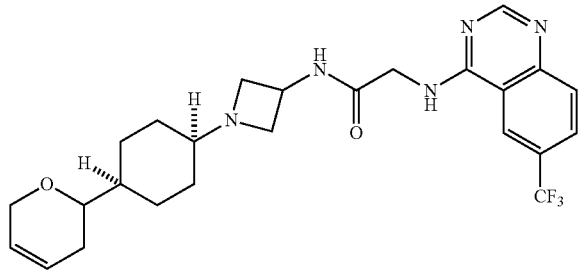

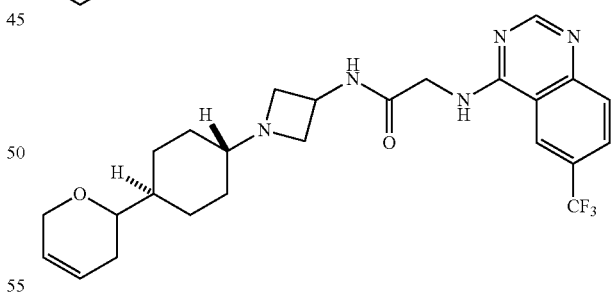

A solution of 4-(3,6-dihydro-2H-pyran-2-yl)cyclohexanone (54 mg, 0.3 mmol), prepared in the previous step, in dry DCM was treated with N-(azetidin-3-yl)-246-(trifluoromethyl)quinazolin-4-yl)amino)acetamide (163 mg, 0.244 mmol, as prepared in Example 1, step G) and TEA (0.100 mL, 0.717 mmol). After stirring at room temperature 30 minutes, NaBH(OAc)₃ (206 mg, 0.972 mmol) was added and the mixture was stirred overnight. Reaction workup and purification as described in Example 1, Step H yielded the product.

cis isomer:

ESI-MS (m/z): Calcd. For $C_{25}H_{30}F_3N_5O_2$: 489.24. found: 490 (M+H).

trans isomer:

ESI-MS (m/z): Calcd. For $C_{25}H_{30}F_3N_5O_2$: 489.24. found: 490 (M+H).

Example 3

N-(1-((1S,4s)-4-(cyclopropyl(hydroxy)methyl)cyclohexyl)azetidin-3-yl)-2-((6-(trifluoromethyl)quinazolin-4-yl)amino)acetamide Step A:
cyclopropyl(1,4-dioxaspiro[4.5]decan-8-yl)methanol

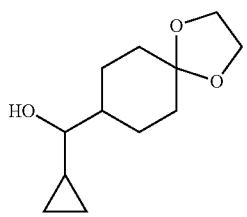 [SMILES: OC(C1CC1)C1CCC2(CC1)OCCO2]

To a solution of 1,4-dioxaspiro[4.5]decane-8-carbaldehyde (1.135 g, 6.668 mmol, prepared as described in Pearson, et al. in *J. Org. Chem.* 1997, 62(16), 5284-5292) cooled to −78° C. under argon was added a cyclopropylmagnesium bromide (40 mL, 20 mmol, 0.5 M in THF) dropwise. After the complete addition, the reaction mixture was allowed to reach room temperature overnight. It was then re-cooled to −78° C. and quenched with saturated NaHCO₃ solution and warmed to room temperature. After extraction with ether, the organic layer was concentrated in vacuo and the residue purified by flash chromatography (silica gel, 0-100% ethyl acetate/heptane) to afford the product.

$^1$H NMR (CHLOROFORM-d) δ: 3.97 (s, 4H), 2.64 (t, J=2.8 Hz, 1H), 1.87-2.01 (m, 2H), 1.76-1.87 (m, 2H), 1.51-1.63 (m, 4H), 1.44 (t, J=12.6 Hz, 2H), 0.84-1.02 (m, 1H), 0.56-0.66 (m, 1H), 0.44-0.56 (m, 1H), 0.19-0.36 (m, 2H)

Step B:
4-(cyclopropyl(hydroxy)methyl)cyclohexanone

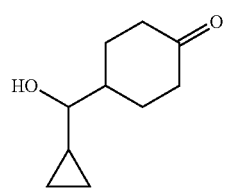

A solution of cyclopropyl(1,4-dioxaspiro[4.5]decan-8-yl)methanol (922 mg, 4.34 mmol), prepared in the previous step, was deprotected as described in example 1, step C to afford the product.

$^1$H NMR (400 MHz, CHLOROFORM-d) δ=2.73 (ddd, J=2.9, 6.2, 9.0 Hz, 1 H), 2.17-2.51 (m, 6 H), 1.94-2.05 (m, 1 H), 1.53-1.70 (m, 4 H), 0.94-1.07 (m, 1 H), 0.61-0.70 (m, 1 H), 0.49-0.59 (m, 1 H), 0.21-0.36 (m, 2 H)

Step C: N-(1-((1S,4s)-4-(cyclopropyl(hydroxy)methyl)cyclohexyl)azetidin-3-yl)-2-((6-(trifluoromethyl)quinazolin-4-yl)amino)acetamide

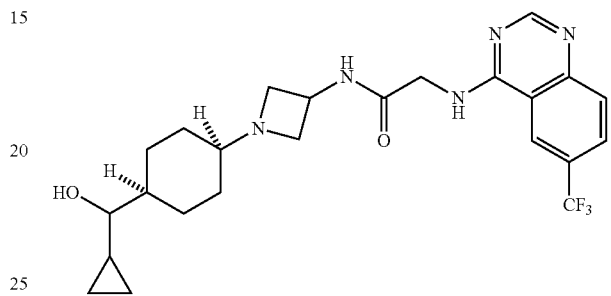

A solution of cyclopropyl(1,4-dioxaspiro[4.5]decan-8-yl) methanol (117 mg, 0.695 mmol), prepared in the previous step, in dry DCM was treated with N-(azetidin-3-yl)-2-((6-(trifluoromethyl)quinazolin-4-yl)amino)acetamide (170 mg, 0.307 mmol, as prepared in Example 1, step G) and TEA (0.080 mL, 0.574 mmol). After stirring at room temperature 30 minutes, NaBH(OAc)₃ (205 mg, 0.967 mmol) was added and the mixture was stirred overnight. Reaction workup and purification as described in Example 1, Step H yielded the product. $^1$H NMR (400 MHz, DMSO-d₆) δ=8.94-9.07 (m, 1 H), 8.72-8.85 (m, 1 H), 8.56 (s, 1 H), 8.30-8.44 (m, 1 H), 8.01-8.10 (m, 1 H), 7.81-7.92 (m, 1 H), 4.18-4.29 (m, 2 H), 4.12 (d, J=5.4 Hz, 2 H), 3.39-3.48 (m, 2 H), 3.17 (d, J=5.1 Hz, 1 H), 2.68-2.76 (m, 2 H), 2.52-2.59 (m, 1 H), 2.10-2.24 (m, 1 H), 1.20-1.56 (m, 9 H), 0.64-0.82 (m, 1 H), 0.33-0.41 (m, 1 H), 0.25-0.33 (m, 1 H), 0.15 (none, 2 H) ESI-MS (m/z): Calcd. For $C_{24}H_{30}F_3N_5O_2$: 477.24. found: 478 (M+H).

Example 4

(+) and (−) N-(1-((1S,4s)-4-(cyclopropyl(hydroxy) methyl)cyclohexyl)azetidin-3-yl)-2-((6-(trifluoromethyl)quinazolin-4-yl)amino)acetamide A solution of N-(1-((1S,4s)-4-(R)-cyclopropyl(hydroxy) methyl)cyclohexyl)azetidin-3-yl)-246-(trifluoromethyl) quinazolin-4-yl)amino)acetamide dissolved in 15% EtOH/ 15% IPA/70% hexane (95% n-hexane from Mallinckrodt) was injected onto a ChiralPak AD column (5×50 cm) using 15% EtOH/15% IPA/70% hexane (95% n-hexane from Mallinckrodt) as a mobile phase. The first peak to elute from the column had (+) rotation and the second had (−) rotation as determined by an in line polarimeter detector.

ESI-MS (m/z): Calcd. For $C_{24}H_{30}F_3N_5O_2$: 477.24. found: 478 (M+H).

Example 5

N-(1-((1S,4s)-4-(cyclopropyl(hydroxy)methyl)1-deuterocyclohexyl)azetidin-3-yl)-2-((6-(trifluoromethyl)quinazolin-4-yl)amino)acetamide

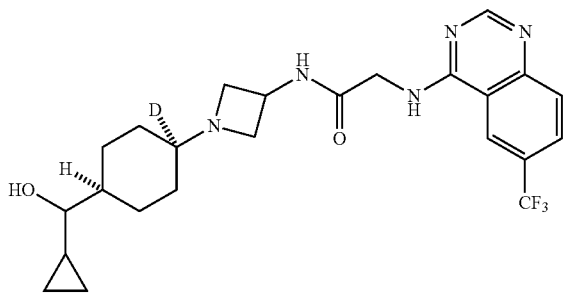 [SMILES: [2H][C@]1(N2CC(NC(=O)CNc3ncnc4ccc(C(F)(F)F)cc34)C2)CC[C@@H](C(O)C2CC2)CC1]

A solution of cyclopropyl(1,4-dioxaspiro[4.5]decan-8-yl)methanol (120 mg, 0.713 mmol), prepared as described in Example 3, step B, in dry DCM was treated with N-(azetidin-3-yl)-2-((6-(trifluoromethyl)quinazolin-4-yl)amino)acetamide (390 mg, 0.705 mmol, as prepared in Example 1, step G) and NMM (0.150 mL, 1.36 mmol). After stirring at room temperature 30 minutes, NaBD(OAc)$_3$ (570 mg, 2.68 mmol) was added and the mixture was stirred overnight. Reaction workup and purification as described in Example 1, Step H yielded the product. ESI-MS (m/z): Calcd. For $C_{24}H_{29}DF_3N_5O_2$: 478.24. found: 479 (M+H).

Example 6

(+) and (−) N-(1-((1S,4s)-4-(cyclopropyl(hydroxy)methyl)1-deuterocyclohexyl)azetidin-3-yl)-2-((6-(trifluoromethyl)quinazolin-4-yl)amino)acetamide A solution of racemic N-(141S,4s)-4-((R)-cyclopropyl(hydroxy)methyl)1-deuterocyclohexyl)azetidin-3-yl)-2-(6-(trifluoromethyl)quinazolin-4-yl)amino)acetamide, as prepared in Example 5, in 15% EtOH/15% IPA/70% hexane (95% n-hexane from Mallinckrodt) was injected onto a ChiralPak AD column (5×50 cm) using 15% EtOH/15% IPA/70% hexane (95% n-hexane from Mallinckrodt) as a mobile phase. The first peak to elute from the column had (+) rotation and the second had (−) rotation as determined by and in line polarimeter detector. ESI-MS (m/z): Calcd. For $C_{24}H_{29}DF_3N_5O_2$: 478.24. found: 479 (M+H).

Example 7

N-(1-((1S,4s)-4-(1-hydroxy-2-methylpropyl)cyclohexyl)azetidin-3-yl)-2-((6-(trifluoromethyl)quinazolin-4-yl)amino)acetamide Step A: 2-methyl-1-(1,4-dioxaspiro[4.5]decan-8-yl)propan-1-ol

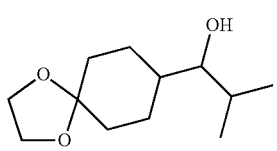

To a solution of 1,4-dioxaspiro[4.5]decane-8-carbaldehyde (693 mg, 4.07 mmol, prepared as described in Pearson, et al. in *J. Org. Chem.* 1997, 62(16), 5284-5292) in THF (20 mL) cooled to −78° C. under argon was added a isopropylmagnesium bromide (6 mL, 12 mmol, 1 M in THF) dropwise. After the complete addition, the reaction mixture was allowed to reach room temperature overnight. It was then re-cooled to −78° C. and quenched with saturated NaHCO$_3$ solution and warmed to room temperature. After extraction with ether, the organic layer was concentrated in vacuo and the residue purified by flash chromatography (silica gel, 0-100% ether/DCM) to afford the product.

$^1$H NMR (400 MHz, CHLOROFORM-d) δ=3.97 (s, 4 H), 3.14 (d, 1 H), 1.73-1.88 (m, 3 H), 1.33-1.69 (m, 7 H), 1.29 (d, J=5.6 Hz, 1 H), 0.94 (dd, 6 H)

Step B: 4-(1-hydroxy-2-methylpropyl)cyclohexanone

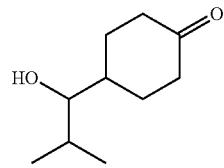

A solution of 2-methyl-1-(1,4-dioxaspiro[4.5]decan-8-yl)propan-1-ol (922 mg, 4.34 mmol), prepared in the previous step, was deprotected as described in example 1, step C to afford the product.

$^1$H NMR (CHLOROFORM-d) δ: 3.05-3.28 (m, 1H), 2.17-2.48 (m, 5H), 1.75-1.99 (m, 3H), 1.45-1.74 (m, 4H), 0.97 (dd, J=7.9, 7.0 Hz, 6H)

Step C: N-(1-((1S,4s)-4-(1-hydroxy-2-methylpropyl)cyclohexyl)azetidin-3-yl)-2-((6-(trifluoromethyl)quinazolin-4-yl)amino)acetamide

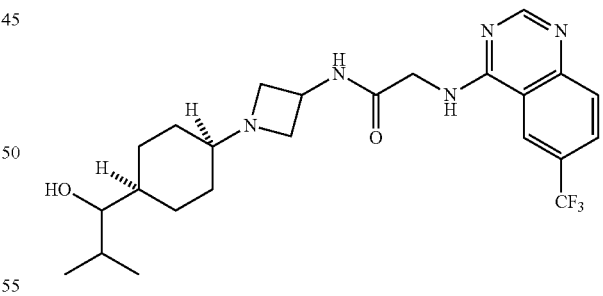

A solution of 4-(1-hydroxy-2-methylpropyl)cyclohexanone (117 mg, 0.695 mmol), as prepared in the previous step, in dry DCM was treated with N-(azetidin-3-yl)-2-((6-(trifluoromethyl)quinazolin-4-yl)amino)acetamide (170 mg, 0.307 mmol, as prepared in Example 1, step G) and TEA (0.080 mL, 0.574 mmol). After stirring at room temperature 30 minutes, NaBH(OAc)$_3$ (205 mg, 0.967 mmol) was added and the mixture was stirred overnight. Reaction workup and purification as described in Example 1, Step H yielded the product. ESI-MS (m/z): Calcd. For $C_{24}H_{32}F_3N_5O_2$: 479.25. found: 480 (M+H).

Example 8

(+) and (−)N-(1-((1S,4s)-4-(1-hydroxy-2-methylpropyl)cyclohexyl)azetidin-3-yl)-2-((6-(trifluoromethyl)quinazolin-4-yl)amino)acetamide A solution of N-(1-((1S,4s)-4-((R)-1-hydroxy-2-methylpropyl)cyclohexyl)azetidin-3-yl)-2-((6-(trifluoromethyl)quinazolin-4-yl)amino)acetamide dissolved in 15% EtOH/15% IPA/70% hexane (95% n-hexane from Mallinckrodt) was injected onto a ChiralPak AD column (5×50 cm) using 15% EtOH/15% IPA/70% hexane (95% n-hexane from Mallinckrodt) as a mobile phase. The first peak to elute from the column had (+) rotation and the second had (−) rotation as determined by and in line polarimeter detector.

ESI-MS (m/z): Calcd. For $C_{24}H_{32}F_3N_5O_2$: 479.25. found: 480 (M+H).

Example 9

2-((6-(trifluoromethyl)quinazolin-4-yl)amino)-N-(1-((1s,4s)-4-vinylcyclohexyl)azetidin-3-yl)acetamide and 2-((6-(trifluoromethyl)quinazolin-4-yl)amino)-N-(1-((1r,4r)-4-vinylcyclohexyl)azetidin-3-yl)acetamide Step A: 8-vinyl-1,4-dioxaspiro[4.5]decane

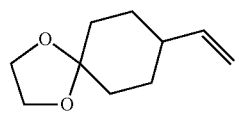

To a flask containing triphenylphosphonium bromide-sodamide complex (20.04 g, 48.10 mmol) was added THF (100 mL). After stirring @ rt for 1 hour, the solution was bright yellow (with some ppt). The rxn mixture was cooled to 0° C. and a solution of 1,4-dioxaspiro[4.5]decane-8-carbaldehyde (693 mg, 4.07 mmol, prepared as described in Pearson, et al. in *J. Org. Chem.* 1997, 62(16), 5284-5292) in THF (20 mL) was added dropwise via syringe. After the complete addition, the reaction mixture turned light peach and was stirred, warming to rt overnight. The reaction was quenched cautiously with saturated aq NaHCO₃ at 0° C. and allowed to warm to room temperature, followed by water and extraction with ether. The concentrated organic layers were purified by flash chrom (silica gel, ether, stains PAA). To avoid losing some material on the rotovap (seems volatile), the bath temperature was kept under 35° C.

¹H NMR (CHLOROFORM-d) δ: 5.65-5.86 (m, 1H), 5.00 (d, J=17.4 Hz, 1H), 4.92 (d, J=10.3 Hz, 1H), 3.94 (s, 4H), 1.92-2.10 (m, 1H), 1.70-1.81 (m, 4H), 1.51-1.65 (m, 2H), 1.37-1.51 (m, 2H)

Step B: 4-vinylcyclohexanone

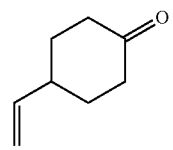

A solution of 8-vinyl-1,4-dioxaspiro[4.5]decane (500 mg, 2.97 mmol), prepared in the previous step, was deprotected as described in example 1, step C to afford the product.

¹H NMR (CHLOROFORM-d) δ: 5.83 (ddd, J=17.2, 10.6, 6.2 Hz, 1H), 4.94-5.16 (m, 2H), 2.30-2.56 (m, 5H), 2.03-2.14 (m, 2H), 1.54-1.70 (m, 2H)

Step C: 2-((6-(trifluoromethyl)quinazolin-4-yl)amino)-N-(1-((1s,4s)-4-vinylcyclohexyl)azetidin-3-yl)acetamide and 2-((6-(trifluoromethyl)quinazolin-4-yl)amino)-N-(1-((1r,4r)-4-vinylcyclohexyl)azetidin-3-yl)acetamide

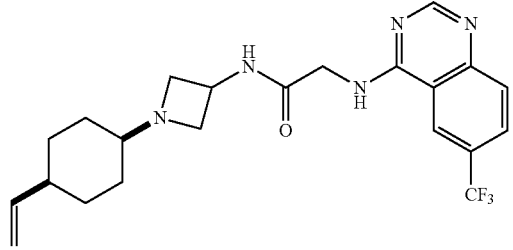

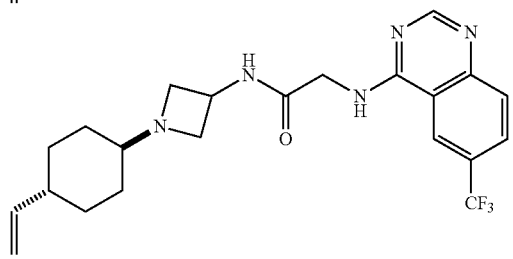

A solution of 4-(vinyl)cyclohexanone (100 mg, 0.805 mmol), prepared in the previous step, in dry DCM was treated with N-(azetidin-3-yl)-2-((6-(trifluoromethyl)quinazolin-4-yl)amino)acetamide (598 mg, 0.896 mmol, as prepared in Example 1, step G) and TEA (0.380 mL, 2.73 mmol). After stirring at room temperature 30 minutes, NaBH(OAc)₃ (622 mg, 2.94 mmol) was added and the mixture was stirred overnight. Reaction workup and purification as described in Example 1, Step H yielded the products, with the syn isomer eluting first.

ESI-MS (m/z): Calcd. For $C_{22}H_{26}F_3N_5O$: 433.21. found: 434 (M+H).

Example 10

N-(1-((1R,4s)-4-(2,5-dihydrofuran-2-yl)cyclohexyl)azetidin-3-yl)-2-((6-(trifluoromethyl)quinazolin-4-yl)amino)acetamide and N-(1-((1R,4r)-4-(2,5-dihydrofuran-2-yl)cyclohexyl)azetidin-3-yl)-2-((6-(trifluoromethyl)quinazolin-4-yl)amino)acetamide Step A:
1-(1,4-dioxaspiro[4.5]decan-8-yl)prop-2-en-1-ol

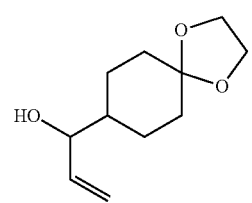

To a solution of 1,4-dioxaspiro[4.5]decane-8-carbaldehyde (860 mg, 5.05 mmol, prepared as described in Pearson, et al. in *J. Org. Chem.* 1997, 62(16), 5284-5292) in THF (6 mL) cooled to −78° C. under argon was added a vinylmagnesium bromide (20 mL, 20 mmol, 1 M in THF) dropwise. After the complete addition, the reaction mixture was allowed to reach room temperature overnight. It was then re-cooled to −78° C. and quenched with saturated NaHCO₃ solution and warmed to room temperature. After extraction with ether, the organic layer was concentrated in vacuo and the residue purified by flash chromatography (silica gel, 0-100% ether/hexanes) to afford the product.

Step B:
8-(1-(allyloxy)allyl)-1,4-dioxaspiro[4.5]decane

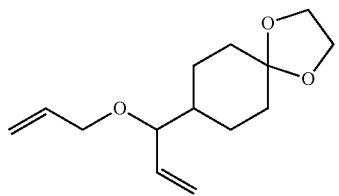 [SMILES: C=CCOC(C=C)C1CCC2(CC1)OCCO2]

A solution of 1-(1,4-dioxaspiro[4.5]decan-8-yl)prop-2-en-1-ol (414 mg, 2.09 mmol), prepared in the previous step, was added to a suspension of sodium hydride (104 mg, 4.12 mmol, 95%) dropwise at 0° C. under argon. After the complete addition, the reaction mixture was allowed to reach room temperature and stirred for 1 hour. Allyl bromide (0.35 mL, 4.05 mmol) was added dropwise and the mixture stirred overnight at room temperature. It was poured onto ice cooled saturated NaHCO$_3$ solution. After extraction with ether, the organic layer was concentrated in vacuo and the residue purified by flash chromatography (silica gel, DCM) to afford the product.

Step C: 8-(2,5-dihydrofuran-2-yl)-1,4-dioxaspiro[4.5]decane

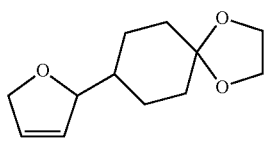 [SMILES: C1=CC(C2CCC3(CC2)OCCO3)OC1]

A solution of 8-(1-(allyloxy)allyl)-1,4-dioxaspiro[4.5]decane (347 mg, 1.46 mmol), prepared in the previous step, and the Grubbs Generation II catalyst (62 mg, 0.07 mmol) in DCM was degassed and heated to 40° C. under argon for 4 hours. After extraction with saturated NaHCO$_3$ solution, the organic layer was concentrated in vacuo and the residue purified by flash chromatography (silica gel, ether) to afford the product.

Step D: 4-(2,5-dihydrofuran-2-yl)cyclohexanone

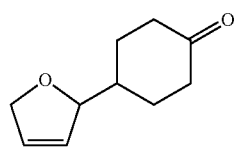 [SMILES: O=C1CCC(C2C=CCO2)CC1]

A solution of 8-(2,5-dihydrofuran-2-yl)-1,4-dioxaspiro[4.5]decane (281 mg, 1.34 mmol), prepared in the previous step, was deprotected as described in example 1, step C to afford the product.

Step E: N-(1-((1R,4s)-4-(2,5-dihydrofuran-2-yl)cyclohexyl)azetidin-3-yl)-2-((6-(trifluoromethyl)quinazolin-4-yl)amino)acetamide and N-(1-((1R,4r)-4-(2,5-dihydrofuran-2-yl)cyclohexyl)azetidin-3-yl)-2-((6-(trifluoromethyl)quinazolin-4-yl)amino)acetamide

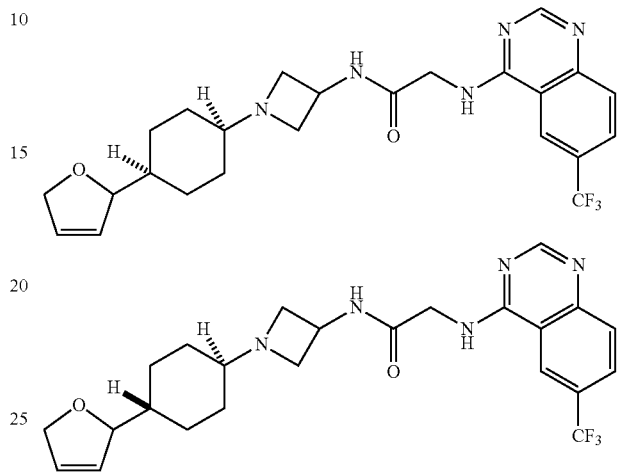

A solution of 4-(2,5-dihydrofuran-2-yl)cyclohexanone (127 mg, 0.764 mmol), prepared in the previous step, in dry DCM was treated with N-(azetidin-3-yl)-246-(trifluoromethyl)quinazolin-4-yl)amino)acetamide (320 mg, 0.48 mmol, as prepared in Example 1, step G) and TEA (0.200 mL, 1.44 mmol). After stirring at room temperature 30 minutes, NaBH(OAc)$_3$ (323 mg, 1.52 mmol) was added and the mixture was stirred overnight. Reaction workup and purification as described in Example 1, Step H yielded the products, with the cis isomer eluting first.

cis isomer:
ESI-MS (m/z): Calcd. For $C_{24}H_{28}F_3N_5O_2$: 475.22. found: 476 (M+H).

trans isomer:
ESI-MS (m/z): Calcd. For $C_{24}H_{28}F_3N_5O_2$: 475.22. found: 476 (M+H).

Example 11

N-(1-((1S,4s)-4-(6-oxo-1,2,3,6-tetrahydropyridin-2-yl)cyclohexyl)azetidin-3-yl)-2-((6-(trifluoromethyl)quinazolin-4-yl)amino)acetamide Step A: (E)-N-(1,4-dioxaspiro[4.5]decan-8-ylmethylene)-2-methylpropane-2-sulfinamide

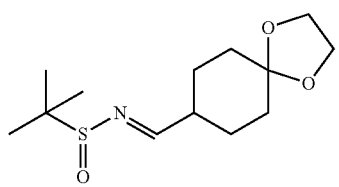 [SMILES: CC(C)(C)S(=O)/N=C/C1CCC2(CC1)OCCO2]

To a solution of 1,4-dioxaspiro[4.5]decane-8-carbaldehyde (6.68 g, 39.2 mmol, prepared as described in Pearson, et al. in *J. Org. Chem.* 1997, 62(16), 5284-5292), racemic 2-methylpropane-2-sulfinamide (3.50 g, 28.0 mmol), tech grade titanium (IV) ethoxide (14 mL, 67.5 mmol) were dissolved in dry THF (100 mL), placed under an argon atmosphere and stirred at ambient temperature for 16 hours. The next day the reaction mixture was diluted with ethyl acetate and poured onto rapidly stirred ice cold brine. The copious white precipitate was removed by filtration through celite and the organic layer removed. After drying over $Na_2SO_4$ and concentration the residue was purified by flash chromatography (silica gel, 0-100% ether/DCM) to afford the product.

$^1$H NMR (CHLOROFORM-d) δ: 8.00 (d, J=4.4 Hz, 1H), 2.41-2.59 (m, 1H), 1.88-2.00 (m, 2H), 1.55-1.86 (m, 7H), 1.19 (s, 9H)

Step B: N-(1-(1,4-dioxaspiro[4.5]decan-8-yl)but-3-en-1-yl)-2-methylpropane-2-sulfinamide

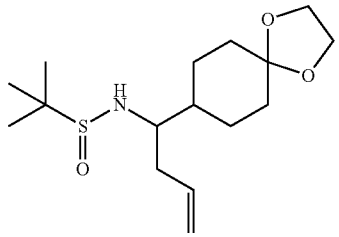 [SMILES: C=CCC(NS(=O)C(C)(C)C)C1CCC2(CC1)OCCO2]

A solution (E)-N-(1,4-dioxaspiro[4.5]decan-8-ylmethylene)-2-methylpropane-2-sulfinamide (1.91 g, 6.99 mmol), prepared in the previous step, in dry THF (48 mL) was treated with a solution of allylmagnesiumm bromide (10.5 mL, 21 mmol, 2N in THF) dropwise at ambient temperature under argon. After the complete addition, the reaction mixture was allowed to stir at room temperature and for 3 hours and then quenched at 0° C. by the cautious addition of saturated ammonium chloride solution. After extraction with ethyl acetate, the organic layer was concentrated in vacuo and the residue purified by flash chromatography (silica gel, 0-5% MeOH/Ethyl Acetate) to afford the product as a mixture of disatereomers.

$^1$H NMR (CHLOROFORM-d) δ: 5.56-5.93 (m, 1H), 5.16-5.35 (m, 2H), 3.85-3.98 (m, 4H), 3.54-3.74 (m, 1H), 2.99-3.25 (m, 1H), 1.66-1.84 (m, 5H), 1.29-1.62 (m, 5H), 1.22 (s, 9H)

Step C:
1-(4,4-dimethoxycyclohexyl)but-3-en-1-amine

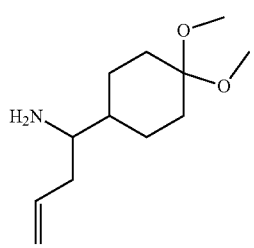

A solution of N-(1-(1,4-dioxaspiro[4.5]decan-8-yl)but-3-en-1-yl)-2-methylpropane-2-sulfinamide (828 mg, 2.63 mmol), prepared in the previous step, was dissolved in methanol (20 mL) and treated with HCl (4.4 mL. 5.5 mmol, 1.25 M in MeOH), stirring overnight at room temperature. The reaction mixture was concentrated in vacuo, triturated with ether, decanting the supernatant several times and the residue dried under high vacuum afford the product as a white foam (HCl salt).

$^1$H NMR (CHLOROFORM-d) δ: 5.66-5.99 (m, 1H), 5.04-5.25 (m, 2H), 3.20 (s, 3H), 3.14 (s, 3H), 2.53-2.78 (m, 1H), 2.23-2.42 (m, 1H), 1.91-2.11 (m, 3H), 1.51-1.75 (m, 2H), 1.15-1.51 (m, 11H)

Step D: N-(1-(4,4-dimethoxycyclohexyl)but-3-en-1-yl)acrylamide

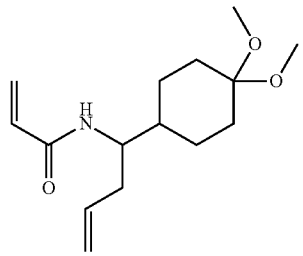 [SMILES: C=CCC(NC(=O)C=C)C1CCC(OC)(OC)CC1]

A solution of 1-(4,4-dimethoxycyclohexyl)but-3-en-1-amine, HCl salt (512 mg, 2.4 mmol), prepared in the previous step, was cooled to −78° C. under argon and treated with triethylamine followed by acryloyl chloride (0.220 mL, 2.64 mmol) dropwise. The reaction was allowed to reach ambient temperature overnight and then poured onto saturated $NaHCO_3$ solution and extracted with ethyl acetate. The organic extracts were concentrated in vacuo and purified by flash chromatography (silica gel, 0-100% ether/DCM) to afford the product.

$^1$H NMR (CHLOROFORM-d) δ: 6.27 (dd, J=16.9, 1.5 Hz, 1H), 5.99-6.15 (m, 1H), 5.68-5.83 (m, 1H), 5.64 (dd, J=10.1, 1.3 Hz, 1H), 5.09 (d, J=2.9 Hz, 1H), 5.06 (d, J=1.0 Hz, 1H), 3.97-4.10 (m, 1H), 3.17-3.21 (m, 3H), 3.10-3.15 (m, 3H), 2.30-2.40 (m, 1H), 2.14-2.26 (m, 1H), 1.96-2.10 (m, 2H), 1.61-1.69 (m, 2H), 1.41-1.53 (m, 1H), 1.17-1.37 (m, 5H)

Step E: 6-(4,4-dimethoxycyclohexyl)-5,6-dihydropyridin-2(1H)-one

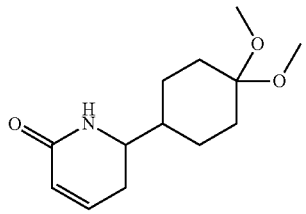 [SMILES: COC1(OC)CCC(C2CC=CC(=O)N2)CC1]

A solution of N-(1-(4,4-dimethoxycyclohexyl)but-3-en-1-yl)acrylamide (512 mg, 2.4 mmol), prepared in the previous step, and the Grubbs Generation II catalyst (97 mg, 0.11 mmol) in DCE (100 mL) was degassed and heated to 50° C. under argon for 2 hours. The reaction mixture was concentrated in vacuo and the residue purified by flash chromatography (silica gel, DCM->0-5% MeOH/ethyl acetate) to afford the product.

¹H NMR (CHLOROFORM-d) δ: 6.51-6.71 (m, 1H), 6.24 (br. s., 1H), 5.90 (d, J=9.5 Hz, 1H), 3.38-3.55 (m, 1H), 3.20 (s, 3H), 3.14 (s, 3H), 2.20-2.40 (m, 2H), 2.00-2.16 (m, 2H), 1.65 (br. s., 2H), 1.45-1.56 (m, 1H), 1.14-1.40 (m, 5H)

Step F:
6-(4-oxocyclohexyl)-5,6-dihydropyridin-2(1H)-one

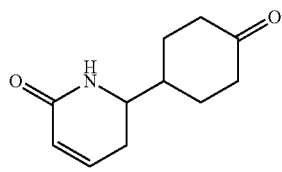 [SMILES: O=C1CCC(C2CC=CC(=O)N2)CC1]

A solution of 6-(4,4-dimethoxycyclohexyl)-5,6-dihydropyridin-2(1H)-one (237 mg, 0.99 mmol), prepared in the previous step, was deprotected as described in example 1, step C to afford the product.

Step G: N-(1-((1S,4s)-4-(6-oxo-1,2,3,6-tetrahydropyridin-2-yl)cyclohexyl)azetidin-3-yl)-2-((6-(trifluoromethyl)quinazolin-4-yl)amino)acetamide

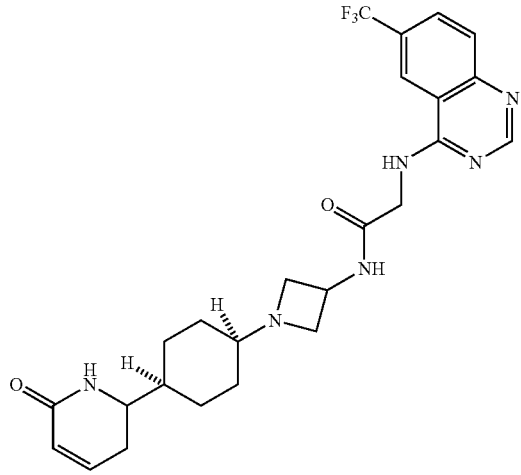 [SMILES: O=C1C=CCC([C@H]2CC[C@@H](N3CC(NC(=O)CNc4ncnc5ccc(C(F)(F)F)cc45)C3)CC2)N1]

A solution of 6-(4-oxocyclohexyl)-5,6-dihydropyridin-2(1H)-one (90 mg, 0.47 mmol), prepared in the previous step, in dry DCM was treated with N-(azetidin-3-yl)-2-((6-(trifluoromethyl)quinazolin-4-yl)amino)acetamide (359 mg, 0.54 mmol, as prepared in Example 1, step G) and TEA (0.220 mL, 1.58 mmol). After stirring at room temperature 30 minutes, NaBH(OAc)₃ (391 mg, 1.85 mmol) was added and the mixture was stirred overnight. Reaction workup and purification as described in Example 1, Step H yielded the products, with the cis isomer eluting first.

cis isomer:

¹H NMR (MeOH) δ: 8.60 (s, 1H), 8.55 (s, 1H), 8.01 (dd, 1H), 7.87 (d, 1H), 6.56-6.79 (m, 1H), 5.69-5.92 (m, 1H), 4.40-4.58 (m, 1H), 4.27 (s, 2H), 3.65 (s, 2H), 3.40-3.53 (m, 2H), 2.80-2.97 (m, 2H), 2.20-2.41 (m, 3H), 1.31-1.73 (m, 9H)
ESI-MS (m/z): Calcd. For C₂₅H₂₉F₃N₆O₂: 502.23. found: 503 (M+H).

Example 12

N-(1-((1S,4s)-4-(6-oxo-1,2,3,6-tetrahydropyridin-2-yl)cyclohexyl)azetidin-3-yl)-2-((6-(trifluoromethyl)quinazolin-4-yl)amino)acetamide

Step A: N-(1-(1,4-dioxaspiro[4.5]decan-8-yl)allyl)-2-methylpropane-2-sulfinamide

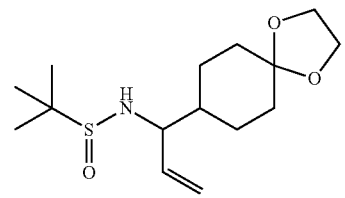 [SMILES: C=CC(NS(=O)C(C)(C)C)C1CCC2(CC1)OCCO2]

A solution (E)-N-(1,4-dioxaspiro[4.5]decan-8-ylmethylene)-2-methylpropane-2-sulfinamide (1.89 g, 5.53 mmol), prepared in Example 11, step A, in dry THF (48 mL) was treated with a solution of vinylmagnesiumm chloride (10.4 mL, 16.6 mmol, 1.6 N in THF) dropwise at ambient temperature under argon. After the complete addition, the reaction mixture was allowed to stir at room temperature and for 3 hours and then quenched at 0° C. by the cautious addition of saturated ammonium chloride solution. After extraction with ethyl acetate, the organic layer was concentrated in vacuo and the residue purified by flash chromatography (silica gel, 0-5% MeOH/Ethyl Acetate) to afford the product as a mixture of disatereomers.

Step B:
1-(1,4-dioxaspiro[4.5]decan-8-yl)prop-2-en-1-amine

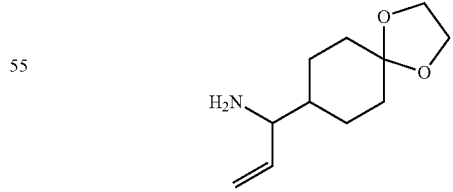

A solution of N-(1-(1,4-dioxaspiro[4.5]decan-8-yl)allyl)-2-methylpropane-2-sulfinamide (1.38 g, 4.58 mmol), prepared in the previous step, was dissolved in methanol (100 mL) and treated with HCl (15 mL. 18.7 mmol, 1.25 M in MeOH), stirring overnight at room temperature. The reaction mixture was concentrated in vacuo, triturated with ether, decanting the supernatant several times and the residue dried under high vacuum afford the product as a white foam (HCl salt).

Step C: N-(1-(1,4-dioxaspiro[4.5]decan-8-yl)allyl)acrylamide

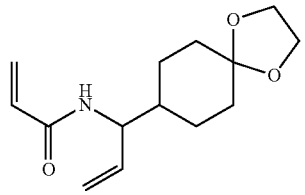 [SMILES: C=CC(=O)NC(C=C)C1CCC2(CC1)OCCO2]

A solution of 1-(1,4-dioxaspiro[4.5]decan-8-yl)prop-2-en-1-amine, HCl salt (966 mg, 4.13 mmol), prepared in the previous step, was cooled to 0° C. under argon and treated with triethylamine (1.71 mL, 12.3 mmol) followed by acryloyl chloride (0.35 mL, 4.2 mmol) dropwise. The reaction was allowed to reach ambient temperature overnight and then poured onto saturated NaHCO$_3$ solution and extracted with ethyl acetate. The organic extracts were concentrated in vacuo and purified by flash chromatography (silica gel, 0-5% MeOH/ethyl acetate) to afford the product.

$^1$H NMR (CHLOROFORM-d) δ: 6.25-6.37 (m, 1H), 6.03-6.18 (m, 1H), 5.72-5.85 (m, 1H), 5.42-5.59 (m, 1H), 5.05-5.30 (m, 2H), 4.44-4.67 (m, 1H), 3.93 (s, 4H), 1.66-1.85 (m, 4H), 1.46-1.64 (m, 4H), 1.37 (m, 2H)

Step D: 5-(1,4-dioxaspiro[4.5]decan-8-yl)-1H-pyrrol-2(5H)-one

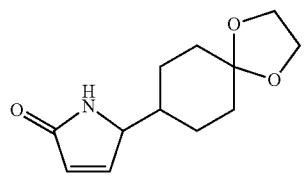 [SMILES: O=C1C=CC(C2CCC3(CC2)OCCO3)N1]

A solution of N-(1-(1,4-dioxaspiro[4.5]decan-8-yl)allyl)acrylamide (560 mg, 2.23 mmol), prepared in the previous step, and the Grubbs Generation II catalyst (95 mg, 0.11 mmol) in DCE (50 mL) was degassed and heated to 50° C. under argon for 2 hours. The reaction mixture was concentrated in vacuo and the residue purified by flash chromatography (silica gel, DCM->0-5% MeOH/ethyl acetate) to afford the product.

$^1$H NMR (CHLOROFORM-d) δ: 7.61 (br. s., 1H), 7.11 (d, J=5.9 Hz, 1H), 6.12 (d, J=5.9 Hz, 1H), 4.09 (d, J=5.9 Hz, 1H), 3.81-4.01 (m, 4H), 1.67-1.88 (m, 4H), 1.31-1.65 (m, 5H)

Step E: 5-(1,4-dioxaspiro[4.5]decan-8-yl)pyrrolidin-2-one

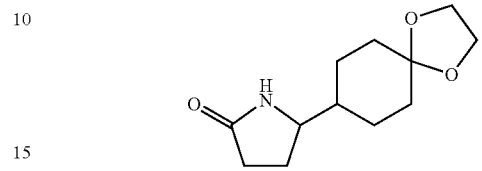

To a mixture of 5-(1,4-dioxaspiro[4.5]decan-8-yl)-1H-pyrrol-2(5H)-one (330 mg, 1.48 mmol), prepared in the previous step, and Palladium on Carbon (299 mg, 0.14 mmol, 5%, "Degussa, wet") was carefully added methanol (30 mL). The reaction flask was evacuated, backfilled with hydrogen via balloon and stirred at room temperature overnight. The catalyst was removed by filtration and the filtrate concentrated in vacuo to afford the product.

Step F: 5-(4-oxocyclohexyl)pyrrolidin-2-one

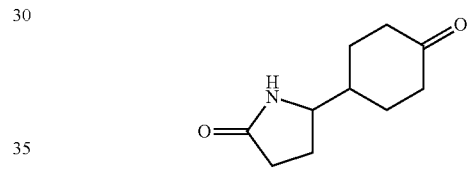

A solution of 5-(1,4-dioxaspiro[4.5]decan-8-yl)pyrrolidin-2-one (319 mg, 1.42 mmol), prepared in the previous step, was deprotected as described in example 1, step C to afford the product.

Step G: N-(1-((1S,4s)-4-(5-oxopyrrolidin-2-yl)cyclohexyl)azetidin-3-yl)-2-((6-(trifluoromethyl)quinazolin-4-yl)amino)acetamide

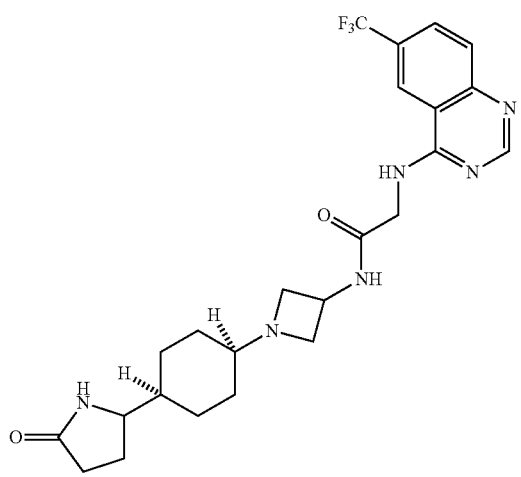 [SMILES: O=C(CNc1ncnc2ccc(C(F)(F)F)cc12)NC1CN([C@H]2CC[C@@H](C3CCC(=O)N3)CC2)C1]

A solution of 6-(4-oxocyclohexyl)-5,6-dihydropyridin-2 (1H)-one (90 mg, 0.47 mmol), prepared in the previous step, in dry DCM was treated with N-(azetidin-3-yl)-2-((6-(trifluoromethyl)quinazolin-4-yl)amino)acetamide (359 mg, 0.54 mmol), as prepared in Example 1, step G) and TEA (0.220 mL, 1.58 mmol). After stirring at room temperature 30 minutes, NaBH(OAc)$_3$ (391 mg, 1.85 mmol) was added and the mixture was stirred overnight. Reaction workup and purification as described in Example 1, Step H yielded the products, with the cis isomer eluting first.

cis isomer:

$^1$H NMR (MeOD) δ: 8.60 (s, 1H), 8.54 (s, 1H), 7.98-8.05 (m, 1H), 7.81-7.90 (m, 1H), 4.40-4.55 (m, 1H), 4.27 (s, 2H), 3.58-3.70 (m, 2H), 3.45-3.57 (m, 1H), 2.83-2.95 (m, 2H), 2.09-2.38 (m, 3H), 1.72-1.89 (m, 1H), 1.42 (d, 8H) ESI-MS (m/z): Calcd. For C$_{24}$H$_{29}$F$_3$N$_6$O$_2$: 490.23. found: 491 (M+H).

Example 13

N-(1-((1S,4s)-4-(6-oxopiperidin-2-yl)cyclohexyl)azetidin-3-yl)-2-((6-(trifluoromethyl)quinazolin-4-yl)amino)acetamide

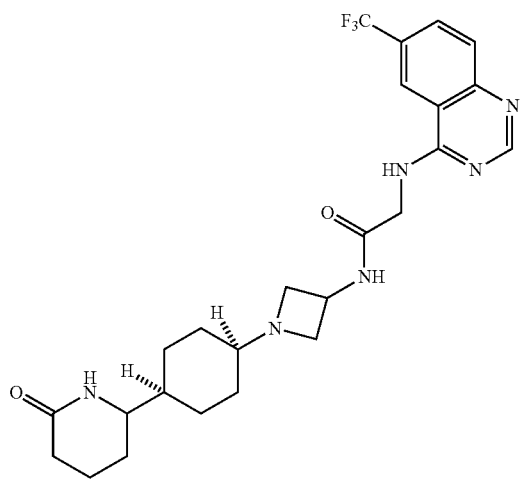 [SMILES: O=C(CNc1ncnc2ccc(C(F)(F)F)cc12)NC1CN([C@H]2CC[C@@H](C3CCCC(=O)N3)CC2)C1]

A solution of N-(1-((1S,4s)-4-((R)-6-oxo-1,2,3,6-tetrahydropyridin-2-yl)cyclohexyl)azetidin-3-yl)-2-(6-(trifluoromethyl)quinazolin-4-yl)amino)acetamide (127 mg, 0.25 mmol), prepared in Example 11, and Palladium on Carbon (299 mg, 0.14 mmol, 5%, "Degussa, wet") was carefully added methanol (30 mL). The reaction flask was evacuated, backfilled with hydrogen via balloon and stirred at room temperature overnight. The catalyst was removed by filtration and the filtrate concentrated in vacuo to afford the product.

ESI-MS (m/z): Calcd. For C$_{25}$H$_{31}$F$_3$N$_6$O$_2$: 504.25. found: 505 (M+H).

Example 14

N-(1-((1S,4s)-4-(tetrahydro-2H-pyran-2-yl)cyclohexyl)azetidin-3-yl)-2-((6-(trifluoromethyl)quinazolin-4-yl)amino)acetamide Step A: 8-(tetrahydro-2H-pyran-2-yl)-1,4-dioxaspiro[4.5]decane

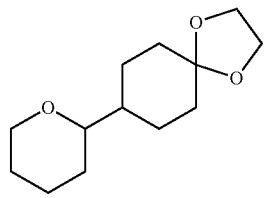 [SMILES: C1CCC(C2CCC3(CC2)OCCO3)OC1]

To a mixture of 8-(3,6-dihydro-2H-pyran-2-yl)-1,4-dioxaspiro[4.5]decane (190 mg, 0.847 mmol), as prepared in Example 2 step C, and Palladium on Carbon (118 mg, 0.055 mmol, 5%, "Degussa, wet") was carefully added methanol (24 mL). The reaction flask was evacuated, backfilled with hydrogen via balloon and stirred at room temperature overnight. The catalyst was removed by filtration and the filtrate concentrated in vacuo to afford the product.

Step B: 4-(tetrahydro-2H-pyran-2-yl)cyclohexanone

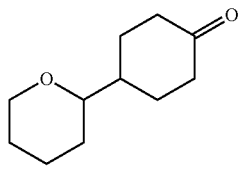 [SMILES: O=C1CCC(C2CCCCO2)CC1]

A solution of 8-(tetrahydro-2H-pyran-2-yl)-1,4-dioxaspiro[4.5]decane (190 mg, 0.84 mmol), prepared in the previous step, was deprotected as described in example 1, step C to afford the product.

Step C: N-(1-((1S,4s)-4-(tetrahydro-2H-pyran-2-yl)cyclohexyl)azetidin-3-yl)-2-((6-(trifluoromethyl)quinazolin-4-yl)amino)acetamide

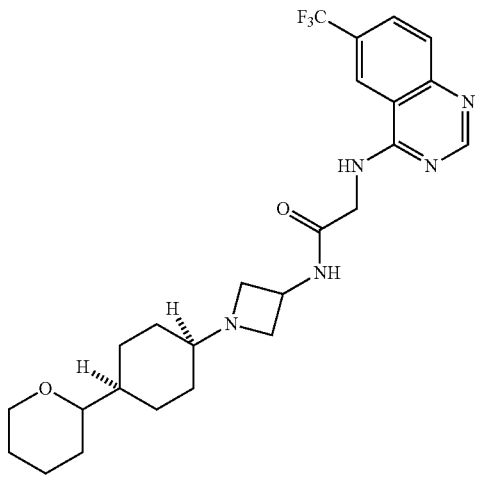 [SMILES: O=C(CNc1ncnc2ccc(C(F)(F)F)cc12)NC1CN([C@H]2CC[C@@H](C3CCCCO3)CC2)C1]

A solution of 4-(tetrahydro-2H-pyran-2-yl)cyclohexanone (116 mg, 0.64 mmol), prepared in the previous step, in dry DCM was treated with N-(azetidin-3-yl)-2-((6-(trifluoromethyl)quinazolin-4-yl)amino)acetamide (132 mg, 0.198 mmol, as prepared in Example 1, step G) and TEA (0.080 mL, 0.57 mmol). After stirring at room temperature 30 minutes, NaBH(OAc)$_3$ (149 mg, 0.70 mmol) was added and the mixture was stirred overnight. Reaction workup and purification as described in Example 1, Step H yielded the products, with the cis isomer eluting first.

cis isomer:
ESI-MS (m/z): Calcd. For $C_{24}H_{29}F_3N_6O_2$: 491.25. found: 492 (M+H).

Example 15

N-(1-((1S,4s)-4-(tetrahydro-2H-pyran-2-yl)cyclohexyl)azetidin-3-yl)-2-((6-(trifluoromethyl)quinazolin-4-yl)amino)acetamide

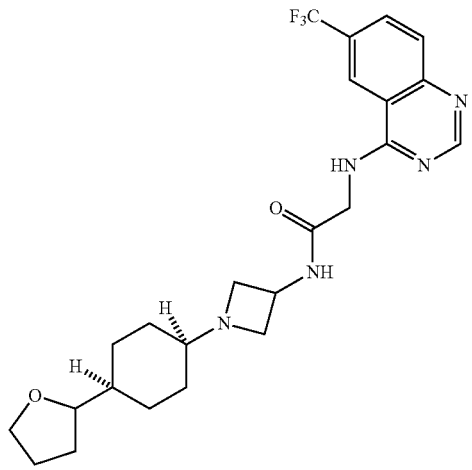 [SMILES: O=C(CNc1ncnc2ccc(C(F)(F)F)cc12)NC1CN([C@H]2CC[C@@H](C3CCCO3)CC2)C1]

A solution of N-(1-((1R,4s)-4-(S)-2,5-dihydrofuran-2-yl)cyclohexyl)azetidin-3-yl)-2-((6-(trifluoromethyl)quinazolin-4-yl)amino)acetamide (126 mg, 0.265 mmol), prepared in Example 10, and Palladium on Carbon (84 mg, 0.04 mmol, 5%, "Degussa, wet") was carefully added methanol (50 mL). The reaction flask was evacuated, backfilled with hydrogen via balloon and stirred at room temperature overnight. The catalyst was removed by filtration and the filtrate concentrated in vacuo to afford the product.

ESI-MS (m/z): Calcd. For $C_{24}H_{30}F_3N_5O_2$: 477.24. found: 478 (M+H).

Example 16

N-(1-((1R,4s)-4-(2-oxooxazolidin-4-yl)cyclohexyl)azetidin-3-yl)-2-((6-(trifluoromethyl)quinazolin-4-yl)amino)acetamide Step A: tert-butyl (1-(1,4-dioxaspiro[4.5]decan-8-yl)allyl)carbamate

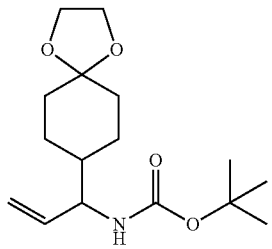 [SMILES: C=CC(NC(=O)OC(C)(C)C)C1CCC2(CC1)OCCO2]

To a flask containing 1-(1,4-dioxaspiro[4.5]decan-8-yl)but-3-en-1-amine (2.12 g, 9.07 mmol, HCl salt), prepared as described in Example 12, step B was added DCM (60 mL) followed by triethylamine (3.83 mL, 27.8 mmol) and Boc-anhydride (2.76 g, 12.3 mmol). The reaction mixture was stirred under argon overnight and then washed with saturated NH$_4$Cl solution. After concentration of the organic layer in vacuo, the residue was purified in via flash chromatography (silica gel, ethyl acetate) to afford the product.

Step B: tert-butyl (2-hydroxy-1-(1,4-dioxaspiro[4.5]decan-8-yl)ethyl)carbamate

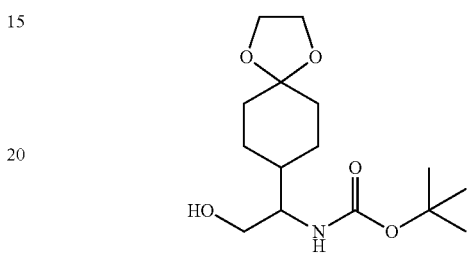

A 250 mL round bottom flask was charged with tert-butyl (1-(1,4-dioxaspiro[4.5]decan-8-yl)allyl)carbamate (5.3 g, 17.8 mmol), prepared in the previous step, and methanol (198 mL). The mixture was cooled to −78° C. and ozone was bubbled through the solution at a rate of 3 L/min for 1 hour. The mixture turned pale blue in color after 30 minutes. After 1 hour air was bubbled through the solution for 30 minutes until the blue color disappeared. Sodium borohydride (2.7 g, 71.3 mmol) was added to the mixture in 4 portions. The mixture was gradually warmed to room temperature. After 6 h at room temperature the mixture quenched with saturated aqueous ammonium chloride. After dilution with water and extraction with ethyl acetate, the organic layer was dried over MgSO$_4$, filtered, and concentrated in vacuo to give the product as a clear oil.

$^1$H NMR (400 MHz, CDCl$_3$) δ 3.89-3.97 (m, 4 H), 3.61-3.78 (m, 2 H), 3.45-3.54 (m, 1 H), 2.06-2.10 (m, 1 H), 1.68-1.84 (m, 4 H), and 1.32-1.64 (m, 13 H).

Step C: 4-(1,4-dioxaspiro[4.5]decan-8-yl)oxazolidin-2-one

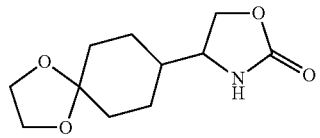 [SMILES: O=C1NC(C2CCC3(CC2)OCCO3)CO1]

A 250 mL round bottom flask was charged with tert-butyl (2-hydroxy-1-(1,4-dioxaspiro[4.5]decan-8-yl)ethyl)carbamate (1.5 g, 4.98 mmol), prepared in the previous step, and tetrahydrofuran (100 mL). The mixture was cooled to 0° C. and potassium tert-butoxide (670 mg, 5.97 mmol) was added. The mixture was stirred at 0° C. for 2 h. The mixture was diluted with ethyl acetate and washed with saturated aqueous ammonium chloride. The organic layer was dried over MgSO$_4$, filtered, and concentrated in vacuo to the product as a clear oil.

$^1$H NMR (400 MHz, CDCl$_3$) δ 4.44-4.49 (m, 1 H), 4.07-4.18 (m, 1 H), 3.87-3.98 (m, 4 H), 3.60-3.68 (m, 1 H), 2.01-2.08 (m, 1 H), and 1.15-1.85 (m, 8 H).

Step D: 4-(4-oxocyclohexyl)oxazolidin-2-one

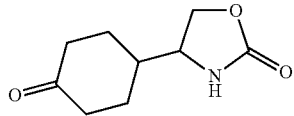 [SMILES: O=C1CCC(C2COC(=O)N2)CC1]

A solution of 4-(1,4-dioxaspiro[4.5]decan-8-yl)oxazolidin-2-one (880 mg, 3.87 mmol) and acetonitrile (65 mL).), prepared in the previous step, was deprotected as described in example 1, step C to afford the product.

$^1$H NMR (400 MHz, CDCl$_3$) δ 4.47-4.56 (m, 1 H), 4.17-4.23 (m, 1 H), 3.74-3.78 (m, 1 H), 2.07-2.14 (m, 1 H), 1.84-2.04 (m, 4 H), and 1.40-1.57 (m, 4 H).

Step E: N-(1-((1R,4s)-4-(2-oxooxazolidin-4-yl)cyclohexyl)azetidin-3-yl)-2-(6-(trifluoromethyl)quinazolin-4-yl)amino)acetamide

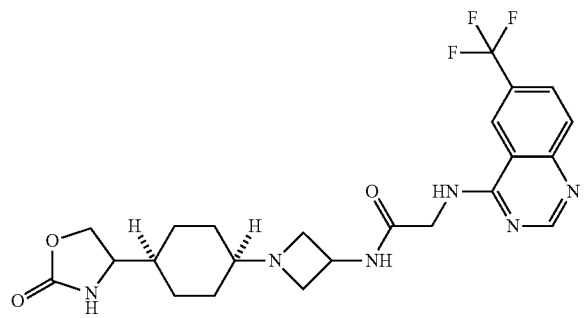 [SMILES: O=C(CNc1ncnc2ccc(C(F)(F)F)cc12)NC1CN([C@H]2CC[C@@H](C3COC(=O)N3)CC2)C1]

A solution of 4-(4-oxocyclohexyl)oxazolidin-2-one (400 mg, 0.60 mmol), prepared in the previous step, and N-(azetidin-3-yl)-2-((6-(trifluoromethyl)quinazolin-4-yl)amino)acetamide (100 mg, 0.56 mmol) as prepared in Example 1, step G) was processed according to the reductive amination procedure to afford the product.

$^1$H NMR (400 MHz, CD$_3$OD) δ 8.83-8.94 (m, 2 H), 8.32 (d, J=7.6 Hz, 1 H), 8.02 (d, J=7.6 Hz, 1 H), 4.68-4.83 (m, 1 H), 4.36-4.59 (m, 5 H), 4.10-4.30 (m, 3 H), 3.75-3.90 (m, 1 H), 3.43-3.52 (m, 1 H), 3.28-3.33 (m, 1 H), 1.70-1.85 (m, 3 H), 1.51-1.68 (m, 3 H), and 1.19-1.49 (m, 2 H); ESI-MS (m/z): Calcd. For C$_{23}$H$_{27}$F$_3$N$_6$O$_3$: 492.21. found: 493 (MH+)

Example 17

N-(1-((1R,4s)-4-(2-oxo-1,3-oxazinan-4-yl)cyclohexyl)azetidin-3-yl)-2-((6-(trifluoromethyl)quinazolin-4-yl)amino)acetamide

Step A: tert-butyl (1-(1,4-dioxaspiro[4.5]decan-8-yl)allyl)carbamate

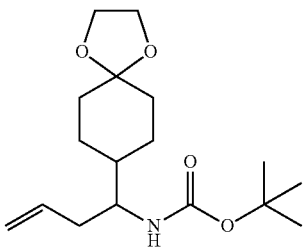 [SMILES: C=CCC(NC(=O)OC(C)(C)C)C1CCC2(CC1)OCCO2]

To a flask containing 1-(1,4-dioxaspiro[4.5]decan-8-yl)but-3-en-1-amine (4.7 g, 19.0 mmol, HCl salt), prepared as described in Example 11, step C was added DCM (126 mL) followed by triethylamine (7.91 mL, 56.9 mmol) and Boc-anhydride (4.70 g, 20.9 mmol). The reaction mixture was stirred under argon overnight and then washed with saturated NH$_4$Cl solution. After concentration of the organic layer in vacuo, the residue was purified in via flash chromatography (silica gel, 5% MeOH/DCM) to afford the product.

Step B: tert-butyl (3-hydroxy-1-(1,4-dioxaspiro[4.5]decan-8-yl)propyl)carbamate

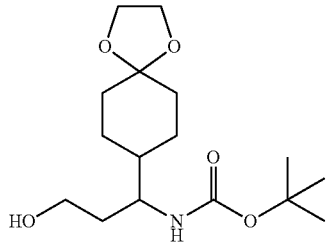 [SMILES: CC(C)(C)OC(=O)NC(CCO)C1CCC2(CC1)OCCO2]

A 250 mL round bottom flask was charge with tert-butyl (1-(1,4-dioxaspiro[4.5]decan-8-yl)allyl)carbamate (5.8 g, 18.6 mmol) and methanol (207 mL). The mixture was cooled to −78° C. and ozone was bubble through the solution at a rate of 3 L/min for 1 hour. The mixture turned pale blue in color after 30 minutes. After 1 hour air was bubble through the solution for 30 minutes until the blue color disappeared. Sodium borohydride (2.82 g, 74.5 mmol) was added to the mixture in 4 portions. The mixture was gradually warmed to room temperature. After 6 h at room temperature the mixture quenched with saturated aqueous ammonium chloride. Dilute with water and extract with ethyl acetate. Dry organic layer with MgSO4, filter, and concentrate in vacuo to give tert-butyl (3-hydroxy-1-(1,4-dioxaspiro[4.5]decan-8-yl)propyl)carbamate (5.1 g, 16.2 mmol) as a clear oil.

$^1$H NMR (400 MHz, CDCl$_3$) δ 3.89-4.10 (m, 4 H), 3.53-3.78 (m, 3 H), 1.94-2.07 (m, 1 H), 1.62-1.91 (m, 6 H), and 1.26-1.61 (m, 13 H).

Step C: 4-(1,4-dioxaspiro[4.5]decan-8-yl)-1,3-oxazinan-2-one

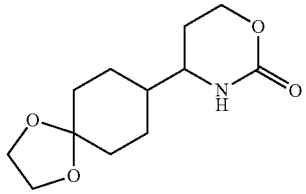 [SMILES: O=C1NC(C2CCC3(CC2)OCCO3)CCO1]

A 250 mL round bottom flask was charge with tert-butyl (3-hydroxy-1-(1,4-dioxaspiro[4.5]decan-8-yl)propyl)carbamate (2.11 g, 6.69 mmol) and tetrahydrofuran (134 mL). The mixture was cooled to 0° C. and potassium tert-butoxide (900 mg, 8.03 mmol) was added. The mixture was stirred at 0° C. for 2 h. The mixture was diluted with ethyl acetate and washed with saturated aqueous ammonium chloride. Dry organic layer with MgSO4, filter, and concentrate in vacuo to give 4-(1,4-dioxaspiro[4.5]decan-8-yl)-1,3-oxazinan-2-one (1.39 g, 5.76 mmol) as a clear oil.

$^1$H NMR (400 MHz, CDCl$_3$) δ 4.28-4.39 (m, 1 H), 4.16-4.24 (m, 1 H), 3.89-4.01 (m, 4 H), 3.26-3.38 (m, 1 H), 1.90-2.12 (m, 2 H), 1.62-1.88 (m, 4 H), and 1.31-1.58 (m, 5 H).

Step D: 4-(4-oxocyclohexyl)-1,3-oxazinan-2-one

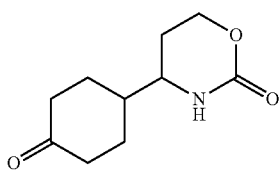 [SMILES: O=C1CCC(C2CCOC(=O)N2)CC1]

A 250 mL round bottom flask was charge with 4-(1,4-dioxaspiro[4.5]decan-8-yl)-1,3-oxazinan-2-one (1.39 g, 5.76 mmol) and acetonitrile (96 mL). A solution of concentrated HCl (6.4 mL) in water (19 mL) was added to the mixture. The mixture was stirred at room temperature for 20 h. Saturated aqueous ammonium bicarbonate was added until the pH was >7. The mixture was extracted with ethyl acetate. Dry organic layer with MgSO$_4$, filter, and concentrate in vacuo to give the target material as a clear oil.

$^1$H NMR (400 MHz, CDCl$_3$) δ 4.31-4.42 (m, 1 H), 4.18-4.28 (m, 1 H), 3.39-3.48 (m, 1 H), 2.39-2.48 (m, 1 H), 1.74-2.21 (m, 6 H), and 1.40-1.72 (m, 4 H).

Step E: N-(1-((1R,4s)-4-(2-oxo-1,3-oxazinan-4-yl)cyclohexyl)azetidin-3-yl)-2-((6-(trifluoromethyl)quinazolin-4-yl)amino)acetamide

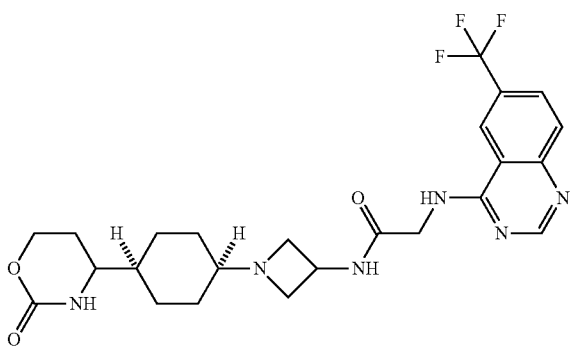 [SMILES: O=C(CNc1ncnc2ccc(C(F)(F)F)cc12)NC1CN([C@H]2CC[C@@H](C3CCOC(=O)N3)CC2)C1]

A solution of 4-(4-oxocyclohexyl)-1,3-oxazinan-2-one (372 mg, 0.56 mmol) prepared in the previous step, and N-(azetidin-3-yl)-2-((6-(trifluoromethyl)quinazolin-4-yl)amino)acetamide (100 mg, 0.56 mmol) as prepared in Example 1, step G) was processed according to the reductive amination procedure to afford the product.

$^1$H NMR (400 MHz, CD$_3$OD) δ 8.84-8.93 (m, 2 H), 8.32 (d, J=7.6 Hz, 1 H), 8.03 (d, J=7.6 Hz, 1 H), 4.70-4.88 (m, 1 H), 4.36-4.59 (m, 4 H), 4.16-4.30 (m, 3 H), 3.42-3.58 (m, 2 H), 3.29-3.34 (m, 1 H), and 1.09-2.01 (m, 11 H); ESI-MS (m/z): Calcd. For C$_{24}$H$_{29}$F$_3$N$_6$O$_3$: 506.23. found: 507 (MH+).

Example 18

N-(1-((1S,4s)-4-(1-hydroxy-2-(methylthio)ethyl)cyclohexyl)azetidin-3-yl)-2-((6-(trifluoromethyl)quinazolin-4-yl)amino)acetamide

Step A: 8-(oxiran-2-yl)-1,4-dioxaspiro[4.5]decane

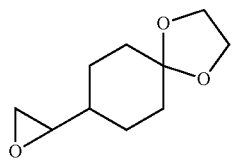 [SMILES: C1COC2(CCC(C3CO3)CC2)O1]

To a solution of 8-vinyl-1,4-dioxaspiro[4.5]decane (370 mg, 2.20 mmol), prepared as described in Example 9 Step A, in DCM (20 mL) cooled to 0° C. was added mCPBA (532 mg, 2.37 mmol, 77%). The mixture was stirred warming to room temperature over 1 hour and then concentrated in vacuo without heating. The residue was purified by flash chromatography (silica gel, 0-50% ether/DCM) to afford the product.

$^1$H NMR (CHLOROFORM-d) δ: 3.95 (s, 4H), 2.75 (d, J=3.9 Hz, 2H), 2.54 (t, J=3.8 Hz, 1H), 1.92 (d, J=10.3 Hz, 1H), 1.75-1.86 (m, 2H), 1.64-1.75 (m, 1H), 1.37-1.59 (m, 4H), 1.14-1.25 (m, 1H)

Step B: 2-(methylthio)-1-(1,4-dioxaspiro[4.5]decan-8-yl)ethanol

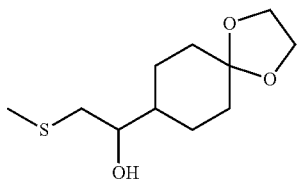

8-(oxiran-2-yl)-1,4-dioxaspiro[4.5]decane (202 mg, 1.10 mmol), prepared in the previous step, in DCM (20 mL) was dissolved in NMP (20 mL) and methanethiol sodium salt (297 mg, 4.24 mmol) was added. The mixture was stirred, heating to 80° C. under argon overnight and then cooled to ambient temperature and poured onto water. After extraction with ethyl acetate, the organic layers were concentrated in vacuo and the residue was purified by flash chromatography (silica gel, 0-50% ether) to afford the product.

$^1$H NMR (CHLOROFORM-d) δ: 3.95 (s, 4H), 3.38-3.53 (m, 1H), 2.76 (dd, J=13.6, 2.8 Hz, 1H), 2.63 (d, J=2.7 Hz, 1H), 2.48 (dd, J=13.4, 9.8 Hz, 1H), 2.10 (s, 3H), 1.88-1.98 (m, 1H), 1.66-1.85 (m, 3H), 1.30-1.62 (m, 5H)

Step C: 4-(1-hydroxy-2-(methylthio)ethyl)cyclohexanone

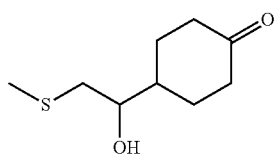

2-(methylthio)-1-(1,4-dioxaspiro[4.5]decan-8-yl)ethanol, prepared in the previous step, was deprotected as described in example 1, step C to afford the product.

$^1$H NMR (400 MHz, CDCl$_3$) δ 4.47-4.56 (m, 1 H), 4.17-4.23 (m, 1 H), 3.74-3.78 (m, 1 H), 2.07-2.14 (m, 1 H), 1.84-2.04 (m, 4 H), and 1.40-1.57 (m, 4 H).

Step D: N-(1-((1S,4s)-4-(1-hydroxy-2-(methylthio)ethyl)cyclohexyl)azetidin-3-yl)-2-((6-(trifluoromethyl)quinazolin-4-yl)amino)acetamide

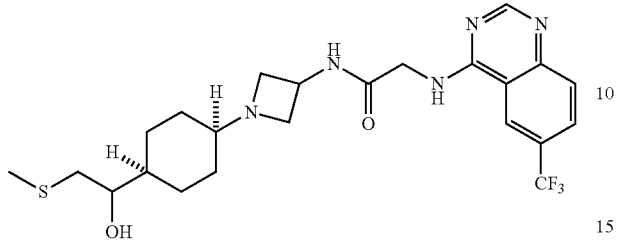

Reaction of 4-(1-hydroxy-2-(methylthio)cyclohexanone, prepared as described above, with N-(azetidin-3-yl)-246-(trifluoromethyl)quinazolin-4-yl)amino)acetamide, prepared as described in Example 1, step G in the presence of TEA and NaBH(OAc)$_3$ as described in Example 1, Step H yielded the product.

$^1$H NMR (MeOH) δ: 8.42-8.61 (m, 2H), 7.97 (dd, J=8.8, 1.7 Hz, 1H), 7.81 (d, J=8.6 Hz, 1H), 4.40-4.55 (m, 1H), 4.27 (s, 2H), 3.50-3.70 (m, 3H), 2.92 (t, J=6.7 Hz, 2H), 2.64-2.76 (m, 1H), 2.43-2.56 (m, 1H), 2.19-2.33 (m, 1H), 2.10 (s, 3H), 1.30-1.68 (m, 8H); ESI-MS (m/z): Calcd. For C$_{23}$H$_{30}$F$_3$N$_5$O$_2$S: 497.21. found: 498 (MH+).

Example 19

N-(1-((1S,4s)-4-(2-azido-1-hydroxyethyl)cyclohexyl)azetidin-3-yl)-2-((6-(trifluoromethyl)quinazolin-4-yl)amino)acetamide Step A:
2-azido-1-(1,4-dioxaspiro[4.5]decan-8-yl)ethanol

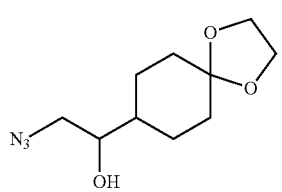 [SMILES: [N-]=[N+]=NCC(O)C1CCC2(CC1)OCCO2]

To a solution of 8-(oxiran-2-yl)-1,4-dioxaspiro[4.5]decane (205 mg, 1.11 mmol), prepared in the previous step, in methanol (5 mL) water (0.5 mL) was added sodium azide (361 mg, 5.56 mmol) and ammonium chloride (119 mg, 2.22 mmol). The mixture was stirred, heating to 80° C. under argon overnight and then cooled to ambient temperature and concentrated in vacuo. The residue was purified by flash chromatography (silica gel, ether) to afford the product.

$^1$H NMR (CHLOROFORM-d) δ: 3.87-4.01 (m, 4H), 3.51-3.61 (m, 1H), 3.40-3.49 (m, 1H), 3.27-3.38 (m, 1H), 2.03 (d, J=4.6 Hz, 1H), 1.90 (dt, J=12.5, 3.1 Hz, 1H), 1.73-1.84 (m, 2H), 1.62-1.71 (m, 1H), 1.30-1.60 (m, 5H)

Step B: 4-(2-azido-1-hydroxyethyl)cyclohexanone

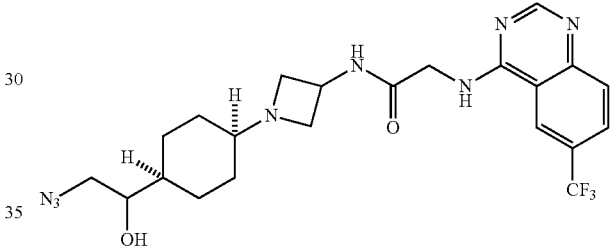

2-azido-1-(1,4-dioxaspiro[4.5]decan-8-yl)ethanol, prepared in the previous step, was deprotected as described in example 1, step C to afford the product $^1$H NMR (CHLOROFORM-d) δ: 3.65 (br. s., 1H), 3.47-3.55 (m, 1H), 3.36-3.44 (m, 1H), 2.19-2.50 (m, 6H), 1.86-2.06 (m, 2H), 1.51-1.65 (m, 2H)

Step C: N-(1-((1S,4s)-4-(2-azido-1-hydroxyethyl)cyclohexyl)azetidin-3-yl)-2-((6-(trifluoromethl)quinazolin-4-yl)amino)acetamide

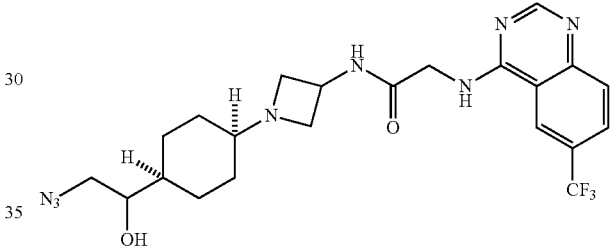

Reaction of 4-(2-azido-1-hydroxyethyl)cyclohexanone, prepared as described above, with N-(azetidin-3-yl)-246-(trifluoromethyl)quinazolin-4-yl)amino)acetamide, prepared as described in Example 1, step G in the presence of TEA and NaBH(OAc)$_3$ as described in Example 1, Step H yielded the product.

$^1$H NMR (MeOD) δ: 8.60 (s, 1H), 8.55 (s, 1H), 7.97-8.07 (m, 1H), 7.82-7.90 (m, 1H), 4.38-4.55 (m, 1H), 4.27 (s, 2H), 3.62 (br. s., 3H), 3.14-3.27 (m, 1H), 2.91 (d, J=1.5 Hz, 2H), 2.17-2.33 (m, 1H), 1.32-1.64 (m, 9H); ESI-MS (m/z): Calcd. For C$_{22}$H$_{27}$F$_3$N$_8$O$_2$: 492.22. found: 493 (MH+).

Example 20

N-(1-((1S,4s)-4-(1-hydroxy-2-methoxyethyl)cyclohexyl)azetidin-3-yl)-2-((6-(trifluoromethyl)quinazolin-4-yl)amino)acetamide Step A:
2-methoxy-1-(1,4-dioxaspiro[4.5]decan-8-yl)ethanol

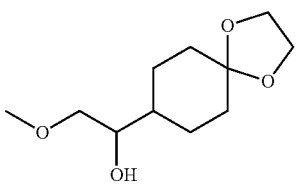

8-(oxiran-2-yl)-1,4-dioxaspiro[4.5]decane (202 mg, 1.10 mmol), prepared in the previous step, in DCM (20 mL) was dissolved in sodium methoxide solution (10 mL, 5 mmol, 0.5 M). The mixture was stirred, heating to reflux under argon overnight and then cooled to ambient temperature and concentrated in vacuo. After addition of saturated ammonium chloride solution and extraction with ethyl acetate, the organic layers were concentrated in vacuo and the residue was purified by flash chromatography (silica gel, 0-50% ether) to afford the product.

$^1$H NMR (CHLOROFORM-d) δ: 3.95 (s, 4H), 3.38-3.53 (m, 1H), 2.76 (dd, J=13.6, 2.8 Hz, 1H), 2.63 (d, J=2.7 Hz, 1H), 2.48 (dd, J=13.4, 9.8 Hz, 1H), 2.10 (s, 3H), 1.88-1.98 (m, 1H), 1.66-1.85 (m, 3H), 1.30-1.62 (m, 5H)

Step B:
4-(1-hydroxy-2-methoxyethyl)cyclohexanone

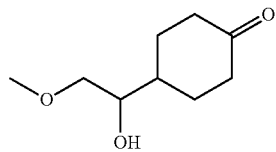

2-methoxy-1-(1,4-dioxaspiro[4.5]decan-8-yl)ethanol, prepared in the previous step, was deprotected as described in example 1, step C to afford the product $^1$H NMR (CHLOROFORM-d) δ: 3.61-3.68 (m, 1H), 3.48-3.54 (m, 1H), 3.34-3.44 (m, 4H), 2.20-2.50 (m, 6H), 1.83-2.04 (m, 2H), 1.50-1.64 (m, 2H).

Step C: N-(1-((1S,4s)-4-(1-hydroxy-2-methoxyethyl)cyclohexyl)azetidin-3-yl)-2-((6-(trifluoromethyl)quinazolin-4-yl)amino)acetamide

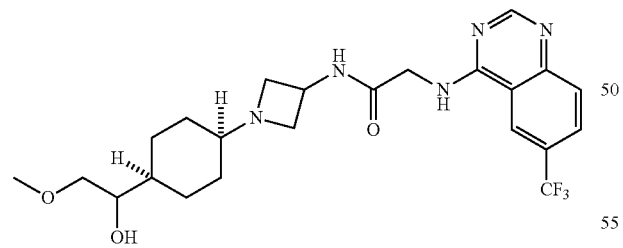

Reaction of 4-(1-hydroxy-2-methoxyethyl)cyclohexanone, prepared as described above, with N-(azetidin-3-yl)-2-(6-(trifluoromethyl)quinazolin-4-yl)amino)acetamide, prepared as described in Example 1, step G) in the presence of TEA and NaBH(OAc)$_3$ as described in Example 1, Step H yielded the product.

$^1$H NMR (MeOD) δ: 8.59-8.64 (m, 1H), 8.56 (s, 1H), 7.97-8.07 (m, 1H), 7.79-7.93 (m, 1H), 4.36-4.59 (m, 1H), 4.27 (s, 2H), 3.50-3.70 (m, 3H), 3.41-3.50 (m, 1H), 3.32-3.37 (m, 4H), 2.84-2.97 (m, 2H), 2.11-2.33 (m, 1H), 1.51 (m, 9H); ESI-MS (m/z): Calcd. For C$_{23}$H$_{30}$F$_3$N$_5$O$_3$: 481.23. found: 482 (MH+).

Example 21

N-(1-((1S,4s)-4-(1-hydroxy-2-((methylsulfinybethyl)cyclohexyl)azetidin-3-yl)-2-((6-(trifluoromethyl)quinazolin-4-yl)amino)acetamide A solution of N-(1-((1S,4s)-4-(1-hydroxy-2-(methylthio)ethyl)cyclohexyl)azetidin-3-yl)-2-((6-(trifluoromethyl)quinazolin-4-yl)amino)acetamide (104 mg, 0.209 mmol), prepared in Example 18, was dissolved in DCM (20 mL), cooled to −10° C. and treated with mCPBA (50 mg, 0.223 mmol). After warming to room temperature and stirring overnight, the reaction mixture was concentrated in vacuo without heat and the residue purified by prep plate chromatography (25% 7N NH$_3$-MeOH/EtOAc).

$^1$H NMR (MeOH) δ: 8.59 (s, 1H), 8.54 (s, 1H), 7.98-8.04 (m, 1H), 7.80-7.89 (m, 1H), 4.40-4.56 (m, 1H), 4.28 (s, 2H), 3.80-3.94 (m, 1H), 3.68 (s, 2H), 3.00 (s, 4H), 2.76-2.88 (m, 1H), 2.68 (d, J=15.7 Hz, 3H), 2.29-2.45 (m, 1H), 1.37-1.70 (m, 9H); ESI-MS (m/z): Calcd. For C$_{23}$H$_{30}$F$_3$N$_5$O$_3$: 481.23. found: 482 (MH+).

Example 22

N-(1-((1S,4s)-4-(2-oxooxazolidin-5-yl)cyclohexyl)azetidin-3-yl)-2-((6-(trifluoromethyl)quinazolin-4-yl)amino)acetamide Step A: N-(1-((1S,4s)-4-(2-amino-1-hydroxyethyl)cyclohexyl)azetidin-3-yl)-2-((6-(trifluoromethyl)quinazolin-4-yl)amino)acetamide A solution of N-(1-((1S,4s)-4-(2-azido-1-hydroxyethyl)cyclohexyl)azetidin-3-yl)-2-((6-(trifluoromethyl)quinazolin-4-yl)amino)acetamide (152 mg, 0.309 mmol), prepared in Example 19, and Palladium on Carbon (370 mg, 0.174 mmol, 5%, "Degussa, wet") was carefully added methanol (20 mL).

The reaction flask was evacuated, backfilled with hydrogen via balloon and stirred at room temperature overnight. The catalyst was removed by filtration and the filtrate concentrated in vacuo to afford the product.

$^1$H NMR (MeOH) δ: 8.58 (s, 1H), 8.54 (s, 1H), 8.00 (dd, J=8.8, 1.7 Hz, 1H), 7.84 (d, J=8.8 Hz, 1H), 4.47 (t, J=7.1 Hz, 1H), 4.27 (s, 2H), 3.57-3.69 (m, 2H), 3.39 (br. s., 1H), 3.31 (dt, J=3.3, 1.5 Hz, 2H), 2.87-2.95 (m, 3H), 2.80 (dd, J=13.2, 2.9 Hz, 1H), 2.51 (dd, J=13.1, 8.7 Hz, 1H), 2.26 (br. s., 1H), 1.24-1.69 (m, 10H); ESI-MS (m/z): Calcd. For $C_{22}H_{29}F_3N_6O_2$: 466.23. found: 467 (M+H).

Step B: N-(1-((1S,4s)-4-(2-oxooxazolidin-5-yl)cyclohexyl)azetidin-3-yl)-2-((6-(trifluoromethyl)quinazolin-4-yl)amino)acetamide

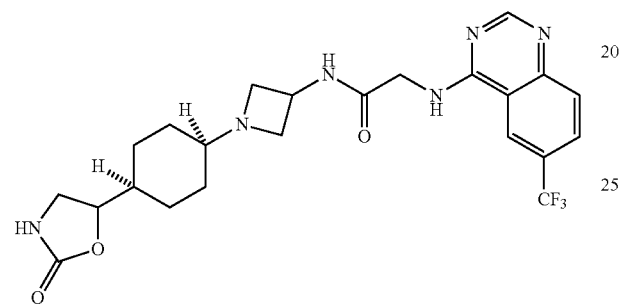

A solution of N-(1-((1S,4s)-4-(2-amino-1-hydroxyethyl)cyclohexyl)azetidin-3-yl)-2-((6-(trifluoromethyl)quinazolin-4-yl)amino)acetamide (53 mg, 0.114 mmol), prepared in step A above, in dry THF (12 mL) was treated with carbonyldiimidazole (32 mg, 0.197) and stirred at room temperature overnight. The reaction was concentrated in vacuo and the residue purified by flash chromatography (silica gel, 0-10% 7 N NH$_3$-MeOH/ethyl acetate) to afford the product.

$^1$H NMR (MeOD) δ: 8.56 (s, 1H), 8.53 (s, 1H), 7.97 (d, J=8.6 Hz, 1H), 7.81 (d, J=8.8 Hz, 1H), 4.40-4.55 (m, 2H), 4.28 (s, 2H), 3.54-3.68 (m, 3H), 3.25-3.37 (m, 2H), 2.92 (br. s., 2H), 2.29 (br. s., 1H), 1.27-1.72 (m, 9H); ESI-MS (m/z): Calcd. For $C_{23}H_{27}F_3N_6O_3$: 492.21. found: 493 (M+H).

Example 23

N-(1-((1S,4s)-4-(2-(dimethylamino)-1-hydroxyethyl)cyclohexyl)azetidin-3-yl)-2-((6-(trifluoromethyl)quinazolin-4-yl)amino)acetamide

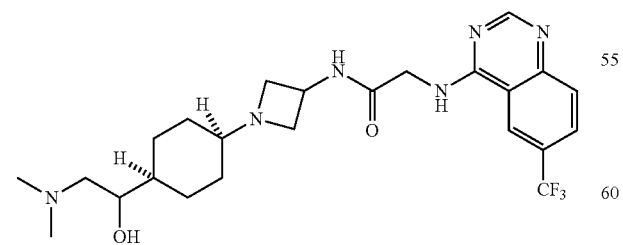

A solution of N-(1-((1S,4s)-4-(2-amino-1-hydroxyethyl)cyclohexyl)azetidin-3-yl)-2-((6-(trifluoromethyl)quinazolin-4-yl)amino)acetamide (16 mg, 0.0343 mmol), prepared in step A example 22 in MeOH (10 mL) was treated with formaldehyde (20 mg, 0.246, 37% w/w in water) and sodium cyanoborohydride (32 mg, 0.509 mmol) and stirred at room temperature overnight. The reaction was concentrated in vacuo and the residue purified by flash chromatography (silica gel, 0-10% 7 N NH$_3$-MeOH/ethyl acetate) to afford the product.

ESI-MS (m/z): Calcd. For $C_{24}H_{33}F_3N_6O_3$: 494.26. found: 495 (M+H).

Example 24

2-((2,6-bis(trifluoromethyl)quinolin-4-yl)amino)-N-(1-((1r-4r)-4-hydroxy-4-(thiazol-2-yl)cyclohexyl)azetidin-3-yl)acetamide Step A:
8-Thiazol-2-yl-1,4-dioxa-spiro[4.5]decan-8-ol

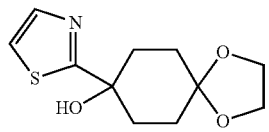

n-BuLi (2.5 M in hexanes, 26 mL, 65 mmol) was dropped slowly into a solution of thiazole (5.0 g, 59 mmol) in THF (50 mL) at −78° C. in 10 min. The reaction was stirred for additional 20 min. at −78° C. A solution of 1,4-dioxa-spiro[4.5]decan-8-one (9.36 g, 60 mmol) in THF (20 mL) was slowly dropped into the reaction. After addition, the reaction was stirred for additional 2 hours at −78° C. The reaction was then quenched with water solution and warmed to room temperature. The solvent was removed in vacuo and the residue was partitioned between ethyl acetate and water. The organic layer was washed with brine, dried over anhydrous Na$_2$SO$_4$, filtered and concentrated to give yellow solid, which was then purified by silica gel column on a CombiFlash system using hexanes and ethyl acetate (from 10% ethyl acetate to 100% ethyl acetate) to afford the title compound as white solid.

$^1$H NMR (400 MHz, CDCl$_3$) δ 7.70 (s, 1H), 7.28 (s, 1H), 4.01 (m, 4H), 3.30 (s, 1H), 2.35 (m, 2H), 2.23 (m, 2H), 2.05 (m, 2H), 1.85 (m, 2H).

Step B: 4-Hydroxy-4-thiazol-2-yl-cyclohexanone

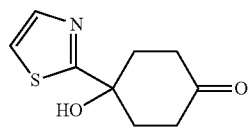 [SMILES: O=C1CCC(O)(c2nccs2)CC1]

The title compound was prepared as white solid from deprotection of 8-thiazol-2-yl-1,4-dioxa-spiro[4.5]decan-8-ol using the similar procedure described in Step C of Example 1.

$^1$H NMR (400 MHz, CDCl$_3$) δ 7.71 (s, 1H), 7.32 (s, 1H), 2.93 (m, 2H), 2.40 (m, 4H), 2.31 (m, 2H).

Step C: tert-butyl 3-(2-((2,6-bis(trifluoromethyl)quinolin-4-yl)amino)acetamido)azetidine-1-carboxylate

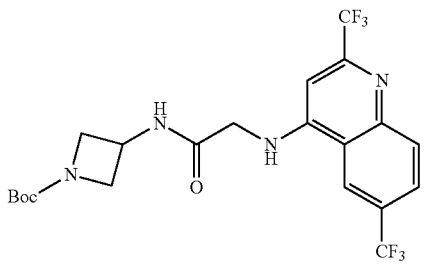 [SMILES: CC(C)(C)OC(=O)N1CC(NC(=O)CNc2cc(C(F)(F)F)nc3ccc(C(F)(F)F)cc23)C1]

A solution of commercially available 2,6-bis(trifluoromethyl)quinolin-4-ol (291 mg, 1.04 mmol) in dry dioxane (5 mL) was treated sequentially with TEA (0.36 mL, 2.58 mmol) and PyBrOP (586 mg, 1.26 mmol). After stirring 1 hour at room temperature under argon, a solution of tert-butyl 3-(2-aminoacetamido)azetidine-1-carboxylate (352, 1.54 mmol), prepared as described in Example 1, Step E in dry dioxane (5 mL) was introduced and the reaction mixture was stirred overnight at room temperature. After concentration in vacuo, the residue was purified by flash chromatography (silica gel, 0-5% MeOH/ethyl acetate) to afford the product. ESI-MS (m/z): Calcd. For C$_{21}$H$_{22}$F$_6$N$_4$O$_3$: 492.11. found: 493 (M+H).

Step D: N-(azetidin-3-yl)-2-((2,6-bis(trifluoromethyl)quinolin-4-yl)amino)acetamide

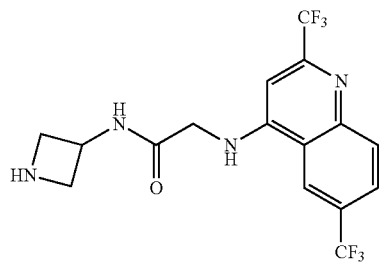 [SMILES: O=C(CNc1cc(C(F)(F)F)nc2ccc(C(F)(F)F)cc12)NC1CNC1]

A solution of tert-butyl 3-(2-((2,6-bis(trifluoromethyl)quinolin-4-yl)amino)acetamido)azetidine-1-carboxylate (291 mg, 1.04 mmol) in dry dioxane (5 mL), prepared in Step C above, was de-protected as described in example to afford the product. ESI-MS (m/z): Calcd. For C$_{16}$H$_{14}$F$_3$N$_4$O: 392.11. found: 393 (M+H).

Step E: 2-((2,6-bis(trifluoromethyl)quinolin-4-yl)amino)-N-(1-((1r,4r)-4-hydroxy-4-(thiazol-2-yl)cyclohexyl)azetidin-3-yl)acetamide

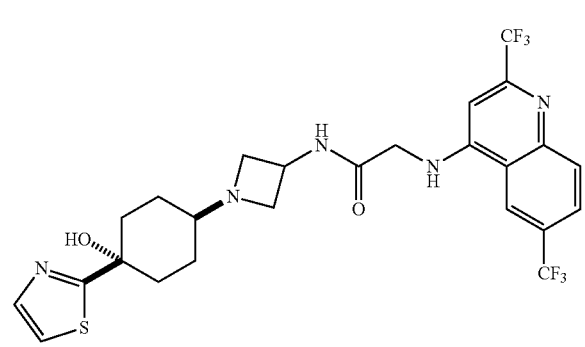

To a suspension of 4-Hydroxy-4-thiazol-2-yl-cyclohexanone (as prepared in Step C, 1 eq.) and N-(azetidin-3-yl)-2-((2,6-bis(trifluoromethyl)quinolin-4-yl)amino)acetamide (as prepared in the previous step, bis TFA salt, 1 eq.) in DCM was added TEA (2 eq.). After stirring at room temperature 30 minutes, NaBH(OAc)$_3$ (3 eq) was added and the mixture was stirred overnight. The reaction was quenched with saturated sodium bicarbonate solution and partially concentrated. Extraction with ethyl acetate followed by concentration of the organic layer in vacuo yielded a residue which was purified by flash chromatography (silica gel, 0-20% 7 N NH$_3$-MeOH/Ethyl acetate) to afford the product as a solid.

ESI-MS (m/z): Calcd. For C$_{25}$H$_{25}$F$_6$N$_5$O$_2$S: 573.16. found: 574 (M+H).

Example 25

2-((2,6-bis(trifluoromethyl)quinolin-4-yl)amino)-N-(1((-1R,4s)-4-(1-hydroxypropyl)cyclohexyl)azetidin-3-yl)acetamide Step A:
1-(1,4-dioxaspiro[4.5]decan-8-yl)propan-1-ol

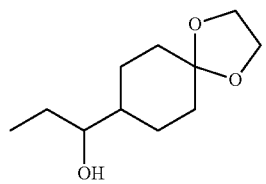

Reacting 1,4-dioxaspiro[4.5]decane-8-carbaldehyde (prepared as described in Pearson, et al. in *J. Org. Chem.* 1997, 62(16), 5284-5292) with ethylmagnesium bromide as described in Example 2, Step A yielded the title compound.

$^1$H NMR (CHLOROFORM-d) δ: 3.94 (s, 4H), 3.25-3.40 (m, 1H), 1.27-1.92 (m, 12H), 0.94-1.00 (m, 3H)

Step B: 4-(1-hydroxypropyl)cyclohexanone

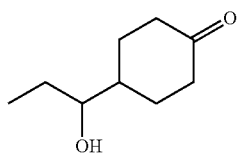

Deprotection of 1-(1,4-dioxaspiro[4.5]decan-8-yl)propan-1-ol (prepared as described in Step A) by the procedure in Example 1, Step C afforded the product.

$^1$H NMR (CHLOROFORM-d) δ: 3.37-3.57 (m, 1H), 2.27-2.55 (m, 4H), 2.18 (ddd, J=13.0, 6.2, 3.1 Hz, 1H), 1.96-2.08 (m, 1H), 1.81 (m, 1H), 1.40-1.73 (m, 6H), 1.00 (t, 3H)

Step C: 2-((2,6-bis(trifluoromethyl)quinolin-4-yl)amino)-N-(1-((1R,4s)-4-(1-hydroxypropyl)cyclohexyl)azetidin-3-yl)acetamide

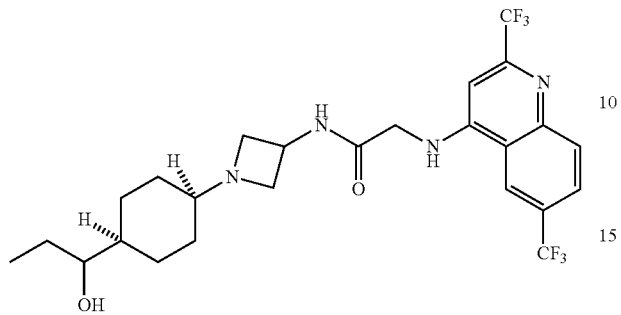

Reaction of 4-(1-hydroxypropyl)cyclohexanone (as prepared in Step B) with N-(azetidin-3-yl)-2-((2,6-bis(trifluoromethyl)quinolin-4-yl)amino)acetamide (as prepared in Example 24, Step D) in the presence of TEA and NaBH(OAc)$_3$ as described in Example 1, Step H) afforded the product. ESI-MS (m/z): Calcd. For $C_{25}H_{30}F_6N_4O_2$: 532.23. found: 533 (M+H).

Example 26

N-(1-((1r,4r)-4-hydroxy-4-(thiazol-5-yl)cyclohexyl)azetidin-3-yl)-2-((6-(trifluoromethyl)quinolin-4-yl)amino)acetamide Step A: 8-(2-Trimethylsilanyl-thiazol-5-yl)-1,4-dioxa-spiro[4.5]decan-8-ol

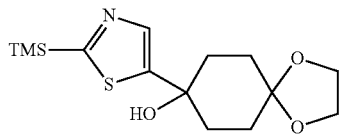 [SMILES: C[Si](C)(C)c1ncc(C2(O)CCC3(CC2)OCCO3)s1]

The title compound was prepared as white solid from 2-trimethylsilanyl-thiazole and 1,4-dioxa-spiro[4.5]decan-8-one using the similar procedure described in Step A of Example 24. ESI-MS (m/z): Calcd. For $C_{14}H_{23}NO_3SSi$, 313. found: 314 (M+H).

Step B: 8-Thiazol-5-yl-1,4-dioxa-spiro[4.5]decan-8-ol

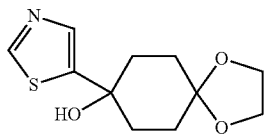 [SMILES: OC1(c2cncs2)CCC2(CC1)OCCO2]

The title compound was prepared as white solid from 8-(2-trimethylsilanyl-thiazol-5-yl)-1,4-dioxa-spiro[4.5]decan-8-ol followed by TBAF work-up.

$^1$H NMR (400 MHz, CDCl$_3$) δ 8.65 (s, 1H), 7.72 (s, 1H), 4.01 (m, 4H), 2.20 (m, 2H), 2.08 (m, 4H), 1.69 (m, 2H).

Step C: 4-Hydroxy-4-thiazol-5-yl-cyclohexanone

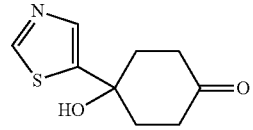 [SMILES: O=C1CCC(O)(c2cncs2)CC1]

The title compound was prepared as white solid from deprotection of 8-thiazol-5-yl-1,4-dioxa-spiro[4.5]decan-8-ol using the similar procedure described in Step C of Example 1.
$^1$H NMR (400 MHz, CDCl$_3$) δ 8.70 (s, 1H), 7.73 (s, 1H), 2.96 (m, 2H), 2.35 (m, 4H), 2.23 (m, 2H).

Step D: benzyl (6-(trifluoromethyl)quinolin-4-yl)carbamate

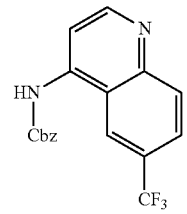

A rapidly stirred mixture of ethyl acetate and saturated aqueous sodium bicarbonate containing commercially available 6-(trifluoromethyl)quinolin-4-amine (558 mg, 2.63 mmol) was cooled to 0° C. and treated dropwise with benzyl chloroformate (1.10 mL, 3.29 mmol). After stirring overnight warming to room temperature, the aqueous layer was removed and the organic layer concentrated in vacuo. Purification of the residue by flash chromatography (silica gel, 0-20% MeOH/Ethyl acetate) yielded the product.
$^1$H NMR (CHLOROFORM-d) δ: 8.95 (d, J=5.4 Hz, 1H), 8.19-8.32 (m, 2H), 8.11 (s, 1H), 7.91 (d, J=8.8 Hz, 1H), 7.58 (br. s., 1H), 7.37-7.54 (m, 5H), 5.33 (s, 2H).

Step E: ethyl 2-(((benzyloxy)carbonyl)(6-(trifluoromethyl)quinolin-4-yl)amino)acetate

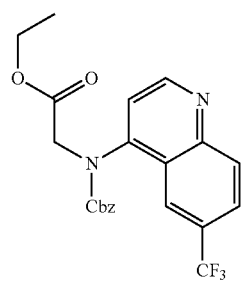 [SMILES: CCOC(=O)CN(C(=O)OCc1ccccc1)c1ccnc2ccc(C(F)(F)F)cc12]

A solution of benzyl (6-(trifluoromethyl)quinolin-4-yl)carbamate (440 mg, 1.27 mmol, prepared in Step D) in dry DMF (20 mL) is treated with cesium carbonate (870 mg, 2.67 mmol) and stirred at room temperature for 1 hour. Ethylbromoacetate (0.15 mL, 1.36 mmol) is added dropwise and the reaction mixture is stirred at room temperature overnight. The reaction mixture was then poured into saturated NH₄Cl solution and extracted with ethyl acetate. After concentration in vacuo, the residue was purified by flash chromatography (silica gel, 0-100% ethyl acetate/DCM) to afford the title compound.

¹H NMR (400 MHz, CDCl₃) δ 8.70 (s, 1H), 7.73 (s, 1H), 2.96 (m, 2H), 2.35 (m, 4H), 2.23 (m, 2H).

Step F: 2-(((benzyloxy)carbonyl)(6-(trifluoromethyl)quinolin-4-yl)amino) acetic acid

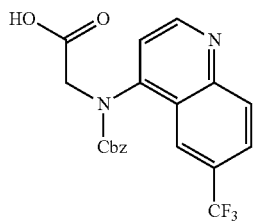 [SMILES: O=C(O)CN(C(=O)OCc1ccccc1)c1ccnc2ccc(C(F)(F)F)cc12]

A solution of ethyl 2-(((benzyloxy)carbonyl)(6-(trifluoromethyl)quinolin-4-yl)amino)acetate (404 mg, 0.934 mmol, prepared in step E) in MeOH (15 mL) and THF (5 mL) and treated with a solution of LiOH (112 mg, 4.67 mol) in water (5 mL). After stirring at room temperature for xx hours, the pH was adjusted to ~5 by the addition of aqueous HCl. After extraction with ethyl acetate, the organic layer was dried over Na₂SO₄ and concentrated in vacuo to yield the product.

¹H NMR (400 MHz, CDCl₃) δ 8.70 (s, 1H), 7.73 (s, 1H), 2.96 (m, 2H), 2.35 (m, 4H), 2.23 (m, 2H).

Step G: tert-butyl 3-(2-(((benzyloxy)carbonyl)(6-(trifluoromethyl)quinolin-4-yl)amino)acetamido)azetidine-1-carboxylate

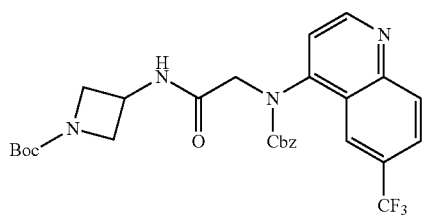 [SMILES: CC(C)(C)OC(=O)N1CC(NC(=O)CN(C(=O)OCc2ccccc2)c2ccnc3ccc(C(F)(F)F)cc23)C1]

A solution of 2-(((benzyloxy)carbonyl)(6-(trifluoromethyl)quinolin-4-yl)amino)acetic acid (306 mg, 0.757 mmol, prepared in step F) and EDCI (217 mg, 1.13 mmol) in DCM (10 mL) was stirred until a clear solution resulted. This solution was added to a suspension of tert-butyl 3-aminoazetidine-1-carboxylate (156 mg, 0.908 mmol) and HOBt (116 mg, 0.757 mmol) in DCM (10 mL). The reaction mixture was stirred overnight at ambient temperature and poured onto saturated aqueous sodium bicarbonate, extracting with ethyl acetate. Concentration of the organic layer followed by purification of the residue by flash chromatopgraphy (silica gel, 0-20% MeOH/ethyl acetate) afforded the product.

Step H: tert-butyl 3-(2-((6-(trifluoromethyl)quinolin-4-yl)amino)acetamido)azetidine-1-carboxylate

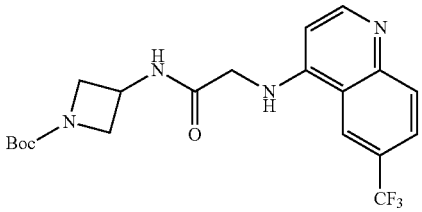 [SMILES: CC(C)(C)OC(=O)N1CC(NC(=O)CNc2ccnc3ccc(C(F)(F)F)cc23)C1]

To flask containing tert-butyl 3-(2-(((benzyloxy)carbonyl)(6-(trifluoromethyl)quinolin-4-yl)amino)acetamido)azetidine-1-carboxylate (306 mg, 0.309 mmol), prepared in Step G, and Palladium on Carbon (98 mg, 0.092 mmol, 5%, "Degussa, wet") was carefully added methanol (40 mL). The reaction flask was evacuated, backfilled with hydrogen via balloon and stirred at room temperature overnight. The catalyst was removed by filtration and the filtrate concentrated in vacuo to afford the product.

¹H NMR (ACETONITRILE-d₃) δ: 8.51-8.61 (m, 1H), 8.39 (s, 1H), 7.95-8.06 (m, 1H), 7.78-7.90 (m, 1H), 7.43-7.56 (m, 1H), 6.64-6.76 (m, 1H), 6.40 (d, J=5.4 Hz, 1H), 4.47-4.62 (m, 1H), 4.01-4.15 (m, 2H), 3.97 (d, J=5.6 Hz, 2H), 3.69 (m, 2H).

Step I: N-(azetidin-3-yl)-2-((6-(trifluoromethyl)quinolin-4-yl)amino)acetamide

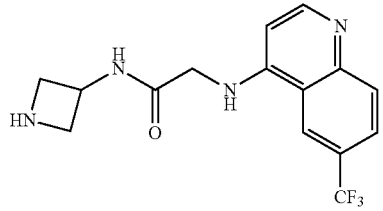 [SMILES: O=C(CNc1ccnc2ccc(C(F)(F)F)cc12)NC1CNC1]

The title compound was prepared by de-protection tert-butyl 3-(2-((6-(trifluoromethyl)quinolin-4-yl)amino)acetamido)azetidine-1-carboxylate, prepared in Step H using a similar procedure as described in Step G of Example 1.

ESI-MS (m/z): Calcd. For C₁₅H₁₅N₄O, 324.12. found: 325 (M+H).

Step J: N-(1-((1r,4r)-4-hydroxy-4-(thiazol-5-yl)cyclohexyl)azetidin-3-yl)-2-((6-(trifluoromethyl)quinolin-4-yl)amino)acetamide

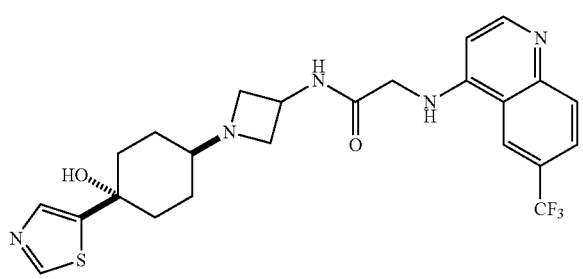

Reaction of: 4-Hydroxy-4-thiazol-5-yl-cyclohexanone (as prepared in Step C) with N-(azetidin-3-yl)-2-((6-(trifluoromethyl)quinolin-4-yl)amino)acetamide (as prepared in Step I) in the presence of TEA and NaBH(OAc)$_3$ as described in Example 1, Step H afforded the product. ESI-MS (m/z): Calcd. For $C_{24}H_{26}F_3N_5O_2S$: 505.18. found: 506 (M+H).

Example 27

N-(1-((1r,4r)-4-hydroxy-4-(thiazol-5-yl)cyclohexyl)azetidin-3-yl)-2-((6-(trifluoromethyl)quinolin-4-yl)amino)acetamide

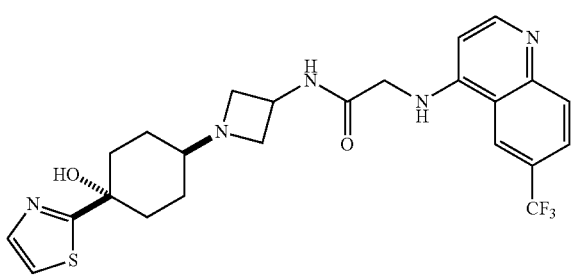

Reaction of 4-Hydroxy-4-thiazol-2-yl-cyclohexanone (as prepared in Example 24 Step B) with N-(azetidin-3-yl)-2-((6-(trifluoromethyl)quinolin-4-yl)amino)acetamide (as prepared in Example 26 Step I) in the presence of TEA and NaBH(OAc)$_3$ as described in Example 1, Step H afforded the product.

$^1$H NMR (DMSO-d$_6$) δ: 8.66-8.78 (m, 1H), 8.40-8.59 (m, 2H), 7.92-8.03 (m, 2H), 7.80-7.90 (m, 1H), 7.62-7.72 (m, 1H), 7.45-7.58 (m, 1H), 6.32-6.43 (m, 1H), 4.17-4.35 (m, 1H), 3.93 (br. s., 2H), 3.41-3.52 (m, 2H), 2.74-2.86 (m, 2H), 2.07-2.26 (m, 3H), 1.60-1.73 (m, 2H), 1.42 (br. s., 4H); ESI-MS (m/z): Calcd. For $C_{24}H_{26}F_3N_5O_2S$: 505.18. found: 506 (M+H).

Example 28

N-(1-((1s,4s)-4-(1-hydroxycyclopent-3-en-1-yl)cyclohexyl)azetidin-3-yl)-2-((6-(trifluoromethyl)quinolin-4-yl)amino)acetamide Step A:
1-(1,4-dioxaspiro[4.5]decan-8-yl)but-3-en-1-ol

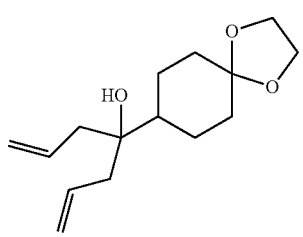 [SMILES: C=CCC(O)(CC=C)C1CCC2(CC1)OCCO2]

To a solution of ethyl 1,4-dioxaspiro[4.5]decane-8-carboxylate (1.12 g, 5.24 mmol, prepared as described in Pearson, et al. in *J. Org. Chem.* 1997, 62(16), 5284-5292) in THF (10 mL) cooled to −78° C. under argon was added a allyl-magnesium bromide (18 mL, 18 mmol, 1 M in THF) dropwise. After the complete addition, the reaction mixture was allowed to reach room temperature overnight. It was then re-cooled to −78° C. and quenched with saturated NaHCO$_3$ solution and warmed to room temperature. After extraction with ether, the organic layer was concentrated in vacuo and the residue purified by flash chromatography (silica gel, 0-100% ether/hexanes) to afford the product.

$^1$H NMR (CHLOROFORM-d) δ: 5.80-5.98 (m, 2H), 5.06-5.22 (m, 4H), 3.96 (s, 4H), 2.28-2.39 (m, 2H), 2.18-2.28 (m, 2H), 1.82 (d, J=9.0 Hz, 4H), 1.35-1.59 (m, 6H)

Step B:
1-(1,4-dioxaspiro[4.5]decan-8-yl)cyclopent-3-enol

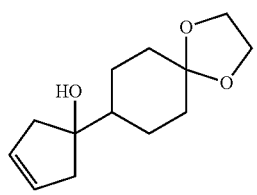 [SMILES: OC1(C2CCC3(CC2)OCCO3)CC=CC1]

A solution of 1-(1,4-dioxaspiro[4.5]decan-8-yl)but-3-en-1-ol (840 mg, 3.33 mmol), prepared in the previous step, and the Grubbs Generation II catalyst (185 mg, 0.218 mmol) in DCM was degassed and heated to 40° C. under argon for 4 hours. After extraction with saturated NaHCO$_3$ solution, the organic layer was concentrated in vacuo and the residue purified by flash chromatography (silica gel, ether) to afford the product.

Step C:
4-(1-hydroxycyclopent-3-en-1-yl)cyclohexanone

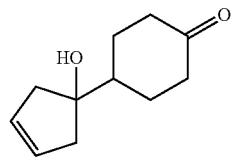 [SMILES: O=C1CCC(C2(O)CC=CC2)CC1]

A solution of 8-(3,6-dihydro-2H-pyran-2-yl)-1,4-dioxaspiro[4.5]decane, prepared in the previous step, was deprotected as described in example 1, step C to afford the product.

Step D: N-(1-((1s,4s)-4-(1-hydroxycyclopent-3-en-1-yl)cyclohexyl)azetidin-3-yl)-2-((6-(trifluoromethyl)quinolin-4-yl)amino)acetamide

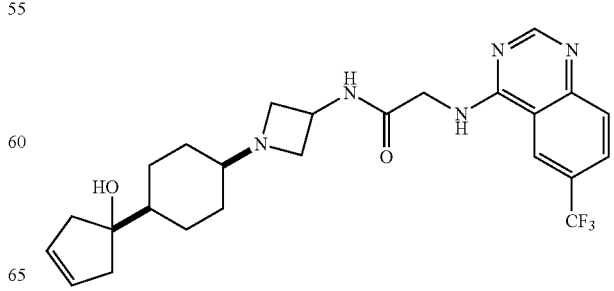

Reaction of 4-(3,6-dihydro-2H-pyran-2-yl)cyclohexanone (as prepared the previous step) with N-(azetidin-3-yl)-2-((6-trifluoromethyl)quinazolin-4-yl)amino)acetamide (as prepared in Example 1 Step G) in the presence of TEA and NaBH(OAc)₃ as described in Example 1, Step H afforded the product.

ESI-MS (m/z): Calcd. For $C_{26}H_{31}F_3N_4O_2$: 488.24. found: 489 (M+H).

Example 29

N-(1-((1s,4s)-4-(2-hydroxypropan-2-yl)cyclohexyl) azetidin-3-yl)-2-((6-(trifluoromethyl)quinazolin-4-yl)amino)acetamide Step A: 2-(1,4-dioxaspiro[4.5]decan-8-yl)propan-2-ol

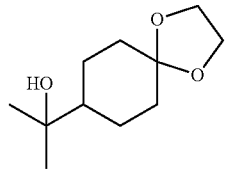

To a solution of ethyl 1,4-dioxaspiro[4.5]decane-8-carboxylate (0.64 g, 2.99 mmol, prepared as described in Pearson, et al. in *J. Org. Chem.* 1997, 62(16), 5284-5292) in THF (20 mL) cooled to −78° C. under argon was added a methylmagnesium chloride (4 mL, 12 mmol, 3 M in THF) dropwise. After the complete addition, the reaction mixture was allowed to reach room temperature overnight. It was then re-cooled to −78° C. and quenched with saturated NaHCO₃ solution and warmed to room temperature. After extraction with ether, the organic layer was concentrated in vacuo and the residue purified by flash chromatography (silica gel, 0-100% ether/hexanes) to afford the product.

Step B: 4-(2-hydroxypropan-2-yl)cyclohexanone

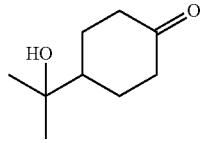

A solution of 2-(1,4-dioxaspiro[4.5]decan-8-yl)propan-2-ol, prepared in the previous step, was de-protected as described in example 1, step C to afford the product.

Step C: N-(1-((1s,4s)-4-(2-hydroxypropan-2-yl)cyclohexyl)azetidin-3-yl)-2-((6-(trifluoromethyl) quinazolin-4-yl)amino)acetamide

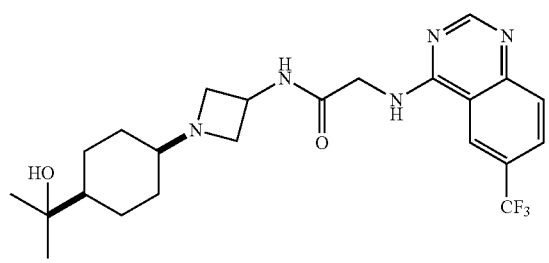

Reaction of 4-(4-hydroxyhepta-1,6-dien-4-yl)cyclohexanone (as prepared in the previous step) with N-(azetidin-3-yl)-2-(6-(trifluoromethyl)quinazolin-4-yl)amino)acetamide (as prepared in Example 1 Step G) in the presence of TEA and NaBH(OAc)₃ as described in Example 1, Step H afforded the product.

ESI-MS (m/z): Calcd. For $C_{24}H_{31}F_3N_4O_2$: 464.24. found: 465 (M+H).

Example 30

N-(1-((1s,4s)-4-(3-hydroxypentan-3-yl)cyclohexyl) azetidin-3-yl)-2-((6-(trifluoromethyl)quinazolin-4-yl)amino)acetamide Step A: 3-(1,4-dioxaspiro[4.5]decan-8-yl)pentan-3-ol

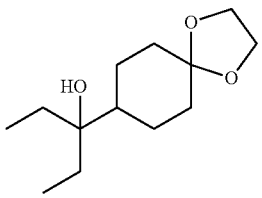 [SMILES: CCC(O)(CC)C1CCC2(CC1)OCCO2]

To a solution of ethyl 1,4-dioxaspiro[4.5]decane-8-carboxylate (0.754 g, 3.52 mmol, prepared as described in Pearson, et al. in *J. Org. Chem.* 1997, 62(16), 5284-5292) in THF (20 mL) cooled to −78° C. under argon was added a ethylmagnesium chloride (9 mL, 18 mmol, 2 M in THF) dropwise. After the complete addition, the reaction mixture was allowed to reach room temperature overnight. It was then re-cooled to −78° C. and quenched with saturated NaHCO₃ solution and warmed to room temperature. After extraction with ether, the organic layer was concentrated in vacuo and the residue purified by flash chromatography (silica gel, 0-100% ether/hexanes) to afford the product.

Step B: 4-(3-hydroxypentan-3-yl)cyclohexanone

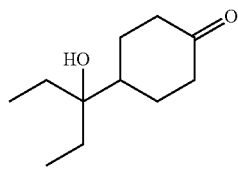

A solution of 2 3-(1,4-dioxaspiro[4.5]decan-8-yl)pentan-3-ol, prepared in the previous step, was de-protected as described in example 1, step C to afford the product.

Step C: N-(1-((1s,4s)-4-(3-hydroxypentan-3-yl)cyclohexyl)azetidin-3-yl)-2-((6-(trifluoromethyl) quinazolin-4-yl)amino)acetamide

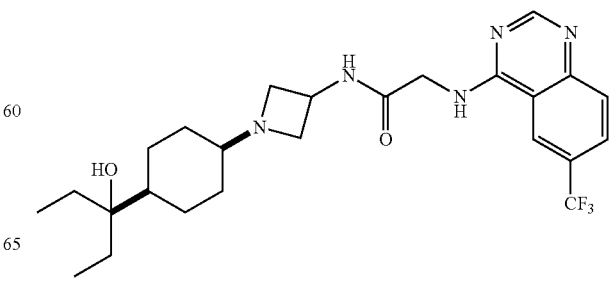

Reaction of 4-(3-hydroxypentan-3-yl)cyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{26}H_{35}F_3N_4O_2$: 492.27. found: 493 (M+H).

Example 31

N-(1-((1s,4s)-4-(4-hydroxyhepta-1,6-dien-4-yl)cyclohexyl)azetidin-3-yl)-2-((6-(trifluoromethyl)quinazolin-4-yl)amino)acetamide Step A: 4-(4-hydroxyhepta-1,6-dien-4-yl)cyclohexanone

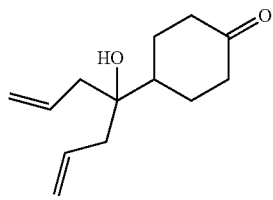

A solution of 1-(1,4-dioxaspiro[4.5]decan-8-yl)but-3-en-1-ol, prepared in Example 28, Step A, was de-protected as described in example 1, step C to afford the product.

Step B: N-(1-((1s,4s)-4-(4-hydroxyhepta-1,6-dien-4-yl)cyclohexyl)azetidin-3-yl)-2-((6-(trifluoromethyl)quinazolin-4-yl)amino)acetamide Reaction of 4-(4-hydroxyhepta-1,6-dien-4-yl)cyclohexanone (as prepared in the previous step) with N-(azetidin-3-yl)-2-(6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{28}H_{35}F_3N_4O_2$: 516.27. found: 517 (M+H).

Example 32

N-(1-((1s,4s)-4-(4-hydroxyheptan-4-yl)cyclohexyl)azetidin-3-yl)-2-((6-(trifluoromethyl)quinazolin-4-yl)amino)acetamide Step A: 4-(1,4-dioxaspiro[4.5]decan-8-yl)heptan-4-ol

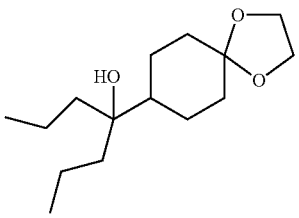 [SMILES: CCCC(O)(CCC)C1CCC2(CC1)OCCO2]

To a flask containing 1-(1,4-dioxaspiro[4.5]decan-8-yl)but-3-en-1-ol (390 mg, 1.54 mmol), prepared in Example 28, Step A, and Palladium on Carbon (244 mg, 0.115 mmol, 5%) was carefully added methanol (25 mL). The reaction flask was evacuated, backfilled with hydrogen via balloon and stirred at room temperature overnight. The catalyst was removed by filtration and the filtrate concentrated in vacuo to afford the product.

Step B: 4-(4-hydroxyheptan-4-yl)cyclohexanone

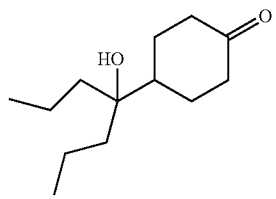

A solution of 4-(1,4-dioxaspiro[4.5]decan-8-yl)heptan-4-ol, prepared in Example 28, Step A, was de-protected as described in example 1, step C to afford the product.

Step C: N-(1-((1s,4s)-4-(4-hydroxyheptan-4-yl)cyclohexyl)azetidin-3-yl)-2-((6-(trifluoromethyl)quinazolin-4-yl)amino)acetamide

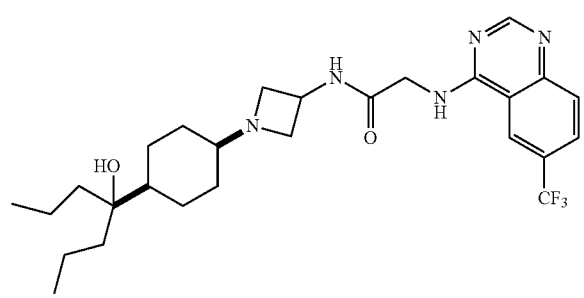 [SMILES: CCCC(O)(CCC)[C@H]1CC[C@@H](N2CC(NC(=O)CNc3ncnc4ccc(C(F)(F)F)cc34)C2)CC1]

Reaction of 4-(4-hydroxyheptan-4-yl)cyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{28}H_{39}F_3N_4O_2$: 520.30. found: 521 (M+H).

Example 33

N-(1-((1s,4s)-4-cyclopentylcyclohexyl)azetidin-3-yl)-2-((6-(trifluoromethyl)quinazolin-4-yl)amino)acetamide Step A: 8-cyclopentyl-1,4-dioxaspiro[4.5]decane

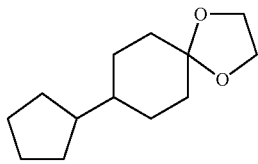 [SMILES: C1CCC(C2CCC3(CC2)OCCO3)C1]

To a flask containing 1-(1,4-dioxaspiro[4.5]decan-8-yl)cyclopent-3-enol (218 mg, 0.972 mmol), prepared in the Example 28 Step B, and Palladium on Carbon (157 mg, 0.074 mmol) was carefully added methanol (24 mL). The reaction flask was evacuated, backfilled with hydrogen via balloon and stirred at room temperature overnight. The catalyst was removed by filtration and the filtrate concentrated in vacuo to afford the product.

Step B: 4-cyclopentylcyclohexanone

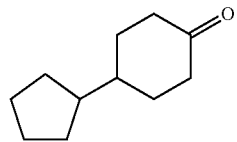 [SMILES: O=C1CCC(C2CCCC2)CC1]

A solution of 8-cyclopentyl-1,4-dioxaspiro[4.5]decane, prepared in the previous step, was de-protected as described in example 1, step C to afford the product.

Step C: N-(1-((1s,4s)-4-cyclopentylcyclohexyl)azetidin-3-yl)-2-((6-(trifluoromethyl)quinazolin-4-yl)amino)acetamide

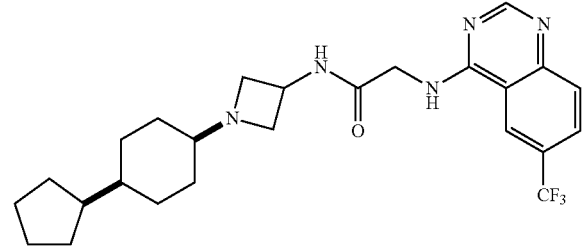 [SMILES: O=C(CNc1ncnc2ccc(C(F)(F)F)cc12)NC1CN([C@H]2CC[C@@H](C3CCCC3)CC2)C1]

Reaction of 4-cyclopentylcyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{26}H_{33}F_3N_4O$: 474.26. found: 475 (M+H).

Example 34

N-(1-((1R,4s)-4-(2,2,2-trifluoro-1-hydroxyethyl)cyclohexyl)azetidin-3-yl)-2-((6-(trifluoromethyl)quinazolin-4-yl)amino)acetamide Step A: trimethyl(2,2,2-trifluoro-1-(1,4-dioxaspiro[4.5]decan-8-yl)ethoxy)silane

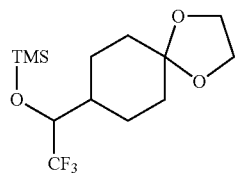 [SMILES: C[Si](C)(C)OC(C1CCC2(CC1)OCCO2)C(F)(F)F]

To a solution of 1,4-dioxaspiro[4.5]decane-8-carbaldehyde (1.46 g, 4.88 mmol, prepared as described in Pearson, et al. in *J. Org. Chem.* 1997, 62(16), 5284-5292) cooled to 0° C. under argon was added TBAF (0.05 eq) followed by trimethyl(trifluoromethyl)silane (0.80 mL, 5.07 mmol, 0.5 M in THF) dropwise. After the complete addition, the reaction mixture was allowed to reach room temperature overnight. It was then re-cooled to −78° C. and quenched with saturated NaHCO$_3$ solution and warmed to room temperature. After extraction with ether, the organic layer was concentrated in vacuo and the residue purified by flash chromatography (silica gel, DCM) to afford the product.

Step B: 2,2,2-trifluoro-1-(1,4-dioxaspiro[4.5]decan-8-yl)ethanol

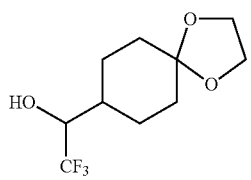

To a solution of trimethyl(2,2,2-trifluoro-1-(1,4-dioxaspiro[4.5]decan-8-yl)ethoxy)silane (792 mg, 2.54 mmol, prepared in the previous step) in THF (10 mL) was added a TBAF (2.6 mL, 2.6 mmol, 1 M in THF) dropwise. After the complete addition, the reaction mixture was at room temperature 2 hours and then concentrated in vacuo. The residue purified by flash chromatography (silica gel, 0-100% ethyl acetate/heptane) to afford the product.

Step C: 4-(2,2,2-trifluoro-1-hydroxyethyl)cyclohexanone

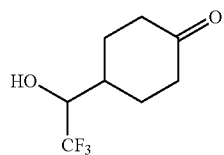

A solution of 2,2,2-trifluoro-1-(1,4-dioxaspiro[4.5]decan-8-yl)ethanol, prepared in the previous step, was deprotected as described in example 1, step C to afford the product.

Step D: N-(1-((1R,4s)-4-(2,2,2-trifluoro-1-hydroxyethyl)cyclohexyl)azetidin-3-yl)-2-((6-(trifluoromethyl)quinazolin-4-yl)amino)acetamide

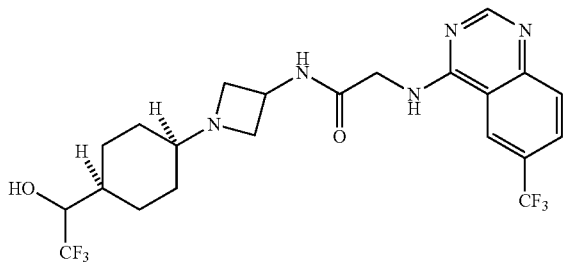 [SMILES: O=C(CNc1ncnc2ccc(C(F)(F)F)cc12)NC1CN([C@H]2CC[C@@H](C(O)C(F)(F)F)CC2)C1]

Reaction of 4-(2,2,2-trifluoro-1-hydroxyethyl)cyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{26}H_{33}F_3N_4O$: 505.19. found: 506 (M+H).

Example 35

N-(1-((1R,4s)-4-(2,2,3,3,4,4,4-heptafluoro-1-hydroxybutyl)cyclohexyl)azetidin-3-yl)-2-((6-(trifluoromethyl)quinazolin-4-yl)amino)acetamide Step A: (2,2,3,3,4,4,4-heptafluoro-1-(1,4-dioxaspiro[4.5]decan-8-yl)butoxy)trimethylsilane

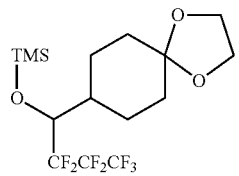

To a solution of 1,4-dioxaspiro[4.5]decane-8-carbaldehyde (350 mg, 2.06 mmol, prepared as described in Pearson, et al. in *J. Org. Chem.* 1997, 62(16), 5284-5292) cooled to 0° C. under argon was added TBAF (0.05 eq) followed by trimethyl(trifluoromethyl)silane (0.45 mL, 2.17 mmol, 0.5 M in THF) dropwise. After the complete addition, the reaction mixture was allowed to reach room temperature overnight. It was then re-cooled to −78° C. and quenched with saturated NaHCO$_3$ solution and warmed to room temperature. After extraction with ether, the organic layer was concentrated in vacuo and the residue purified by flash chromatography (silica gel, DCM) to afford the product.

Step B: 2,2,3,3,4,4,4-heptafluoro-1-(1,4-dioxaspiro[4.5]decan-8-yl)butan-1-ol

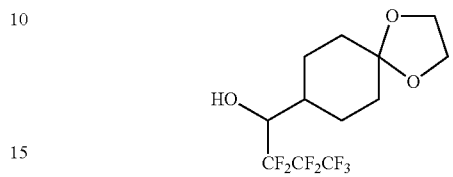

To a solution of trimethyl (2,2,3,3,4,4,4-heptafluoro-1-(1,4-dioxaspiro[4.5]decan-8-yl)butoxy)trimethylsilane (265 mg, 0.643 mmol, prepared in the previous step) in THF (10 mL) was added a TBAF (0.64 mL, 0.64 mmol, 1 M in THF) dropwise. After the complete addition, the reaction mixture was at room temperature 2 hours and then concentrated in vacuo. The residue purified by flash chromatography (silica gel, 0-100% ethyl acetate/heptane) to afford the product.

Step C: 4-(2,2,3,3,4,4,4-heptafluoro-1-hydroxybutyl)cyclohexanone

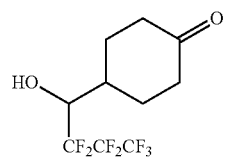

A solution of 2 2,2,3,3,4,4,4-heptafluoro-1-(1,4-dioxaspiro[4.5]decan-8-yl)butan-1-ol, prepared in the previous step, was de-protected as described in example 1, step C to afford the product.

Step D: N-(1-((1R,4s)-4-(2,2,3,3,4,4,4-heptafluoro-1-hydroxybutyl)cyclohexyl)azetidin-3-yl)-2-((6-(trifluoromethyl)quinazolin-4-yl)amino)acetamide

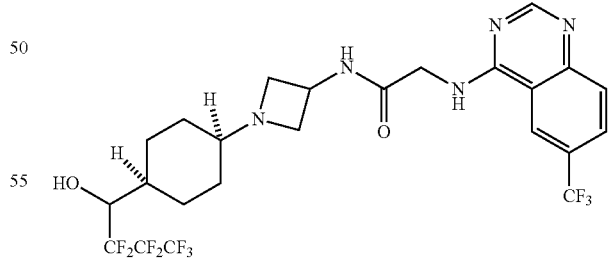

Reaction of 4-(2,2,3,3,4,4,4-heptafluoro-1-hydroxybutyl)cyclohexanone (as prepared in the previous step) with N-(azetidin-3-yl)-2-(6-(trifluoromethyl)quinazolin-4-yl) amino)acetamide (as prepared in Example 1 Step G) in the presence of TEA and NaBH(OAc)$_3$ as described in Example 1, Step H afforded the product.

ESI-MS (m/z): Calcd. For $C_{26}H_{33}F_3N_4O$: 605.18. found: 606 (M+H).

Example 36

N-(1-((1s,4s)-4-(prop-1-en-2-yl)cyclohexyl)azetidin-3-yl)-2-((6-(trifluoromethyl)quinazolin-4-yl)amino)acetamide Step A: 8-(prop-1-en-2-yl)-1,4-dioxaspiro[4.5]decane

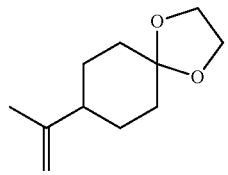

To a solution 2-(1,4-dioxaspiro[4.5]decan-8-yl)propan-2-ol (164 mg, 0.82 mmol, prepared in the Example 29, Step A) in THF (10 mL) cooled to 0° C. under argon was added Burgess Reagent (214 mg, 0.87 mmol). After the complete addition, the reaction mixture was at room temperature 1 hour and then concentrated in vacuo. The residue purified by flash chromatography (silica gel, DCM) to afford the product.

Step B: 4-(prop-1-en-2-yl)cyclohexanone

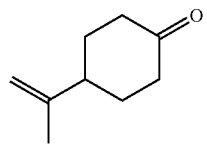

A solution of 2 8-(prop-1-en-2-yl)-1,4-dioxaspiro[4.5]decane, prepared in the previous step, was de-protected as described in example 1, step C to afford the product.

Step C: N-(1-((1s,4s)-4-(prop-1-en-2-yl)cyclohexyl)azetidin-3-yl)-2-((6-(trifluoromethyl)quinazolin-4-yl)amino)acetamide

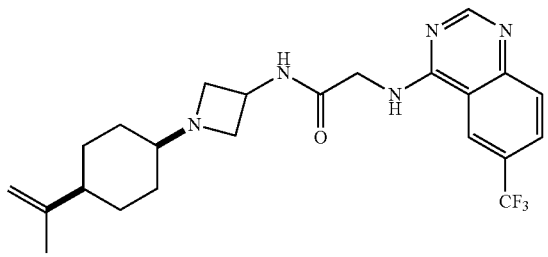 [SMILES: C=C(C)[C@H]1CC[C@@H](N2CC(NC(=O)CNc3ncnc4ccc(C(F)(F)F)cc34)C2)CC1]

Reaction of 4-(prop-1-en-2-yl)cyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{23}H_{28}F_3N_5O$: 447.22. found: 448 (M+H).

Example 37

N-(1-((1r,4r)-4-hydroxy-4-isopropylcyclohexyl)azetidin-3-yl)-2-((6-(trifluoromethyl)quinazolin-4-yl)amino)acetamide Step A: 8-isopropyl-1,4-dioxaspiro[4.5]decan-8-ol

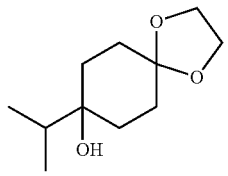

To a solution of commercially available 1,4-dioxaspiro[4.5]decan-8-one (3.00 g, 19.2 mmol, in THF (20 mL) cooled to −78° C. under argon was added a isopropylmagnesium chloride (10 mL, 20 mmol, 2 M in THF) dropwise. After the complete addition, the reaction mixture was allowed to reach room temperature overnight. It was then re-cooled to −78° C. and quenched with saturated NaHCO$_3$ solution and warmed to room temperature. After extraction with ether, the organic layer was concentrated in vacuo and the residue purified by flash chromatography (silica gel, 0-100% ether/hexanes) to afford the product.

Step B: 4-hydroxy-4-isopropylcyclohexanone

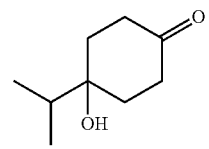

A solution of 8-isopropyl-1,4-dioxaspiro[4.5]decan-8-ol, prepared in the previous step, was de-protected as described in example 1, step C to afford the product.

Step C: N-(1-((1r,4r)-4-hydroxy-4-isopropylcyclohexyl)azetidin-3-yl)-2-((6-(trifluoromethyl)quinazolin-4-yl)amino)acetamide

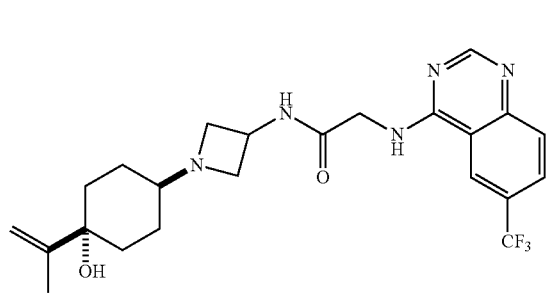 [SMILES: C=C(C)[C@]1(O)CC[C@H](N2CC(NC(=O)CNc3ncnc4ccc(C(F)(F)F)cc34)C2)CC1]

Reaction of 4-hydroxy-4-isopropylcyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)₃ as described in Example 1, Step H afforded the product.

ESI-MS (m/z): Calcd. For $C_{24}H_{31}F_3N_4O_2$: 464.24. found: 465 (M+H).

Example 38

N-(1-((1s,4s)-4-(tetrahydro-2H-pyran-4-yl)cyclohexyl)azetidin-3-yl)-2-((6-(trifluoromethyl)quinazolin-4-yl)amino)acetamide Step A: 8-(3,6-dihydro-2H-pyran-4-yl)-1,4-dioxaspiro[4.5]dec-7-ene

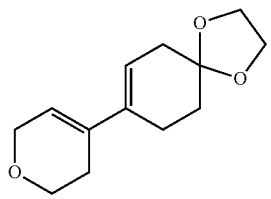 [SMILES: C1=C(C2=CCC3(CC2)OCCO3)CCOC1]

8-(4,4,5,5-Tetramethyl-[1,3,2]dioxaborolan-2-yl)-1,4-dioxa-spiro[4.5]dec-7-ene (prepared as described in PCT Int. Appl. WO2006064189, 1.57 g, 5.90 mmol), commercially available 3,6-dihydro-2H-pyran-4-yltrifluoromethane-sulfonate (5.23 mmol), and tetrakis (triphenylphosphino)palladium(0) (302 mg, 0.262 mmol) were dissolved in 1,4-dioxane (20 mL), treated with 2M aqueous Na₂CO₃ (14 mL, 28 mmol), bubbled with argon for a few minutes, and heated to 100° C. under reflux condenser for 24 h. After cooling to ambient temperature, the reaction was diluted with water (30 mL), extracted thrice with dichloromethane, aqueous layer acidified to ca. pH 7, extracted twice more with dichloromethane, and the combined organic layers washed with brine, dried over Na₂SO₄, filtered, and concentrated in vacuo to give an orange oil. This was purified by flash chromatography (silica gel, EtOAc) to give the title compound as a colorless crystalline solid.

¹H NMR (CHLOROFORM-d) δ: 5.75 (br. s., 1H), 5.68-5.73 (m, 1H), 4.26 (br. s., 2H), 4.01 (s, 3H), 3.79-3.90 (m, 2H), 2.38-2.50 (m, 3H), 2.25-2.34 (m, 2H), 1.86 (t, J=6.6 Hz, 2H).

Step B: 8-(tetrahydro-2H-pyran-4-yl)-1,4-dioxaspiro[4.5]decane

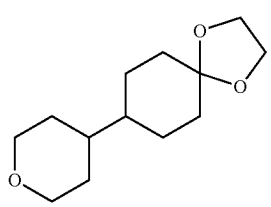 [SMILES: C1CC(C2CCC3(CC2)OCCO3)CCO1]

To a flask containing 8-(3,6-dihydro-2H-pyran-4-yl)-1,4-dioxaspiro[4.5]dec-7-ene (218 mg, 0.972 mmol), prepared in the Example 28 Step B, and Palladium on Carbon (157 mg, 0.074 mmol) was carefully added methanol (24 mL). The reaction flask was evacuated, backfilled with hydrogen via balloon and stirred at room temperature overnight. The catalyst was removed by filtration and the filtrate concentrated in vacuo to afford the product.

¹H NMR (CHLOROFORM-d) δ: 3.91-4.05 (m, 6H), 3.37 (br. s., 2H), 1.70-1.84 (m, 3H), 1.46-1.68 (m, 4H), 1.21-1.44 (m, 6H), 1.13 (br. s., 1H)

Step C: 4-(tetrahydro-2H-pyran-4-yl)cyclohexanone

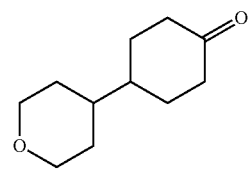 [SMILES: O=C1CCC(C2CCOCC2)CC1]

A solution of 8-(tetrahydro-2H-pyran-4-yl)-1,4-dioxaspiro[4.5]decane, prepared in the previous step, was de-protected as described in example 1, step C to afford the product.

¹H NMR (CHLOROFORM-d) δ: 4.03 (dd, J=11.6, 3.3 Hz, 2H), 3.31-3.45 (m, 2H), 2.27-2.48 (m, 3H), 2.02-2.17 (m, 2H), 1.21-1.71 (m, 8H)

Step D: N-(1-(((1r,4r)-4-hydroxy-4-isopropylcyclohexyl)azetidin-3-yl)-2-((6-(trifluoromethyl)quinazolin-4-yl)amino)acetamide

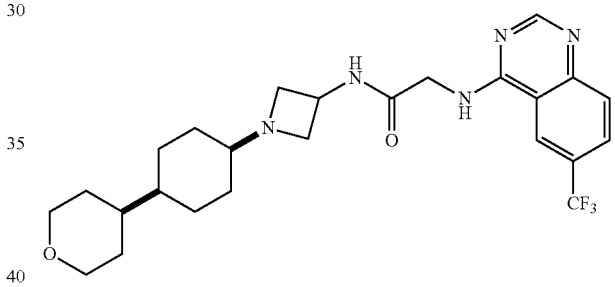

Reaction of 4-(tetrahydro-2H-pyran-4-yl)cyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)₃ as described in Example 1, Step H afforded the product.

ESI-MS (m/z): Calcd. For $C_{25}H_{32}F_3N_5O_2$: 491.25. found: 492 (M+H).

Example 39

N-(1-((1S,4s)-4-(1-methyl-5-oxopyrrolidin-2-yl)cyclohexyl)azetidin-3-yl)-2-((6-(trifluoromethyl)quinazolin-4-yl)amino)acetamide Step A: 1-methyl-5-(1,4-dioxaspiro[4.5]decan-8-yl)pyrrolidin-2-one

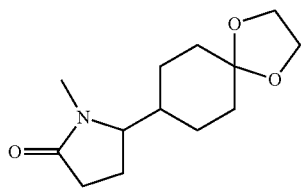 [SMILES: CN1C(=O)CCC1C1CCC2(CC1)OCCO2]

To a suspension of sodium hydride (27 mg, 1.07 mmol, 95%) in THF under argon was added 5-(1,4-dioxaspiro[4.5]decan-8-yl)pyrrolidin-2-one (135 mg, 0.60 mmol, prepared in the Example 12 Step E). After stirring 1 hour at room temperature, Methyl iodide (0.07 mL, 1.12 mmol) was added dropwise and the reaction stirred at room temperature overnight. The reaction mixture was poured onto saturated NaHCO$_3$ and extracted with ethyl acetate. The organic layer was concentrated in vacuo and the residue purified by flash chromatography (silica gel, 0-100% ethyl acetate/DCM).

Step B: 5-(4-oxocyclohexyl)pyrrolidin-2-one

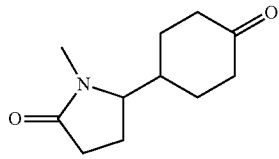

A solution of 1-methyl-5-(1,4-dioxaspiro[4.5]decan-8-yl)pyrrolidin-2-one, prepared in the previous step, was deprotected as described in example 1, step C to afford the product.

Step C: N-(1-((1S,4s)-4-(5-oxopyrrolidin-2-yl)cyclohexyl)azetidin-3-yl)-2-((6-(trifluoromethyl)quinazolin-4-yl)amino)acetamide

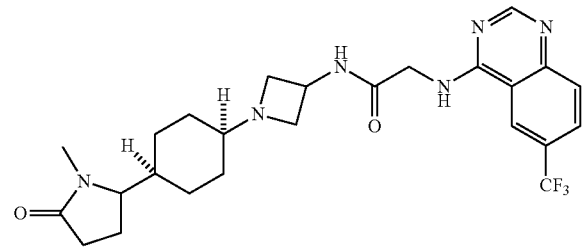 [SMILES: CN1C(=O)CCC1[C@H]1CC[C@@H](N2CC(NC(=O)CNc3ncnc4ccc(C(F)(F)F)cc34)C2)CC1]

Reaction of 4-(tetrahydro-2H-pyran-4-yl)cyclohexanone (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MeOD) δ: 8.45-8.62 (m, 2H), 7.97 (d, 1H), 7.82 (d, J=8.6 Hz, 1H), 4.40-4.56 (m, 1H), 4.27 (s, 2H), 3.46-3.73 (m, 3H), 3.31 (br. s., 1H), 2.84-2.95 (m, 2H), 2.77 (s, 3H), 2.23-2.47 (m, 3H), 1.90-2.07 (m, 2H), 1.74 (br. s., 3H), 1.19-1.54 (m, 5H), 0.99-1.14 (m, 1H)ESI-MS (m/z): Calcd. For C$_{25}$H$_{31}$F$_3$N$_6$O$_2$: 504.25. found: 505 (M+H).

Example 40

N-(1-(4-(2-oxopyrrolidin-1-yl)cyclohexyl)azetidin-3-yl)-2-((6-(trifluoromethyl)quinazolin-4-yl)amino)acetamide

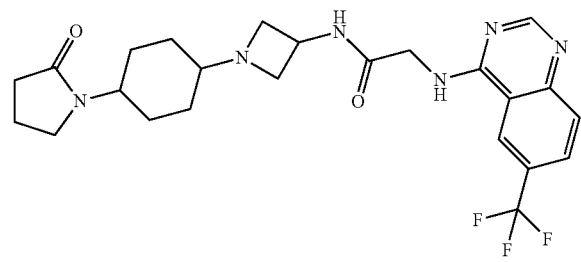 [SMILES: O=C(CNc1ncnc2ccc(C(F)(F)F)cc12)NC1CN(C2CCC(N3CCCC3=O)CC2)C1]

Step A: 1,4-dioxaspiro[4.5]decan-8-yl methanesulfonate

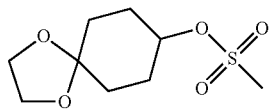

1,4-dioxaspiro[4.5]decan-8-ol (1 g, 6.32 mmol) and triethylamine (1.3 mL, 9.48 mmol) taken in anhydrous THF and treated with methanesulfonyl chloride (0.73 mL, 9.48 mmol). Stirred for 18 h. Diluted with water and extracted with EtOAc. The ethyl acetate layer washed with sat NaCl, dried over Na$_2$SO$_4$ and evaporated to give the expected product. Used without further purification.

Step B: 1-(1,4-dioxaspiro[4.5]decan-8-yOpyrrolidin-2-one

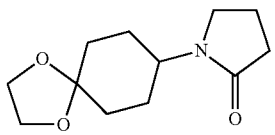 [SMILES: O=C1CCCN1C1CCC2(CC1)OCCO2]

Pyrrolidin-2-one (720 mg, 8.46 mmol) in DMF (5 mL) was treated with NaH (203 mg, 8.46 mmol) at room temperature. The mixture allowed to stir for 30 min. 1,4-dioxaspiro[4.5]decan-8-yl methanesulfonate (500 mg, 2.12 mmol) from above step A, in DMF (3 mL) was added to the mixture and stirred at 130° C. for 3 h. The mixture was cooled to room temperature, quenched with NH$_4$Cl, and extracted into EtOAc. Washed the EtOAc layer with saturated NaCl, dried over Na$_2$SO$_4$ and evaporated. Purified by silica prep TLC to give 55 mg (11.5%) of 1-(1,4-dioxaspiro[4.5]decan-8-yl)pyrrolidin-2-one.

Step C: 1-(4-oxocyclohexyl)pyrrolidin-2-one

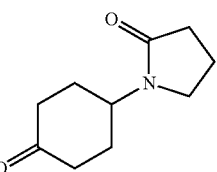

1-(1,4-dioxaspiro[4.5]decan-8-yl)pyrrolidin-2-one (143 mg, 0.64 mmol) from above step B, was dissolved in acetonitrile, treated with 6N HCl, and stirred at room temperature for 18 h. reaction mixture was concentrated in vacuo, treated with saturated NaHCO$_3$ to pH 6. The solvents were removed under vacuum and the residue treated with saturated NaCl (2 mL) and extracted with 4:1 EtOAc/iPrOH (x4). The organic fractions were combined, filtered and evaporated to give 115 mg of 1-(4-oxocyclohexyl)pyrrolidin-2-one.

Step C: N-(1-(4-(2-oxopyrrolidin-1-yl)cyclohexyl)azetidin-3-yl)-2-((6-(trifluoromethyl)quinazolin-4-yl)amino)acetamide N-(azetidin-3-yl)-2-((6-(trifluoromethyl)quinazolin-4-yl)amino)acetamide TFA salt (100 mg, 0.22 mmol) from example 1, step G, and 1-(4-oxocyclohexyl)pyrrolidin-2-one (40.5 mg, 0.22 mmol) from above step B, Sodium triacetoxyborohydride (138 mg, 0.64 mmol), were taken in acetonitrile and stirred for 24 h at room temperature. The mixture was treated with MeOH and concentrated under vacuum. The residue was purified by preparative TLC (nBuOH/aq NH4OH 4:1) and reverse phase HPLC to give the title compound as a white solid. ESI-MS (m/z): Calcd. for $C_{24}H_{29}F_3N_6O_2$: 490.23. found: 491.23 (M+1).

Example 41

N-(1-((1s,4s)-4-acetamidocyclohexyl)azetidin-3-yl)-2-((6-(trifluoromethyl)quinazolin-4-yl)amino)acetamide

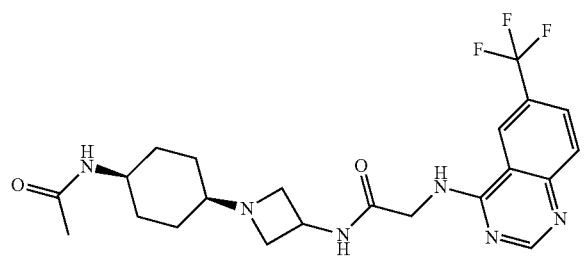 [SMILES: CC(=O)N[C@H]1CC[C@@H](N2CC(NC(=O)CNc3ncnc4ccc(C(F)(F)F)cc34)C2)CC1]

N-(azetidin-3-yl)-2-((6-(trifluoromethyl)quinazolin-4-yl)amino)acetamide (100 mg, 0.31 mmol), from example 1, step G, and N-(4-oxocyclohexyl)acetamide (47.45 mg, 0.31 mmol, TCI AMERICA Fine Chemical), Sodium triacetoxyborohydride (189 mg, 0.89 mmol), were taken in acetonitrile and stirred for 18 h at room temperature. The mixture was treated with MeOH and concentrated under vacuum. The residue was purified by preparative TLC (nBuOH/aq NH4OH 4:1) and reverse phase HPLC (0% to 30% CH3CN over 25 min) to give the title compound as a white solid. ESI-MS (m/z): Calcd. for C22H27F3N6O2: 464.21. found: 465.21 (M+1).

Example 42 benzyl methyl((1s,4s)-4-(3-(2-((6-(trifluoromethybquinazolin-4-yl)amino)acetamido)azetidin-1-yl)cyclohexyl)carbamate

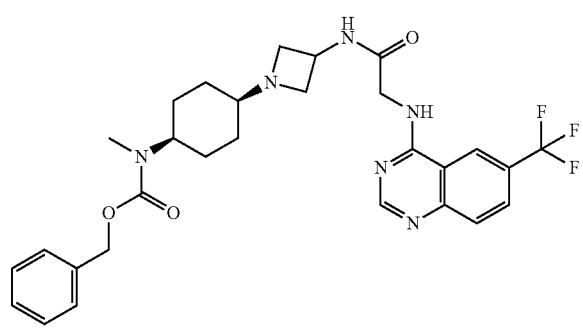 [SMILES: CN(C(=O)OCc1ccccc1)[C@H]1CC[C@@H](N2CC(NC(=O)CNc3ncnc4ccc(C(F)(F)F)cc34)C2)CC1]

Step A: benzyl methyl(4-oxocyclohexyl)carbamate

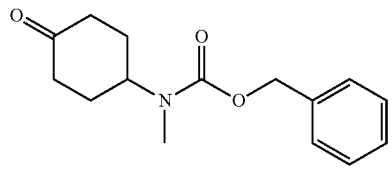 [SMILES: CN(C(=O)OCc1ccccc1)C1CCC(=O)CC1]

Benzyl (4-oxocyclohexyl)carbamate (500 mg, 2.0 mmol) in DMF was treated with lithium hexamethyldisilazid (2.0 mmol) at room temperature. This solution was stirred for 30 min and was then treated with iodomethane (0.25 mL, 4.0 mmol) and stirred for 18 h. DMF was removed under vacuum and the residue was purified by silica column chromatography to give the title compound.

Step B: benzyl methyl((1s,4s)-4-(3-(2-((6-(trifluoromethyl)quinazolin-4-yl)amino)acetamido)azetidin-1-yl)cyclohexyl)carbamate N-(azetidin-3-yl)-2-((6-(trifluoromethyl)quinazolin-4-yl)amino)acetamide 2.7 TFA salt (350 mg, 0.55 mmol), from example 1, step G, and N-(4-oxocyclohexyl)acetamide (143.0 mg, 0.55 mmol) from step A, sodium triacetoxyborohydride (337 mg, 1.59 mmol) and TEA (0.21 mL, 1.5 mmol), were taken in acetonitrile and stirred for 18 h at room temperature. The mixture concentrated under vacuum and the residue basified with NaHCO3, saturated with solid NaCl and extracted with EtOAc/iPrOH (4:1) four times. Organic layer separated, dried over Na2SO4 and evaporated. The residue was purified by silica prep TLC. silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C29H33F3N6O3: 570.26. found: 571.26 (M+1).

Example 43

N-methyl-N-((1s,4s)-4-(3-(2-((6-(trifluoromethyl)quinazolin-4-yl)amino)acetamido)azetidin-1-yl)cyclohexybisobutyramide

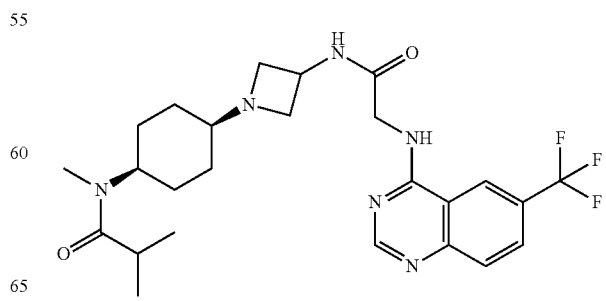

Step A: N-(1-((1s,4s)-4-(methylamino)cyclohexyl)azetidin-3-yl)-2-((6-(trifluoromethyl)quinazolin-4-yl)amino)acetamide

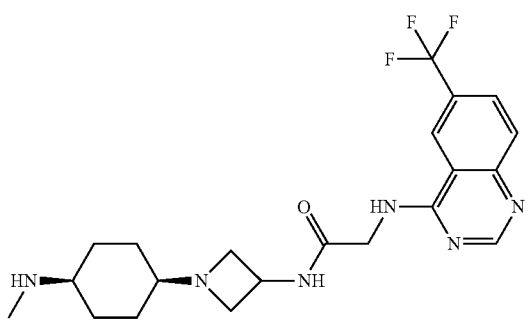 [SMILES: CN[C@H]1CC[C@@H](N2CC(NC(=O)CNc3ncnc4ccc(C(F)(F)F)cc34)C2)CC1]

Benzyl methyl((1s,4s)-4-(3-(2-((6-(trifluoromethyl)quinazolin-4-yl)amino)acetamido)azetidin-1-yl)cyclohexyl)carbamate (126 mg, 0.22 mmol) from example 3, step B was dissolved in MeOH and treated with 5% Pd/C (220 mg). This solution was stirred in a H₂ atmosphere (H2 balloon) for 18 h. Catalyst was removed by filtration and solvent removed under vacuum to give the title compound as an oil.

Step B: N-methyl-N-((1s,4s)-4-(3-(2-((6-(trifluoromethyl)quinazolin-4-yl)amino)acetamido)azetidin-1-yl)cyclohexylfisobutyramide A solution of N-(1-((1s,4s)-4-(methylamino)cyclohexyl)azetidin-3-yl)-2-((6-(trifluoromethyl)quinazolin-4-yl)amino)acetamide (19 mg, 0.04 mmol) from above step A in THF is treated with TEA (18 µL, 0.13 mmol) and cooled to −10° C. To this solution isobutyryl chloride (9.3 mg, 0.09 mmol) was added and the mixture was allowed to warm to room temperature and stirred for 5 h. The reaction mixture was diluted with saturated NaHCO₃ and extracted with EtOAc. The ethyl acetate layer was washed with saturated NaCl, dried over Na₂SO₄ and evaporated. The residue was purified by silica prep TLC to give the title compound.
ESI-MS (m/z): Calcd. for C25H33F3N6O2: 506.26. found: 507.26 (M+1).

Example 44

N-methyl-N-((1s,4s)-4-(3-(2-((6-(trifluoromethyl)quinazolin-4-yl)amino)acetamido)azetidin-1-yl)cyclohexybacetamide

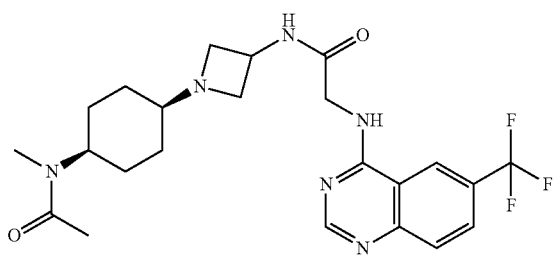 [SMILES: CC(=O)N(C)[C@H]1CC[C@@H](N2CC(NC(=O)CNc3ncnc4ccc(C(F)(F)F)cc34)C2)CC1]

A solution of N-(1-((1s,4s)-4-(methylamino)cyclohexyl)azetidin-3-yl)-2-((6-(trifluoromethyl)quinazolin-4-yl)amino)acetamide (19 mg, 0.04 mmol) from example 4, step A and acetic anhydride (8.3 µL, 0.09 mmol) was added and the mixture was allowed to warm to room temperature and stirred for 5h. The reaction mixture was diluted with saturated NaHCO₃ and extracted with EtOAc. The ethyl acetate layer was washed with saturated NaCl, dried over Na₂SO₄ and evaporated. The residue was purified by silica prep TLC to give the title compound.
ESI-MS (m/z): Calcd. for C23H29F3N6O2: 478.23. found: 479.23 (M+1).

Example 45

N-Methyl-N-((1s,4s)-4-(3-(2-((6-(trifluoromethyl)quinazolin-4-yl)amino)acetamido)azetidin-1-yl)cyclohexyl)propionamide

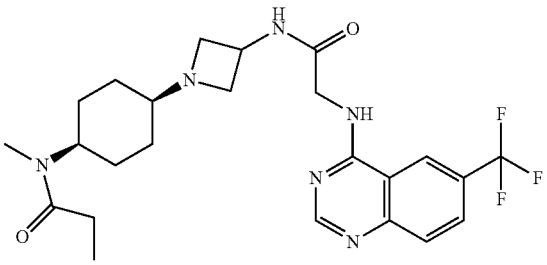 [SMILES: CCC(=O)N(C)[C@H]1CC[C@@H](N2CC(NC(=O)CNc3ncnc4ccc(C(F)(F)F)cc34)C2)CC1]

A solution of N-(1-((1s,4s)-4-(methylamino)cyclohexyl)azetidin-3-yl)-2-((6-(trifluoromethyl)quinazolin-4-yl)amino)acetamide (19 mg, 0.04 mmol) from example 4, step A in THF is treated with TEA (18 µL, 0.13 mmol) and cooled to −10° C. To this solution propyl chloride (8.8 µL, 0.1 mmol) was added and the mixture was allowed to warm to room temperature and stirred for 5h. The reaction mixture was diluted with saturated NaHCO₃ and extracted with EtOAc. The ethyl acetate layer was washed with saturated NaCl, dried over Na₂SO₄ and evaporated. The residue was purified by silica prep TLC to give the title compound.
ESI-MS (m/z): Calcd. for C24H31F3N6O2: 492.25. found: 493.25 (M+1).

Example 46

N-methyl-N-((1s,4s)-4-(3-(2-((6-(trifluoromethyl)quinazolin-4-yl)amino)acetamido)azetidin-1-yl)cyclohexyl)butyramide

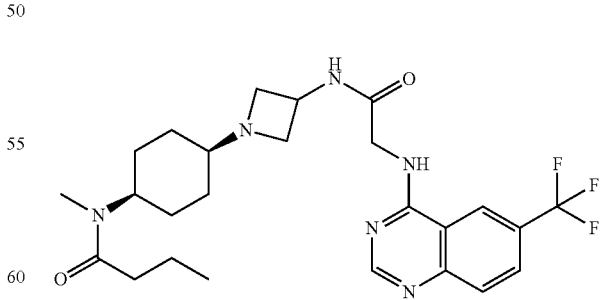

A solution of N-(1-((1s,4s)-4-(methylamino)cyclohexyl)azetidin-3-yl)-2-((6-(trifluoromethyl)quinazolin-4-yl)amino)acetamide (19 mg, 0.04 mmol) from example 4, step A in THF is treated with TEA (18 µL, 0.13 mmol) and cooled to −10° C. To this solution butyryl chloride (9 µL, 0.1 mmol) was added and the mixture was allowed to warm to room temperature and stirred for 5 h. The reaction mixture was diluted with saturated NaHCO₃ and extracted with EtOAc. The ethyl acetate layer was washed with saturated NaCl, dried over Na₂SO₄ and evaporated. The residue was purified by silica prep TLC to give the title compound. ESI-MS (m/z): Calcd. for C25H33F3N6O2: 506.26. found: 507.26 (M+1).

Example 47

Benzyl ethyl((1s,4s)-4-(3-(2-((6-(trifluoromethyl)quinazolin-4-yl)amino)acetamido)azetidin-1-yl)cyclohexyl)carbamate

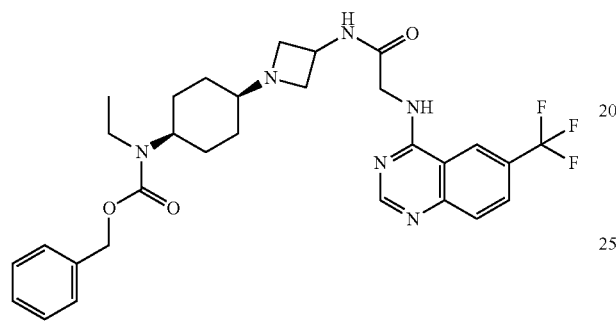

Step A: N-ethyl-1,4-dioxaspiro[4.5]decan-8-amine

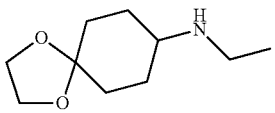

1,4-dioxaspiro[4.5]decan-8-one (2 g, 12.8 mmol), and ethylamine (6.4 mL, 12.8 mmol), and sodium triacetoxyborohydride (8 g, 38 mmol) were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated to give the title compound.

Step B: Benzyl ethyl(1,4-dioxaspiro[4.5]decan-8-yl)carbamate

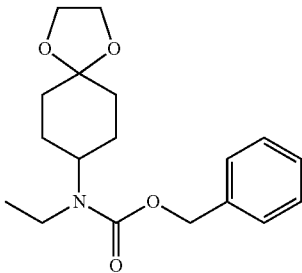 [SMILES: CCN(C(=O)OCc1ccccc1)C1CCC2(CC1)OCCO2]

A solution of N-ethyl-1,4-dioxaspiro[4.5]decan-8-amine (1.8 g, 9.9 mmol) from above step a in THF is treated with TEA (1.4, 9.9 mmol) and benzyloxycarbonyl chloride (1.4 mL, 9.9 mmol). The mixture was stirred for 18 h at room temperature. THF was removed under vacuum and the residue was taken EtOAc and washed with 10% citric acid, saturated NaHCO₃, and saturated NaCl. The solution was dried over Na₂SO₄ and evaporated under vacuum. The residue was purified by silica column chromatography to give the title compound.

Step C: Benzyl ethyl(4-oxocyclohexyl)carbamate

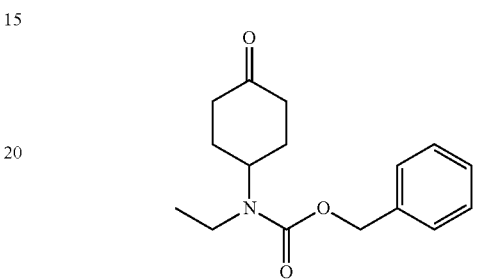

Benzyl ethyl(1,4-dioxaspiro[4.5]decan-8-yl)carbamate (350 mg, 1.1 mmol) was dissolved in acetonitrile, treated with 6N HCl, and stirred at room temperature for 18 h. reaction mixture was concentrated in vacuo, treated with saturated NaHCO₃ to pH 6. The solvents were removed under vacuum and the residue treated with saturated NaCl (2 mL) and extracted with 4:1 EtOAc/iPrOH (x4). The organic fractions were combined, filtered and evaporated to give the title compound.

Step D: benzyl ethyl((1s,4s)-4-(3-(2-((6-(trifluoromethyl)quinazolin-4-yl)amino)acetamido)azetidin-1-yl)cyclohexyl)carbamate N-(azetidin-3-yl)-2-((6-(trifluoromethyl)quinazolin-4-yl)amino)acetamide 2.7 TFA salt (350 mg, 0.55 mmol), from example 1, step G, and benzyl ethyl(4-oxocyclohexyl)carbamate (150.9 mg, 0.55 mmol) from step C, sodium triacetoxyborohydride (337 mg, 1.59 mmol) and TEA (0.21 mL, 1.5 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C30H35F3N6O3: 584.27. found: 585.27 (M+1).

Example 48 benzyl propyl((1s,4s)-4-(3-(2-((6-(trifluoromethyl) quinazolin-4-yl)amino)acetamido)azetidin-1-yl)cyclohexyl)carbamate

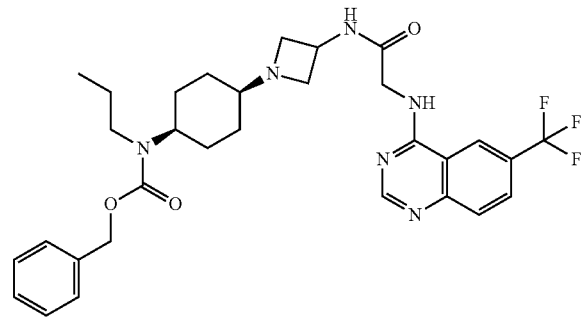 [SMILES: CCCN(C(=O)OCc1ccccc1)[C@H]1CC[C@@H](N2CC(NC(=O)CNc3ncnc4ccc(C(F)(F)F)cc34)C2)CC1]

Step A: N-propyl-1,4-dioxaspiro[4.5]decan-8-amine

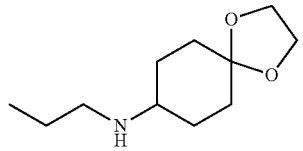

1,4-dioxaspiro[4.5]decan-8-one (2 g, 12.8 mmol), and propylamine (1.05 mL, 12.8 mmol), and sodium triacetoxyborohydride (8 g, 38 mmol) were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated to give the title compound.

Step B: Benzyl propyl(1,4-dioxaspiro[4.5]decan-8-yl)carbamate

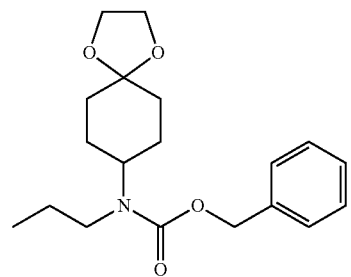 [SMILES: CCCN(C(=O)OCc1ccccc1)C1CCC2(CC1)OCCO2]

A solution of N-propyl-1,4-dioxaspiro[4.5]decan-8-amine (2.97 g, 14.9 mmol) from above step A in THF is treated with TEA (2.1, 14.9 mmol) and benzyloxycarbonyl chloride (2.1 mL, 14.9 mmol). The mixture was stirred for 18 h at room temperature. THF was removed under vacuum and the residue was taken EtOAc and washed with 10% citric acid, saturated NaHCO₃, and saturated NaCl. The solution was dried over Na₂SO₄ and evaporated under vacuum. The residue was purified by silica column chromatography to give the title compound.

Step C: Benzyl (4-oxocyclohexyl) (propyl)carbamate

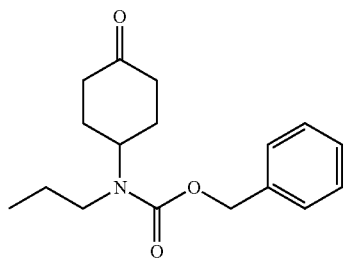 [SMILES: CCCN(C(=O)OCc1ccccc1)C1CCC(=O)CC1]

Benzyl propyl(1,4-dioxaspiro[4.5]decan-8-yl)carbamate (350 mg, 1.1 mmol) was dissolved in acetonitrile, treated with 6N HCl, and stirred at room temperature for 18 h. reaction mixture was concentrated in vacuo, treated with saturated NaHCO₃ to pH 6. The solvents were removed under vacuum and the residue treated with saturated NaCl (2 mL) and extracted with 4:1 EtOAc/iPrOH (x4). The organic fractions were combined, filtered and evaporated to give the title compound.

Step D: benzyl propyl((1s,4s)-4-(3-(2-((6-(trifluoromethyl)quinazolin-4-yl)amino)acetamido)azetidin-1-yl)cyclohexyl)carbamate N-(azetidin-3-yl)-2-((6-(trifluoromethyl)quinazolin-4-yl) amino)acetamide 2.7 TFA salt (350 mg, 0.55 mmol), from example 1, step G, and benzyl (4-oxocyclohexyl)(propyl) carbamate (158.5 mg, 0.55 mmol) from step C, sodium triacetoxyborohydride (337 mg, 1.59 mmol) and TEA (0.21 mL, 1.5 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C31H37F3N6O3: 598.29. found: 599.29 (M+1).

Example 49

N-(1-((1s,4s)-4-(N-methylmethylsulfonamido)cyclohexyl)azetidin-3-yl)-2-((6-(trifluoromethyl)quinazolin-4-yl)amino)acetamide

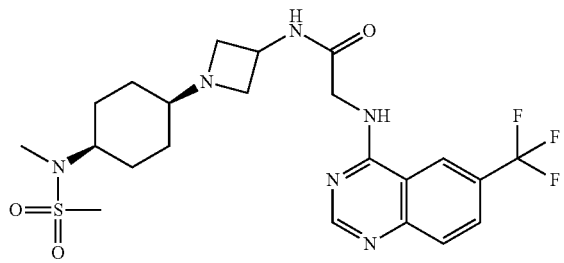 [SMILES: CN([C@H]1CC[C@@H](N2CC(NC(=O)CNc3ncnc4ccc(C(F)(F)F)cc34)C2)CC1)S(C)(=O)=O]

A solution of N-(1-((1s,4s)-4-(methylamino)cyclohexyl)azetidin-3-yl)-2-((6-(trifluoromethyl)quinazolin-4-yl)amino)acetamide (19 mg, 0.04 mmol) from example 4, step A in THF was treated with TEA (18 μL, 0.13 mmol) and cooled to −10° C. To this solution methanesulfonyl chloride (6.3 μL, 0.08 mmol) was added and the mixture was allowed to warm to room temperature and stirred for 5 h. The reaction mixture was diluted with saturated NaHCO$_3$ and extracted with EtOAc. The ethyl acetate layer was washed with saturated NaCl, dried over Na$_2$SO$_4$ and evaporated. The residue was purified by silica prep TLC to give the title compound. ESI-MS (m/z): Calcd. for C22H29F3N6O3S: 514.20. found: 515.20 (M+1).

Example 50

N-ethyl-N-((1s,4s)-4-(3-(2-((6-(trifluoromethyl)quinazolin-4-yl)amino)acetamido)azetidin-1-yl)cyclohexyl)acetamide

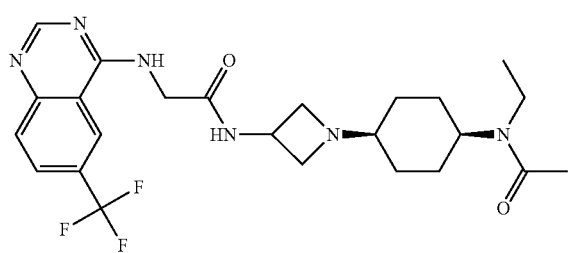 [SMILES: CCN(C(C)=O)[C@H]1CC[C@@H](N2CC(NC(=O)CNc3ncnc4ccc(C(F)(F)F)cc34)C2)CC1]

A solution of N-(1-((1s,4s)-4-(ethylamino)cyclohexyl)azetidin-3-yl)-2-((6-(trifluoromethyl)quinazolin-4-yl)amino)acetamide (32 mg, 0.07 mmol) in THF was treated with pyridine (11.4 μL, 0.14 mmol) and cooled to −10° C. To this solution acetic anhydride (13.4 μL, 0.14 mmol) was added and the mixture was allowed to warm to room temperature and stirred for 5h. The reaction mixture was diluted with saturated NaHCO$_3$ and extracted with EtOAc. The ethyl acetate layer was washed with saturated NaCl, dried over Na$_2$SO$_4$ and evaporated. The residue was purified by silica prep TLC to give the title compound. ESI-MS (m/z): Calcd. for C24H31F3N6O2: 492.25. found: 493.25 (M+1).

Example 51

N-(1-((1s,4s)-4-(N-propylformamido)cyclohexyl)azetidin-3-yl)-2-((6-(trifluoromethyl)quinazolin-4-yl)amino)acetamide

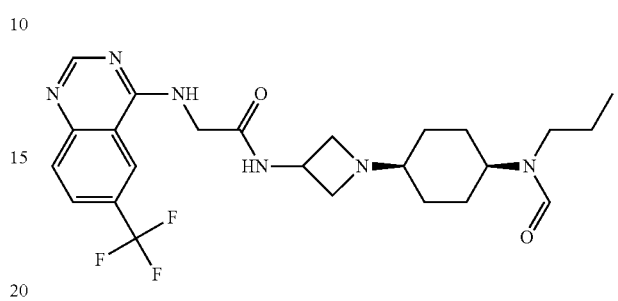

To a solution of acetic anhydride (30.5 μL, 0.32 mmol) in DCM was added formic acid (12.3 μL,). 32 mmol) and pyridine (26 μL, 0.32 mmol). This solution was stirred at room temperature for 1 h. To this a DCM solution of N-(1-((1s,4s)-4-(propylamino)cyclohexyl)azetidin-3-yl)-2-((6-(trifluoromethyl)quinazolin-4-yl)amino)acetamide (30 mg, 0.06 mmol) and TEA (36 μL, 0.26 mmol) was added and the resulting solution was stirred at room temperature for 18 h. The reaction mixture was diluted with DCM and washed with saturated NaHCO3, saturated NaCl and dried over Na$_2$SO$_4$. DCM was removed under vacuum and the residue was purified by preparative TLC to give the title compound. ESI-MS (m/z): Calcd. for C24H31F3N6O2: 492.25. found: 493.25 (M+1).

Example 52

N-(1-((1s,4s)-4-(1,2-oxazinan-2-yl)cyclohexyl)azetidin-3-yl)-2-((6-(trifluoromethyl)quinazolin-4-yl)amino)acetamide

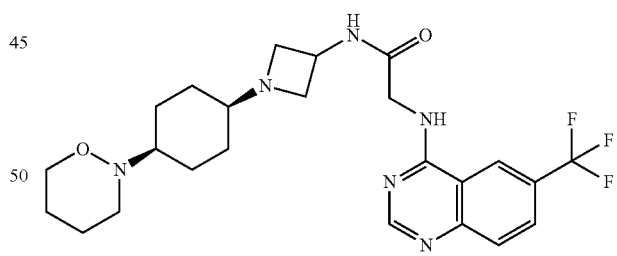

Step A:
2-(1,4-dioxaspiro[4.5]decan-8-yl)-1,2-oxazinane

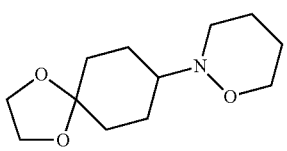 [SMILES: C1CCN(C2CCC3(CC2)OCCO3)OC1]

1,4-dioxaspiro[4.5]decan-8-one (358.5 mg, 2.3 mmol), and 1,2-oxazinane (200 mg, 2.3 mmol), and sodium triacetoxyborohydride (1.46 g, 6.9 mmol) were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. Residue purified by silica column chromatography to give the title compound.

Step B: 4-(1,2-oxazinan-2-yl)cyclohexanone

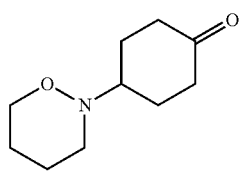 [SMILES: O=C1CCC(N2CCCCO2)CC1]

2-(1,4-dioxaspiro[4.5]decan-8-yl)-1,2-oxazinane (350 mg, 1.54 mmol) from above step A, was dissolved in acetonitrile, treated with 6N HCl, and stirred at room temperature for 18 h. reaction mixture was concentrated in vacuo, treated with saturated NaHCO₃ to pH 6. The solvents were removed under vacuum and the residue treated with saturated NaCl (2 mL) and extracted with 4:1 EtOAc/iPrOH (x4). The organic fractions were combined, filtered and evaporated to give the title compound.

Step C: benzyl ethyl((1s,4s)-4-(3-(2-((6-(trifluoromethyl)quinazolin-4-yl)amino)acetamido)azetidin-1-yl)cyclohexyl)carbamate N-(azetidin-3-yl)-2-((6-(trifluoromethyl)quinazolin-4-yl)amino)acetamide 2.0 TFA salt (100 mg, 0.18 mmol), from example 1, step G, and 4-(1,2-oxazinan-2-yl)cyclohexanone (33 mg, 0.18 mmol) from step B, sodium triacetoxyborohydride (111 mg, 0.52 mmol) and TEA (50 μL, 0.36 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C24H31F3N6O2: 492.25. found: 493.25 (M+1).

¹H NMR (MeOD) δ: 8.18 (s, 1H), 8.00 (s, 1H), 7.37-7.54 (m, 2H), 4.03-4.15 (m, 1H), 3.86 (s, 2H), 3.49 (t, J=4.6 Hz, 2H), 3.15 (t, J=7.8 Hz, 2H), 2.68 (dd, J=8.3, 4.9 Hz, 2H), 2.11 (t, J=6.4 Hz, 1H), 1.76-1.90 (m, 1H), 1.43 (br. s., 1H), 1.35 (quin, J=5.7 Hz, 3H), 0.95-1.20 (m, 9H)

Example 53

N-(1-((1s,4s)-4-(isoxazolidin-2-yl)cyclohexyl)azetidin-3-yl)-2-((6-(trifluoromethyl)quinazolin-4-yl)amino)acetamide

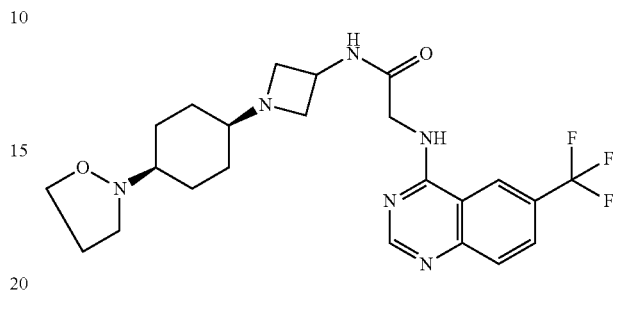

Step A:
2-(1,4-dioxaspiro[4.5]decan-8-yl)isoxazolidine

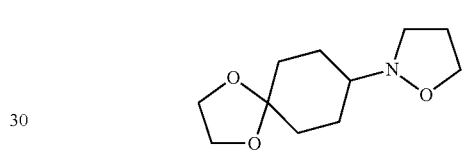

1,4-dioxaspiro[4.5]decan-8-one (358.5 mg, 2.3 mmol), and isoxazolidine (168 mg, 2.3 mmol), and sodium triacetoxyborohydride (1.46 g, 6.9 mmol) were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. Residue purified by silica column chromatography to give the title compound.

Step B: 4-(isoxazolidin-2-yl)cyclohexanone

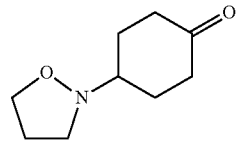 [SMILES: O=C1CCC(N2CCCO2)CC1]

2-(1,4-dioxaspiro[4.5]decan-8-yl)isoxazolidine (350 mg, 1.64 mmol) from above step A, was dissolved in acetonitrile, treated with 6N HCl, and stirred at room temperature for 18 h. reaction mixture was concentrated in vacuo, treated with saturated NaHCO₃ to pH 6. The solvents were removed under vacuum and the residue treated with saturated NaCl (2 mL) and extracted with 4:1 EtOAc/iPrOH (x4). The organic fractions were combined, filtered and evaporated to give the title compound.

Step C: N-(1-0 s,4s)-4-(isoxazolidin-2-yl)cyclohexyl)azetidin-3-yl)-2-((6-(trifluoromethyl)-quinazolin-4-yl)amino)acetamide N-(azetidin-3-yl)-2-((6-(trifluoromethyl)quinazolin-4-yl)amino)acetamide 2.0 TFA salt (100 mg, 0.18 mmol), from example 1, step G, and 4-(isoxazolidin-2-yl)cyclohexanone (111 mg, 0.52 mmol) from step B, sodium triacetoxyborohydride (111 mg, 0.52 mmol) and TEA (50 µL, 0.36 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C23H29F3N6O2: 478.23. found: 479.23 (M+1).

Example 54

N-(1-((1s,4s)-4-((2-oxopiperidin-1-yl)methyl)cyclohexyl)azetidin-3-yl)-2-((6-(trifluoromethyl)quinazolin-4-yl)amino)acetamide

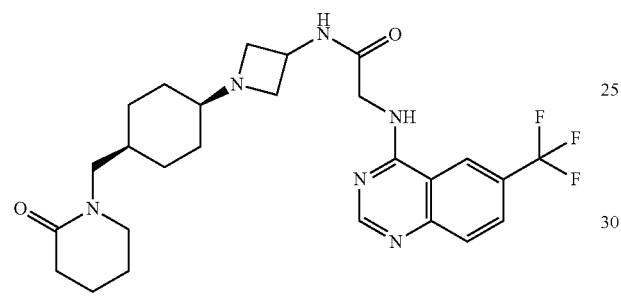

N-(azetidin-3-yl)-2-((6-(trifluoromethyl)quinazolin-4-yl)amino)acetamide 2.0 TFA salt (80 mg, 0.15 mmol), from example 1, step G, and 1-((4-oxocyclohexyl)methyl)piperidin-2-one (30.3 mg, 0.15 mmol), sodium triacetoxyborohydride (88.8 mg, 0.42 mmol) and TEA (40 µL, 0.29 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C26H33F3N6O2: 518.26. found: 519.26 (M+1).

Example 55

N-(1-((1s,4s)-4-(2-oxopyridin-1-(2H)-yl)cyclohexyl)azetidin-3-yl)-2-((6-(trifluoromethyl)quinazolin-4-yl)amino)acetamide

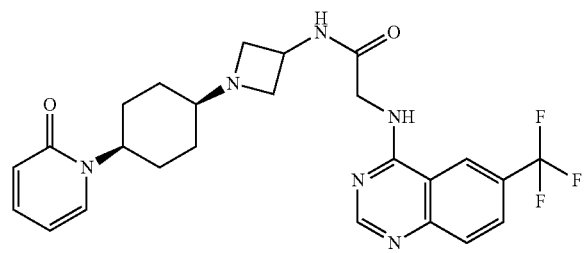 [SMILES: O=C(CNc1ncnc2ccc(C(F)(F)F)cc12)NC1CN([C@H]2CC[C@@H](n3ccccc3=O)CC2)C1]

Step A:
1-(1,4-dioxaspiro[4.5]decan-8-yl)pyridin-2(1H)-one

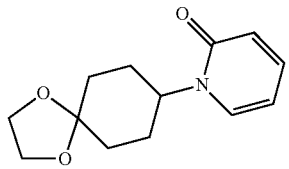 [SMILES: O=c1ccccn1C1CCC2(CC1)OCCO2]

A solution of 4-dioxaspiro[4.5]decan-8-yl methanesulfonate (497 mg, 2 mmol) from example 1, step A and pyridin-2(1H)-one (200 mg, 2 mmol) in DMF was treated with Cs₂CO₃ (1 g, 3 mmol) and heated at 80° C. for 18 h. DMF was removed under vacuum and the residue was purified by silica column chromatography to give the title compound.

Step B: 1-(4-oxocyclohexyl)pyridin-2(1H)-one

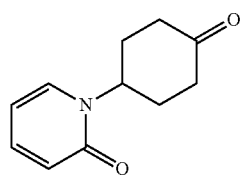 [SMILES: O=C1CCC(n2ccccc2=O)CC1]

1-(1,4-dioxaspiro[4.5]decan-8-yl)pyridin-2(1H)-one (150 mg, 0.64 mmol) from above step A, was dissolved in acetonitrile, treated with 6N HCl, and stirred at room temperature for 18 h. reaction mixture was concentrated in vacuo, treated with saturated NaHCO₃ to pH 6. The solvents were removed under vacuum and the residue treated with saturated NaCl (2 mL) and extracted with 4:1 EtOAc/iPrOH (x4). The organic fractions were combined, filtered and evaporated to give the title compound.

Step C: N-(1-((1s,4s)-4-(2-oxopyridin-1(2H)-yl)cyclohexyl)azetidin-3-yl)-2-((6-(trifluoromethyl)quinazolin-4-yl)amino)acetamide N-(azetidin-3-yl)-2-((6-(trifluoromethyl)quinazolin-4-yl)amino)acetamide 2.0 TFA salt (100 mg, 0.18 mmol), from example 1, step G, and 1-(4-oxocyclohexyl)pyridin-2(1H)-one (34.6 mg, 0.18 mmol) from step B, sodium triacetoxyborohydride (111 mg, 0.52 mmol) and TEA (50 µL, 0.36 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C25H27F3N6O2: 500.21. found: 501.21 (M+1).

¹H NMR (MeOH) δ: 8.62 (s, 1H), 8.56 (s, 1H), 8.03 (dd, J=8.8, 2.0 Hz, 1H), 7.88 (d, J=8.8 Hz, 1H), 7.79 (dd, J=7.1, 1.7 Hz, 1H), 7.47 (ddd, J=8.9, 6.7, 2.0 Hz, 1H), 6.53 (d, J=8.3 Hz, 1H), 6.43 (td, J=6.8, 1.3 Hz, 1H), 4.85 (t, J=3.5 Hz, 1H), 4.53 (t, J=7.2 Hz, 1H), 4.29 (s, 2H), 3.71-3.80 (m, 2H), 3.00 (t, J=7.7 Hz, 2H), 2.48 (br. s., 1H), 1.83-1.95 (m, 4H), 1.52-1.67 (m, 4H)

Example 56

N-(1-((1s,4s)-4-(2-oxopiperidin-1-yl)cyclohexyl)azetidin-3-yl)-2-((6-(trifluoromethyl)quinazolin-4-yl)amino)acetamide

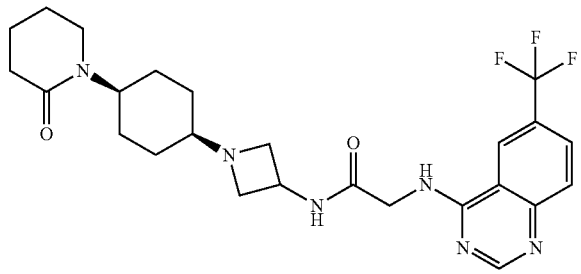 [SMILES: O=C(CNc1ncnc2ccc(C(F)(F)F)cc12)NC1CN([C@H]2CC[C@@H](N3CCCCC3=O)CC2)C1]

N-(azetidin-3-yl)-2-((6-(trifluoromethyl)quinazolin-4-yl)amino)acetamide 2.0 TFA salt (100 mg, 0.18 mmol), from example 1, step G, and 1-(4-oxocyclohexyl)piperidin-2-one (35 mg, 0.18 mmol), sodium triacetoxyborohydride (111 mg, 0.52 mmol) and TEA (50 µL, 0.36 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C25H31F3N6O2: 504.25. found: 505.25 (M+1).

Example 57

N-(1-((1s,4s)-4-(2,5-dioxopyrrolidin-1-yl)cyclohexyl)azetidin-3-yl)-2-((6-(trifluoromethyl)quinazolin-4-yl)amino)acetamide

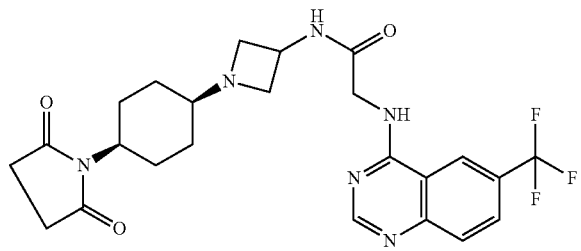 [SMILES: O=C(CNc1ncnc2ccc(C(F)(F)F)cc12)NC1CN([C@H]2CC[C@@H](N3C(=O)CCC3=O)CC2)C1]

Step A: 1-(1,4-dioxaspiro[4.5]decan-8-yl)pyrrolidine-2,5-dione

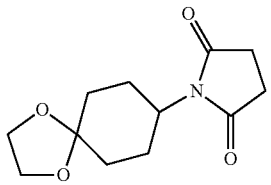 [SMILES: O=C1CCC(=O)N1C1CCC2(CC1)OCCO2]

A solution of pyrrolidine-2,5-dione (210 mg, 2 mmol) in DMF was treated with sodiumhexamethyldisilazid (1.5 eq), stirred for 30 min and treated with 4-dioxaspiro[4.5]decan-8-yl methanesulfonate (250 mg, 1 mmol) from example 1, step A, and heated at 80° C. for 18 h. DMF was removed under vacuum and the residue was purified by silica column chromatography to give the title compound.

Step B: 1-(4-oxocyclohexyl)pyrrolidine-2,5-dione

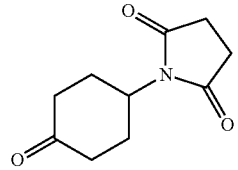 [SMILES: O=C1CCC(N2C(=O)CCC2=O)CC1]

1-(1,4-dioxaspiro[4.5]decan-8-yl)pyrrolidine-2,5-dione (60 mg, 0.25 mmol) from above step A, was dissolved in acetonitrile, treated with 6N HCl, and stirred at room temperature for 18 h. The reaction mixture was concentrated in vacuo, treated with saturated NaHCO₃ to pH 6. The solvents were removed under vacuum and the residue treated with saturated NaCl (2 mL) and extracted with 4:1 EtOAc/iPrOH (x4). The organic fractions were combined, filtered and evaporated to give the title compound.

Step C: N-(1-0s,4s)-4-(2,5-dioxopyrrolidin-1-yl)cyclohexyl)azetidin-3-yl)-2-((6-(trifluoromethyl)-quinazolin-4-yl)amino)acetamide N-(azetidin-3-yl)-2-((6-(trifluoromethyl)quinazolin-4-yl)amino)acetamide 2.0 TFA salt (139 mg, 0.25 mmol), from example 1, step G, and 1-(4-oxocyclohexyl)pyrrolidine-2,5-dione (49 mg, 0.25 mmol) from step B, sodium triacetoxyborohydride (154 mg, 0.73 mmol) and TEA (70 µL, 0.5 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter

Example 58

N-(1-((1s,4s)-4-(2-oxopyridin-1(2H)-yl)cyclohexyl)azetidin-3-yl)-2-((6-(trifluoromethyl)quinolin-4-yl)amino)acetamide

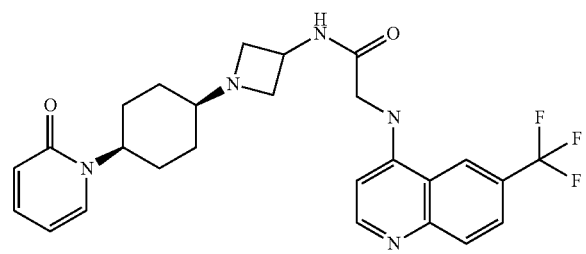 [SMILES: O=C(CNc1ccnc2ccc(C(F)(F)F)cc12)NC1CN([C@H]2CC[C@@H](n3ccccc3=O)CC2)C1]

N-(azetidin-3-yl)-2-((6-(trifluoromethyl)quinolin-4-yl)amino)acetamide 2.0 TFA salt (100 mg, 0.18 mmol) from example 26, step I, and 1-(4-oxocyclohexyl)pyridin-2(1H)-one (34.6 mg, 0.18 mmol) from example 16 step b, sodium triacetoxyborohydride (142 mg, 0.67 mmol) and TEA (50 µL, 0.36 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C26H28F3N5O2: 499.22. found: 500.22 (M+1).

$^1$H NMR (MeOD) δ: 8.61 (s, 1H), 8.49 (d, J=5.6 Hz, 1H), 7.95-8.01 (m, 1H), 7.85-7.93 (m, 1H), 7.78 (d, J=6.8 Hz, 1H), 7.41-7.51 (m, 1H), 6.47-6.58 (m, 2H), 6.43 (t, J=6.7 Hz, 1H), 4.79-4.86 (m, 1H), 4.55 (t, J=7.1 Hz, 1H), 4.12 (s, 2H), 3.74 (t, J=7.6 Hz, 2H), 2.99 (t, J=7.5 Hz, 2H), 2.47 (br. s., 1H), 1.80-1.93 (m, 4H), 1.51-1.66 (m, 4H)

Example 59

2-((2,6-bis(trifluoromethyl)quinolin-4-yl)amino)-N-(1-((1s,4s)-4-(2-oxopyridin-1(2H)-yl)cyclohexyl)azetidin-3-yl)acetamide

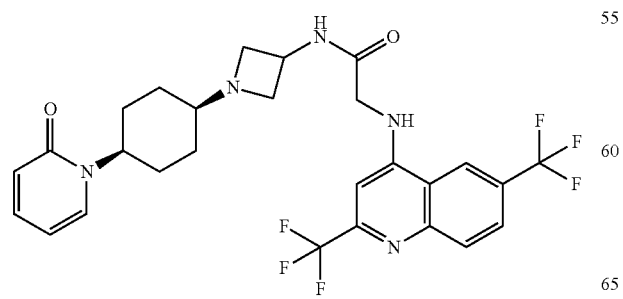

N-(azetidin-3-yl)-2-((2,6-bis(trifluoromethyl)quinolin-4-yl)amino)acetamide 2.0 TFA salt (100 mg, 0.16 mmol) from example 24, step D and 1-(4-oxocyclohexyl)pyridin-2(1H)-one (31 mg, 0.16 mmol) from example 16 step b, sodium triacetoxyborohydride (126 mg, 0.60 mmol) and TEA (45 µL, 0.32 mmol), were taken in acetonitrile and stirred for 18 h at room temperature. The mixture concentrated under vacuum and the residue basified with NaHCO₃, saturated with solid NaCl and extracted with EtOAc/iPrOH (4:1) four times. Organic layer separated, dried over Na₂SO₄ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C27H27F6N5O2: 567.21. found: 568.21 (M+1).

Example 60

2-((2-cyano-6-(trifluoromethyl)quinolin-4-yl)amino)-N-(1-((1s,4s)-4-(2-oxopyridin-1(2H)-yl)cyclohexyl)azetidin-3-yl)acetamide

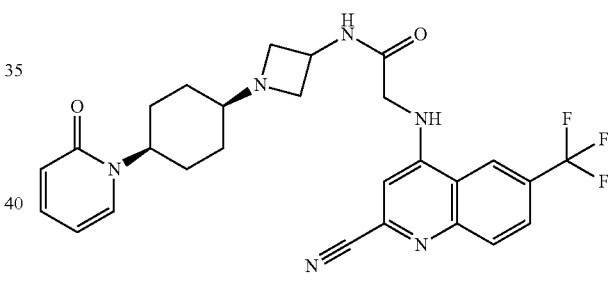

Step A: Ethyl 4((4-methoxybenzyl)oxy)-6-(trifluoromethyl)quinoline-2-carboxylate

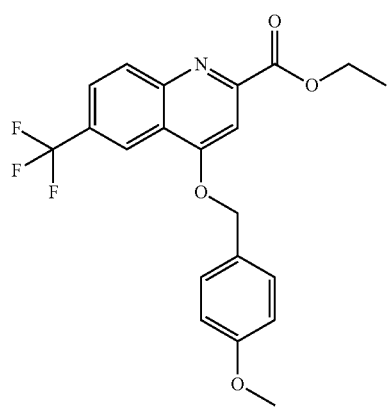 [SMILES: CCOC(=O)c1cc(OCc2ccc(OC)cc2)c2cc(C(F)(F)F)ccc2n1]

An acetonitrile solution of ethyl 4-hydroxy-6-(trifluoromethyl)quinoline-2-carboxylate (50 g, 175 mmol) and 1-(chloromethyl)-4-methoxybenzene (33 ml, 245 mmol), is treated with Cs$_2$CO$_3$ (80 g, 245 mmol) and heated at 70° C. for 18 h. Salts were removed by filtration and the solvent removed under vacuum. The residue was dissolved in EtOAc and washed with water and sat NaCl. Organic layer dried over Na$_2$SO$_4$ and evaporated under vacuum. The resulting solid was recrystallized from EtOAc/Hex to give the title compound.

Step B: 4-((4-methoxybenzyl)oxy)-6-(trifluoromethyl)quinoline-2-carboxamide

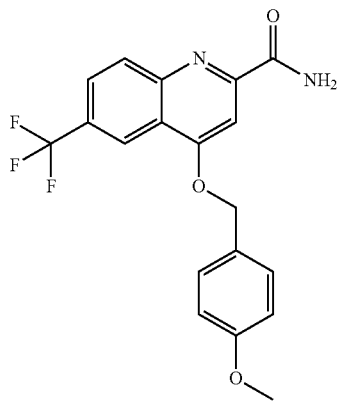 [SMILES: COc1ccc(COc2cc(C(N)=O)nc3ccc(C(F)(F)F)cc23)cc1]

A methanolic solution of ethyl 4-((4-methoxybenzyl)oxy)-6-(trifluoromethyl)quinoline-2-carboxylate (53 g, 131 mmol) from above step A, was cooled in an ice bath and saturated with ammonia by bubbling in ammonia. The flask was capped and stirred at room temp for 20 h. The white precipitate that formed was collected by filtration and washed with a small amount of MeOH and dried under vacuum to give the title compound.

Step C: 4-((4-methoxybenzyl)oxy)-6-(trifluoromethyl)quinoline-2-carbonitrile

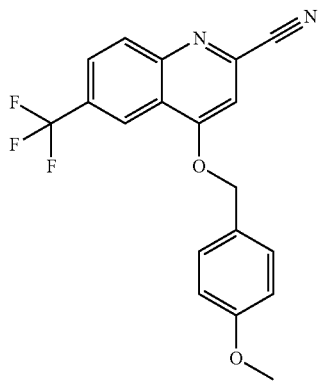 [SMILES: COc1ccc(COc2cc(C#N)nc3ccc(C(F)(F)F)cc23)cc1]

A solution of 4-((4-methoxybenzyl)oxy)-6-(trifluoromethyl)quinoline-2-carboxamide (9 g, 24 mmol) from above step B, and TEA (10 mL, 72 mmol) was treated with trifluoroacetic anhydride (4.35 mL, 31.3 mmol) at room temperature and stirred for 2 h (completion of reaction monitored by LCMS). Solvent was removed under vacuum and the residue was purified by recrystallization from EtOAc/Hex to give the title compound.

Step D: 4-hydroxy-6-(trifluoromethyl)quinoline-2-carbonitrile

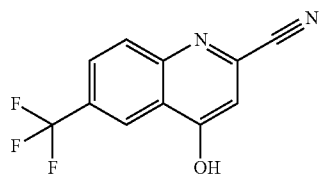 [SMILES: N#Cc1cc(O)c2cc(C(F)(F)F)ccc2n1]

A solution of 4-((4-methoxybenzyl)oxy)-6-(trifluoromethyl)quinoline-2-carbonitrile (5 g, 14 mmol) from above step C, in 15 mL DCM and 45 mL TFA was stirred for 2 h. Solvent was removed under vacuum and the residue was evaporated form toluene twice. The residue was dried under high vacuum. The resulting yellow solid was triturated with hot toluene, filtered and washed with ether to provide the title compound as a white solid.

Step E: tert-butyl 3-(2((2-cyano-6-(trifluoromethyl)quinolin-4-yl)amino)acetamido)azetidine-1-carboxylate

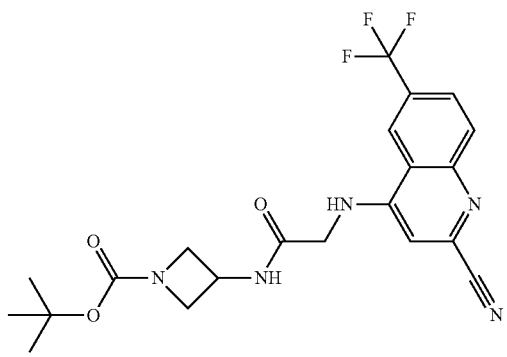 [SMILES: CC(C)(C)OC(=O)N1CC(NC(=O)CNc2cc(C#N)nc3ccc(C(F)(F)F)cc23)C1]

To a solution of 4-hydroxy-6-(trifluoromethyl)quinoline-2-carbonitrile (2 g, 8.4 mmol) from above step D, in dry dioxane was added TEA (2.9 mL, 21 mmol) and PyBroP (4.75 g, 10 mmol) and stirred at 50 C for 2 hour. To this solution tert-butyl 3-(2-aminoacetamido)azetidine-1-carboxylate (2.9 g, 12.45 mmol) from example 1, step E, was added and stirred at room temperature for 48 h. The solution was concentrated in vacuo. Water was added to the residue and extracted with EtOAc. The ethyl acetate was removed under vacuum and the residue was purified by flash chromatography (silica gel, 0 to 80% EtOAc in hexane) to give the title compound.

Step F: N-(azetidin-3-yl)-2-((2-cyano-6-(trifluoromethyl)quinolin-4-yl)amino)acetamide

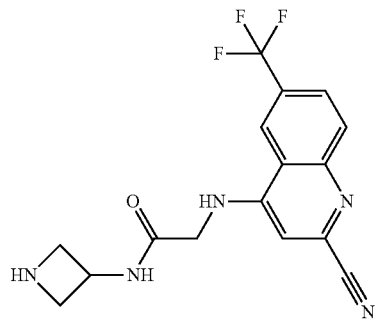 [SMILES: N#Cc1cc(NCC(=O)NC2CNC2)c2cc(C(F)(F)F)ccc2n1]

A solution of tert-butyl 3-(2-((2-cyano-6-(trifluoromethyl)quinolin-4-yl)amino)acetamido)azetidine-1-carboxylate (3.35 g, 7.45 mmol) from above step E, in DCM (50 mL) was treated with thioanisole (0.25 mL, 2 mmol) and stirred for 10 min and then treated with trifluoroacetic acid (50 mL) dropwise. The resulting opaque solution was stirred for 2.5 h at room temperature and diluted with Et$_2$O (200 mL). Precipitate was formed. This mixture was cooled in the refrigerator and the solvent decanted (solid sticks to the flask). The solid was dried under high vacuum and recrystallized from iPrOH to give the title compound.

Step G: 2-((2-cyano-6-(trifluoromethyl)quinolin-4-yl)amino)-N-(1-((1s,4s)-4-(2-oxopyridin-1(2H)-yl)cyclohexyl)azetidin-3-yl)acetamide N-(azetidin-3-yl)-2-((2-cyano-6-(trifluoromethyl)quinolin-4-yl)amino)acetamide 2.0 TFA salt (223 mg, 0.39 mmol) from above step F, and 1-(4-oxocyclohexyl)pyridin-2(1H)-one (74 mg, 0.39 mmol) from example 16 step b, sodium triacetoxyborohydride (303 mg, 1.43 mmol) and TEA (107 μL, 0.77 mmol), were taken in acetonitrile and stirred for 18 h at room temperature. The mixture concentrated under vacuum and the residue basified with NaHCO$_3$, saturated with solid NaCl and extracted with EtOAc/iPrOH (4:1) four times. Organic layer separated, dried over Na$_2$SO$_4$ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. ESI-MS (m/z): Calcd. for C27H27F3N6O2: 524.21. found: 525.21 (M+1).
$^1$H NMR (MeOD) δ: 8.66 (s, 1H), 7.97-8.10 (m, 2H), 7.66 (s, 1H), 7.43-7.56 (m, 1H), 6.85-6.96 (m, 1H), 6.56 (d, J=8.8 Hz, 1H), 6.42-6.50 (m, 1H), 4.71-4.81 (m, 1H), 4.47-4.62 (m, 2H), 4.32 (s, 1H), 4.27 (s, 1H), 4.21 (s, 2H), 3.62 (br. s., 1H), 1.92 (d, J=3.7 Hz, 3H), 1.82 (br. s., 4H)

Example 61

2-((2-cyano-6-(trifluoromethyl)quinolin-4-yl)amino)-N-(1-((1r,4r)-4-hydroxy-4-(thiazol-5-yl)cyclohexyl)azetidin-3-yl)acetamide citrate salt

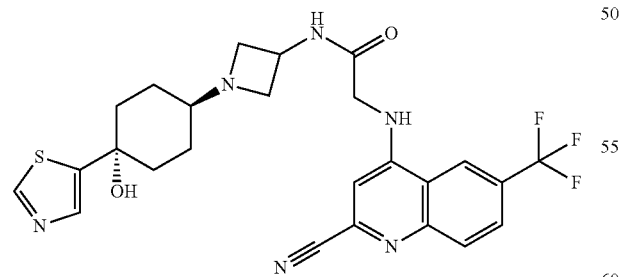

N-(azetidin-3-yl)-2-((2-cyano-6-(trifluoromethyl)quinolin-4-yl)amino)acetamide 2.0 TFA salt (223 mg, 0.39 mmol) from example 21, step F, and 4-hydroxy-4-(thiazol-5-yl)cyclohexanone (76 mg, 0.39 mmol) from example 26 step, C, sodium triacetoxyborohydride (303 mg, 1.43 mmol) and TEA (107 μL, 0.77 mmol), were taken in acetonitrile and stirred for 18 h at room temperature. The mixture concentrated under vacuum and the residue basified with NaHCO$_3$, saturated with solid NaCl and extracted with EtOAc/iPrOH (4:1) four times. Organic layer separated, dried over Na$_2$SO$_4$ and evaporated. The residue was purified by silica prep TLC. Silica band scraped off plate extracted with 20% MeOH in DCM. The solvents were removed under vacuum and the residue was taken in MeOH and transferred into a scintillation vial and evaporated under vacuum. The residue was dried under vacuum and taken in 10% MeOH in DCM and filtered through 0.45 micron filter and evaporated to give the title compound. This was dissolved in MeOH and treated with 1 equivalent of citric acid (0.5 M citrate solution) and evaporated to give the citrate salt. ESI-MS (m/z): Calcd. For C25H25F3N6O2S: 530.17. found: 531.17 (M+1).
$^1$H NMR (MeOD) δ: 8.93 (s, 1H), 8.65 (br. s., 1H), 7.92-8.08 (m, 2H), 7.86 (s, 1H), 6.87 (s, 1H), 4.65 (t, J=7.2 Hz, 1H), 4.25-4.36 (m, 2H), 4.21 (s, 2H), 4.01-4.17 (m, 2H), 2.26 (d, J=9.0 Hz, 2H), 2.02-2.15 (m, 2H), 1.80-1.95 (m, 3H), 1.54 (br. s., 2H)

Example 62

4-((2-(((1r,4r)-4-hydroxy-4-(thiazol-5-yl)cyclohexyl)azetidin-3-yl)amino)-2-oxoethyl)amino)-6-(trifluoromethyl)quinoline-2-carboxamide

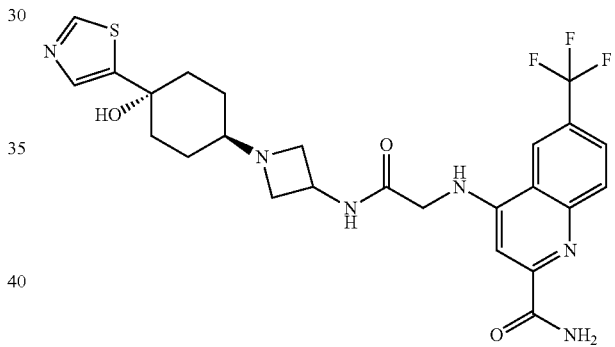

Step A: tert-butyl 2-((2-cyano-6-(trifluoromethyl)quinolin-4-yl)amino)acetate

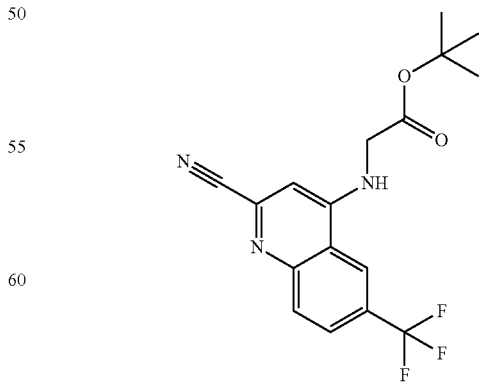

To a solution of 4-hydroxy-6-(trifluoromethyl)quinoline-2-carbonitrile (2 g, 8.4 mmol) from example 21, step D, in dry dioxane was added TEA (2.9 mL, 21 mmol) and PyBroP (4.75 g, 10 mmol) and stirred at 50 C for 2 hour. To this solution tert-butyl 2-aminoacetate (1.3 g, 10.1 mmol) was added and stirred at 30° C. for 24 h. The solution was concentrated in vacuo. Water was added to the residue and extracted with EtOAc. The ethyl acetate was removed under vacuum and the residue was purified by flash chromatography (silica gel, 0 to 80% EtOAc in hexane) to give the title compound.

Step B: Tert-butyl 2-((2-carbamoyl-6-(trifluoromethyl)quinolin-4-yl)amino)acetate

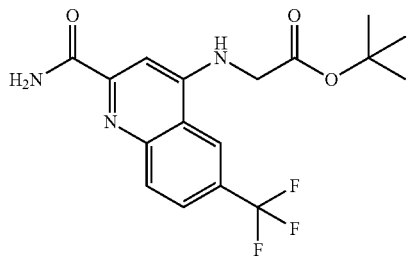 [SMILES: CC(C)(C)OC(=O)CNc1cc(C(N)=O)nc2ccc(C(F)(F)F)cc12]

A solution of tert-butyl 2-((2-cyano-6-(trifluoromethyl)quinolin-4-yl)amino)acetate (329 mg, 0.94 mmol) from above step A, in EtOH (3 mL) water (600 uL) and THF (5 mL) was added hydrido(dimethylphosphinous acid-kp)[hydrogen bis(dimethylphosphinito-kp)]platinum(ii) (80 mg, 0.18 mmol) and stirred at 75° C. for 3 h. The mixture was filtered to remove the white solid that had formed and the filtrate was evaporated under vacuum. The residue was purified by silica column chromatography to give the title compound.

Step C: 2-((2-carbamoyl-6-(trifluoromethyl)quinolin-4-yl)amino)acetic acid

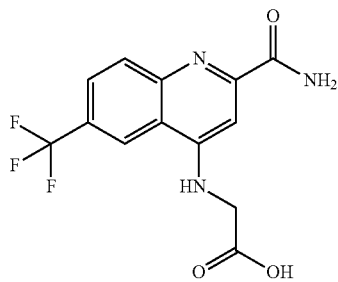 [SMILES: NC(=O)c1cc(NCC(=O)O)c2cc(C(F)(F)F)ccc2n1]

A solution of tert-butyl 2-((2-carbamoyl-6-(trifluoromethyl)quinolin-4-yl)amino)acetate (200 mg, 0.54 mmol) above step B, in DCM (5 mL) was treated with thioanisole (0.05 mL) and stirred for 10 min and then treated with trifluoroacetic acid (5 mL) dropwise. The resulting opaque solution was stirred for 2.5 h at room temperature and diluted with Et₂O (200 mL). Precipitate was formed. The solid was dried under high vacuum to give the title compound.

Step D: 4-((2-((1-((1r,4r)-4-hydroxy-4-(thiazol-5-yl)cyclohexyl)azetidin-3-yl)amino)-2-oxoethyl)amino)-6-(trifluoromethyl)quinoline-2-carboxamide A solution of 2-((2-carbamoyl-6-(trifluoromethyl)quinolin-4-yl)amino)acetic acid (125 mg, 0.4 mmol), from above step C, (1r,4r)-4-(3-aminoazetidin-1-yl)-1-(thiazol-5-yl)cyclohexanol (162 mg, 0.44 mmol), 1-hydroxybenzotriazole (59 mg, 0.44 mmol), and TEA (0.17 mL, 1.2 mmol) in THF was cooled in an ice bath and treated with ((3-(dimethylamino)propyl)ethyl carbodiimide hydrochloride (77 mg, 0.4 mmol). This solution was allowed to warm to room temperature and stirred for 24 h. THF was removed under vacuum and the residue was taken in water and extracted twice with EtOAc/iPrOH (4:1). The organic fractions were combined dried over Na₂SO₄ and evaporated. The residue was purified by preparative TLC to give the title compound. ESI-MS (m/z): Calcd. For C25H27F3N6O3S: 548.18. found: 549.18 (M+1).

Example 63

N-(1-((1r,4r)-4-hydroxy-4-(thiazol-5-yl)cyclohexyl)azetidin-3-yl)-2-((7-(trifluoromethybisoquinolin-1-yl)amino)acetamide

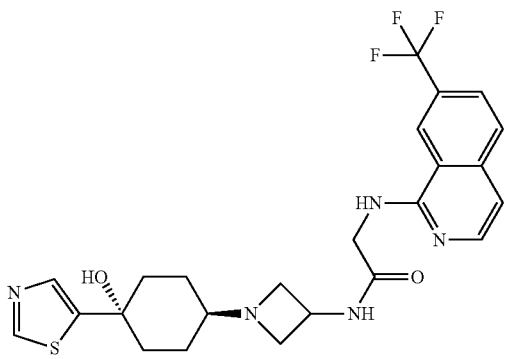 [SMILES: O=C(CNc1nccc2ccc(C(F)(F)F)cc12)NC1CN([C@H]2CC[C@@](O)(c3cncs3)CC2)C1]

Step A: 1-Chloro-7-iodoisoquinoline

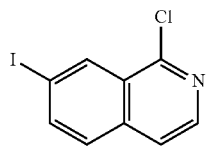 [SMILES: Clc1nccc2ccc(I)cc12]

To a stirred solution of 7-bromo-1-chloroisoquinoline (15 g, 62 mmol) in THF at −78° C., n-BuLi (123.7 mmol) was added. The resulting solution was stirred for 15 min. and, I₂ (31.4 mg, 123.7 mmol) in THF was slowly added by syringe over a period of 5 min. The solution was then allowed to reach room temperature and treated with a saturated aqueous Na₂S₂O₃ solution. The resulting mixture was extracted with diethyl ether (2×). The extracted organic layer was washed with brine, dried over Na₂SO₄ and concentrated in vacuum. The residue was purified by flash chromatography to give the title compound.

Step B: 1-Methoxy-7-(trifluoromethyl)isoquinoline

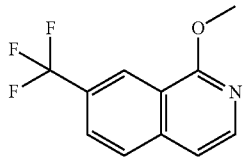 [SMILES: COc1nccc2ccc(C(F)(F)F)cc12]

To a solution of 1-chloro-7-iodoisoquinoline (9.2 g, 32 mmol) from above step A, in DMF was added methyl 2,2-difluoro-2-(fluorosulfonyl)acetate (8.6 mg, 66 mmol) and Cu (2.2 g, 35 mmol). The reaction mixture was stirred at 80° C. for 48 h. The reaction mixture was filtered through Celite, which was washed with DMF (2×25 mL). The filtrate was evaporated under reduced pressure and the residue was purified by flash chromatography (40% EtOAc in hex) to give the title compound.

Step C: 1-Chloro-7-(trifluoromethyl)isoquinoline

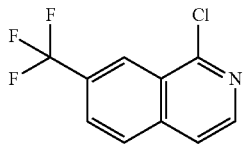 [SMILES: FC(F)(F)c1ccc2ccnc(Cl)c2c1]

A solution of 1-Methoxy-7-(trifluoromethyl)isoquinoline (50 mg, 0.22 mmol) from above step B in phosphorus oxychloride (1 mL) was heated at 150° C. for 18 h. Phosphorus oxychloride was removed under vacuum and the residue was purified by silica column chromatography to give the title compound.

Step D: 1-Phenoxy-7-(trifluoromethyl)isoquinoline

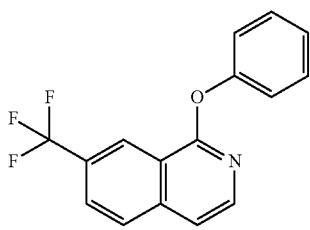 [SMILES: FC(F)(F)c1ccc2ccnc(Oc3ccccc3)c2c1]

A mixture of 1-chloro-7-(trifluoromethyl)isoquinoline (1.5 g, 6.5 mmol), from above step C, KOH (0.73 g, 13 mmol) and phenol (6.1 g, 65 mmol) were heated at 100° C. for 72 h. The resulting mixture was cooled to room temperature and taken in Et$_2$O and extracted with 4N NaOH (x3). The organic fraction was washed with water, saturated NaCl, dried over Na$_2$SO$_4$ and evaporated to give the title compound.

Step E: 7-(trifluoromethyl)isoquinolin-1-amine

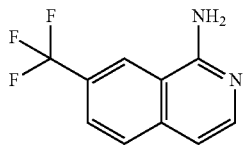 [SMILES: Nc1nccc2ccc(C(F)(F)F)cc12]

A mixture of 1-phenoxy-7-(trifluoromethyl)isoquinoline (670 mg, 2.3 mmol), from above step D, and ammonium acetate (1.8 g, 23 mmol) was heated at 160° C. for 4 h. The mixture was cooled to room temperature and dissolved in water. Sodium hydroxide (1N solution) was added until the solution was basic and extracted with EtOAc (x4). The combined organic fractions were washed with saturated NaCl, dried over Na$_2$SO$_4$ and evaporated under vacuum to give the title compound.

Step F: Benzyl (7-(trifluoromethyl)isoquinolin-1-yl)carbamate

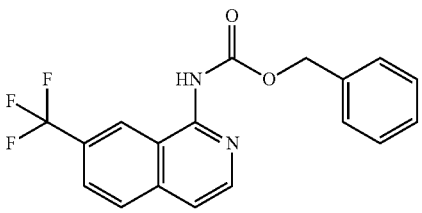 [SMILES: O=C(Nc1nccc2ccc(C(F)(F)F)cc12)OCc1ccccc1]

A solution of 7-(trifluoromethyl)isoquinolin-1-amine (410 mg, 1.9 mmol), from above step E, and benzyl chloroformate (0.33 mL, 2.3 mmol) in DCM was treated with N-methylmorpholine (0.23 mL, 2.1 mmol) and stirred at room temperature for 18 h. Reaction mixture was diluted with DCM and washed with water and dried over Na$_2$SO$_4$. DCM was removed under vacuum and the residue was purified by silica column chromatography to give the title compound.

Step G: Methyl 2-(((benzyloxy)carbonyl)(7-(trifluoromethyl)isoquinolin-1-yl)amino)acetate

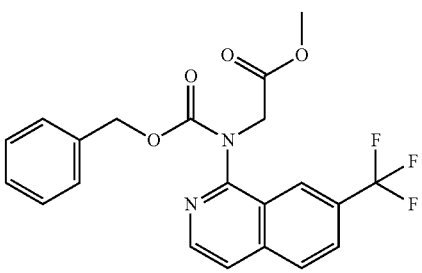 [SMILES: COC(=O)CN(C(=O)OCc1ccccc1)c1nccc2ccc(C(F)(F)F)cc12]

A solution of benzyl (7-(trifluoromethyl)isoquinolin-1-yl)carbamate (212 mg, 0.61 mmol), from above step F in DMF (5 mL) was cooled in an ice bath and treated with NaH (27 mg, 0.67 mmol), and the mixture was stirred for 30 min and was treated with methyl bromoacetate (64 µL, 0.67 mmol).

This solution was stirred and allowed to warm to room temperature over 18 h. The reaction was quenched with saturated NH₄Cl and DMF was removed under vacuum. The residue was taken in EtOAc and washed with water, sat NaCl and dried over Na₂SO₄. EtOAc was removed under vacuum and the residue was purified by silica column chromatography to give the title compound.

Step H: 2-(((Benzyloxy)carbonyl)(7-(trifluoromethyl)isoquinolin-1-yl)amino)acetic acid

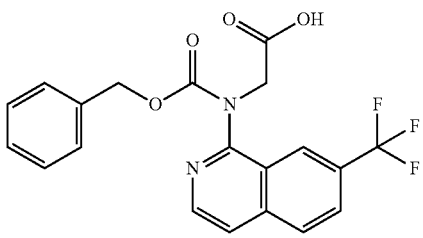 [SMILES: O=C(O)CN(C(=O)OCc1ccccc1)c1nccc2ccc(C(F)(F)F)cc12]

A methanolic solution of methyl 2-(((benzyloxy)carbonyl)(7-(trifluoromethyl)isoquinolin-1-yl)amino)acetate (241 mg, 0.58 mmol) from above step G was cooled in an ice bath and treated with a solution of 1N NaOH (2.88 ml, 2.88 mmol). The solution was stirred for 4 h (monitored with TLC for completion), MeOH evaporated under vacuum (no heat), and the residue treated with 1N HCl and extracted with EtOAc. The EtOAc layer was washed with saturated NaCl, dry over Na₂SO₄ and evaporated to give the title compound.

Step I: Benzyl (2-((1-((1r,4r)-4-hydroxy-4-(thiazol-5-yl)cyclohexyl)azetidin-3-yl)amino)-2-oxoethyl)(7-(trifluoromethyl)isoquinolin-1-yl)carbamate

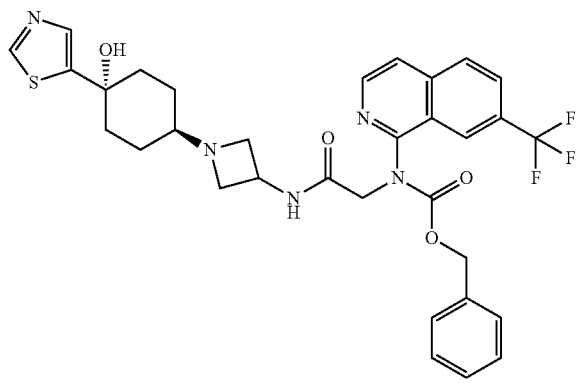 [SMILES: O=C(CN(C(=O)OCc1ccccc1)c1nccc2ccc(C(F)(F)F)cc12)NC1CN([C@H]2CC[C@@](O)(c3cncs3)CC2)C1]

A solution of 2-(((benzyloxy)carbonyl)(7-(trifluoromethyl)isoquinolin-1-yl)amino)acetic acid (88 mg, 0.22 mmol), from above step H, (1r,4r)-4-(3-aminoazetidin-1-yl)-1-(thiazol-5-yl)cyclohexanol (130 mg, 0.22 mmol), 1-hydroxybenzotriazole (33 mg, 0.22 mmol), and DIEA (0.19 mL, 1.1 mmol) in THF was cooled in an ice bath and treated with ((3-(dimethylamino)propyl)ethyl carbodiimide hydrochloride (42 mg, 0.22 mmol). This solution was allowed to warm to room temperature and stirred for 24 h. THF was removed under vacuum and the residue was taken in water and extracted twice with EtOAc/iPrOH (4:1). The organic fractions were combined dried over Na₂SO₄ and evaporated. The residue was purified by preparative TLC to give the title compound.

Step J. N-(1-((1r,4r)-4-hydroxy-4-(thiazol-5-yl)cyclohexyl)azetidin-3-yl)-2-((7-(trifluoromethyl)isoquinolin-1-yl)amino)acetamide A solution of benzyl (2-((1-((1r,4r)-4-hydroxy-4-(thiazol-5-yl)cyclohexyl)azetidin-3-yl)amino)-2-oxoethyl)(7-(trifluoromethyl)isoquinolin-1-yl)carbamate (40 mg, 0.06 mmol), from above step I, in MeOH was treated with a 5% Pd/C (100 mg), and the mixture was stirred under a H₂ atmosphere for 18 h. The catalyst was removed by filtration and MeOH removed under vacuum. The residue was purified by prep TLC to give the title compound. ESI-MS (m/z): Calcd. For $C_{24}H_{26}F_3N_5O_2S$: 505.18. found: 506.18 (M+1).

Example 64

N-(1-((1r,4r)-4-hydroxy-4-(thiazol-2-yl)cyclohexyl)azetidin-3-yl)-2-(methyl(6-(trifluoromethyl)quinazolin-4-yl)amino)acetamide Step A: ethyl 2-(((benzyloxy)carbonyl)(methyl)amino)acetate

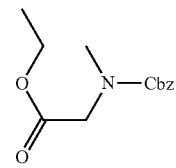 [SMILES: CCOC(=O)CN(C)C(=O)OCc1ccccc1]

A rapidly stirred mixture of ethyl acetate and saturated aqueous sodium bicarbonate containing commercially available commercially available 2 ethyl 2-(methylamino)acetate (1.91 g, 12.4 mmol, HCl salt) was cooled to 0° C. and treated dropwise with benzyl chloroformate (4.10 mL, 12.3 mmol). After stirring overnight warming to room temperature, the aqueous layer was removed and the organic layer concentrated in vacuo. Purification of the residue by flash chromatography (silica gel, DCM) yielded the product.

Step B: 2-(((benzyloxy)carbonyl)(methyl)amino)acetic acid

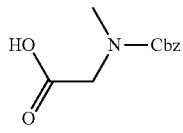

A solution of ethyl 2-(((benzyloxy)carbonyl)(methyl)amino)acetate (2.66 mg, 10.6 mmol, prepared the previous step) in MeOH (24 mL) and THF (5 mL) and treated with a solution of LiOH (12 mL, 54 mmol, 4.52 M in water). After stirring at room temperature for 3 hours, the pH was adjusted to ~5 by the addition of aqueous HCl. After extraction with ethyl acetate, the organic layer was dried over Na$_2$SO$_4$ and concentrated in vacuo to yield the product.

Step C: tert-butyl 3-(2-(((benzyloxy)carbonyl)(methyl)amino)acetamido)azetidine-1-carboxylate

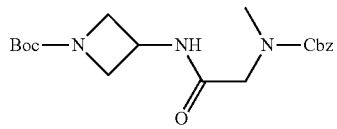 [SMILES: CN(CC(=O)NC1CN(C(=O)OC(C)(C)C)C1)C(=O)OCc1ccccc1]

A mixture of 2-(((benzyloxy)carbonyl)(methyl)amino)acetate (2.12 g, 9.50 mmol, prepared the previous step) and EDCI (1.99 g, 10.4 mmol) were stirred in anhydrous DCM (10 mL) for 15 minutes and then added to a solution of commercially available tert-butyl 3-aminoazetidine-1-carboxylate (1.64 g, 9.52 mmol) and DMAP (220 mg, 1.80 mmol) in DCM (90 mL). The reaction mixture was stirred at room temperature overnight and then concentrated in vacuo. The residue was dissolved in ethyl acetate, washed with saturated ammonium chloride solution, 1 N NaOH solution, brine and the organic layer dried over Na$_2$SO$_4$. After concentration in vacuo, the residue was purified by flash chromatography (silica gel, 0%-5% MeOH/EtOAc) to give a white solid after drying under high vacuum.

Step D: tert-butyl 3-(2-(methylamino)acetamido)azetidine-1-carboxylate

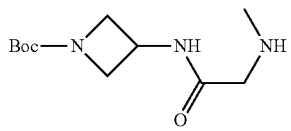 [SMILES: CNCC(=O)NC1CN(C(=O)OC(C)(C)C)C1]

To a flask containing tert-butyl 3-(2-(((benzyloxy)carbonyl)(methyl)amino)acetamido)azetidine-1-carboxylate (3.10 g, 8.21 mmol, prepared in the previous step) and a stirbar, was added 10% Pd/C (136 g, 0.127 mmol). The flask was evacuated and back filled with argon. Methanol (100 mL) was carefully added via syringe and the flask was evacuated with stirring. It was then back filled with hydrogen and stirred 2 days under a hydrogen balloon. After evacuation with stirring and back filling with argon, the catalyst was removed by filtration over Celite 521 and concentrated in vacuo to afford the product.

Step E: tert-butyl 3-(2-(methyl(6-(trifluoromethyl)quinazolin-4-yl)amino)acetamido)azetidine-1-carboxylate

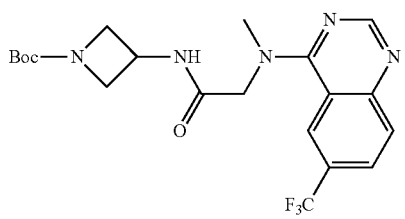 [SMILES: CN(CC(=O)NC1CN(C(=O)OC(C)(C)C)C1)c1ncnc2ccc(C(F)(F)F)cc12]

A mixture of tert-butyl 3-(2-(methylamino)acetamido)azetidine-1-carboxylate (348 mg, 1.43 mmol) as prepared in the previous step and commercially available 4-chloro-6-(trifluoromethyl)quinazoline (327 mg, 1.41 mmol) were stirred in anhydrous iPrOH and triethylamine at 90° C. under argon for 1 hour. The reaction mixture was concentrated in vacuo and the residue purified by flash chromatography (silica gel, 0%-5% MeOH/EtOAc) to give a yellow solid after drying under high vac.

Calcd. For C$_{20}$H$_{24}$F$_3$N$_5$O$_3$: 439.18. found: 440 (M+H).

Step F: N-(azetidin-3-yl)-2-(methyl(6-(trifluoromethyl)quinazolin-4-yl)amino)acetamide TFA salt

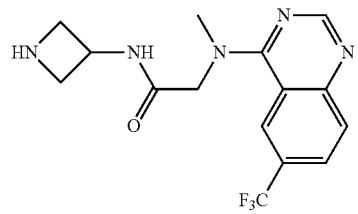 [SMILES: CN(CC(=O)NC1CNC1)c1ncnc2ccc(C(F)(F)F)cc12]

3-[2-(3-Trifluoromethyl-benzoylamino)-acetylamino]-azetidine-1-carboxylic acid tert-butyl ester (8.35 g, 19.6 mmol) as prepared in the previous step was dissolved in DCM (250 mL) and treated with TFA (17 mL, 229 mmol) at room temperature. The reaction was stirred overnight at room temperature. The solvent was removed in vacuo and the residue first triturated with ether, decanting the supernatant, and dried on the high vacuum to give the title compound as a TFA salt containing extra TFA (colorless foam). The amount of TFA varied from run to run and was determined by integration of the $^{19}$F NMR signals of the aryl CF$_3$ and the CF$_3$ from TFA.

ESI-MS (m/z): Calcd. For C$_{15}$H$_{16}$F$_3$N$_5$O: 339.19. found: 340 (M+H).

Step G: N-(1-((1r,4r)-4-hydroxy-4-(thiazol-2-yl)cyclohexyl)azetidin-3-yl)-2-(methyl(6-(trifluoromethyl)quinazolin-4-yl)amino)acetamide

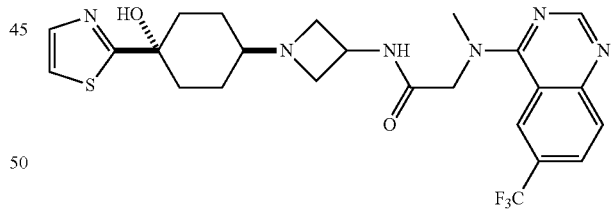

To a suspension of 4-(3-hydroxy-pyridin-2-yl)-cyclohexanone (as prepared in step C, 1 eq.) and N-(azetidin-3-yl)-2-(methyl(6-(trifluoromethyl)quinazolin-4-yl)amino)acetamide (as prepared in the previous step, tris TFA salt, 3 eq.) in DCM was added TEA (3 eq.). After stirring at room temperature 30 minutes, NaBH(OAc)$_3$ (3 eq) was added and the mixture was stirred overnight. The reaction was quenched with saturated sodium bicarbonate solution and partially concentrated. Extraction with ethyl acetate followed by concentration of the organic layer in vacuo yielded a residue which was purified by flash chromatography (silica gel, 0-20% 7 N NH$_3$-MeOH/Ethyl acetate) to afford the product as a solid.

ESI-MS (m/z): Calcd. For C$_{24}$H$_{27}$F$_3$N$_6$O$_2$S: 520.19. found: 521 (M+H).

Example 65

N-(1-(4-(pyridin-3-yl)cyclohexyl)azetidin-3-yl)-2-((6-(trifluoromethyl)quinazolin-4-yl)amino)acetamide

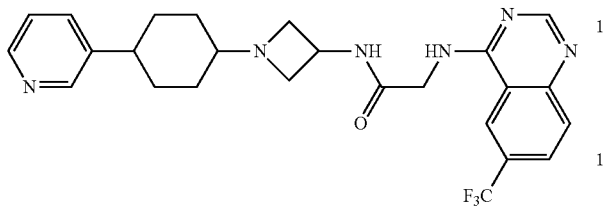

Reaction of 4-(pyridin-3-yl)cyclohexanone (prepared by the reaction of 3-bromopyridine with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (MeOD) δ: 8.62 (s, 1 H), 8.56 (s, 1 H), 8.43 (d, J=2.0 Hz, 1 H), 8.33 (dd, J=5.1, 1.5 Hz, 1 H), 8.04 (dd, J=8.8, 1.8 Hz, 1 H), 7.88 (d, J=8.8 Hz, 1 H), 7.77 (dt, J=7.8, 1.8 Hz, 1 H), 7.35 (dd, J=7.7, 5.2 Hz, 1 H), 4.51 (quin, J=7.1 Hz, 1 H), 4.28 (s, 2 H), 3.65-3.73 (m, 2 H), 2.95 (t, J=7.6 Hz, 2 H), 2.56-2.69 (m, 1 H), 2.43 (d, J=2.8 Hz, 1 H), 1.68-1.92 (m, 4 H), 1.49-1.62 (m, 4 H); ESI-MS (m/z): Calcd. For C$_{25}$H$_{27}$F$_3$N$_6$O: 484.22. found: 485 (M+H).

Example 66

N-(1-(4-(pyridin-2-yl)cyclohexyl)azetidin-3-yl)-2-((6-(trifluoromethyl)quinazolin-4-yl)amino)acetamide

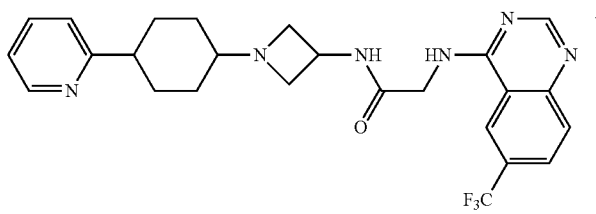

Reaction of 4-(pyridin-3-yl)cyclohexanone (prepared by the reaction of 2-bromopyridine with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (MeOD) δ: 8.99 (t, J=5.7 Hz, 1 H), 8.80 (s, 1 H), 8.56 (s, 1 H), 8.46 (d, J=4.0 Hz, 1 H), 8.05 (dd, J=8.8, 1.8 Hz, 1 H), 7.88 (d, J=8.8 Hz, 1 H), 7.67 (td, J=7.6, 1.9 Hz, 1 H), 7.21 (d, J=7.8 Hz, 1 H), 7.16 (td, J=6.2, 1.0 Hz, 1 H), 4.27 (m, J=6.3 Hz, 1 H), 4.14 (d, J=5.8 Hz, 2 H), 3.48 (br. s., 2 H), 2.78 (br. s., 2 H), 2.57-2.71 (m, 1 H), 2.22-2.35 (m, 1 H), 1.76-1.96 (m, 2H), 1.62 (d, J=13.1 Hz, 2 H), 1.45 (m, J=14.7, 14.7 Hz, 4 H)]); ESI-MS (m/z): Calcd. For C$_{25}$H$_{27}$F$_3$N$_6$O: 484.22. found: 485 (M+H).

Example 67

N-(1-(4-(5-hydroxypyridin-2-yl)cyclohexyl)azetidin-3-yl)-2-((6-(trifluoromethyl)quinazolin-4-yl)amino)acetamide

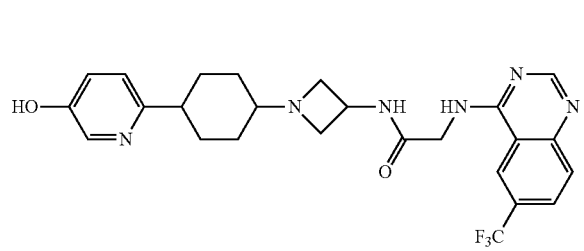

Reaction of 4-(5-hydroxypyridin-2-yl)cyclohexanone (prepared by the reaction of 5-(benzyloxy)-2-bromopyridine with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.
$^1$H NMR (MeOD) δ: 8.60 (s, 1 H), 8.49 (s, 1 H), 8.02 (d, J=2.8 Hz, 1 H), 7.90-7.95 (m, 1 H), 7.84-7.90 (m, 1 H), 7.18-7.24 (m, 1 H), 7.12-7.18 (m, 1 H), 4.76 (quin, J=7.5 Hz, 1 H), 4.31 (s, 2 H), 4.12-4.27 (m, 4 H), 3.14 (q, J=7.3 Hz, 2 H), 2.66-2.80 (m, 1 H), 1.98-2.06 (m, 2 H), 1.64-1.90 (m, 7 H), 1.32 (t, J=7.3 Hz, 3 H); ESI-MS (m/z): Calcd. For C$_{25}$H$_{27}$F$_3$N$_6$O$_2$: 500.21. found: 501 (M+H).

Example 68

N-(1-(4-(3-methoxypyridin-4-yl)cyclohexyl)azetidin-3-yl)-2-((6-(trifluoromethyl)quinazolin-4-yl)amino)acetamide

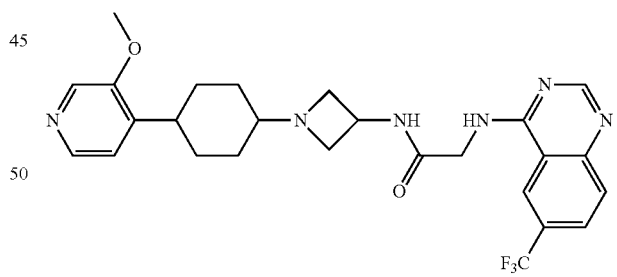

Reaction of 4-(3-methoxypyridin-4-yl)cyclohexanone (prepared by the reaction of 4-bromo-3-methoxypyridine with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-246-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (MeOD) δ: 8.62 (s, 1 H), 8.37 (s, 1 H), 8.09-8.17 (m, 2 H), 7.86-7.96 (m, 2 H), 7.22 (d, J=4.8 Hz, 1 H), 4.47-4.60 (m, 1 H), 4.23 (s, 2 H), 3.86-3.96 (m, 3 H), 3.61 (t, J=6.9 Hz, 2H), 2.95 (dd, J=7.5, 2.7 Hz, 2 H), 1.82-1.94 (m, 1 H), 1.71 (d, J=11.9 Hz, 3 H), 1.54 (d, J=9.3 Hz, 3 H), 1.08-1.47 (m, 1 H); ESI-MS (m/z): Calcd. For $C_{26}H_{29}F_3N_6O_2$: 514.23. found: 515 (M+H).

Example 69

N-(1-(4-(2-hydroxyphenyl)cyclohexyl)azetidin-3-yl)-2-((6-(trifluoromethyl)quinazolin-4-yl)amino)acetamide

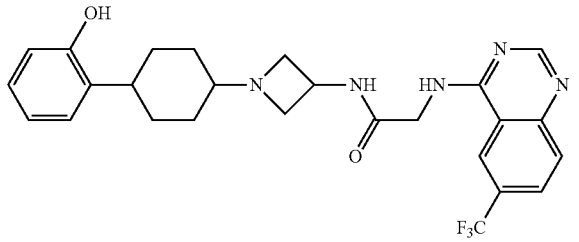 [SMILES: O=C(CNc1ncnc2ccc(C(F)(F)F)cc12)NC1CN(C2CCC(c3ccccc3O)CC2)C1]

Reaction of 4-(2-hydroxyphenyl)cyclohexanone (prepared by the reaction of 2-iodophenol with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)₃ as described in Example 1, Step H afforded the product.

¹H NMR (ACETONITRILE-d3) δ: 8.58 (s, 1 H), 8.39 (s, 1 H), 7.95 (m, J=8.8, 1.8 Hz, 1 H), 7.85 (m, J=8.8 Hz, 1 H), 7.56 (t, J=5.4 Hz, 1 H), 7.13-7.24 (m, 1 H), 7.11 (dd, J=7.6, 1.5 Hz, 1 H), 6.99 (td, J=7.6, 1.6 Hz, 1 H), 6.80 (td, J=7.5, 1.0 Hz, 1 H), 6.74 (dd, J=8.0, 1.1 Hz, 1 H), 4.38 (sxt, J=6.9 Hz, 1 H), 4.18 (d, J=5.8 Hz, 2 H), 3.55 (t, J=7.1 Hz, 2 H), 2.73-2.88 (m, 3 H), 2.27-2.35 (m, 1 H), 1.61-1.76 (m, 4 H), 1.36-1.50 (m, 4 H); ESI-MS (m/z): Calcd. For $C_{26}H_{28}F_3N_5O_2$: 499.22. found: 500 (M+H).

Example 70

N-(1-(4-(5-aminopyridin-2-yl)cyclohexyl)azetidin-3-yl)-2-((6-(trifluoromethyl)quinazolin-4-yl)amino)acetamide

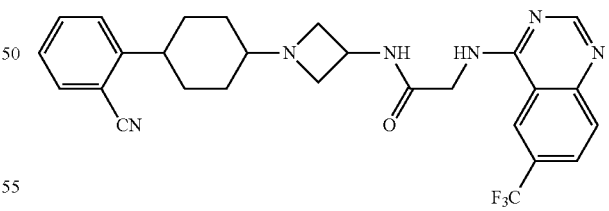

Reaction of 4-(5-aminopyridin-2-yl)cyclohexanone (prepared by the reaction of 6-bromopyridin-3-amine with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)₃ as described in Example 1, Step H afforded the product.

¹H NMR (ACETONITRILE-d3) δ: 8.57 (s, 1 H), 8.38 (s, 1 H), 7.91 (m, J=2.0 Hz, 2 H), 7.78-7.87 (m, 1 H), 7.68 (t, J=5.2 Hz, 1 H), 7.36 (d, J=6.8 Hz, 1 H), 6.90 (d, J=2.0 Hz, 2 H), 4.31-4.43 (m, 1 H), 4.19 (d, J=5.8 Hz, 2 H), 3.56 (t, J=7.6 Hz, 2 H), 2.87 (t, J=7.1 Hz, 2 H), 2.52 (tt, J=11.4, 3.5 Hz, 1 H), 2.32 (d, J=3.0 Hz, 1 H), 1.75-1.90 (m, 2 H), 1.57-1.69 (m, 2 H), 1.35-1.51 (m, 4 H); ESI-MS (m/z): Calcd. For $C_{25}H_{28}F_3N_7O$: 499.23. found: 500 (M+H).

Example 71

N-(1-((1s,4s)-4-(3-aminopyridin-2-yl)cyclohexyl)azetidin-3-yl)-2-((6-(trifluoromethyl)quinazolin-4-yl)amino)acetamide

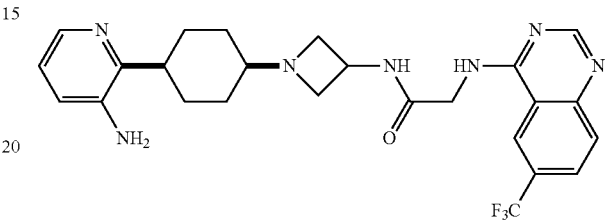

Reaction of 4-(3-aminopyridin-2-yl)cyclohexanone (prepared by the reaction of 2-bromopyridin-3-amine with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)₃ as described in Example 1, Step H afforded the product.

¹H NMR (MEOD) δ: 8.62 (s, 1 H), 8.55 (s, 1 H), 8.02 (dd, J=8.8, 1.8 Hz, 1 H), 7.86 (d, J=8.8 Hz, 1 H), 7.79 (dd, J=4.8, 1.5 Hz, 1 H), 7.02-7.10 (m, 1 H), 6.97 (dd, J=8.0, 4.7 Hz, 1 H), 4.56 (quin, J=7.1 Hz, 1 H), 4.31 (s, 2 H), 3.98 (t, J=7.5 Hz, 2 H), 3.42-3.58 (m, 2 H), 2.83-2.98 (m, 2 H), 1.78-1.98 (m, 4 H), 1.53-1.78 (m, 4 H); ESI-MS (m/z): Calcd. For $C_{25}H_{28}F_3N_7O$: 499.23. found: 500 (M+H).

Example 72

N-(1-(4-(2-cyanophenyl)cyclohexyl)azetidin-3-yl)-2-((6-(trifluoromethyl)quinazolin-4-yl)amino)acetamide Reaction of 2-(4-oxocyclohexyl)benzonitrile (prepared by the reaction of 2-bromobenzonitrile with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)₃ as described in Example 1, Step H afforded the product.

¹H NMR (ACETONITRILE-d3) δ: 8.60 (s, 1 H), 8.46 (s, 1 H), 8.00 (dd, J=8.8, 1.8 Hz, 1 H), 7.89 (d, J=8.6 Hz, 1 H), 7.65

(dd, J=7.8, 1.0 Hz, 1 H), 7.57-7.63 (m, 1 H), 7.50 (d, J=7.8 Hz, 1 H), 7.33 (td, J=7.6, 1.3 Hz, 1 H), 4.44 (quin, J=6.9 Hz, 1 H), 4.21 (s, 2 H), 3.65 (t, J=7.3 Hz, 2 H), 2.91-3.00 (m, 3 H), 2.46 (br. s., 1 H), 1.70-1.89 (m, 4 H), 1.45-1.62 (m, 4 H); ESI-MS (m/z): Calcd. For $C_{27}H_{27}F_3N_6O$: 508.22. found: 509 (M+H).

Example 73

N-(1-((1s,4s)-4-(2-(hydroxymethyl)phenyl)cyclohexyl)azetidin-3-yl)-2-((6-(trifluoromethyl)quinazolin-4-yl)amino)acetamide

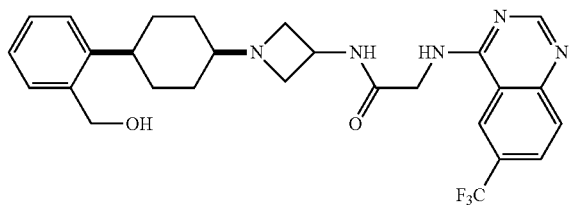

Reaction of 2-(4-oxocyclohexyl)benzonitrile (prepared by the reaction of 2-bromobenzonitrile with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (DMSO-d6) δ: 9.01 (t, J=5.7 Hz, 1 H), 8.81 (s, 1 H), 8.57 (s, 1 H), 8.44 (d, J=7.1 Hz, 1H), 8.06 (dd, J=8.7, 1.9 Hz, 1 H), 7.88 (d, J=8.6 Hz, 1 H), 7.32 (d, J=7.6 Hz, 1 H), 7.21 (d, J=5.1 Hz, 2 H), 7.07-7.16 (m, 1 H), 5.01 (t, J=5.4 Hz, 1 H), 4.52 (d, J=5.6 Hz, 2 H), 4.25-4.37 (m, 1 H), 4.15 (d, J=5.8 Hz, 2 H), 3.52 (br. s., 2 H), 2.65-2.85 (m, 3 H), 2.32 (m, J=1.8 Hz, 1 H), 1.57-1.84 (m, 4 H), 1.40 (m, J=11.9 Hz, 4 H); ESI-MS (m/z): Calcd. For $C_{27}H_{30}F_3N_5O_2$: 513.24. found: 514 (M+H).

Example 74

N-(1-(4-(3-(methylamino)pyridin-4-yl)cyclohexyl)azetidin-3-yl)-2-((6-(trifluoromethyl)quinazolin-4-yl)amino)acetamide

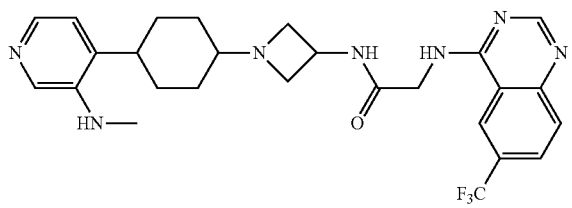 [SMILES: CNc1cnccc1C1CCC(N2CC(NC(=O)CNc3ncnc4ccc(C(F)(F)F)cc34)C2)CC1]

Reaction of 4-(3-(methylamino)pyridin-4-yl)cyclohexanone (prepared by the reaction of 4-bromo-N-methylpyridin-3-amine with 8-(4,4,5,5-Tetramethyl-[1,3,2]dioxaborolan-2-yl)-1,4-dioxa-spiro[4.5]dec-7-ene using the sequence described in Example 1 Step A-C) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MEOD) δ: 8.51-8.62 (m, 3 H), 7.94-8.05 (m, 2 H), 7.84-7.94 (m, 3 H), 7.75-7.84 (m, 1 H), 4.23 (d, J=2.5 Hz, 3 H), 4.13-4.20 (m, 2 H), 4.05-4.11 (m, 3 H), 4.01 (dd, J=11.2, 6.4 Hz, 0 H), 3.72-3.85 (m, 1 H), 2.91-2.98 (m, 1 H), 1.92 (br. s., 2 H), 1.67-1.80 (m, 2 H), 1.53-1.67 (m, 2 H), 1.24-1.32 (m, 2 H); ESI-MS (m/z): Calcd. For $C_{26}H_{30}F_3N_7O$: 513.25. found: 514 (M+H).

Example 75

N-(1-((1r,4r)-4-hydroxy-4-(6-methylpyridin-3-yl)cyclohexyl)azetidin-3-yl)-2-((6-(trifluoromethyl)quinazolin-4-yl)amino)acetamide

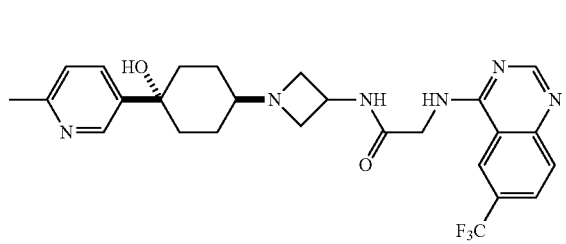

Reaction of 4-hydroxy-4-(6-methylpyridin-3-yl)cyclohexanone (prepared by the reaction of 5-bromo-2-methylpyridine with 1,4-dioxaspiro[4.5]decan-8-one using the sequence described in Example 24 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MEOD) δ: 8.62 (s, 1 H), 8.50-8.59 (m, 2 H), 8.03 (dd, J=8.8, 1.8 Hz, 1 H), 7.78-7.91 (m, 2 H), 7.26 (dd, J=8.1, 2.5 Hz, 2 H), 4.50 (quin, J=7.1 Hz, 1 H), 4.28 (s, 2 H), 3.70 (t, J=7.3 Hz, 2 H), 3.00 (t, J=6.9 Hz, 2 H), 2.47-2.53 (m, 3 H), 2.43 (br. s., 1 H), 2.09-2.26 (m, 2 H), 1.96-2.09 (m, 1 H), 1.76-1.95 (m, 2 H), 1.34-1.71 (m, 4 H); ESI-MS (m/z): Calcd. For $C_{26}H_{29}F_3N_6O_2$: 514.23. found: 515 (M+H).

Example 76

N-(1-(4-hydroxy-4-(6-methoxypyridin-3-yl)cyclohexyl)azetidin-3-yl)-2-((6-(trifluoromethyl)quinazolin-4-yl)amino)acetamide

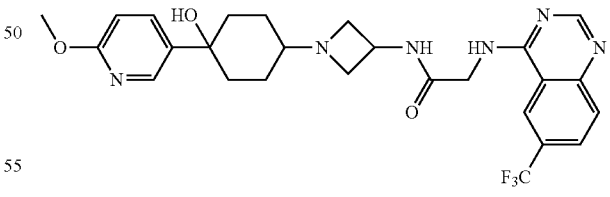

Reaction of 4-hydroxy-4-(6-methoxypyridin-3-yl)cyclohexanone (prepared by the reaction of 5-bromo-2-methoxypyridine with 1,4-dioxaspiro[4.5]decan-8-one using the sequence described in Example 24 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MEOD) δ: 8.62 (s, 1 H), 8.50-8.59 (m, 2 H), 8.03 (dd, J=8.8, 1.8 Hz, 1 H), 7.78-7.91 (m, 2 H), 7.26 (dd, J=8.1, 2.5 Hz, 2 H), 4.50 (quin, J=7.1 Hz, 1 H), 4.28 (s, 2 H), 3.70 (t, J=7.3 Hz, 2 H), 3.00 (t, J=6.9 Hz, 2 H), 2.47-2.53 (m, 3 H), 2.43 (br. s., 1 H), 2.09-2.26 (m, 2H), 1.96-2.09 (m, 1 H), 1.76-1.95 (m, 2 H), 1.34-1.71 (m, 4 H); ESI-MS (m/z): Calcd. For $C_{26}H_{29}F_3N_6O_2$: 514.23. found: 515 (M+H).

Example 77

N-(1-(4-hydroxy-4-(6-methoxypyridin-2-yl)cyclohexyl)azetidin-3-yl)-2-((6-(trifluoromethyl)quinazolin-4-yl)amino)acetamide

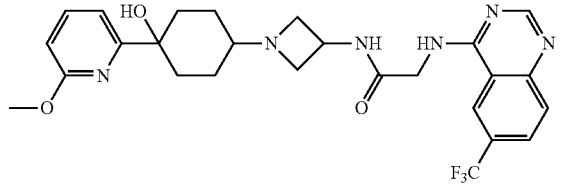 [SMILES: COc1cccc(C2(O)CCC(N3CC(NC(=O)CNc4ncnc5ccc(C(F)(F)F)cc45)C3)CC2)n1]

Reaction of 4-hydroxy-4-(6-methoxypyridin-2-yl)cyclohexanone (prepared by the reaction of 2-bromo-6-methoxypyridine with 1,4-dioxaspiro[4.5]decan-8-one using the sequence described in Example 24 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MEOD) δ: 8.65 (s, 1 H), 8.16 (s, 1 H), 7.85 (s, 1 H), 7.53-7.67 (m, 2 H), 6.94-7.04 (m, 1 H), 6.90 (d, J=7.3 Hz, 1 H), 6.58-6.67 (m, 2 H), 4.56-4.64 (m, 0 H), 4.30 (d, J=5.1 Hz, 2 H), 3.90-3.94 (m, 3 H), 3.74 (dt, J=9.5, 4.7 Hz, 1 H), 3.63 (t, J=7.5 Hz, 2 H), 2.95 (dd, J=7.5, 6.2 Hz, 2 H), 1.65-2.01 (m, 30H [mostly ketone s.m.]), 1.26-1.61 (m, 30H [mostly ketone s.m.]); ESI-MS (m/z): Calcd. For $C_{26}H_{29}F_3N_6O_2$: 514.23. found: 515 (M+H).

Example 78

N-(1-((1r,4r)-4-hydroxy-4-phenylcyclohexyl)azetidin-3-yl)-2-((6-(trifluoromethyl)quinazolin-4-yl)amino)acetamide

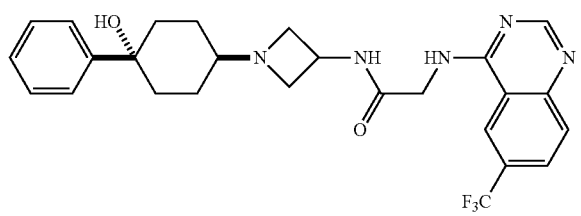

Reaction of 4-hydroxy-4-phenylcyclohexanone (prepared by the reaction of phenylmagnesium bromide with 1,4-dioxaspiro[4.5]decan-8-one using the sequence described in Example 24

Step A-B) with N-(azetidin-3-yl)-2-(6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (CHLOROFORM-d) δ: 8.63 (s, 1 H), 8.11 (s, 1 H), 7.77-7.86 (m, 2 H), 7.66 (t, J=5.2 Hz, 1 H), 7.51-7.56 (m, 2 H), 7.32-7.39 (m, 3 H), 4.52-4.64 (m, 1 H), 4.27 (d, J=5.1 Hz, 2 H), 3.62 (t, J=7.5 Hz, 2 H), 2.94 (t, J=6.6 Hz, 2 H), 2.21-2.37 (m, 3 H), 2.02-2.12 (m, 1 H), 1.79-1.92 (m, 3 H), 1.52-1.74 (m, 5 H), 1.44 (dt, J=9.3, 4.6 Hz, 2 H); ESI-MS (m/z): Calcd. For $C_{26}H_{28}F_3N_5O_2$: 499.22. found: 500 (M+H).

Example 79

N-(1-(4-hydroxy-4-(2-methylthiazol-5-yl)cyclohexyl)azetidin-3-yl)-2-((6-(trifluoromethyl)quinazolin-4-yl)amino)acetamide

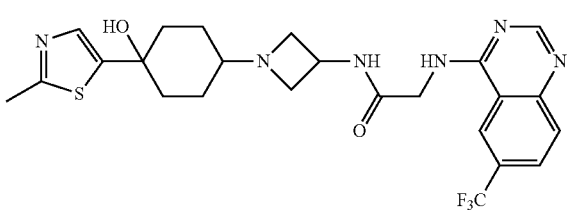 [SMILES: Cc1ncc(C2(O)CCC(N3CC(NC(=O)CNc4ncnc5ccc(C(F)(F)F)cc45)C3)CC2)s1]

Reaction of 4-hydroxy-4-(2-methylthiazol-5-yl)cyclohexanone (prepared by the reaction of 5-bromo-2-methylthiazole with 1,4-dioxaspiro[4.5]decan-8-one using the sequence described in Example 24 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (CHLOROFORM-d) δ: 8.57 (s, 1 H), 8.43 (s, 1 H), 7.88-7.94 (m, 1 H), 7.81-7.88 (m, 1 H), 7.46 (s, 1 H), 4.54 (quin, J=6.5 Hz, 1 H), 4.24 (s, 2 H), 3.30 (br. s., 2 H), 3.13 (q, J=7.3 Hz, 6 H), 2.64 (s, 3 H), 2.55 (br. s., 1 H), 2.17 (td, J=8.5, 3.7 Hz, 2 H), 1.56-1.92 (m, 6 H), 1.32 (t, J=7.3 Hz, 9 H); ESI-MS (m/z): Calcd. For $C_{24}H_{27}F_3N_6O_2S$: 520.19. found: 521 (M+H).

Example 80

N-(1-(4-hydroxy-4-(2-isopropylthiazol-5-yl)cyclohexyl)azetidin-3-yl)-2-((6-(trifluoromethyl)quinazolin-4-yl)amino)acetamide

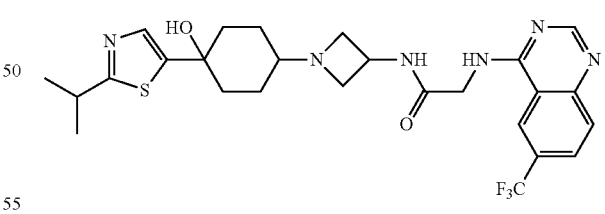

Reaction of 4-hydroxy-4-(2-isopropylthiazol-5-yl)cyclohexanone (prepared by the reaction of 5-bromo-2-isopropylthiazole with 1,4-dioxaspiro[4.5]decan-8-one using the sequence described in Example 24 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (CHLOROFORM-d) δ: 8.59-8.64 (m, 1 H), 8.39-8.48 (m, 1 H), 7.85-7.99 (m, 2 H), 7.38-7.53 (m, 1 H), 7.32 (s, 2 H), 4.42-4.61 (m, 1 H), 4.20-4.29 (m, 2 H), 3.81 (t, J=8.2 Hz,

2 H), 3.43-3.52 (m, 1 H), 3.10 (q, J=7.3 Hz, 5 H), 2.48 (br. s., 1 H), 2.23 (d, J=8.6 Hz, 1 H), 2.00-2.13 (m, 2 H), 1.55-1.91 (m, 6 H), 1.30-1.40 (m, 8 H); ESI-MS (m/z): Calcd. For C$_{26}$H$_{31}$F$_3$N$_6$O$_2$S: 548.22. found: 549 (M+H).

Example 81

N-(1-(4-hydroxy-4-(isothiazol-5-yl)cyclohexyl)azetidin-3-yl)-2-((6-(trifluoromethyl)quinazolin-4-yl)amino)acetamide

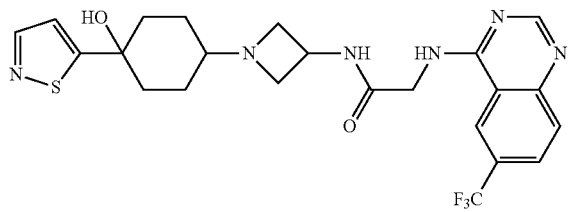 [SMILES: O=C(CNc1ncnc2ccc(C(F)(F)F)cc12)NC1CN(C2CCC(O)(c3ccns3)CC2)C1]

Reaction of 4-hydroxy-4-(isothiazol-5-yl)cyclohexanone (prepared by the reaction of 5-bromoisothiazole with 1,4-dioxaspiro[4.5]decan-8-one using the sequence described in Example 24 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 8.61 (s, 1 H), 8.45-8.51 (m, 1 H), 8.35 (d, J=1.8 Hz, 1 H), 7.92-7.98 (m, 1 H), 7.87-7.92 (m, 1 H), 7.04 (d, J=1.8 Hz, 1 H), 4.62 (t, J=6.8 Hz, 1 H), 4.21-4.31 (m, 2 H), 3.97-4.09 (m, 2 H), 3.79-3.88 (m, 1 H), 3.13 (q, J=7.3 Hz, 6 H), 2.05-2.26 (m, 2 H), 1.78 (d, J=12.9 Hz, 6 H), 1.35 (t, J=7.3 Hz, 9 H); ESI-MS (m/z): Calcd. For C$_{23}$H$_{25}$F$_3$N$_6$O$_2$S: 506.17. found: 507 (M+H).

Example 82

2-((2,6-bis(trifluoromethyl)quinolin-4-yl)amino)-N-(1-((1r,4r)-4-hydroxy-4-(thiazol-5-yl)cyclohexyl)azetidin-3-yl)acetamide

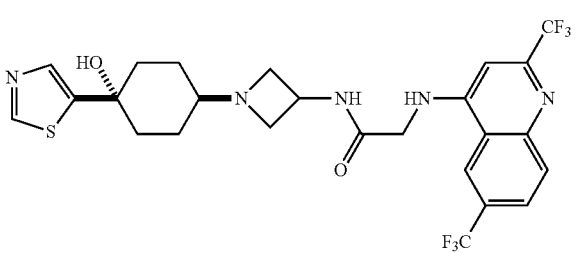

Reaction of 4-Hydroxy-4-thiazol-2-yl-cyclohexanone (prepared as described in Example 26 Step C) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MeOD) δ: 1.34 (s, 5 H) 1.70-1.80 (m, 1 H) 1.82-2.01 (m, 11 H) 2.18-2.27 (m, 1 H) 2.31 (s, 1 H) 3.71 (br. s., 1 H) 4.15 (s, 2 H) 4.47 (s, 1 H) 4.63 (s, 2 H) 6.73 (s, 1 H) 7.81 (s, 1 H) 7.93-8.03 (m, 1 H) 8.12 (s, 1 H) 8.67 (s, 1 H) 8.90 (s, 1 H); ESI-MS (m/z): Calcd. For C$_{25}$H$_{25}$F$_6$N$_5$O$_2$S: 573.16. found: 574 (M+H).

Example 83

N-(1-1r,4r)-4-hydroxy-4-(thiazol-2-yl)cyclohexyl)azetidin-3-yl)-2-((6-(trifluoromethyl)quinazolin-4-yl)amino)acetamide

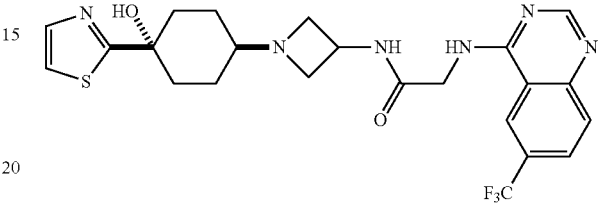

Reaction of 4-Hydroxy-4-thiazol-2-yl-cyclohexanone (prepared as described in Example 24 Step B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MeOD) δ: 8.63 (s, 1 H), 8.56 (s, 1 H), 8.04 (d, J=8.8 Hz, 1 H), 7.88 (d, J=8.6 Hz, 1 H), 7.67 (d, J=3.3 Hz, 1 H), 7.47 (d, J=3.3 Hz, 1 H), 4.44 (quin, J=7.0 Hz, 1 H), 4.28 (s, 2 H), 3.62 (t, J=6.9 Hz, 2 H), 2.93-3.09 (m, 2 H), 2.30-2.42 (m, 3 H), 1.80 (m, J=3.8 Hz, 2 H), 1.59-1.74 (m, 2 H), 1.39-1.54 (m, 2 H); ESI-MS (m/z): Calcd. For C$_{25}$H$_{25}$F$_6$N$_5$O$_2$S: 506.17. found: 507 (M+H).

Example 84

N-(1-1-((1r,4r)-4-hydroxy-1-deutero-4-(thiazol-2-yl)cyclohexyl)azetidin-3-yl)-2-((6-(trifluoromethyl)quinazolin-4-yl)amino)acetamide

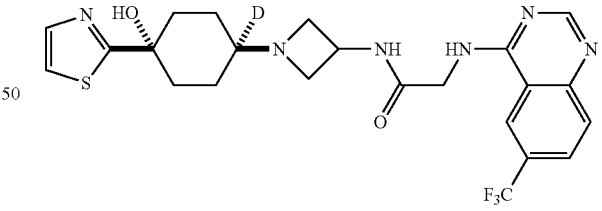

Reaction of 4-Hydroxy-4-thiazol-2-yl-cyclohexanone (prepared as described in Example 24 Step B) with N-(azetidin-3-yl)-2-((6-(trifluoromethyl)quinazolin-4-yl)amino)acetamide (as prepared in Example 1 Step G) in the presence of TEA and NaBD(OAc)$_3$ as described in Example 1, Step H afforded the product.

$^1$H NMR (MeOD) δ: 8.63 (s, 1 H), 8.56 (s, 1 H), 8.04 (d, J=8.8 Hz, 1 H), 7.88 (d, J=8.6 Hz, 1 H), 7.67 (d, J=3.3 Hz, 1 H), 7.47 (d, J=3.3 Hz, 1 H), 4.44 (quin, J=7.0 Hz, 1 H), 4.28 (s, 2 H), 3.62 (t, J=6.9 Hz, 2 H), 2.93-3.09 (m, 2 H), 2.30-2.42 (m, 3 H), 1.80 (m, J=3.8 Hz, 2 H), 1.59-1.74 (m, 2 H), 1.39-1.54 (m, 2 H); ESI-MS (m/z): Calcd. For C$_{25}$H$_{24}$DF$_6$N$_5$O$_2$S: 507.18. found: 508 (M+H).

Example 85

N-(1-1-((1r,4r)-4-hydroxy-4-(thiazol-5-yl)cyclohexyl)azetidin-3-yl)-2-((6-(trifluoromethyl)quinazolin-4-yl)amino)acetamide

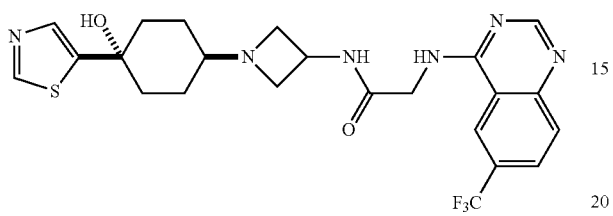

Reaction of 4-hydroxy-4-(thiazol-5-yl)cyclohexanone (prepared as described in Example 26 Step C) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (ACETONITRILE-d3) δ: 1.53 (br. s., 2 H) 1.57-1.68 (m, 2 H) 1.74 (dd, J=13.64, 3.54 Hz, 4 H) 1.85-1.91 (m, 1 H) 2.02 (dd, J=11.12, 3.79 Hz, 3 H) 3.32-3.41 (m, 1 H) 3.50 (d, J=2.27 Hz, 1 H) 3.74 (br. s., 1 H) 3.86 (br. s., 1 H) 3.91-4.01 (m, 2 H) 4.21 (br. s., 2 H) 4.25 (d, J=8.08 Hz, 2 H) 4.69 (s, 2 H) 7.62 (br. s., 1 H) 7.75 (s, 1 H) 7.87-7.97 (m, 2 H) 7.97-8.03 (m, 1 H) 8.51 (s, 1 H) 8.61 (s, 1 H) 8.70 (s, 1 H) 8.73 (s, 1 H); ESI-MS (m/z): Calcd. For C$_{25}$H$_{25}$F$_6$N$_5$O$_2$S: 506.17. found: 507 (M+H).

Example 86

N-(1-((1r,4r)-4-hydroxy-1-deutero-4-(thiazol-5-yl)cyclohexyl)azetidin-3-yl)-2-((6-(trifluoromethyl)quinazolin-4-yl)amino)acetamide

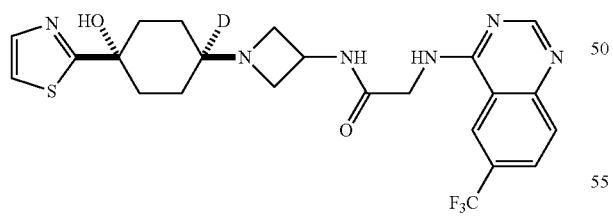

Reaction of 4-Hydroxy-4-thiazol-2-yl-cyclohexanone (prepared as described in Example 26 Step C) with N-(azetidin-3-yl)-2-((6-(trifluoromethyl)quinazolin-4-yl)amino)acetamide (as prepared in Example 1 Step G) in the presence of TEA and NaBD(OAc)$_3$ as described in Example 1, Step H afforded the product.

$^1$H NMR (MeOD) δ: $^1$H NMR (MeOD) δ: 8.89 (s, 1H), 8.58 (s, 1H), 8.54 (s, 1H), 7.97-8.03 (m, 1H), 7.78-7.88 (m, 2H), 4.46 (s, 1H), 4.27 (s, 2H), 3.63 (t, J=7.3 Hz, 2H), 2.97 (t, J=7.6 Hz, 2H), 2.21 (br. s., 2H), 1.67-1.90 (m, 4H), 1.32 (none, 2H); ESI-MS (m/z): Calcd. For C$_{25}$H$_{24}$DF$_6$N$_5$O$_2$S: 507.18. found: 508 (M+H).

Example 87

2-((2,6-bis(trifluoromethyl)quinazolin-4-yl)amino)-N-(1-((1r,4r)-4-hydroxy-4-(thiazol-5-yl)cyclohexyl)azetidin-3-yl)acetamide Step A: 2,6-bis(trifluoromethyl)quinazolin-4-ol

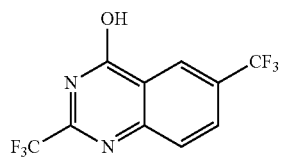 [SMILES: FC(F)(F)c1ccc2nc(C(F)(F)F)nc(Cl)c2c1]

A mixture of Trifluoroacetic anhydride (0.882 mL, 6.35 mmol) and 2-amino-5-(trifluoromethyl)benzoic acid (425 mg, 2.01 mmol) were suspended in heptane (40 mL) and heated under Dean-Stark conditions at 110° C. for 18 hours. After cooling to room temperature, reaction mixture was concentrated in vacuo to 15 mL volume, treated acetic acid, concentrated again to 30 mL total volume, ammonium acetate (1 g, 13 mmol) was added and the mixture was heated to for 4 days. After cooling to room temperature, the reaction was concentrated to dryness in vacuo, and the residue slowly quenched with saturated aqueous NaHCO$_3$. The resulting precipitate was collected by filtration, washed with water and heptanes and dried in vacuo to afford the product as a gold solid.

$^1$H NMR [(400 MHz, ACETONITRILE-d3) δ ppm 7.98 (d, J=8.59 Hz, 1 H) 8.15 (d, J=8.34 Hz, 1 H) 8.53 (s, 1 H); ESI-MS (m/z): Calcd. For C$_{10}$H$_4$F$_6$N$_2$O: 280.02. found: 281 (M+H).

Step B: 4-chloro-2,6-bis(trifluoromethyl)quinazoline

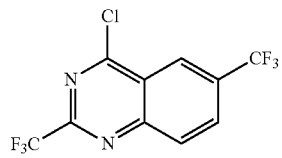

A mixture of 2,6-bis(trifluoromethyl)quinazolin-4-ol (200 mg, 0.666 mmol, prepared in the previous step), DMF (0.01 mL, 0.129 mmol) and diisopropylethylamine (0.17 mL, 0.986 mmol) suspended in dry DCM (10 mL) and treated dropwise with oxalyl chloride (0.11 mL, 1.26 mmol) under argon. After the addition, the reaction mixture was heated to reflux for 4 hours. After cooling to room temperature, the reaction was quenched by the cautious addition of potassium phosphate dibasic solution (20% w/w) and extracted with dichloromethane. The combined organic layers were washed with brine and dried over Na$_2$SO$_4$ and concentrated to yield the product as a white solid.

¹H NMR [(400 MHz, CHLOROFORM-d) δ ppm 8.28 (d, J=8.84 Hz, 1 H) 8.39 (d, J=8.84 Hz, 1 H) 8.68 (s, 1 H).

Step C: tert-butyl 3-(24((2,6-bis(trifluoromethyl) quinazolin-4-yl)amino)acetamido)azetidine-1-carboxylate

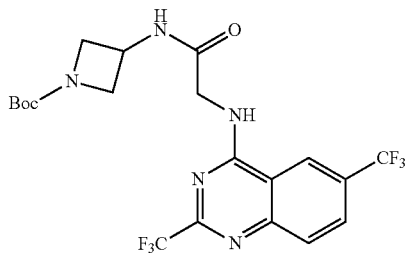 [SMILES: CC(C)(C)OC(=O)N1CC(NC(=O)CNc2nc(C(F)(F)F)nc3ccc(C(F)(F)F)cc23)C1]

A mixture of 4-chloro-2,6-bis(trifluoromethyl)quinazoline (120 mg, 0.399 mmol, prepared in the previous step), tert-butyl 3-(2-aminoacetamido)azetidine-1-carboxylate (133 mg, 0.58 mmol, prepared in Example 1, Step E) and TEA (0.12 mL, 0.863 mmol) was dissolved in dry THF (10 mL) and heated to reflux under argon for 18 hours. The reaction mixture as concentrated in vacuo and the residue purified by flash chromatography (silica gel, 50% EtOAc/Heptane).

¹H NMR [(400 MHz, CHLOROFORM-d) δ ppm 8.78 (br. s., 1 H), 8.22 (br. s., 1 H), 7.92 (d, J=8.8 Hz, 1 H), 7.86 (d, J=8.8 Hz, 1 H), 7.37 (d, J=6.3 Hz, 1 H), 4.68 (br. s., 1 H), 4.21-4.35 (m, 4 H), 3.86 (br. s., 2 H), 1.67 (s, 1 H), 1.46 (br. s., 9 H); ESI-MS (m/z): Calcd. For $C_{20}H_{21}F_6N_5O_3$: 493.15. found: 494 (M+H).

Step D: N-(azetidin-3-yl)-2-((2,6-bis(trifluoromethyl)quinazolin-4-yl)amino)acetamide

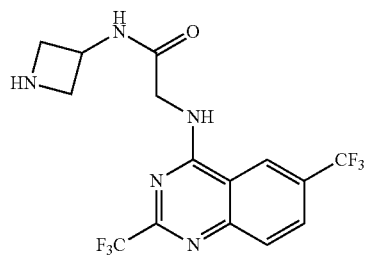 [SMILES: O=C(CNc1nc(C(F)(F)F)nc2ccc(C(F)(F)F)cc12)NC1CNC1]

A solution of tert-butyl 3-(2-((2,6-bis(trifluoromethyl) quinazolin-4-yl)amino)acetamido)azetidine-1-carboxylate (197 mg, 0.399 mmol, prepared in the previous step) was de-protected using the method outlined in Example 1, Step G to afford the title compound.

¹H NMR [(400 MHz, ACETONITRILE-d3) δ ppm 2.09 (s, 2 H) 2.18 (s, 1 H) 4.01 (dd, J=10.99, 6.19 Hz, 2 H) 4.24 (d, J=5.56 Hz, 2 H) 4.29 (dd, 2 H) 4.66-4.77 (m, 1 H) 7.96 (d, 1 H) 8.05 (d, 1 H) 8.50 (d, J=7.58 Hz, 1 H) 8.60 (s, 1 H) 8.73 (t, J=5.05 Hz, 1 H); ESI-MS (m/z): Calcd. For $C_{20}H_{21}F_6N_5O_3$: 393.15. found: 394 (M+H).

Step E: 2-((2,6-bis(trifluoromethyl)quinazolin-4-yl) amino)-N-(1-((1r,4r)-4-hydroxy-4-(thiazol-5-yl)cyclohexyl)azetidin-3-yl)acetamide

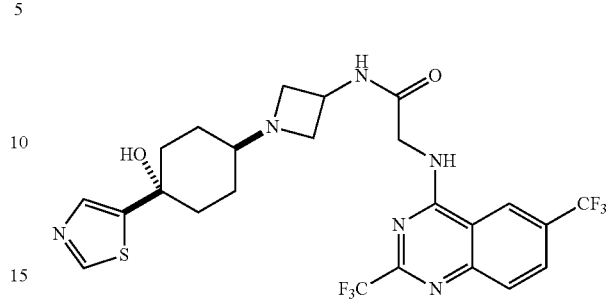

Reaction of N-(azetidin-3-yl)-2-((2,6-bis(trifluoromethyl) quinazolin-4-yl)amino)acetamide (197 mg, 0.399 mmol, prepared in the previous step) with 4-hydroxy-4-(thiazol-5-yl) cyclohexanone (prepared as described in Example 26 Step C) in the presence of TEA and NaBH(OAc)₃ as described in Example 1, Step H afforded the product.

¹H NMR [(400 MHz, THF-d8) δ ppm 0.88 (d, J=6.32 Hz, 2 H) 1.45 (dd, J=13.52, 3.41 Hz, 2 H) 1.54-1.67 (m, 2 H) 1.80-1.91 (m, 2 H) 2.14 (td, J=12.51, 3.54 Hz, 2 H) 2.25 (br. s., 1 H) 2.52 (d, J=8.84 Hz, 2 H) 2.82 (t, J=6.32 Hz, 2 H) 3.48-3.56 (m, 2 H) 4.27 (d, J=5.05 Hz, 2 H) 4.42-4.50 (m, 1 H) 7.67 (s, 1 H) 7.90 (d, J=7.33 Hz, 1 H) 7.95-8.01 (m, 1 H) 8.01-8.07 (m, 1 H) 8.59 (s, 1 H) 8.68 (s, 1 H) 8.74 (t, J=5.05 Hz, 1 H); ESI-MS (m/z): Calcd. For $C_{24}H_{24}F_6N_6O_2S$: 574.14. found: 575 (M+H).

Example 88

N-(1-((1-((1r,4r)-4-hydroxy-4-(thiazol-5-yl)cyclohexyl)azetidin-3-yl)-2-((2-isopropyl-6-(trifluoromethyl)quinazolin-4-yl)amino)acetamide

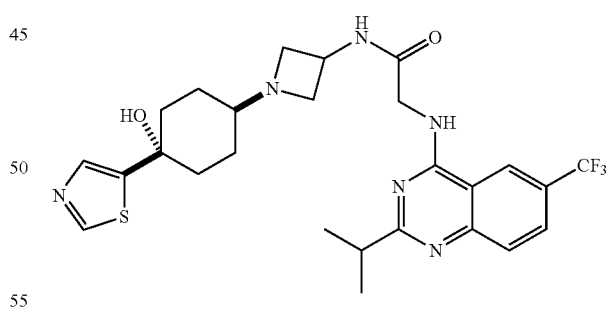

Reaction of 4-hydroxy-4-(thiazol-5-yl)cyclohexanone (prepared as described in Example 26 Step C) with N-(azetidin-3-yl)-2-((2-isopropyl-6-(trifluoromethyl)quinazolin-4-yl)amino)acetamide (prepared by the reaction of 2-amino-5-(trifluoromethyl)benzoic acid with isobutyric anhydride using the sequence described in Example 87 Step A-D) in the presence of TEA and NaBH(OAc)₃ as described in Example 1, Step H afforded the product.

¹H NMR (DMSO-d6) δ: 1.23 (d, J=6.82 Hz, 6 H) 1.29-1.41 (m, 2 H) 1.59-1.71 (m, 2 H) 1.80-1.90 (m, 2 H) 2.05 (br. s., 2

H) 2.53-2.71 (m, 7 H) 2.94 (quin, J=6.82 Hz, 1 H) 3.89-4.03 (m, 1 H) 4.08 (d, J=5.05 Hz, 2 H) 4.35-4.50 (m, 1 H) 5.56 (s, 1 H) 7.77 (s, 1 H) 7.82 (d, J=8.59 Hz, 1H) 8.00 (dd, J=8.84, 1.52 Hz, 1 H) 8.52 (d, J=7.07 Hz, 1 H) 8.75 (s, 1 H) 8.94-9.01 (m, 2 H); ESI-MS (m/z): Calcd. For $C_{26}H_{31}F_3N_6O_2S$: 548.22. found: 549 (M+H).

Example 89

N-(1-((1r,4r)-4-hydroxy-4-(thiazol-5-yl)cyclohexyl)azetidin-3-yl)-2-((2-methyl-6-(trifluoromethyl)quinazolin-4-yl)amino)acetamide

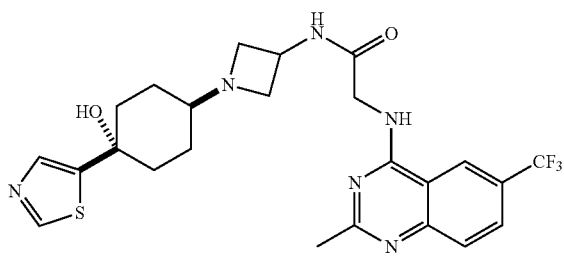

Reaction of 4-hydroxy-4-(thiazol-5-yl)cyclohexanone (prepared as described in Example 26 Step C) with N-(azetidin-3-yl)-2-((2-methyl-6-(trifluoromethyl)quinazolin-4-yl)amino)acetamide (prepared by the reaction of 2-amino-5-(trifluoromethyl)benzoic acid with acetic anhydride using the sequence described in Example 87 Step A-D) in the presence of TEA and NaBH(OAc)$_3$ as described in Example 1, Step H afforded the product.

$^1$H NMR (THF-d8) δ: 1.36-1.48 (m, 2 H) 1.61 (d, J=12.88 Hz, 2 H) 1.83 (t, J=12.76 Hz, 2 H) 2.13 (td, J=12.38, 3.54 Hz, 2 H) 2.23 (br. s., 0 H) 2.51 (s, 3 H) 2.79 (t, J=6.57 Hz, 2 H) 3.54 (t, J=6.95 Hz, 2 H) 4.20 (d, J=5.05 Hz, 2 H) 4.46 (s, 1 H) 7.67 (s, 1 H) 7.69-7.77 (m, 2 H) 7.86 (dd, J=8.84, 1.77 Hz, 1 H) 8.03 (t, J=5.31 Hz, 1 H) 8.40 (s, 1 H) 8.67 (s, 1 H); ESI-MS (m/z): Calcd. For $C_{24}H_{27}F_3N_6O_2S$: 520.19. found: 521 (M+H).

Example 90

N-(1-((1S,4s)-4-(1-hydroxybutyl)cyclohexyl)azetidin-3-yl)-2-((6-(trifluoromethyl)quinazolin-4-yl)amino)acetamide

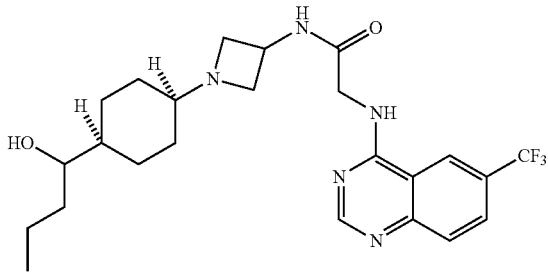 [SMILES: CCCC(O)[C@H]1CC[C@@H](N2CC(NC(=O)CNc3ncnc4ccc(C(F)(F)F)cc34)C2)CC1]

Reaction of 4-(1-hydroxybutyl)cyclohexanone (prepared by the reaction of 1,4-dioxaspiro[4.5]decane-8-carbaldehyde with propylmagnesium chloride using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. ESI-MS (m/z): Calcd. For $C_{24}H_{32}F_3N_5O_2$: 479.25. found: 480 (M+H).

Example 91

N-(1-((1S,4s)-4-(1-hydroxybut-3-en-1-yl)cyclohexyl)azetidin-3-yl)-2-((6-(trifluoromethyl)quinazolin-4-yl)amino)acetamide

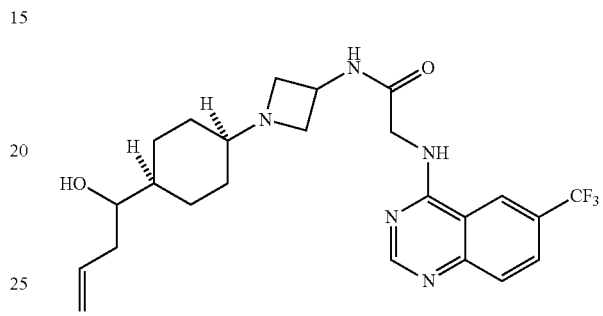

Reaction of 4-(1-hydroxybut-3-en-1-yl)cyclohexanone (prepared by the reaction of 1,4-dioxaspiro[4.5]decane-8-carbaldehyde with allylmagnesium chloride using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{24}H_{30}F_3N_5O_2$: 477.24. found: 478 (M+H).

Example 92

N-(1-((1S,4s)-4-(1-hydroxyallyl)cyclohexyl)azetidin-3-yl)-2-((6-(trifluoromethyl)quinazolin-4-yl)amino)acetamide

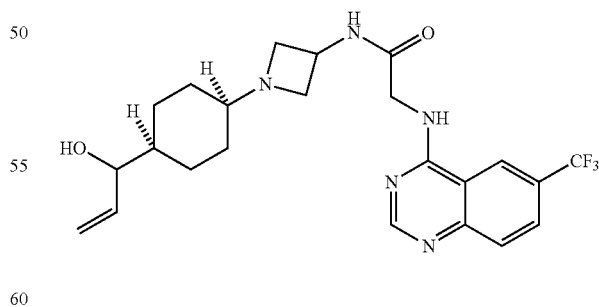

Reaction of 4-(1-hydroxyallyl)cyclohexanone (prepared by the reaction of 1,4-dioxaspiro[4.5]decane-8-carbaldehyde with vinylmagnesium chloride using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{23}H_{28}F_3N_5O_2$: 463.22. found: 464 (M+H).

Example 93

N-(1-((1S,4s)-4-(1-hydroxypropyl)cyclohexyl)azetidin-3-yl)-2-((6-(trifluoromethyl)quinazolin-4-yl)amino)acetamide

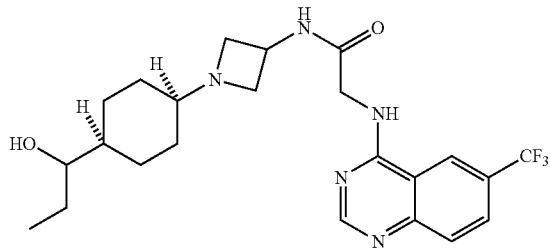 [SMILES: CCC(O)[C@H]1CC[C@@H](N2CC(NC(=O)CNc3ncnc4ccc(C(F)(F)F)cc34)C2)CC1]

Reaction of 4-(1-hydroxypropyl)cyclohexanone (prepared by the reaction of 1,4-dioxaspiro[4.5]decane-8-carbaldehyde with ethylmagnesium chloride using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MeOH) δ: 8.59 (s, 1H), 8.54 (s, 1H), 7.97-8.04 (m, 1H), 7.85 (d, J=8.8 Hz, 1H), 4.47 (s, 1H), 4.27 (s, 2H), 3.61 (t, J=7.2 Hz, 2H), 2.91 (s, 2H), 2.18-2.31 (m, 1H), 1.26-1.67 (m, 12H), 0.94 (t, 3H); ESI-MS (m/z): Calcd. For $C_{23}H_{30}F_3N_5O_2$: 465.24. found: 466 (M+H).

Example 94

N-(1-((1S,4s)-4-(cyclopentyl(hydroxy)methyl)cyclohexyl)azetidin-3-yl)-2-((6-(trifluoromethyl)quinazolin-4-yl)amino)acetamide

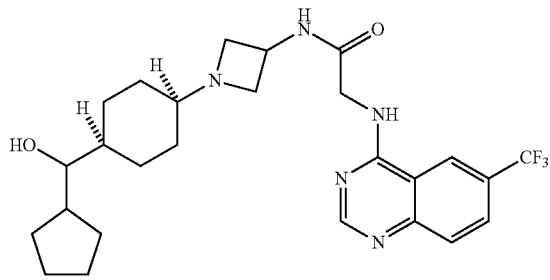 [SMILES: O=C(CNc1ncnc2ccc(C(F)(F)F)cc12)NC1CN([C@H]2CC[C@@H](C(O)C3CCCC3)CC2)C1]

Reaction of 4-(cyclopentyl(hydroxy)methyl)cyclohexanone (prepared by the reaction of 1,4-dioxaspiro[4.5]decane-8-carbaldehyde with cyclopentylmagnesium chloride using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{26}H_{34}F_3N_5O_2$: 505.27. found: 506 (M+H).

Example 95

N-(1-((1R,4s)-4-(1-hydroxyprop-2-yn-1-yl)cyclohexyl)azetidin-3-yl)-2-((6-(trifluoromethyl)quinazolin-4-yl)amino)acetamide

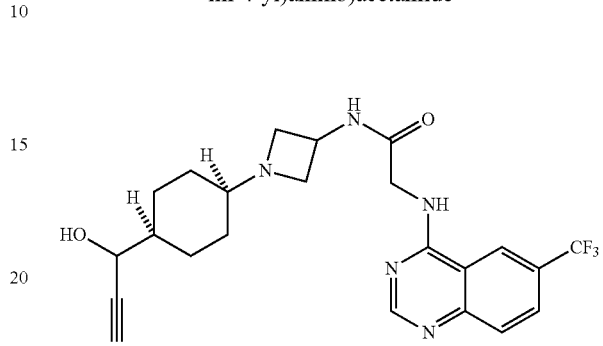

Reaction of 4-(1-hydroxyprop-2-yn-1-yl)cyclohexanone (prepared by the reaction of 1,4-dioxaspiro[4.5]decane-8-carbaldehyde with ethynylmagnesium bromide using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{23}H_{26}F_3N_5O_2$: 461.20. found: 462 (M+H).

Example 96

N-(1-((1R,4s)-4-(1-hydroxy-2-methylallyl)cyclohexyl)azetidin-3-yl)-2-((6-(trifluoromethyl)quinazolin-4-yl)amino)acetamide

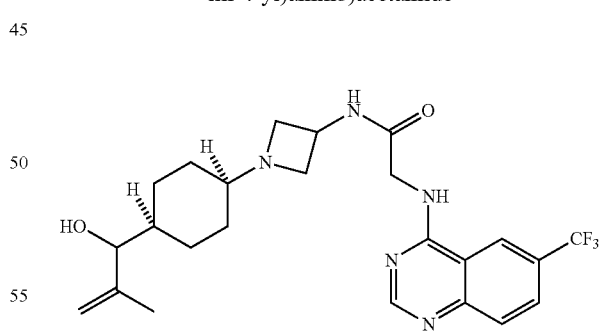

Reaction of 4-(1-hydroxy-2-methylallyl)cyclohexanone (prepared by the reaction of 1,4-dioxaspiro[4.5]decane-8-carbaldehyde with isopropenylmagnesium chloride using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For $C_{24}H_{30}F_3N_5O_2$: 477.24. found: 478 (M+H).

Example 97

N-(1-((1S,4s)-4-(1-hydroxyethyl)cyclohexyl)azetidin-3-yl)-2-((6-(trifluoromethyl)quinazolin-4-yl)amino)acetamide

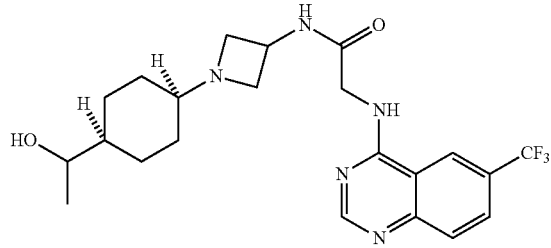 [SMILES: CC(O)[C@H]1CC[C@@H](N2CC(NC(=O)CNc3ncnc4ccc(C(F)(F)F)cc34)C2)CC1]

Reaction of 4-(1-hydroxyethyl)cyclohexanone (prepared by the reaction of 1,4-dioxaspiro[4.5]decane-8-carbaldehyde with methylmagnesium chloride using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. Calcd. For $C_{22}H_{28}F_3N_5O_2$: 451.22. found: 452 (M+H).

Example 98

N-(1-((1R,4s)-4-(1-hydroxy-2,2-dimethylpropyl)cyclohexyl)azetidin-3-yl)-2-((6-(trifluoromethyl)quinazolin-4-yl)amino)acetamide

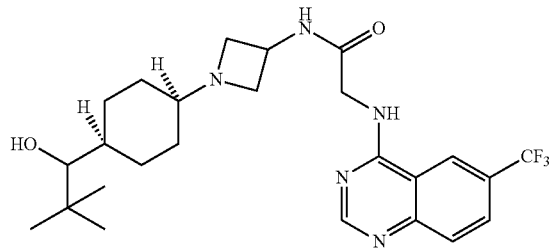 [SMILES: CC(C)(C)C(O)[C@H]1CC[C@@H](N2CC(NC(=O)CNc3ncnc4ccc(C(F)(F)F)cc34)C2)CC1]

Reaction of 4-(1-hydroxy-2,2-dimethylpropyl)cyclohexanone (prepared by the reaction of 1,4-dioxaspiro[4.5]decane-8-carbaldehyde with tert-butylmagnesium chloride using the sequence described in Example 3 Step A-B) with N-(azetidin-3-yl)-2-(6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MeOH) δ: 8.60 (s, 1H), 8.55 (s, 1H), 7.98-8.04 (m, 1H), 7.83-7.89 (m, 1H), 4.41-4.52 (m, 1H), 4.27 (s, 2H), 3.57-3.66 (m, 2H), 3.00-3.05 (m, 1H), 2.85-2.95 (m, 2H), 2.18-2.29 (m, 1H), 1.25 (s, 10H), 0.90 (s, 9H); ESI-MS (m/z): Calcd. For $C_{25}H_{34}F_3N_5O_2$: 493.27; found: 494 (M+H).

Example 99

N-(1-((1R,4s)-4-(hydroxy(thiazol-5-yl)methyl)cyclohexyl)azetidin-3-yl)-2-((6-(trifluoromethyl)quinazolin-4-yl)amino)acetamide

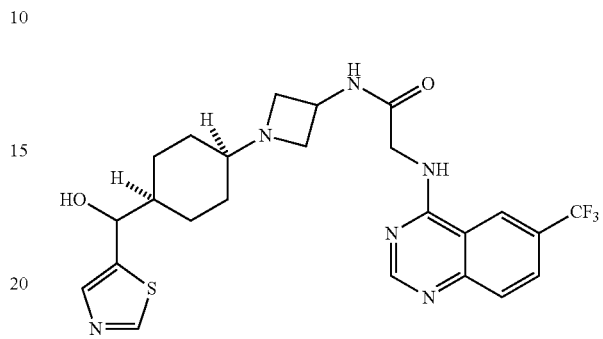

Reaction of 4-(hydroxy(thiazol-5-yl)methyl)cyclohexanone (prepared by the reaction of 1,4-dioxaspiro[4.5]decane-8-carbaldehyde with (2-(tert-butyldimethylsilyl)thiazol-5-yl)lithium using the sequence described in Example 3 Step A-B) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (MeOH) δ: 8.92 (s, 1H), 8.59 (s, 1H), 8.54 (s, 1H), 7.96-8.05 (m, 1H), 7.82-7.89 (m, 1H), 7.73 (s, 1H), 4.82 (d, J=8.1 Hz, 1H), 4.41-4.53 (m, 1H), 4.27 (s, 2H), 4.05-4.15 (m, 1H), 3.62 (d, J=8.3 Hz, 3H), 2.92 (d, J=7.1 Hz, 3H), 2.19-2.30 (m, 1H), 1.24 (m, 11H); ESI-MS (m/z): Calcd. For $C_{24}H_{27}F_3N_6O_2S$: 520.19. found: 521 (M+H).

Example 100

1-((1s,4S)-4-(3-(2-((6-(trifluoromethyl)quinazolin-4-yl)amino)acetamido)azetidin-1-yl)cyclohexyl)propyl acetate

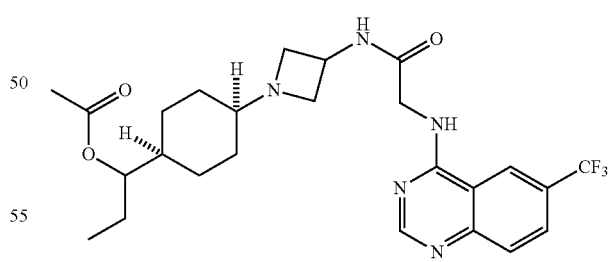

Reaction of 1-(4-oxocyclohexyl)propyl acetate with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (MeOD) δ: 8.58-8.63 (m, 1H), 8.54 (s, 1H), 7.98-8.06 (m, 1H), 7.86 (d, J=8.8 Hz, 1H), 4.75-4.86 (m, 1H), 4.46 (s, 1H), 4.27 (s, 2H), 3.56-3.67 (m, 2H), 3.31 (d, J=1.5 Hz, 3H), 2.87-2.96 (m, 2H), 2.26 (br. s., 1H), 2.02-2.08 (s, 3H), 1.61-1.72 (m, 1H), 1.40 (m., 12H), 0.85 (t, 3H); ESI-MS (m/z): Calcd. For C$_{25}$H$_{32}$F$_3$N$_5$O$_3$: 507.25. found: 508 (M+H).

Example 101

N-(1-cyclohexylazetidin-3-yl)-2-((6-(trifluoromethyl)quinazolin-4-yl)amino)acetamide

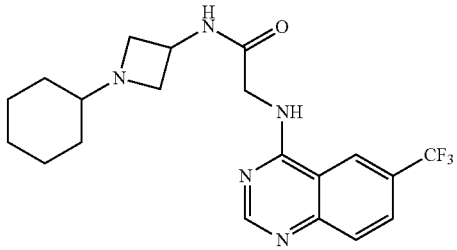 [SMILES: O=C(CNc1ncnc2ccc(C(F)(F)F)cc12)NC1CN(C2CCCCC2)C1]

Reaction of cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For C$_{20}$H$_{24}$F$_3$N$_5$O: 407.19. found: 408 (M+H).

Example 102

N-(1-((1s,4s)-1~1,1'-bi(cyclohexan)1-4-yl)azetidin-3-yl)-2-((6-(trifluoromethyl)quinazolin-4-yl)amino)acetamide

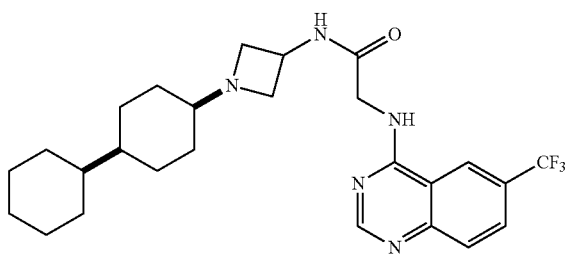 [SMILES: O=C(CNc1ncnc2ccc(C(F)(F)F)cc12)NC1CN([C@H]2CC[C@@H](C3CCCCC3)CC2)C1]

Reaction of cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For C$_{26}$H$_{34}$F$_3$N$_5$O: 489.27. found: 490 (M+H).

Example 103

N-(1-(4-oxocyclohexyl)azetidin-3-yl)-2-((6-(trifluoromethyl)quinazolin-4-yl)amino)acetamide

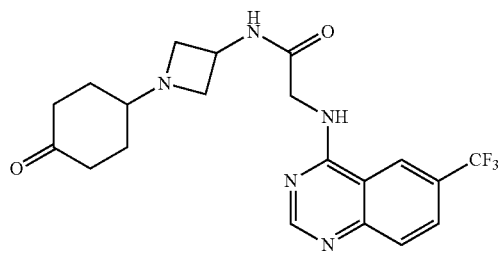 [SMILES: O=C1CCC(N2CC(NC(=O)CNc3ncnc4ccc(C(F)(F)F)cc34)C2)CC1]

Reaction of 1,4-dioxaspiro[4.5]decan-8-one with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H followed by acidic deprotection of the ketal afforded the product.

ESI-MS (m/z): Calcd. For C$_{20}$H$_{22}$F$_3$N$_5$O$_2$: 421.17. found: 422 (M+H).

Example 104: methyl (–1-((1s,4S)-4-(3-(2-((6-(trifluoromethyl)quinazolin-4-yl)amino)acetamido)azetidin-1-yl)cyclohexyl)propyl)carbamate Step A: N-(1-(1,4-dioxaspiro[4.5]decan-8-yl)propyl)-2-methylpropane-2-sulfinamide

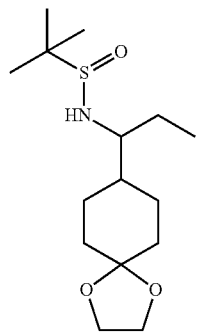 [SMILES: CCC(NS(=O)C(C)(C)C)C1CCC2(CC1)OCCO2]

A solution of (E)-N-(1,4-dioxaspiro[4.5]decan-8-ylmethylene)-2-methylpropane-2-sulfinamide (as prepared in of Example 11 Step A, 3.66 g, 13.4 mmol) in dry THF (100 mL) was placed under an argon atmosphere and treated with ethylmagnesium chloride dropwise. After stirring at ambient temperature for 2 hours, the reaction mixture was cooled to –10° C. and cautiously quenched by the addition of saturated ammonium chloride solution. After dilution with water and ether extraction, the organic layer was concentrated in vacuo. Purification of the residue by flash chrom (silica gel, ethyl acetate) afforded the titled compound as a solid. $^1$H NMR (CHLOROFORM-d) δ: 3.80-4.00 (m, 4H), 2.85-3.15 (series of m, 2H), 1.71 (series of m, 11H), 1.20-1.25 (s, 9H), 0.97 (t, J=7.5 Hz, 3H)

Step B: 1-(1,4-dioxaspiro[4.5]decan-8-yl)propan-1-amine HCl salt

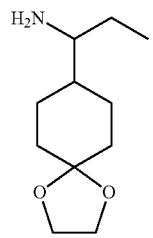

To a solution of N-(1-(1,4-dioxaspiro[4.5]decan-8-yl)propyl)-2-methylpropane-2-sulfinamide (as prepared in the previous step, 2.55 g, 8.39 mmol) in dry MeOH (50 mL) was added HCl (14 mL, 17.5 mmol, 1.25 M in MeOH) at room temperature. After stirring overnight at ambient temperature, the reaction mixture was concentrated in vacuo. Trituration of the residue with ether, followed by decantation of the supernatant and drying the residue under high vacuum afforded the product as a white foam.

MS: 200 (MH$^+$)

Step C: methyl N-(1-1,4-dioxaspiro[4.5]decan-8-ylpropyl)carbamate

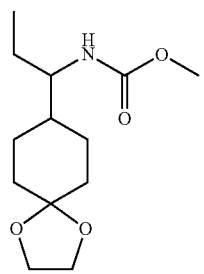 [SMILES: CCC(NC(=O)OC)C1CCC2(CC1)OCCO2]

Into a 50 mL round-bottom flask was placed a solution of 1-1,4-dioxaspiro[4.5]decan-8-ylpropan-1-amine hydrochloride (as prepared in the previous step, 50 mg, 0.21 mmol, 1.00 equiv) in dichloromethane (10 mL) and TEA (42.8 mg, 0.42 mmol, 2.00 equiv). This was followed by the addition of methyl carbonochloridate (23.9 mg, 0.25 mmol, 1.20 equiv) dropwise with stirring at 0° C. The resulting solution was stirred overnight at room temperature. The reaction was then quenched by the addition of 20 mL of water. The resulting solution was extracted with 2×20 mL of dichloromethane. The organic layers were combined, dried over anhydrous sodium sulfate and concentrated under vacuum to give the title compound as a yellow oil.

Step D: methyl 1-(4-oxocyclohexyl)propylcarbamate

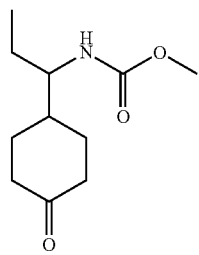

A solution of methyl N-(1-1,4-dioxaspiro[4.5]decan-8-ylpropyl)carbamate (as prepared in the previous step, 39 mg, 0.15 mmol, 1.00 equiv) in CH$_3$CN (5 mL) and HCl (2M, 1 mL) was stirred for 2 h at room temperature. The resulting mixture was concentrated under vacuum. The residue was diluted with 10 mL of aq. sodium bicarbonate (1M). The resulting solution was extracted with 2×20 mL of dichloromethane. The organic layers were combined, dried over anhydrous sodium sulfate and concentrated under vacuum to give the title compound as a yellow oil.

Step E: methyl (−1-((1s,4S)-4-(3-(2-((6-(trifluoromethyl)quinazolin-4-yl)amino)acetamido)azetidin-1-yl)cyclohexyl)propyl)carbamate

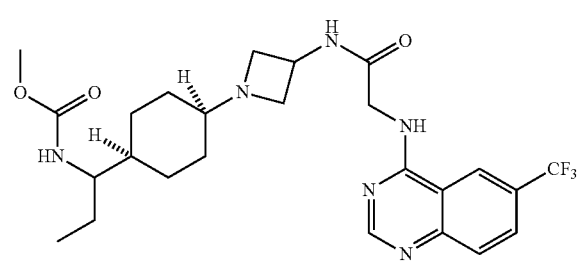 [SMILES: CCC(NC(=O)OC)[C@H]1CC[C@@H](N2CC(NC(=O)CNc3ncnc4ccc(C(F)(F)F)cc34)C2)CC1]

Reaction of methyl (1-(4-oxocyclohexyl)propyl)carbamate (as prepared in the previous step) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

ESI-MS (m/z): Calcd. For C$_{22}$H$_{33}$F$_3$N$_6$O$_3$: 522.26. found: 523 (M+H).

Example 105

N-(1-(4-(ethoxymethyl)cyclohexyl)azetidin-3-yl)-2-((6-(trifluoromethyl)quinazolin-4-yl)amino)acetamide

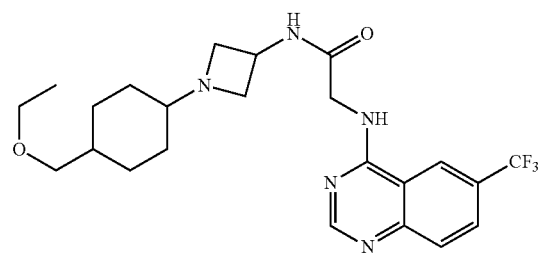 [SMILES: CCOCC1CCC(N2CC(NC(=O)CNc3ncnc4ccc(C(F)(F)F)cc34)C2)CC1]

Reaction of 4-(ethoxymethyl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 0.79-1.04 (m, 2 H) 1.02-1.16 (m, 5 H) 1.22-1.39 (m, 8 H) 1.47 (d, J=4.04 Hz, 4 H) 1.66-1.79 (m, 1 H) 2.71 (t, J=7.33 Hz, 2 H) 3.14-3.21 (m, 3 H) 3.30-3.44 (m, 3 H) 3.48 (t, J=7.33 Hz, 2 H) 4.15 (d, J=5.81 Hz, 2 H) 4.23-4.39 (m, 1 H) 7.03 (br. s., 1 H) 7.33-7.47 (m, 1 H) 7.85-7.94 (m, 1 H) 7.98 (dd, J=8.84, 1.52 Hz, 1 H) 8.39 (s, 1 H) 8.59 (s, 1 H); ESI-MS (m/z): Calcd. For C$_{23}$H$_{30}$F$_3$N$_5$O$_2$: 465.24. found: 466 (M+H).

Example 106

(1s,4s)-ethyl 4-(3-(2-((6-(trifluoromethyl)quinazolin-4-yl)amino)acetamido)azetidin-1-yl)cyclohexanecarboxylate

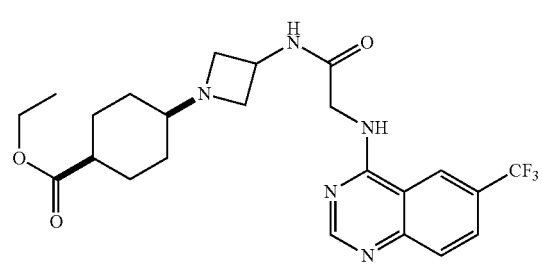 [SMILES: CCOC(=O)[C@H]1CC[C@@H](N2CC(NC(=O)CNc3ncnc4ccc(C(F)(F)F)cc34)C2)CC1]

Reaction of ethyl 4-oxocyclohexanecarboxylate with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 8.58 (s, 1 H), 8.45 (s, 1 H), 8.20 (br. s., 1 H), 7.96 (m, J=8.8, 1.8 Hz, 1 H), 7.87 (m, J=8.8 Hz, 1 H), 7.77 (br. s., 1 H), 4.46-4.61 (m, 1 H), 4.18 (s, 2 H), 4.07 (q, J=7.1 Hz, 2 H), 3.96 (t, J=8.7 Hz, 2 H), 3.51 (dd, J=9.2, 6.2 Hz, 2 H), 2.70 (m, J=8.6, 4.5, 3.5, 3.5 Hz, 1 H), 2.47 (quin, J=5.1 Hz, 1 H), 1.96-2.02 (m, 2 H), 1.89 (s, 2 H), 1.57-1.67 (m, 2 H), 1.45-1.55 (m, 2 H), 1.32-1.45 (m, 2 H), 1.19 (t, J=7.1 Hz, 3 H); ESI-MS (m/z): Calcd. For C$_{23}$H$_{28}$F$_3$N$_5$O$_3$: 479.21. found: 480 (M+H).

Example 107

N-(1-((1s,4s)-4-phenylcyclohexyl)azetidin-3-yl)-2-((6-(trifluoromethyl)quinazolin-4-yl)amino)acetamide

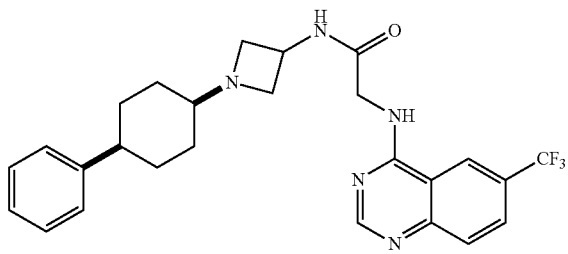 [SMILES: O=C(CNc1ncnc2ccc(C(F)(F)F)cc12)NC1CN([C@H]2CC[C@@H](c3ccccc3)CC2)C1]

Reaction of 4-phenylcyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (MEOD) δ: 8.64 (s, 1 H), 8.36 (s, 1 H), 7.91 (dd, J=8.8, 1.8 Hz, 1 H), 7.90 (d, J=8.8 Hz, 1 H), 7.24-7.30 (m, 4 H), 7.13-7.22 (m, 1 H), 4.58 (br. s., 1 H), 4.26 (s, 2 H), 3.67 (br. s., 2 H), 3.10 (br. s., 1 H), 2.50-2.60 (m, 1 H), 1.77-1.92 (m, 2 H), 1.69 (d, J=2.0 Hz, 2 H), 1.43-1.65 (m, 4 H); ESI-MS (m/z): Calcd. For C$_{26}$H$_{28}$F$_3$N$_5$O: 483.22. found: 484 (M+H).

Example 108

N-(1-((1s,4s)-4-(2-hydroxyethyl)cyclohexyl)azetidin-3-yl)-2-((6-(trifluoromethyl)quinazolin-4-yl)amino)acetamide

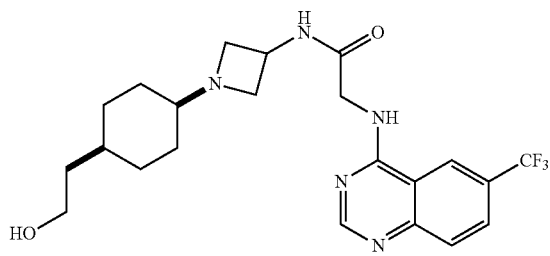 [SMILES: O=C(CNc1ncnc2ccc(C(F)(F)F)cc12)NC1CN([C@H]2CC[C@@H](CCO)CC2)C1]

Reaction of 4-(2-hydroxyethyl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (DMSO-d6) δ: 1.17-1.35 (m, 8 H) 1.35-1.48 (m, 3 H) 2.16 (br. s., 0 H) 2.74 (br. s., 2 H) 3.38-3.50 (m, 4 H) 4.12 (d, J=5.81 Hz, 2 H) 4.18-4.34 (m, 2 H) 7.88 (d, J=8.59 Hz, 1 H) 8.06 (dd, J=8.84, 1.52 Hz, 1 H) 8.42 (d, J=7.07 Hz, 1 H) 8.56 (s, 1 H) 8.80 (s, 1 H) 9.01 (t, J=5.68 Hz, 1 H); ESI-MS (m/z): Calcd. For C$_{22}$H$_{28}$F$_3$N$_5$O$_2$: 451.22. found: 452 (M+H).

Example 109

N-(1-((1s,4s)-4-(hydroxymethyl)cyclohexyl)azetidin-3-yl)-2-((6-(trifluoromethyl)quinazolin-4-yl)amino)acetamide

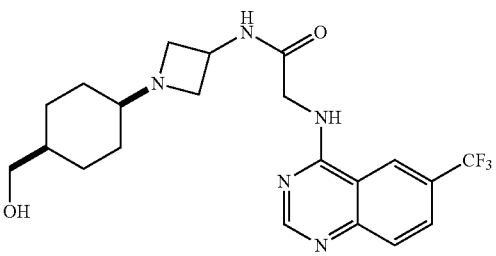 [SMILES: O=C(CNc1ncnc2ccc(C(F)(F)F)cc12)NC1CN([C@H]2CC[C@@H](CO)CC2)C1]

Reaction of 4-(hydroxymethyl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 8.59 (s, 1 H), 8.39 (s, 1 H), 7.92-8.02 (m, 1 H), 7.83-7.92 (m, 1 H), 7.38-7.51 (m, 1 H), 7.00-7.15 (m, 1 H), 4.33 (m, J=14.7, 7.1, 7.1, 7.1, 7.1 Hz, 1 H), 4.15 (d, J=5.8 Hz, 2 H), 3.45-3.54 (m, 2 H), 3.22-3.31 (m, 3 H), 2.79 (t, J=7.3 Hz, 1 H), 2.73 (t, J=7.2 Hz, 1 H), 1.79-1.91 (m, 1 H), 1.65-1.79 (m, 2 H), 1.21-1.53 (m, 5 H), 1.07-1.23 (m, 1 H), 0.80-1.01 (m, 2 H); ESI-MS (m/z): Calcd. For C$_{21}$H$_{26}$F$_3$N$_5$O$_2$: 437.20. found: 438 (M+H).

Example 110

N-(1-((1s,4s)-4-hydroxycyclohexyl)azetidin-3-yl)-2-((6-(trifluoromethyl)quinazolin-4-yl)amino)acetamide

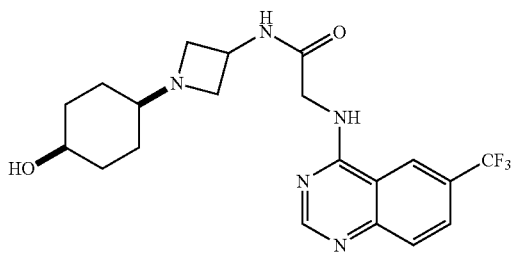 [SMILES: O=C(CNc1ncnc2ccc(C(F)(F)F)cc12)NC1CN([C@H]2CC[C@@H](O)CC2)C1]

Reaction of 4-hydroxycyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 0.88-1.06 (m, 1 H) 1.06-1.21 (m, 1 H) 1.32-1.50 (m, 4 H) 1.52-1.66 (m, 1 H)

1.72 (d, J=11.87 Hz, 1 H) 1.77-1.88 (m, 1 H) 1.99-2.26 (m, 1 H) 3.00 (ddd, J=17.94, 8.34, 6.57 Hz, 2 H) 3.35-3.74 (m, 3 H) 4.18 (d, J=2.78 Hz, 2 H) 4.39 (sxt, J=6.97 Hz, 1 H) 7.88 (m, J=8.84 Hz, 1 H) 7.98 (dd, J=8.72, 1.89 Hz, 1 H) 8.43 (s, 1 H) 8.58 (s, 1 H);

ESI-MS (m/z): Calcd. For $C_{20}H_{24}F_3N_5O_2$: 423.19. found: 424 (M+H).

Example 111

N-(1-((1s,4s)-4-(acetamidomethyl)cyclohexyl)azetidin-3-yl)-2-((6-(trifluoromethyl)quinazolin-4-yl)amino)acetamide

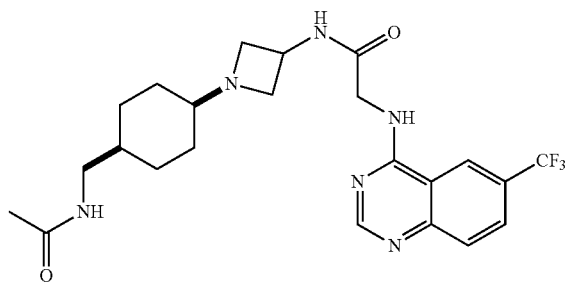 [SMILES: CC(=O)NC[C@H]1CC[C@@H](N2CC(NC(=O)CNc3ncnc4ccc(C(F)(F)F)cc34)C2)CC1]

Reaction of N-((4-oxocyclohexyl)methyl)acetamide with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 1.35-1.75 (m, 9 H) 1.84 (s, 3 H) 2.99-3.10 (m, 2 H) 3.14-3.22 (m, 1 H) 3.92 (br. s., 2 H) 4.22 (s, 4 H) 4.62 (br. s., 1 H) 6.95 (br. s., 1 H) 7.84-8.06 (m, 2 H) 8.51 (s, 1 H) 8.64 (s, 1 H); ESI-MS (m/z): Calcd. For $C_{23}H_{29}F_3N_6O_2$: 478.23. found: 479 (M+H).

Example 112

2,2,2-trifluoro-N-(((1s,4s)-4-(3-(2-((6-(trifluoromethyl)quinazolin-4-yl)amino)acetamido)azetidin-1-yl)cyclohexyl)methyl)acetamide

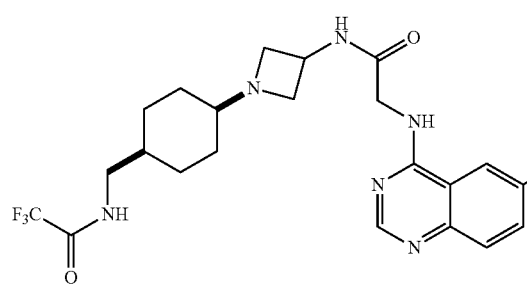

Reaction of 2,2,2-trifluoro-N-((4-oxocyclohexyl)methyl) acetamide with N-(azetidin-3-yl)-2-((6-(trifluoromethyl) quinazolin-4-yl)amino)acetamide (as prepared in Example 1 Step G) in the presence of TEA and NaBH(OAc)$_3$ as described in Example 1, Step H afforded the product.

$^1$H NMR (ACETONITRILE-d3) δ: 1.40-1.69 (m, 8 H) 1.80 (br. s., 1 H) 3.06-3.25 (m, 3 H) 4.04 (m, J=8.34 Hz, 4 H) 4.21 (s, 2 H) 4.55 (br. s., 1 H) 7.79-7.91 (m, 2 H) 8.37 (s, 1 H) 8.56 (s, 1 H); ESI-MS (m/z): Calcd. For $C_{23}H_{26}F_6N_6O_2$: 532.20. found: 533 (M+H).

Example 113 tert-butyl (((1s,4s)-4-(3-(2-((6-(trifluoromethyl)quinazolin-4-yl)amino)acetamido)azetidin-1-yl)cyclohexyl)methyl)carbamate

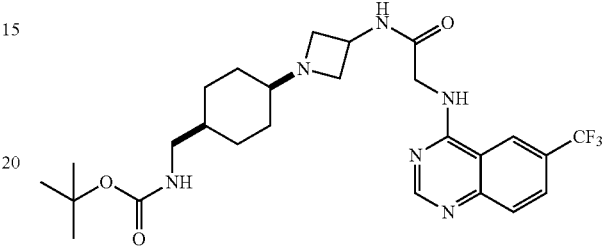

Reaction of tert-butyl ((4-oxocyclohexyl)methyl)carbamate with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 8.70 (s, 1 H), 8.25 (s, 1 H), 7.91 (s, 2 H), 7.27-7.33 (m, 1 H), 4.75-4.84 (m, 1 H), 4.68 (d, J=4.5 Hz, 1 H), 4.35 (d, J=5.1 Hz, 2 H), 3.71 (br. s., 2 H), 3.47 (br. s., 2 H), 3.07 (t, J=6.1 Hz, 2 H), 2.53 (br. s., 1 H), 1.46-1.70 (m, 8 H), 1.44 (s, 12 H); ESI-MS (m/z): Calcd. For $C_{23}H_{26}F_3N_6O_2$: 536.27. found: 537 (M+H).

Example 114

N-(((1s,4s)-4-(3-(2-((6-(trifluoromethyl)quinazolin-4-yl)amino)acetamido)azetidin-1-yl)cyclohexyl)methyl)isobutyramide

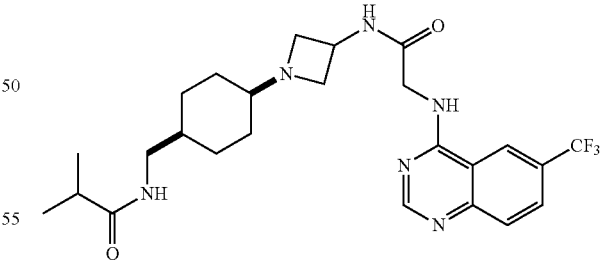

Reaction of N-((4-oxocyclohexyl)methyl)isobutyramide with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 1.02 (d, J=6.65 Hz, 6 H) 1.34 (br. s., 6 H) 1.48 (d, J=18.00 Hz, 3 H) 2.28-2.35 (m, 2 H) 2.90-3.02 (m, 3 H) 3.61 (br. s., 2 H) 4.16 (d, J=5.48 Hz, 2 H) 4.38 (br. s., 1 H) 6.37 (br. s., 1 H) 7.45 (br. s., 1 H) 7.85-7.94 (m, 1 H) 7.94-8.04 (m, 1 H)

8.43 (br. s., 1 H) 8.60 (s, 1 H); ESI-MS (m/z): Calcd. For $C_{25}H_{33}F_3N_6O_2$: 506.26. found: 507 (M+H).

Example 115

N-isopropyl-N-(((1s,4s)-4-(3-(2-((6-(trifluoromethyl)quinazolin-4-yl)amino)acetamido)azetidin-1-yl)cyclohexyl)methyl)acetamide

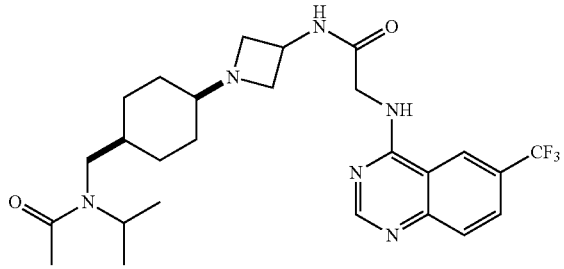 [SMILES: CC(=O)N(C[C@H]1CC[C@@H](N2CC(NC(=O)CNc3ncnc4ccc(C(F)(F)F)cc34)C2)CC1)C(C)C]

Reaction of N-isopropyl-N-((4-oxocyclohexyl)methyl)acetamide (prepared from isopropylamine and 1,4-dioxaspiro[4.5]decane-8-carbaldehyde via sequential reductive amination, acylation and deprotection) with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (DMSO-d6) δ: 9.04 (br. s., 1 H), 8.82 (s, 1 H), 8.56 (s, 1 H), 8.36-8.53 (m, 1 H), 8.06 (d, J=8.8 Hz, 1 H), 7.89 (d, J=8.8 Hz, 1 H), 7.74 (br. s., 2 H), 4.13 (d, J=5.6 Hz, 2 H), 2.67 (d, J=6.8 Hz, 2 H), 1.40 (br. s., 8 H); ESI-MS (m/z): Calcd. For $C_{26}H_{35}F_3N_6O_2$: 520.28. found: 521 (M+H).

Example 116

N-(1-((1s,4s)-4-(aminomethyl)cyclohexyl)azetidin-3-yl)-2-((6-(trifluoromethyl)quinazolin-4-yl)amino)acetamide

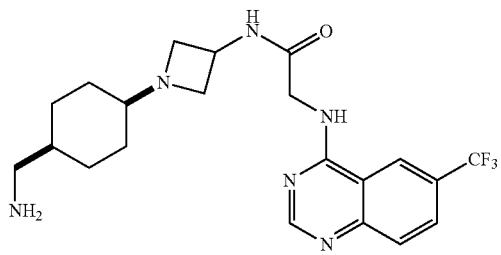 [SMILES: NC[C@H]1CC[C@@H](N2CC(NC(=O)CNc3ncnc4ccc(C(F)(F)F)cc34)C2)CC1]

Reaction of tert-butyl (((1s,4s)-4-(3-(2-((6-(trifluoromethyl)quinazolin-4-yl)amino)acetamido)azetidin-1-yl)cyclohexyl)methyl)carbamate with TFA in DCM as described in Example 1, Step G afforded the product.

$^1$H NMR (DMSO-d6) δ: 9.04 (br. s., 1 H), 8.82 (s, 1 H), 8.56 (s, 1 H), 8.36-8.53 (m, 1 H), 8.06 (d, J=8.8 Hz, 1 H), 7.89 (d, J=8.8 Hz, 1 H), 7.74 (br. s., 2 H), 4.13 (d, J=5.6 Hz, 2 H), 2.67 (d, J=6.8 Hz, 2 H), 1.40 (br. s., 8 H); ESI-MS (m/z): Calcd. For $C_{21}H_{27}F_3N_6O$: 436.22. found: 437 (M+H).

Example 117

N-(1-((1s,4s)-4-isopropylcyclohexyl)azetidin-3-yl)-2-((6-(trifluoromethyl)quinazolin-4-yl)amino)acetamide

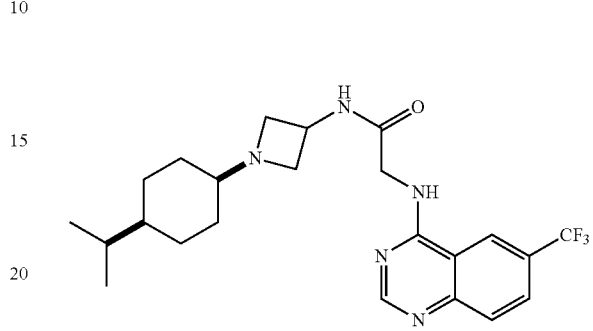

Reaction of 4-isopropylcyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (CHLOROFORM-d) δ: 8.67 (s, 1 H), 8.11 (s, 1 H), 7.86 (s, 2 H), 7.38 (t, J=4.8 Hz, 1 H), 6.54 (d, J=7.8 Hz, 1 H), 4.50-4.62 (m, 1 H), 4.29 (d, J=4.8 Hz, 2 H), 3.52-3.60 (m, 2 H), 2.86-2.95 (m, 2 H), 2.19 (d, J=3.0 Hz, 1 H), 1.26-1.55 (m, 8 H), 1.02 (dd, J=6.9, 3.2 Hz, 1 H), 0.86 (d, J=6.8 Hz, 6 H); ESI-MS (m/z): Calcd. For $C_{23}H_{30}F_3N_5O$: 449.24. found: 450 (M+H).

Example 118

N-(1-deutero-1-((1s,4s)-4-isopropylcyclohexyl)azetidin-3-yl)-2-((6-(trifluoromethyl)quinazolin-4-yl)amino)acetamide

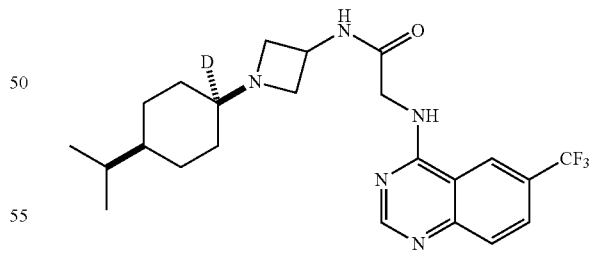

Reaction of 4-isopropylcyclohexanone with N-(azetidin-3-yl)-2-((6-(trifluoromethyl)quinazolin-4-yl)amino)acetamide (as prepared in Example 1 Step G) in the presence of TEA and NaBD(OAc)$_3$ as described in Example 1, Step H afforded the product. $^1$H NMR (DMSO-d6) δ: 0.81 (d, J=6.82 Hz, 6 H) 0.91-1.04 (m, 1 H) 1.15-1.33 (m, 6 H) 1.38 (dq, J=13.36, 6.66 Hz, 1 H) 1.44-1.54 (m, 2 H) 2.71 (t, J=7.20 Hz, 2 H) 3.43 (t, J=7.20 Hz, 2 H) 4.12 (s, 2 H) 4.23 (sxt, J=6.97 Hz, 1 H) 7.87 (d, J=8.84 Hz, 1 H) 8.04 (dd, J=8.72, 1.90 Hz, 1 H)

8.51 (d, J=7.07 Hz, 1 H) 8.55 (s, 1 H) 8.83 (s, 1 H) 9.30 (br. s., 1 H); ESI-MS (m/z): Calcd. For $C_{23}H_{29}DF_3N_5O$: 450.25. found: 451 (M+H).

Example 119

N-(1-(4-methylcyclohexyl)azetidin-3-yl)-2-((6-(trifluoromethyl)quinazolin-4-yl)amino)acetamide

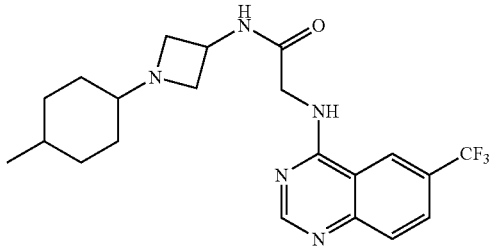 [SMILES: CC1CCC(N2CC(NC(=O)CNc3ncnc4ccc(C(F)(F)F)cc34)C2)CC1]

Reaction of 4-methylcyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 8.61 (s, 1 H), 8.11 (s, 1 H), 8.04 (t, J=4.9 Hz, 1 H), 7.71-7.82 (m, 2 H), 6.80 (d, J=7.3 Hz, 1 H), 4.59 (sxt, J=6.4 Hz, 1 H), 4.27 (d, J=5.3 Hz, 2 H), 3.60 (t, J=7.3 Hz, 2 H), 2.95 (t, J=6.6 Hz, 2 H), 2.15 (br. s., 1 H), 1.49-1.61 (m, 1 H), 1.27-1.49 (m, 8H), 0.91 (d, J=6.8 Hz, 3 H); ESI-MS (m/z): Calcd. For $C_{21}H_{26}F_3N_5O$: 421.21. found: 422 (M+H).

Example 120

N-(1-((1s,4s)-4-(1-methoxypropyl)cyclohexyl)azetidin-3-yl)-2-((6-(trifluoromethyl)quinazolin-4-yl)amino)acetamide

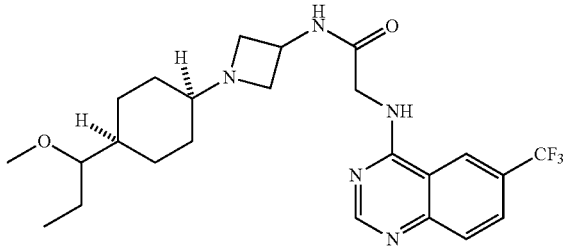 [SMILES: CCC(OC)[C@H]1CC[C@@H](N2CC(NC(=O)CNc3ncnc4ccc(C(F)(F)F)cc34)C2)CC1]

Reaction of 4-(1-methoxypropyl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 0.89 (t, J=7.45 Hz, 3 H) 1.27-1.46 (m, 5 H) 1.51-1.65 (m, 3H) 2.26 (br. s., 3 H) 2.90-3.04 (m, 3 H) 3.35 (s, 3 H) 3.56 (t, J=7.33 Hz, 2 H) 4.29 (d, J=5.31 Hz, 2 H) 4.48-4.63 (m, 1 H) 4.73 (s, 1 H) 6.92 (d, J=7.07 Hz, 1 H) 7.73-7.84 (m, 2 H) 7.92 (t, J=4.93 Hz, 1 H) 8.13 (s, 1 H) 8.62 (s, 1 H); ESI-MS (m/z): Calcd. For $C_{24}H_{32}F_3N_5O_2$: 479.25. found: 480 (M+H).

Example 121

N-(1-((1s,4s)-4-(2-methoxyethyl)cyclohexyl)azetidin-3-yl)-2-((6-(trifluoromethyl)quinazolin-4-yl)amino)acetamide

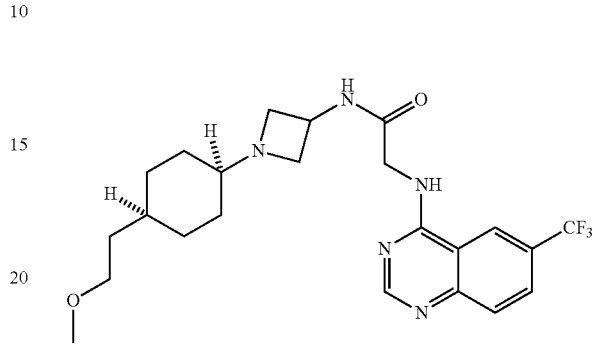

Reaction of 4-(2-methoxyethyl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (DMSO-d6) δ: 1.17-1.48 (m, 11 H) 2.15 (br. s., 1 H) 2.66-2.77 (m, 2 H) 3.19 (s, 3 H) 3.30 (t, J=6.19 Hz, 2 H) 3.43 (t, J=6.44 Hz, 2 H) 4.12 (d, J=5.81 Hz, 2 H) 4.17-4.29 (m, 1 H) 7.88 (d, J=8.84 Hz, 1 H) 8.06 (d, J=8.84 Hz, 1 H) 8.41 (d, J=7.07 Hz, 1 H) 8.56 (s, 1 H) 8.80 (s, 1 H) 9.01 (t, J=5.68 Hz, 1 H); ESI-MS (m/z): Calcd. For $C_{23}H_{30}F_3N_5O_2$: 465.24. found: 466 (M+H).

Example 122 ethyl 2-(4-(3-(2-((6-(trifluoromethyl)quinazolin-4-yl)amino)acetamido)azetidin-1-yl)cyclohexyl)acetate

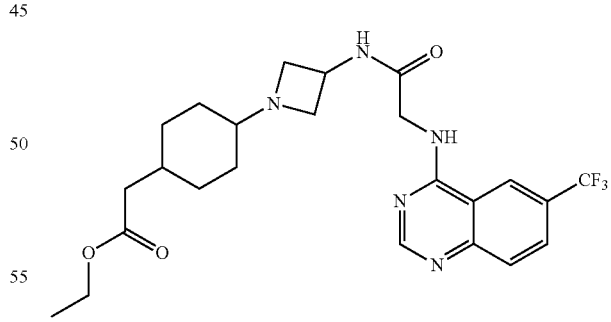

Reaction of ethyl 2-(4-oxocyclohexyl)acetate with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 8.55 (s, 1 H), 8.12 (s, 1 H), 7.99-8.10 (m, 1 H), 7.94 (t, J=5.1 Hz, 1 H), 7.64-7.76 (m, 2 H), 4.60 (dt, J=7.6, 4.5 Hz, 1 H), 4.23 (d, J=5.1 Hz, 2 H), 4.05 (q, J=7.1 Hz, 2 H), 3.68 (t, J=8.1 Hz, 2 H), 3.33 (br. s., 2 H), 2.42 (br. s., 1 H), 2.21 (d, J=7.3 Hz, 2 H), 1.44 (br. s., 9 H), 1.18 (t, J=7.1 Hz, 4 H); ESI-MS (m/z): Calcd. For $C_{24}H_{30}F_3N_5O_3$: 493.23; found: 494 (M+H).

Example 123

N-(1-(4-(trifluoromethyl)cyclohexyl)azetidin-3-yl)-2-((6-(trifluoromethyl)quinazolin-4-yl)amino)acetamide

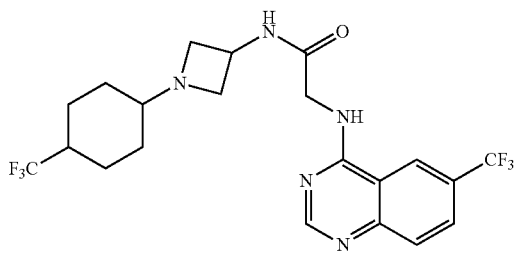 [SMILES: O=C(CNc1ncnc2ccc(C(F)(F)F)cc12)NC1CN(C2CCC(C(F)(F)F)CC2)C1]

Reaction of ethyl 4-(trifluoromethyl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 8.60 (s, 1 H), 8.21 (t, J=5.4 Hz, 1 H), 8.12 (s, 1 H), 7.71-7.81 (m, 2 H), 6.92 (d, J=7.8 Hz, 1 H), 4.49-4.66 (m, 1 H), 4.28 (d, J=5.6 Hz, 2 H), 3.57 (t, J=7.5 Hz, 2 H), 2.85-3.00 (m, 2 H), 2.31 (t, J=3.2 Hz, 1 H), 1.89-2.14 (m, 2 H), 1.53-1.78 (m, 5 H), 1.28-1.42 (m, 2 H); ESI-MS (m/z): Calcd. For $C_{21}H_{23}F_6N_5O$: 475.18. found: 476 (M+H).

Example 124

((1s,4s)-4-(3-(2-((6-(trifluoromethyl)quinazolin-4-yl)amino)acetamido)azetidin-1-yl)cyclohexyl)methyl dimethylcarbamate

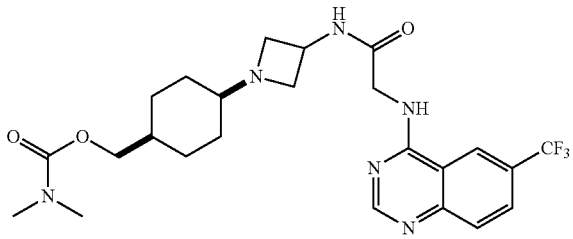 [SMILES: CN(C)C(=O)OC[C@H]1CC[C@@H](N2CC(NC(=O)CNc3ncnc4ccc(C(F)(F)F)cc34)C2)CC1]

Reaction of ethyl (4-oxocyclohexyl)methyl dimethylcarbamate with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 1.21-1.39 (m, 6 H) 1.46 (br. s., 2 H) 1.60 (br. s., 1 H) 2.19 (br. s., 1 H) 2.69-2.77 (m, 2 H) 2.82 (br. s., 6 H) 3.39-3.50 (m, 2 H) 3.79 (d, J=6.85 Hz, 2 H) 4.12 (d, J=5.14 Hz, 2 H) 4.24 (br. s., 1 H) 7.88 (d, J=8.56 Hz, 1 H) 8.04 (br. s., 1 H) 8.39 (d, J=6.85 Hz, 1 H) 8.55 (s, 1 H) 8.80 (br. s., 1 H) 8.99 (br. s., 1 H); ESI-MS (m/z): Calcd. For $C_{24}H_{31}F_3N_6O_3$: 508.24. found: 509 (M+H).

Example 125 tert-butyl (4-(3-(2-((6-(trifluoromethyl)quinazolin-4-yl)amino)acetamido)azetidin-1-yl)cyclohexyl)carbamate

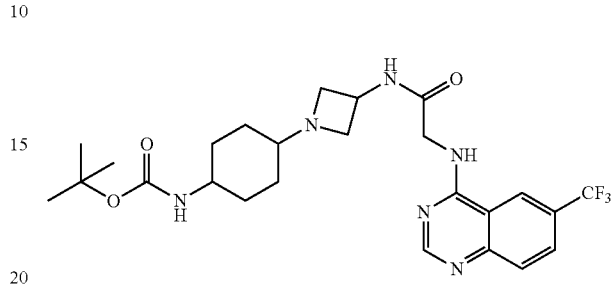

Reaction of ethyl tert-butyl (4-oxocyclohexyl)carbamate with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (CHLOROFORM-d) δ: 1.12-1.29 (m, 12 H) 1.36 (s, 9 H) 1.40-1.62 (m, 6 H) 1.62-1.75 (m, 2 H) 3.59 (br. s., 2 H) 3.86 (d, J=6.06 Hz, 1 H) 4.29 (d, J=5.31 Hz, 2 H) 4.55-4.68 (m, 1 H) 4.74 (d, J=7.83 Hz, 1 H) 7.20-7.28 (m, 1 H) 7.82 (s, 2 H) 8.19 (s, 1 H) 8.62 (s, 1 H); ESI-MS (m/z): Calcd. For $C_{25}H_{33}F_3N_6O_3$: 522.26. found: 523 (M+H).

Example 126

N-methoxy-N-methyl-4-(3-(2-((6-(trifluoromethybquinazolin-4-yl)amino)acetamido)azetidin-1-yl)cyclohexanecarboxamide

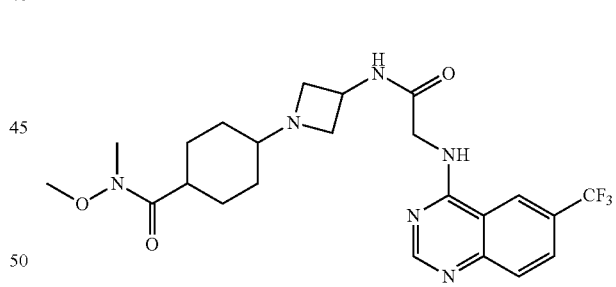

To a suspension of N,O-dimethylhydroxylamine hydrochloride (42 mg, 0.431 mmol) in dry toluene (5 mL) was added trimethylaluminum (0.200 mL, 0.40 mmol) dropwise under argon. After stirring 30 minutes at room temperature, a solution of (1s,4s)-ethyl 4-(3-(2-((6-(trifluoromethyl)quinazolin-4-yl)amino)acetamido)azetidin-1-yl)cyclohexanecarboxylate (80 mg, 0.167 mmol) in dry toluene (5 mL) was added and the reaction heated to 110° C. for 20 hours. After cooling to room temperature, the reaction was quenched by the addition of aqueous saturated Rochelle's salt and extracted with EtOAc. Concentration of the organic layer in vacuo followed by flash chromatography of the residue (silica gel, 7% 7N NH3-MeOH/DCM) yielded the product.

$^1$H NMR (CHLOROFORM-d) δ: 8.66 (s, 1 H), 8.33 (s, 1 H), 7.79-7.92 (m, 4 H), 4.56 (br. s., 1 H), 4.31-4.42 (m, 3 H), 3.56-3.76 (m, 2 H), 3.03 (s, 3 H), 2.89 (s, 3 H), 2.58 (br. s., 1 H), 1.81-1.97 (m, 2 H), 1.73 (br. s., 2 H), 1.38-1.54 (m, 4 H).

Example 127

N-ethyl-4-(3-(2-((6-(trifluoromethyl)quinazolin-4-yl)amino)acetamido)azetidin-1-yl)cyclohexanecarboxamide

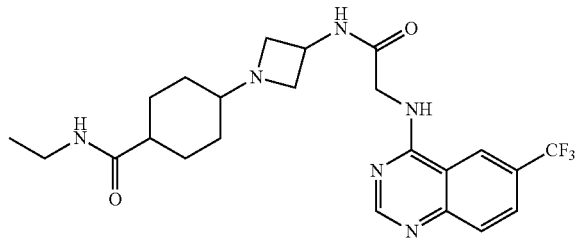 [SMILES: CCNC(=O)C1CCC(N2CC(NC(=O)CNc3ncnc4ccc(C(F)(F)F)cc34)C2)CC1]

Reaction of N-ethyl-4-oxocyclohexanecarboxamide with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (DMSO-d6) δ: 0.97 (t, J=7.20 Hz, 3 H) 1.25 (d, J=16.93 Hz, 5 H) 1.48 (br. s., 2 H) 1.67 (br. s., 2 H) 1.97-2.08 (m, 1 H) 2.17 (br. s., 1 H) 2.74 (t, J=7.07 Hz, 2 H) 3.01 (m, J=7.07, 5.81 Hz, 2 H) 3.43 (t, J=7.20 Hz, 2 H) 4.12 (d, J=5.56 Hz, 2 H) 4.17-4.30 (m, 1 H) 7.61 (t, J=5.56 Hz, 1 H) 7.88 (d, J=8.59 Hz, 1 H) 8.05 (dd, J=8.97, 1.39 Hz, 1 H) 8.44 (d, J=7.33 Hz, 1 H) 8.55 (s, 1 H) 8.81 (s, 1 H) 9.05 (t, J=5.43 Hz, 1 H); ESI-MS (m/z): Calcd. For C$_{23}$H$_{29}$F$_3$N$_6$O$_2$: 478.23. found: 479 (M+H).

Example 128

(1s,4s)-N,N-dimethyl-4-(3-(2-((6-(trifluoromethyl)quinazolin-4-yl)amino)acetamido)azetidin-1-yl)cyclohexanecarboxamide

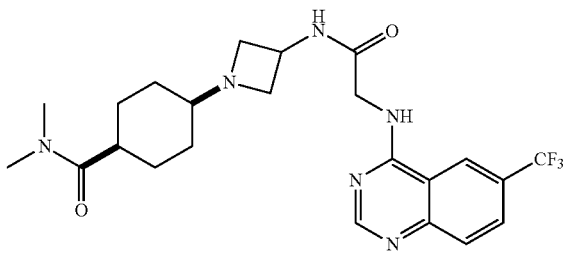

Reaction of N,N-dimethyl-4-oxocyclohexanecarboxamide with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (DMSO-d6) δ: 1.31 (t, J=7.83 Hz, 6 H) 1.43 (br. s., 2 H) 1.75 (br. s., 1 H) 2.16 (d, J=6.82 Hz, 2 H) 2.74 (br. s., 1 H) 2.79 (s, 3 H) 2.94 (s, 3 H) 3.46 (br. s., 2 H) 4.13 (d, J=5.81 Hz, 2 H) 4.25 (d, J=6.82 Hz, 1 H) 7.88 (d, J=8.84 Hz, 1 H) 8.04 (dd, J=8.72, 1.64 Hz, 1 H) 8.38 (d, J=7.33 Hz, 1 H) 8.56 (s, 1 H) 8.80 (s, 1 H) 9.00 (t, J=5.68 Hz, 1 H); ESI-MS (m/z): Calcd. For C$_{23}$H$_{29}$F$_3$N$_6$O$_2$: 478.23. found: 479 (M+H).

Example 129

N-(2,4-dimethoxybenzyl)-4-(3-(2-((6-(trifluoromethyl)quinazolin-4-yl)amino)acetamido)azetidin-1-yl)cyclohexanecarboxamide

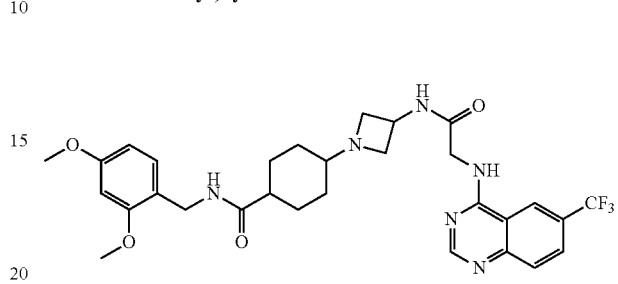

Reaction of N-(2,4-dimethoxybenzyl)-4-oxocyclohexanecarboxamide with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (ACETONITRILE-d3) δ: 1.23-1.46 (m, 4 H) 1.49-1.62 (m, 2 H) 1.65-1.81 (m, 2 H) 2.05-2.13 (m, 1 H) 2.72-2.84 (m, 2 H) 3.52 (t, J=7.20 Hz, 2 H) 3.73-3.78 (m, 3 H) 3.80 (s, 3 H) 4.16 (d, J=5.81 Hz, 2 H) 4.19 (d, J=5.81 Hz, 2 H) 4.28-4.41 (m, 1 H) 6.44 (dd, J=8.21, 2.40 Hz, 1 H) 6.50 (d, J=2.53 Hz, 2 H) 7.06 (d, J=8.34 Hz, 2 H) 7.40 (br. s., 1 H) 7.86-7.94 (m, 1 H) 7.95-8.03 (m, 1 H) 8.40 (s, 1 H) 8.60 (s, 1 H); ESI-MS (m/z): Calcd. For C$_{30}$H$_{35}$F$_3$N$_6$O$_4$: 600.27. found: 601 (M+H).

Example 130

N-(1-((1s,4s)-4-(pyrrolidine-1-carbonyl)cyclohexyl)azetidin-3-yl)-2-((6-(trifluoromethyl)quinazolin-4-yl)amino)acetamide

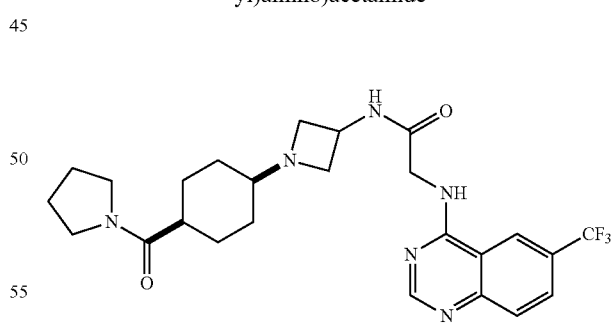

Reaction of 4-(pyrrolidine-1-carbonyl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 1.39-1.67 (m, 3 H) 1.72-1.82 (m, 4 H) 1.86-1.91 (m, 0 H) 2.52 (br. s., 1 H) 3.04 (br. s., 1 H) 3.29 (t, J=6.82 Hz, 2 H) 3.41 (t, J=6.69 Hz, 2 H) 3.70-3.84 (m, 1 H) 4.01-4.16 (m, 1 H) 4.20 (d, J=5.56 Hz, 2 H) 4.58 (br. s., 1 H) 7.68 (br. s., 1 H) 7.91

(d, J=8.59 Hz, 1 H) 7.96-8.04 (m, 1 H) 8.51 (s, 1 H) 8.61 (s, 1 H); ESI-MS (m/z): Calcd. For $C_{25}H_{31}F_3N_6O_2$: 504.25. found: 505 (M+H).

Example 131

N-(1-((1s,4s)-4-(3,3-difluoropyrrolidin-1-yl)cyclohexyl)azetidin-3-yl)-2-((6-(trifluoromethyl)quinazolin-4-yl)amino)acetamide

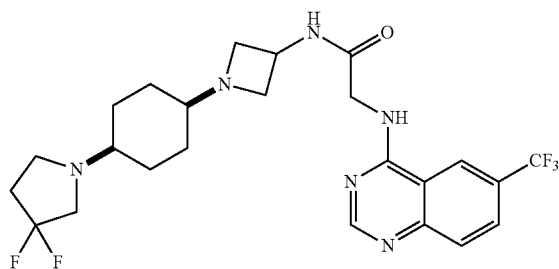

Reaction of 4-(3,3-difluoropyrrolidin-1-yl)cyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (MeOD) δ: 1.29-1.47 (m, 6 H) 1.56-1.68 (m, 2 H) 2.04-2.26 (m, 4 H) 2.69 (t, J=6.97 Hz, 2 H) 2.77-2.85 (m, 2 H) 2.86 (s, 1 H) 2.89 (s, 1 H) 3.44-3.52 (m, 2 H) 4.17 (s, 2 H) 4.35 (quin, J=6.72 Hz, 1 H) 7.86-7.93 (m, 1 H) 8.00 (dd, J=8.80, 1.96 Hz, 1 H) 8.42 (s, 1 H) 8.59 (s, 1 H); ESI-MS (m/z): Calcd. For $C_{24}H_{29}F_5N_6O$: 512.23. found: 513 (M+H).

Example 132

N-(1-((1s,4s)-4-morpholinocyclohexyl)azetidin-3-yl)-2-((6-(trifluoromethyl)quinazolin-4-yl)amino)acetamide

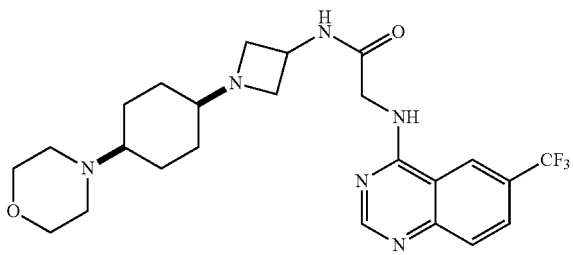

Reaction of 4-morpholinocyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product. $^1$H NMR (ACETONITRILE-d3) δ: 1.22-1.34 (m, 2 H) 1.40 (m, J=12.38 Hz, 2 H) 1.45-1.68 (m, 4 H) 2.07-2.14 (m, 2 H) 2.37-2.46 (m, 4 H) 2.76 (t, J=7.20 Hz, 3 H) 3.43-3.52 (m, 2 H) 3.52-3.64 (m, 4 H) 4.16 (d, J=5.81 Hz, 2 H) 4.33 (sxt, J=6.92 Hz, 1 H) 7.13 (d, J=7.58 Hz, 1 H) 7.45 (t, J=5.18 Hz, 1 H) 7.84-7.94 (m, 1 H) 7.94-8.04 (m, 1 H) 8.42 (s, 1 H) 8.59 (s, 1 H); ESI-MS (m/z): Calcd. For $C_{24}H_{31}F_3N_6O_2$: 492.25. found: 493 (M+H).

Example 133

N-(1-((1s,4s)-4-thiomorpholinocyclohexyl)azetidin-3-yl)-2-((6-(trifluoromethyl)quinazolin-4-yl)amino)acetamide

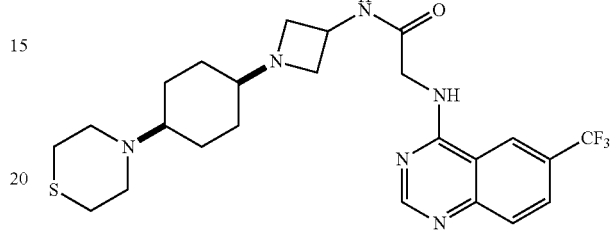

Reaction of 4-thiomorpholinocyclohexanone with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1, Step H afforded the product.

$^1$H NMR (ACETONITRILE-d3) δ: 1.16-1.38 (m, 4 H) 1.50-1.68 (m, 3 H) 2.24 (m, J=8.34 Hz, 1 H) 2.49-2.60 (m, 4 H) 2.64-2.80 (m, 6 H) 3.27 (s, 3 H) 3.41-3.54 (m, 2 H) 4.15 (d, J=5.81 Hz, 2 H) 4.24-4.37 (m, 1 H) 7.03 (d, J=5.81 Hz, 1 H) 7.36 (t, J=5.56 Hz, 1 H) 7.86-7.95 (m, 1 H) 7.95-8.03 (m, 1 H) 8.39 (s, 1 H) 8.60 (s, 1 H); ESI-MS (m/z): Calcd. For $C_{24}H_{31}F_3N_6OS$: 508.22. found: 509 (M+H).

Example 134

N-(1-((1s,4s)-4-(1,1-dioxidothiomorpholino)cyclohexyl)azetidin-3-yl)-2-((6-(trifluoromethyl)quinazolin-4-yl)amino)acetamide

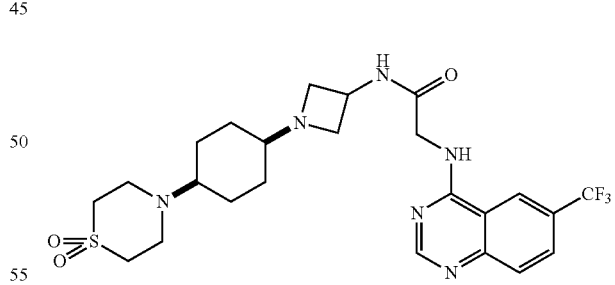

Reaction of 4-(4-oxocyclohexyl)thiomorpholine 4-oxide 1,1-dioxide with N-(azetidin-3-yl)-2-((6-(trifluoromethyl)quinazolin-4-yl)amino)acetamide (as prepared in Example 1 Step G) in the presence of TEA and NaBH(OAc)$_3$ as described in Example 1 Step H afforded the product.

$^1$H NMR (ACETONITRILE-d3) δ: 1.21-1.43 (m, 4 H) 1.51-1.65 (m, 4 H) 2.11-2.16 (m, 1 H) 2.45 (m, J=10.61, 7.14, 3.38, 3.38 Hz, 1 H) 2.72 (t, J=7.20 Hz, 2 H) 2.86-3.04 (m, 9 H) 3.48 (t, J=7.33 Hz, 2 H) 4.15 (d, J=5.81 Hz, 2 H) 4.32 (sxt, J=6.92 Hz, 1 H) 7.09 (d, J=7.58 Hz, 1 H) 7.47 (t, J=5.56 Hz, 1 H) 7.83-7.91 (m, 1 H) 7.93-8.00 (m, 1 H) 8.37 (s, 1 H) 8.58 (s, 1 H); ESI-MS (m/z): Calcd. For $C_{24}H_{31}F_3N_6O_3S$: 540.21. found: 541 (M+H).

Example 135

2,2,2-trifluoro-N-((S)-1-((1s,4R)-4-(3-(2-((6-(trifluoromethyl)quinazolin-4-yl)amino)acetamido)azetidin-1-yl)cyclohexyl)propyl)acetamide Step A: N-(1-{1,4-dioxaspiro[4.5]decan-8-yl}propyl)-2,2,2-trifluoroacetamide

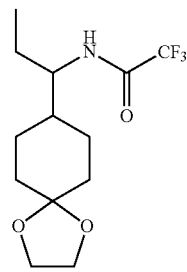 [SMILES: CCC(NC(=O)C(F)(F)F)C1CCC2(CC1)OCCO2]

Into a 50 mL round-bottom flask was placed a solution of 1-1,4-dioxaspiro[4.5]decan-8-ylpropan-1-amine hydrochloride (as prepared in Example 104, Step B) (100 mg, 0.42 mmol, 1.00 equiv) in dichloromethane (10 mL) and TEA (85.6 mg, 0.85 mmol, 2.00 equiv). This was followed by the addition of 2,2,2-trifluoroacetyl 2,2,2-trifluoroacetate (107 mg, 0.51 mmol, 1.20 equiv) dropwise with stirring at 0° C. The resulting solution was stirred overnight at room temperature, then quenched by the addition of 20 mL of water. The resulting solution was extracted with 2×20 mL of dichloromethane. The organic layers were combined, dried over anhydrous sodium sulfate and concentrated under vacuum. This resulted in 89 mg (crude) of N-(1-{1,4-dioxaspiro[4.5]decan-8-yl}propyl)-2,2,2-trifluoroacetamide as a yellow solid.

Step B: 2,2,2-trifluoro-N-(1-(4-oxocyclohexyl)propyl)acetamide

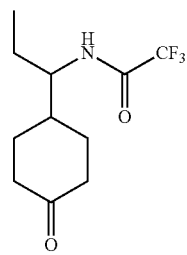 [SMILES: CCC(NC(=O)C(F)(F)F)C1CCC(=O)CC1]

A solution of N-(1-{1,4-dioxaspiro[4.5]decan-8-yl}propyl)-2,2,2-trifluoroacetamide (89 mg, 0.30 mmol, 1.00 equiv) in $CH_3CN$ (5 mL) and HCl (2M, 1 mL) was stirred for 2 h at room temperature. The resulting mixture was concentrated under vacuum. The residue was diluted with 10 mL of aq. sodium bicarbonate (1M). The resulting solution was extracted with 2×20 mL of dichloromethane. The organic layers were combined, dried over anhydrous sodium sulfate and concentrated under vacuum to give the title compound as a yellow oil.

Step C: 2,2,2-trifluoro-N—((S)-1-((1s,4R)-4-(3-(2-((6-(trifluoromethyl)quinazolin-4-yl)amino)acetamido)azetidin-1-yl)cyclohexyl)propyl)acetamide

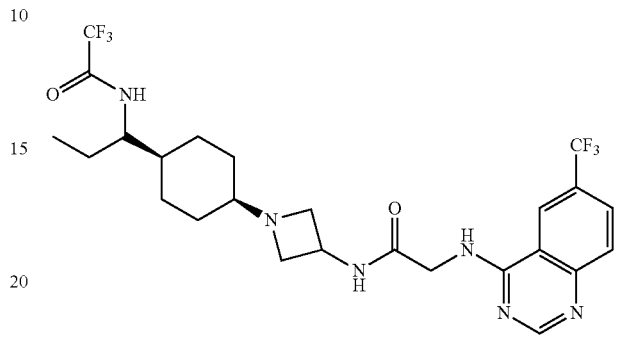

Into a 50 mL round-bottom flask were placed a solution of 2,2,2-trifluoro-N-(1-(4-oxocyclohexyl)propyl)acetamide (66 mg, 0.26 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (as prepared in Example 1, Step G) (126 mg, 0.29 mmol, 1.10 equiv) and TEA (27 mg, 0.27 mmol, 1.00 equiv). The resulting solution was stirred for 30 min at room temperature, then added NaBH(OAc)$_3$ (201 mg, 0.95 mmol, 3.60 equiv). The resulting solution was stirred for an additional 2 h at room temperature, then it was concentrated under vacuum. The crude product was purified by Prep-HPLC with the following conditions: Column, Xbridge phenyl, 5 μm, 19×150 mm; mobile phase, water (0.03% $NH_3H_2O$) and $CH_3CN$; Detector, UV 254 nm. The title compound was obtained as a white solid.

LC-MS (ES, m/z) 561 [M+H]$^+$ $^1$H-NMR (300 MHz, CD$_3$OD) δ 8.63 (s, 1H), 8.57 (s, 1H), 8.06-8.03 (m, 1H), 7.91-7.88 (d, J=8.7 Hz, 1H), 4.49-4.45 (m, 1H), 4.28 (s, 2H), 3.77-3.75 (d, J=7.2 Hz, 1H), 3.67-3.62 (m, 2H), 3.00-2.96 (m, 2H), 2.31 (s, 1H), 1.79-1.71 (m, 1H), 1.48-1.36 (m, 11H), 0.91-0.86 (m, 3H).

Example 136

N-(1-((1R,4s)-4-((S)-1-aminopropyl)cyclohexyl)azetidin-3-yl)-2-((6-(trifluoromethyl)quinazolin-4-yl)amino)acetamide

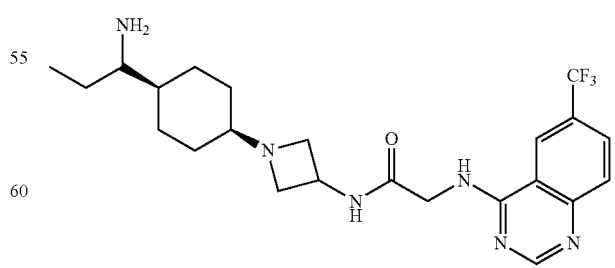

A solution of 2,2,2-trifluoro-N-(1-4-[3-(2-[6-(trifluoromethyl)quinazolin-4-yl]aminoacetamido)azetidin-1-yl]cyclohexylpropyl)acetamide (as prepared in Example 135, 40 mg, 0.07 mmol, 1.00 equiv) in methanol (5 mL) and aq. potassium carbonate (2M, 10 mL) was stirred overnight at 70° C. The reaction mixture was cooled and concentrated under vacuum. The crude product (50 mg) was purified by Prep-HPLC with the following conditions: Column, Xbridge Prep phenyl 5 µm, 19×150 mm; mobile phase, water (0.03% NH$_3$.H$_2$O) and CH$_3$CN; Detector, UV 254 nm. This resulted in 17.7 mg (49%) of N-(1-41S,4s)-4-(R)-1-aminopropyl)cyclohexyl) azetidin-3-yl)-2-(6-(trifluoromethyl)quinazolin-4-ylamino) acetamide as a white solid.

LC-MS (ES, m/z) 465 [M+H]$^+$ $^1$H-NMR (300 MHz, CD$_3$OD) δ 8.63 (s, 12H), 8.57 (s, 1H), 8.07-8.03 (m, 1H), 7.91-7.88 (d, J=8.7 Hz, 1H), 4.53-4.43 (m, 1H), 4.28 (s, 2H), 3.67-3.55 (m, 2H), 2.93-2.88 (m, 2H), 2.70-2.68 (m, 1H), 2.32 (s, 1H), 1.68-1.57 (m, 11H), 1.46-1.41 (m, 3H).

Example 137

N-(1-((1S,4s)-4-((R)-1-(dimethylamino)propyl)cyclohexyl)azetidin-3-yl)-2-(6-(trifluoromethyl)quinazolin-4-ylamino)acetamide Step A: (1-{1,4-dioxaspiro[4.5]decan-8-yl}propyl)dimethylamine

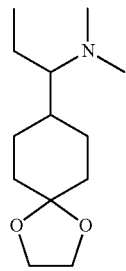 [SMILES: CCC(C1CCC2(CC1)OCCO2)N(C)C]

Into a 50 ml, round-bottom flask were placed a solution of 1-1,4-dioxaspiro[4.5]decan-8-ylpropan-1-amine hydrochloride (as prepared in Example 104, Step B) (100 mg, 0.42 mmol, 1.00 equiv) in dichloromethane (2 mL), HCHO (30%, 106 mg, 3.53 mmol, 2.50 equiv), AcOH (25 mg, 0.42 mmol, 1.00 equiv) and NaBH(OAc)$_3$ (269 mg, 1.27 mmol, 3.00 equiv). The resulting solution was stirred for 3 h at room temperature, then quenched by the addition of 10 mL of water. The resulting solution was extracted with 2×10 mL of dichloromethane. The organic layers were combined, dried and concentrated under vacuum, to give the title compound as a yellow oil.

Step B: 4-(1-(dimethylamino)propyl)cyclohexanone

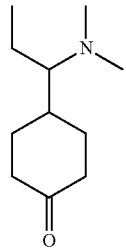

A solution of (1-{1,4-dioxaspiro[4.5]decan-8-yl}propyl) dimethylamine (as prepared in the previous step, 80 mg, 0.35 mmol, 1.00 equiv) in CH$_3$CN (5 mL) and HCl (1M, 1 mL) was stirred for 2 h at room temperature. The resulting mixture was concentrated under vacuum. The residue was diluted with 10 mL of aq. sodium bicarbonate (1M). The resulting solution was extracted with 2×20 mL of dichloromethane. The organic layers were combined, dried over anhydrous sodium sulfate and concentrated under vacuum to give the title compound as a yellow oil.

Step C: N-(1-((1S,4s)-4-((R)-1-(dimethylamino)propyl)cyclohexyl)azetidin-3-yl)-2-(6-(trifluoromethyl)quinazolin-4-ylamino)acetamide

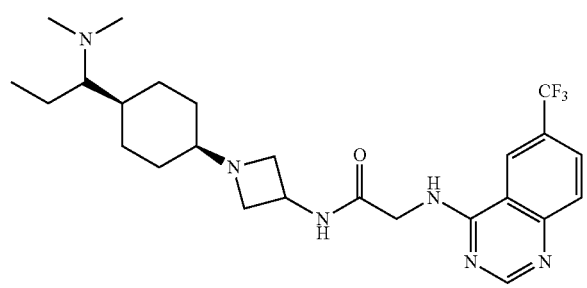 [SMILES: CCC([C@H]1CC[C@@H](N2CC(NC(=O)CNc3ncnc4ccc(C(F)(F)F)cc34)C2)CC1)N(C)C]

Into a 50 mL round-bottom flask were placed a solution of 4-(1-(dimethylamino)propyl)cyclohexanone (as prepared in the previous step, 60 mg, 0.33 mmol, 1.00 equiv) in dichloromethane (10 mL), N-(azetidin-3-yl)-2-(6-(trifluoromethyl) quinazolin-4-ylamino)acetamide 2,2,2-trifluoroacetic acid (as prepared in Example 1, Step G) (158 mg, 0.36 mmol, 1.10 equiv) and TEA (33 mg, 0.33 mmol, 1.00 equiv). The resulting solution was stirred for 30 min at room temperature, followed by addition of NaBH(OAc)$_3$ (250 mg, 1.18 mmol, 3.60 equiv). The resulting solution was stirred for an additional 2 h at room temperature, then concentrated under vacuum. The crude product was purified by Prep-HPLC to give the title compound as a white solid. HPLC conditions: Column, Xbridge Prep phenyl, 5 µm, 19×150 mm; mobile phase, water (0.03% NH$_3$.H$_2$O) and CH$_3$CN; Detector, UV 254 nm.

LC-MS (ES, m/z) 493 [M+H]$^+$.

$^1$H-NMR (300 MHz, CD$_3$OD) δ 8.64 (s, 1H), 8.57 (s, 1H), 8.07-8.03 (m, 1H), 7.91-7.89 (d, J=8.7 Hz, 1H), 4.50-4.45 (m, 1H), 4.28 (s, 2H), 3.63-3.61 (m, 2H), 2.95-2.90 (m, 2H), 2.30 (m, 8H), 1.57-1.40 (m, 11H), 1.00-0.95 (m, 3H).

Example 138

N-(1-((1R,4s)-4-((S)-1-acetamidopropyl)cyclohexyl) azetidin-3-yl)-2-((6-(trifluoromethyl)quinazolin-4-yl)amino)acetamide Step A: N-(azetidin-3-yl)-2-(6-(trifluoromethyl) quinazolin-4-ylamino)acetamide 2,2,2-trifluoroacetic acid

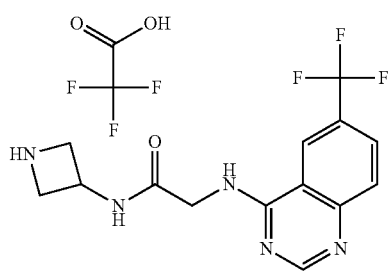

A solution of tert-butyl 3-(2-(6-(trifluoromethyl)quinazo-lin-4-ylamino)acetamido)azetidine-1-carboxylate (prepared as described in Example 1, Step F) (1 g, 2.35 mmol, 1.00 equiv) in dichloromethane (10 mL) and TFA (25% in DCM, 1 mL) was stirred for 3 h at room temperature. The resulting mixture was concentrated under vacuum, and the title compound was obtained as a white solid.

Step B:
N-(1-1,4-dioxaspiro[4.5]decan-8-ylpropyl)acetamide

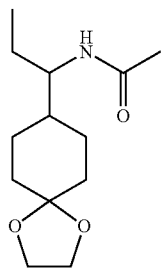

Into a 50 mL round-bottom flask were placed a solution of 1-1,4-dioxaspiro[4.5]decan-8-ylpropan-1-amine hydrochloride (as prepared in Example 104 Step B) (50 mg, 0.21 mmol, 1.00 equiv) in dichloromethane (10 mL) and TEA (42.8 mg, 0.42 mmol, 2.00 equiv). This was followed by the addition of acetyl chloride (19.8 mg, 0.25 mmol, 1.20 equiv) dropwise with stirring at 0° C. The resulting solution was stirred overnight at room temperature. The reaction was then quenched by the addition of 20 mL of water. The resulting solution was extracted with 2×20 ml of dichloromethane. The organic layers were combined, dried over anhydrous sodium sulfate and concentrated under vacuum to give the title compound as a yellow oil.

Step C: N-(1-(4-oxocyclohexyl)propyl)acetamide

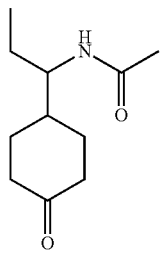

A solution of N-(1-1,4-dioxaspiro[4.5]decan-8-ylpropyl)acetamide (as prepared in the previous step, 39 mg, 0.16 mmol, 1.00 equiv) in $CH_3CN$ (5 mL) and HCl (1M, 1 mL) was stirred for 2 h at room temperature. The resulting mixture was concentrated under vacuum. The residue was diluted with 10 mL of aq. sodium bicarbonate (1M). The resulting solution was extracted with 2×20 mL of dichloromethane.

The organic layers were combined, dried over anhydrous sodium sulfate and concentrated under vacuum to give the title compound as a yellow oil.

Step D: N-(1-((1R,4s)-4-((S)-1-acetamidopropyl)cyclohexyl)azetidin-3-yl)-2-((6-(trifluoromethyl)quinazolin-4-yl)amino)acetamide

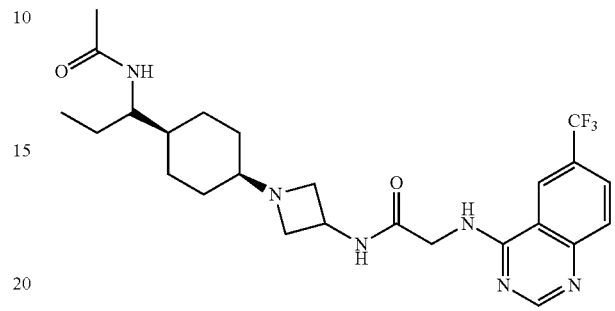

Into a 50 mL round-bottom flask were placed a solution of N-(1-(4-oxocyclohexyl)propyl)acetamide (as prepaed in the previous step, 31 mg, 0.16 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (prepared as described in Step A, 76 mg, 0.17 mmol, 1.10 equiv) and TEA (15.9 mg, 0.16 mmol, 1.00 equiv). The resulting solution was stirred for 30 min at room temperature, then added $NaBH(OAc)_3$ (120 mg, 0.57 mmol, 3.60 equiv). The resulting solution was stirred for an additional 2 h at room temperature. The resulting mixture was concentrated under vacuum. The crude product (50 mg) was purified by Prep-HPLC with the following conditions: Column, Xbridge Prep phenyl, 5 μm, 19×150 mm; mobile phase, water (0.03% $NH_3.H_2O$) and $CH_3CN$; Detector, UV 254 nm. The title compound was obtained as a white solid.

LC-MS (ES, m/z) 507 [M+H]$^+$.

$^1$H-NMR (400 MHz, $CD_3OD$) δ 8.64 (s, 1H), 8.58 (s, 1H), 8.08-8.05 (m, 1H), 7.92-7.90 (d, J=8.8 Hz, 1H), 4.57-4.52 (m, 1H), 4.30 (s, 2H), 4.04 (s, 2H), 3.760 (s, 1H), 3.60-3.50 (d, J=40.4 Hz, 2H), 2.84 (s, 1H), 1.97 (s, 3H), 1.70-1.1.49 (m, 10H), 1.35-1.29 (m, 1H), 0.95-0.80 (m, 3H).

Example 139

N-(1-(1-((1R,4s)-4-((S)-1-(methylsulfonamido)propyl)cyclohexyl)azetidin-3-yl)-2-((6-(trifluoromethyl)quinazolin-4-yl)amino)acetamide Step A: N-(1-(1,4-dioxaspiro[4.5]decan-8-yl)propyl)methanesulfonamide

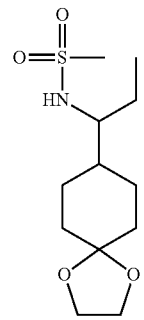

Into a 50 mL round-bottom flask was placed a solution of 1-1,4-dioxaspiro[4.5]decan-8-ylpropan-1-amine hydrochloride (as prepared in Example 104 Step B) (50 mg, 0.21 mmol, 1.00 equiv) in dichloromethane (10 mL) and TEA (42.8 mg, 0.42 mmol, 2.00 equiv). This was followed by the addition of methanesulfonyl chloride (29.1 mg, 0.25 mmol, 1.20 equiv) dropwise with stirring at 0° C. The resulting solution was stirred overnight at room temperature. The reaction was then quenched by the addition of 20 mL of water. The resulting solution was extracted with 2×20 mL of dichloromethane. The organic layers were combined, dried over anhydrous sodium sulfate and concentrated under vacuum to give the title compound as a yellow oil.

Step B:
N-(1-(4-oxocyclohexyl)propyl)methanesulfonamide

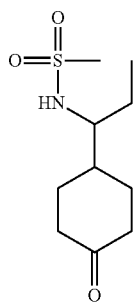

A solution of N-(1-1,4-dioxaspiro[4.5]decan-8-ylpropyl)methanesulfonamide (as prepared in the previous step, 38 mg, 0.14 mmol, 1.00 equiv) in $CH_3CN$ (5 mL) and HCl (2M, 1 mL) was stirred for 2 h at room temperature. The resulting mixture was concentrated under vacuum. The residue was diluted with 10 mL of aq. sodium bicarbonate (1M). The resulting solution was extracted with 2×20 mL of dichloromethane. The organic layers were combined, dried over anhydrous sodium sulfate and concentrated under vacuum to give the title compound as a yellow oil.

Step C: N-(1-((1R,4s)-4-((S)-1-(methylsulfonamido)propyl)cyclohexyl)azetidin-3-yl)-2-((6-(trifluoromethyl)quinazolin-4-yl)amino)acetamide

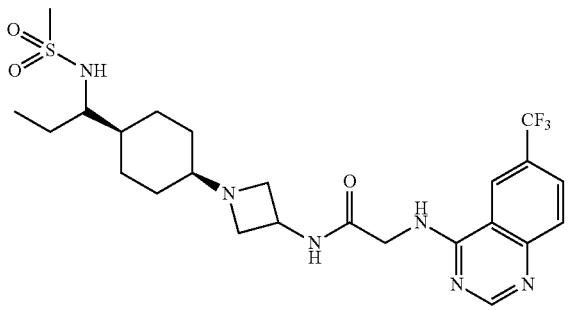 [SMILES: CCC(NS(C)(=O)=O)[C@H]1CC[C@@H](N2CC(NC(=O)CNc3ncnc4ccc(C(F)(F)F)cc34)C2)CC1]

Into a 50 mL round-bottom flask were placed a solution of N-(1-(4-oxocyclohexyl)propyl)methanesulfonamide (as prepared in the previous step, 29 mg, 0.12 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (as prepared in Example 1, Step G) (60 mg, 0.14 mmol, 1.10 equiv) and TEA (13 mg, 0.13 mmol, 1.00 equiv). The resulting solution was stirred for 30 min at room temperature, then added $NaBH(OAc)_3$ (95 mg, 0.45 mmol, 3.60 equiv). The resulting solution was stirred for 2 h at room temperature, then it was concentrated under vacuum. The crude product (80 mg) was purified by Prep-HPLC with the following conditions: Column, Xbridge Prep Phenyl, 5 μm, 19×150 mm; mobile phase, water (0.03% $NH_3H_2O$) and $CH_3CN$ (25% $CH_3CN$ up to 65% in 8 min, up to 100% in 0.1 min, hold at 100% for 1.9 min, down to 25% in 0.1 min, hold at 25% for 0.9 min); Detector, UV 220 & 254 nm. The title compound was obtained as a white solid.
LC-MS (ES, m/z) 543 [M+H]$^+$.
$^1$H-NMR (300 MHz, $CD_3OD$) δ 8.63 (s, 1H), 8.57 (s, 1H), 8.06-8.03 (m, 1H), 7.79-7.88 (d, J=28.2 Hz, 1H), 4.50-4.45 (m, 1H), 4.28 (s, 2H), 3.67-3.62 (m, 2H), 3.18 (s, 1H), 2.96-2.91 (m, 5H), 2.32 (s, 1H), 1.68-1.43 (m, 11H), 0.97-0.93 (m, 3H).

Example 140

2-((6-(trifluoromethyl)quinazolin-4-yl)amino)-N-(1-((1R,4s)-4-((S)-1-(trifluoromethylsulfonamido)propyl)cyclohexyl)azetidin-3-yl)acetamide Step A: N-(1-{1,4-dioxaspiro[4.5]decan-8-yl}propyl)-1,1,1-trifluoromethanesulfonamide

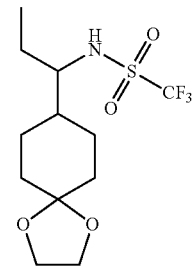 [SMILES: CCC(NS(=O)(=O)C(F)(F)F)C1CCC2(CC1)OCCO2]

Into a 50 mL round-bottom flask was placed a solution of 1-1,4-dioxaspiro[4.5]decan-8-ylpropan-1-amine hydrochloride (as prepared in Example 104 Step B) (50 mg, 0.21 mmol, 1.00 equiv) in dichloromethane (10 mL) and TEA (42.8 mg, 0.42 mmol, 2.00 equiv). This was followed by the addition of (trifluoromethane)sulfonyl trifluoromethanesulfonate (72 mg, 0.26 mmol, 1.20 equiv) dropwise with stirring at 0° C. The resulting solution was stirred overnight at room temperature. The reaction was then quenched by the addition of 20 mL of water. The resulting solution was extracted with 2×20 mL of dichloromethane. The organic layers were combined, dried over anhydrous sodium sulfate and concentrated under vacuum to give the title compound as a yellow oil.

Step B: trifluoro-N-(1-(4-oxocyclohexyl)propyl)methanesulfonamide

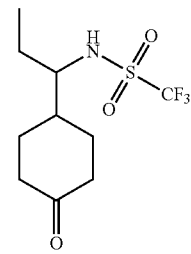 [SMILES: CCC(NS(=O)(=O)C(F)(F)F)C1CCC(=O)CC1]

A solution of N-(1-1,4-dioxaspiro[4.5]decan-8-ylpropyl)-1,1,1-trifluoromethanesulfonamide (as prepared in the previous step, 47 mg, 0.14 mmol, 1.00 equiv) in CH₃CN (5 mL) and HCl (2M, 1 mL) was stirred for 2 h at room temperature. The resulting mixture was concentrated under vacuum. The residue was diluted with 10 mL of aq. sodium bicarbonate (1M). The resulting solution was extracted with 2×20 mL of dichloromethane. The organic layers were combined, dried over anhydrous sodium sulfate and concentrated under vacuum to give the title compound as a yellow oil.

Step C: 2-((6-(trifluoromethyl)quinazolin-4-yl) amino)-N-(1-((1R,4s)-4-((S)-1-(trifluoromethylsulfonamido)propyl)cyclohexyl)azetidin-3-yl)acetamide

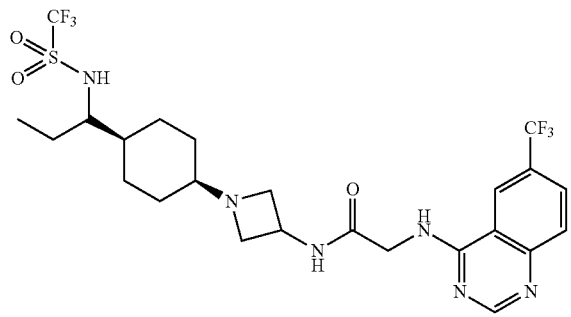 [SMILES: CCC(NS(=O)(=O)C(F)(F)F)[C@H]1CC[C@@H](N2CC(NC(=O)CNc3ncnc4ccc(C(F)(F)F)cc34)C2)CC1]

Into a 50 mL round-bottom flask were placed a solution of trifluoro-N-(1-(4-oxocyclohexyl)propyl)methanesulfonamide (as prepared in the previous step, 30 mg, 0.10 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (as prepared in Example 1, Step G) (50.5 mg, 0.12 mmol, 1.10 equiv) and TEA (11 mg, 0.11 mmol, 1.00 equiv). The resulting solution was stirred for 30 min at room temperature, then added NaBH(OAc)₃ (80 mg, 0.38 mmol, 3.60 equiv). The resulting solution was stirred for an additional 2 h at room temperature, then it was concentrated under vacuum. The crude product (60 mg) was purified by Prep-HPLC with the following conditions: Column, Xbridge Prep Phenyl, 5 μm, 19×150 mm; mobile phase, water (0.03% NH₃H₂O) and CH₃CN (25% CH₃CN up to 45% in 8 min, up to 100% in 0.1 min, hold at 100% for 1.9 min, down to 25% in 0.1 min, hold at 25% for 0.9 min); Detector, UV 254 nm. The title compound was obtained as a white solid.

LC-MS (ES, m/z) 597 [M+H]⁺.

¹H-NMR (300 MHz, CD₃OD) δ 8.64 (s, 1H), 8.58 (s, 1H), 8.08-8.05 (m, 1H), 7.93-7.90 (d, J=8.7 Hz, 1H), 4.62-4.59 (d, J=6.9 Hz, 1H), 4.3214.25 (d, J=19.2 Hz, 4H), 3.95 (s, 2H), 3.39-3.37 (d, J=4.5 Hz, 1H), 3.24-3.21 (d, J=3.2 Hz, 1H), 1.78-1.30 (m, 11H), 0.98-0.93 (m, 3H).

Example 141

1-((R)-1-((1S,4S)-4-(3-(2-(6-(trifluoromethyl) quinazolin-4-ylamino)acetamido)azetidin-1-yl)cyclohexyl)propyburea Step A: (1-{1,4-dioxaspiro[4.5]decan-8-yl}propyl) urea

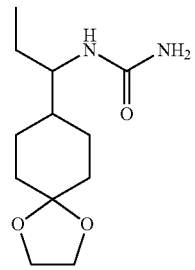 [SMILES: CCC(NC(N)=O)C1CCC2(CC1)OCCO2]

Into a 50 mL round-bottom flask were placed a solution of 1-1,4-dioxaspiro[4.5]decan-8-ylpropan-1-amine hydrochloride (as prepared in Example 104 Step B) (100 mg, 0.42 mmol, 1.00 equiv) in water (3 mL) and KOCN (38 mg, 0.47 mmol, 1.10 equiv). The resulting solution was stirred overnight at 70° C. The resulting solution was cooled and extracted with 3×10 mL of dichloromethane. The organic layers were combined, dried and concentrated under vacuum to give the title compound as a white solid.

Step B: 1-(1-(4-oxocyclohexyl)propyl)urea

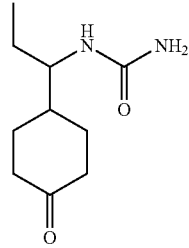

A solution of (1-1,4-dioxaspiro[4.5]decan-8-ylpropyl)urea (as prepared in the previous step, 89 mg, 0.37 mmol, 1.00 equiv) in CH₃CN (2 mL) and HCl (2M, 2 mL) was stirred for 2 h at room temperature. The resulting mixture was concentrated under vacuum. The residue was diluted with 20 mL of aq. sodium bicarbonate (1M). The resulting solution was extracted with 2×20 ml, of dichloromethane. The organic layers were combined, dried and concentrated under vacuum to give the title compound as a yellow oil.

Step C: 2((6-(trifluoromethyl)quinazolin-4-yl) amino)-N-(1-((1R,4s)-4-((S)-1-ureidopropyl)cyclohexyl)azetidin-3-yl)acetamide

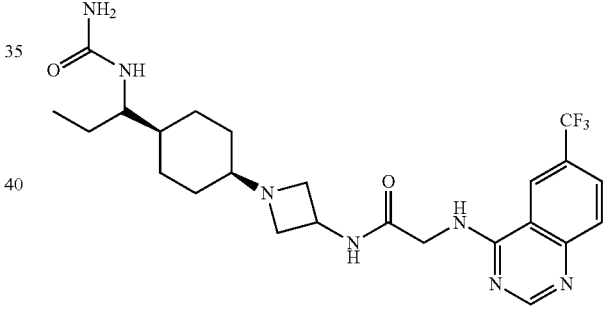

Into a 50 mL round-bottom flask were placed a solution of 1-(1-(4-oxocyclohexyl)propyl)urea (as prepared in the previous step, 62 mg, 0.31 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (as prepared in Example 1, Step G) (151 mg, 0.34 mmol, 1.10 equiv) and TEA (32 mg, 0.32 mmol, 1.00 equiv). The resulting solution was stirred for 30 min at room temperature, then added NaBH(OAc)₃ (239 mg, 1.13 mmol, 3.60 equiv). The resulting solution was stirred for an additional 2 h at room temperature. Then it was concentrated under vacuum. The crude product (50 mg) was purified by Prep-HPLC with the following conditions: Column, Xbridge Prep phenyl 5 μm, 19×150 mm; mobile phase, water (0.03% NH₃H₂O) and CH₃CN; Detector, UV 254 nm. The title compound was obtained as a white solid.

LC-MS (ES, m/z) 508 [M+H]⁺.

¹H-NMR (300 MHz, CD₃OD) δ 8.64 (s, 1H), 8.57 (s, 1H), 8.07-8.04 (m, 1H), 7.92-7.89 (d, J=8.7 Hz, 1H), 4.61 (s, 1H), 4.50-4.45 (m, 1H), 4.28 (s, 2H), 3.70-3.66 (m, 2H), 3.56-3.50 (m, 1H), 3.09-3.01 (m, 2H), 2.36 (s, 1H), 1.63-1.44 (m, 9H), 1.35-1.30 (m, 2H), 1.24-0.92 (m, 3H).

Example 142

N-(1-((1R,4s)-4-((S)-1-(3-methylureido)propyl)cyclohexyl)azetidin-3-yl)-2-((6-(trifluoromethyl)quinazolin-4-yl)amino)acetamide Step A: 4-(hydroxynitroso)phenyl N-(1-{1,4-dioxaspiro[4.5]decan-8-yl}propyl)carbamate

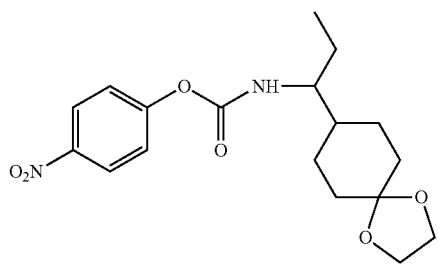 [SMILES: CCC(NC(=O)Oc1ccc([N+](=O)[O-])cc1)C1CCC2(CC1)OCCO2]

Into a 50 mL round-bottom flask was placed a solution of 1-1,4-dioxaspiro[4.5]decan-8-ylpropan-1-amine hydrochloride (as prepared in Example 104 Step B) (50 mg, 0.21 mmol, 1.00 equiv) in dichloromethane (5 mL), TEA (53.4 mg, 0.53 mmol, 2.50 equiv). This was followed by the addition of 4-nitrophenyl carbonochloridate (53.9 mg, 0.27 mmol, 1.20 equiv) dropwise with stirring at 0° C. The resulting solution was stirred for 2 hr at room temperature. The reaction was then quenched by the addition of 10 mL of sodium bicarbonate (1M). The resulting solution was extracted with 2×10 mL of dichloromethane. The organic layers were combined, and concentrated under vacuum. The title compound was obtained as a yellow oil.

Step B: 1-(1-{1,4-dioxaspiro[4.5]decan-8-yl}propyl)-3-methylurea

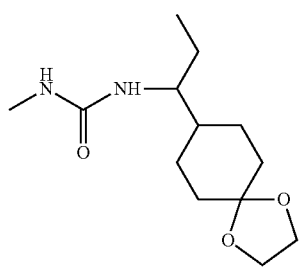 [SMILES: CCC(NC(=O)NC)C1CCC2(CC1)OCCO2]

Into a 50 mL round-bottom flask was placed a solution of 4-(hydroxynitroso)phenyl N-(1-1,4-dioxaspiro[4.5]decan-8-ylpropyl)carbamate (as prepared in the previous step, 88 mg, 0.24 mmol, 1.00 equiv) in tetrahydrofuran (10 mL), methanamine hydrochloride (32.3 mg, 0.47 mmol, 2.00 equiv), N-ethyl-N-isopropylpropan-2-amine (62 mg, 0.48 mmol, 2.00 equiv). The resulting solution was stirred overnight at room temperature. The reaction was then quenched by the addition of 10 mL of sodium bicarbonate (1M). The resulting solution was extracted with 3×10 ml, of dichloromethane. The organic layers were combined, and concentrated under vacuum. The title compound was obtained as a yellow solid.

Step C: 1-methyl-3-(1-(4-oxocyclohexyl)propyl)urea

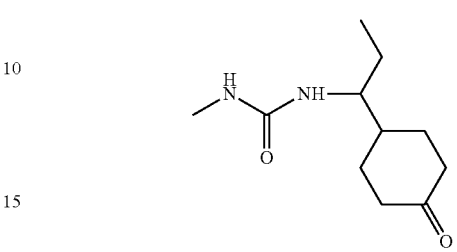

Into a 50 mL round-bottom flask was placed a solution of 1-(1-1,4-dioxaspiro[4.5]decan-8-ylpropyl)-3-methylurea (as prepared in the previous step, 48 mg, 0.19 mmol, 1.00 equiv) in CH$_3$CN (2 mL), hydrogen chloride (aq,2M) (2 mL). The resulting solution was stirred for 2 h at room temperature. The pH value of the solution was adjusted to 8 with potassium carbonate (1 mol/L). The resulting solution was extracted with 3×10 mL of dichloromethane. The organic layers were combined, dried over anhydrous sodium sulfate and concentrated under vacuum. The title compound was obtained as a yellow solid.

Step D: N-(1-((1R,4s)-4-((S)-1-(3-methylureido)propyl)cyclohexyl)azetidin-3-yl)-2-((6-(trifluoromethyl)quinazolin-4-yl)amino)acetamide

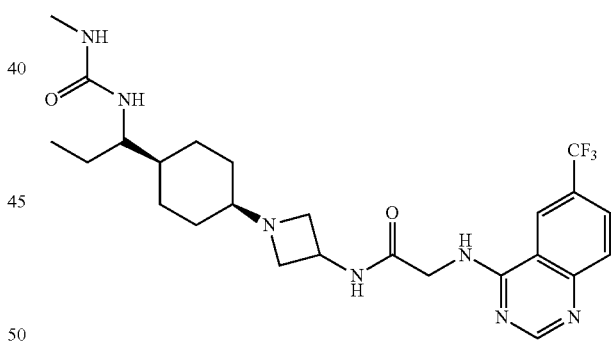

Into a 50 mL round-bottom flask was placed a solution of 1-methyl-3-(1-(4-oxocyclohexyl)propyl)urea (as prepared in the previous step, 35 mg, 0.17 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (as prepared in Example 1, Step G) (80 mg, 0.18 mmol, 1.10 equiv), TEA (17 mg, 0.17 mmol, 1.00 equiv). The resulting solution was stirred for 30 min at room temperature. NaBH(OAc)$_3$ (126 mg, 0.59 mmol, 3.60 equiv) was added. The resulting solution was allowed to react, with stirring, for an additional 2 h at room temperature. The resulting mixture was concentrated under vacuum. The crude product (50 mg) was purified by Prep-HPLC with the following conditions: Column, Xbridge Prep phenyl 5 µm,19×150 mm Prep C012(T); mobile phase, Phase A: water with 0.03% NH$_3$.H$_2$O Phase B:

CH₃CN; Detector, UV 254 nm. The title compound was obtained as a white solid.

LC-MS [M+H]⁺ 523

¹H-NMR (300 MHz, CD₃OD) δ 8.63 (s, 1H), 8.57 (s, 1H), 8.07-8.03 (m, 1H), 7.91-7.88 (d, J=8.7 Hz, 1H), 4.51-4.42 (m, 1H), 4.28 (s, 2H), 3.67-3.62 (m, 2H), 3.56-3.51 (m, 1H), 2.95 (s, 2H), 2.69 (s, 3H), 2.31 (s, 1H), 1.64-1.30 (m, 11H).

Example 143

N-(1-((1R,4s)-4-((S)-1-(3,3-dimethylureido)propyl)cyclohexyl)azetidin-3-yl)-2-((6-(trifluoromethyl)quinazolin-4-yl)amino)acetamide Step A: 1-(1-{1,4-dioxaspiro[4.5]decan-8-yl}propyl)-3,3-dimethylurea

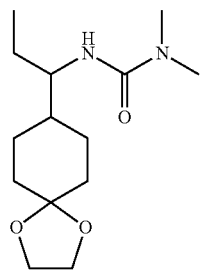 [SMILES: CCC(NC(=O)N(C)C)C1CCC2(CC1)OCCO2]

Into a 50 mL round-bottom flask was placed a solution of 1-1,4-dioxaspiro[4.5]decan-8-ylpropan-1-amine hydrochloride (as prepared in Example 104 Step B) (50 mg, 0.21 mmol, 1.00 equiv) in dichloromethane (10 mL) and TEA (42.8 mg, 0.42 mmol, 2.00 equiv). This was followed by the addition of dimethylcarbamic chloride (27.5 mg, 0.25 mmol, 1.20 equiv) dropwise with stirring at 0° C. The resulting solution was stirred overnight at room temperature. The reaction was then quenched by the addition of 20 mL of water. The resulting solution was extracted with 2×20 mL of dichloromethane. The organic layers were combined, dried over anhydrous sodium sulfate and concentrated under vacuum. The title compound was obtained as a yellow oil.

Step B: 1,1-dimethyl-3-(1-(4-oxocyclohexyl)propyl)urea

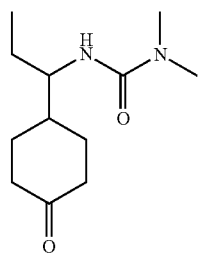 [SMILES: CCC(NC(=O)N(C)C)C1CCC(=O)CC1]

A solution of 1-(1-1,4-dioxaspiro[4.5]decan-8-ylpropyl)-3,3-dimethylurea (as prepared in the previous step, 36 mg, 0.13 mmol, 1.00 equiv) in CH₃CN (5 mL) and HCl (2M, 1 mL) was stirred for 2 h at room temperature. The resulting mixture was concentrated under vacuum. The residue was diluted with 10 mL of aq. sodium bicarbonate (1M). The resulting solution was extracted with 2×20 mL of dichloromethane. The organic layers were combined, dried over anhydrous sodium sulfate and concentrated under vacuum. The title compound was obtained as a yellow oil.

Step C: N-(1-((1R,4s)-4-((S)-1-(3,3-dimethylureido)propyl)cyclohexyl)azetidin-3-yl)-2-((6-(trifluoromethyl)quinazolin-4-yl)amino)acetamide

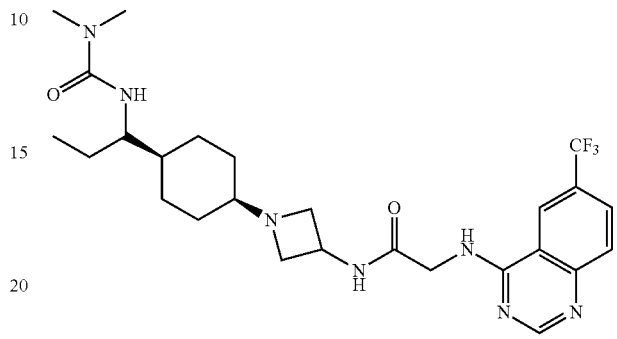

Into a 50 mL round-bottom flask were placed a solution of 1,1-dimethyl-3-(1-(4-oxocyclohexyl)propyl)urea (as prepared in the previous step, 28 mg, 0.12 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (as prepared in Example 1, Step G) (59.9 mg, 0.14 mmol, 1.10 equiv) and TEA (12.5 mg, 0.12 mmol, 1.00 equiv). The resulting solution was stirred for 30 min at room temperature, then added NaBH(OAc)₃ (95 mg, 0.45 mmol, 3.60 equiv). The resulting solution was stirred for an additional 2 h at room temperature. The resulting mixture was concentrated under vacuum. The crude product (80 mg) was purified with Prep-HPLC with the following conditions: Column, Xbridge Prep Phenyl, 5 μm, 19×150 mm; mobile phase, water (0.03% NH₃H₂O and CH₃CN (30% CH₃CN up to 50% in 8 min, up to 100% in 0.1 min, hold at 100% for 1.9 min, down to 30% in 0.1 min, hold at 30% for 0.9 min); Detector, UV 220 & 254 nm. The title compound was obtained as a white solid.

LC-MS (ES, m/z) 536 [M+H]⁺.

¹H-NMR (400 MHz, CD₃OD) δ 8.64 (s, 1H), 8.58 (s, 1H), 8.07-8.04 (d, J=10.4 Hz, 1H), 7.92-7.90 (d, J=8.8 Hz, 1H), 5.62-5.64 (d, J=8.8 Hz, 1H), 4.49-4.43 (m, 1H), 4.29 (s, 2H), 3.63-3.61 (d, J=6.8 Hz, 3H), 2.95 (s, 8H), 2.30 (s, 1H), 1.66-1.60 (m, 2H), 1.54-1.33 (m, 9H), 0.90-0.86 (m, 3H).

Example 144 methyl ((S)-1-((1s,4R)-4-(3-(2-((6-(trifluoromethyl)quinazolin-4-yl)amino)acetamido)azetidin-1-yl)cyclohexyl)propyl)carbamate

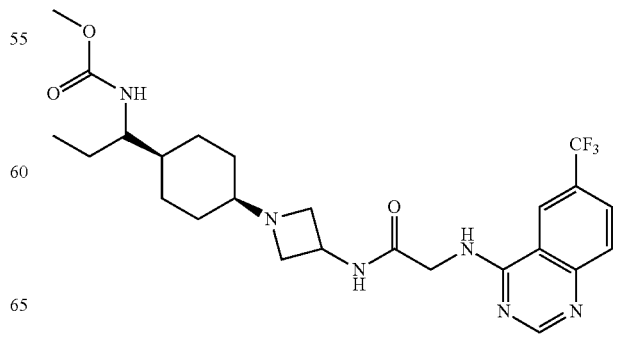

Into a 50 mL round-bottom flask were placed a solution of methyl 1-(4-oxocyclohexyl)propylcarbamate (as prepared in Example 104 Step D) (31 mg, 0.15 mmol, 1.00 equiv) in dichloromethane (10 mL), N-(azetidin-3-yl)-2-(6-(trifluoromethyl)quinazolin-4-ylamino)acetamide 2,2,2-trifluoroacetic acid (as prepared in Example 1, Step G) (70.3 mg, 0.16 mmol, 1.10 equiv) and TEA (15 mg, 0.15 mmol, 1.00 equiv). The resulting solution was stirred for 30 min at room temperature, followed by addition of NaBH(OAc)$_3$ (111 mg, 0.52 mmol, 3.60 equiv). The resulting solution was stirred for an additional 2 h at room temperature. Then it was concentrated under vacuum. The crude product (80 mg) was purified by Prep-HPLC with the following conditions: Column, Xbridge Prep Phenyl, 5 μm, 19×150 mm; mobile phase, water (0.03% NH$_3$H$_2$O and CH$_3$CN (30% CH$_3$CN up to 60% in 8 min, up to 100% in 0.1 min, hold at 100% for 1.9 min, down to 30% in 0.1 min, hold at 30% for 0.9 min); Detector, UV 220 & 254 nm. The title compound was obtained as a white solid.

LC-MS (ES, m/z) 523 [M+H]$^+$.

$^1$H-NMR (400 MHz, CD$_3$OD) δ 8.52 (s, 1H), 8.46 (s, 1H), 7.95-7.93 (d, J=8.8 Hz, 1H), 4.37-4.33 (m, 1H), 4.17 (s, 2H), 3.53-3.48 (m, 5H), 3.27-3.26 (d, J=3.2 Hz, 1H), 2.82-2.79 (m, 2H), 2.16 (s, 1H), 1.50-1.19 (m, 11H), 0.78 (s, 3H).

Examples 145 and 146

N-(1-((1r,4r)-4-hydroxy-4-(thiazol-5-yl)cyclohexyl)azetidin-3-yl)-2-((3-(trifluoromethyl)-1,6-naphthyridin-5-yl)amino)acetamide and N-(1-((1s,4s)-4-hydroxy-4-(thiazol-5-yl)cyclohexyl)azetidin-3-yl)-2-((3-(trifluoromethyl)-1,6-naphthyridin-5-yl)amino)acetamide Step A: tert-butyl 3-(trifluoromethyl)-7,8-dihydro-1,6-naphthyridine-6(5H)-carboxylate

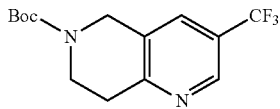 [SMILES: CC(C)(C)OC(=O)N1CCc2ncc(C(F)(F)F)cc2C1]

Into a 100 mL round-bottom flask, was placed a solution of 3-(trifluoromethyl)-5,6,7,8-tetrahydro-1,6-naphthyridine hydrochloride (5 g, 18.21 mmol, 1.00 equiv) in dichloromethane (40 mL), di-tert-butyl dicarbonate (4.76 g, 21.83 mmol, 1.20 equiv) and triethylamine (5.45 g, 53.96 mmol, 5.00 equiv). The resulting solution was stirred for 1.5 h at room temperature, and then was washed with 2×30 mL of H$_2$O. The organic portions was dried over sodium sulfate and concentrated under vacuum. The residue was purified by chromatography over a silica gel column with ethyl acetate/petroleum ether (1:50-1:10). The title compound was obtained as a white solid.

Step B: tert-butyl 5-oxo-3-(trifluoromethyl)-7,8-dihydro-1,6-naphthyridine-6(5H)-carboxylate

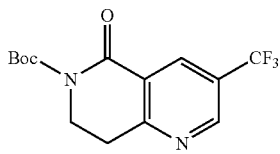 [SMILES: CC(C)(C)OC(=O)N1CCc2ncc(C(F)(F)F)cc2C1=O]

Into a 250 mL round-bottom flask, was placed a solution of tert-butyl 3-(trifluoromethyl)-7,8-dihydro-1,6-naphthyridine-6(5H)-carboxylate (as prepared in the previous step, 3.84 g, 0.01 mol, 1.00 equiv) in CCl$_4$/CH$_3$CN=10/1 (66 mL), a solution of sodium periodate (8.135 g, 38.01 mmol, 3.00 equiv) in water (20 mL) and Ruthenium(III)Chloride Hydrate (0.992 g, 0.30 equiv). The resulting solution was stirred for 12 h at room temperature, and then the mixture was diluted with 50 mL of CH$_2$Cl$_2$. The solids were filtered out. The filtrate was concentrated under vacuum. The residue was purified by chromatography over a silica gel column with ethyl acetate/petroleum ether (1:50-1:10). The title compound was obtained as a white solid.

Step C: 3-(trifluoromethyl)-7,8-dihydro-1,6-naphthyridin-5(6H)-one

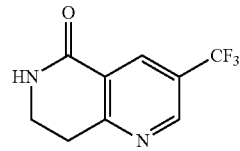

Into a 100 mL round-bottom flask, was placed a solution of tert-butyl 5-oxo-3-(trifluoromethyl)-7,8-dihydro-1,6-naphthyridine-6(5H)-carboxylate (as prepared in the previous step, 2.7 g, 8.54 mmol, 1.00 equiv) in dichloromethane (20 g) and CF$_3$COOH (4 g). The reaction mixture was stirred for 2 h at room temperature. The pH value of the solution was adjusted to 8 with sodium bicarbonate. The resulting solution was extracted with 3×30 mL of dichloromethane, and the combined organic layers was washed with 1×50 mL of brine, dried over anhydrous sodium sulfate, and concentrated under vacuum. The title compound was obtained a yellow solid.

Step D: 3-(trifluoromethyl)-1,6-naphthyridin-5(6H)-one

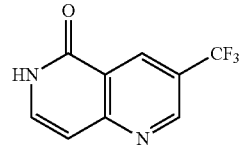

Into a 100 mL round-bottom flask, was placed a solution of 3-(trifluoromethyl)-7,8-dihydro-1,6-naphthyridin-5(6H)-one (as prepared in the previous step, 1.7 g, 7.87 mmol, 1.00 equiv) in dioxane (20 mL) and 2,3-Dichloro-5,6-dicyano-1,4-benzoquinone (2.68 g, 11.81 mmol, 1.50 equiv). The reaction mixture was stirred for 6 h at 100° C. in an oil bath. The resulting mixture was concentrated under vacuum and the residue was dissolved in 20 mL of sodium bicarbonate. The resulting solution was extracted with 3×100 mL of dichloromethane, and the combined organic layers dried over sodium sulfate and concentrated under vacuum. The residue was purified by chromatography over a silica gel column with ethyl acetate/petroleum ether (1:10-1:2). The title compound was obtained as a light yellow solid.

Step E: 5-chloro-3-(trifluoromethyl)-1,6-naphthyridine

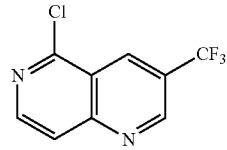 [SMILES: FC(F)(F)c1cnc2ccnc(Cl)c2c1]

Into a 50 mL round-bottom flask, was placed a solution of 3-(trifluoromethyl)-1,6-naphthyridin-5(6H)-one (as prepared in the previous step, 1 g, 4.67 mmol, 1.00 equiv) in acetonitrile (10 mL) and phosphoryl trichloride (10 mL). The reaction mixture was stirred for 2 h at 90° C. in an oil bath. The resulting mixture was concentrated under vacuum. The residue was purified by chromatography over a silica gel column with ethyl acetate/petroleum ether (1:20). The title compound was obtained as a yellow solid.

Step F: tert-butyl 3-(2-(3-(trifluoromethyl)-1,6-naphthyridin-5-ylamino)acetamido)azetidine-1-carboxylate

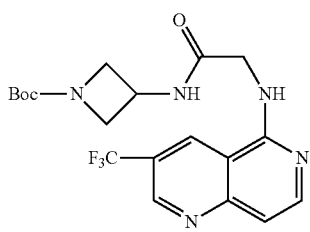 [SMILES: CC(C)(C)OC(=O)N1CC(NC(=O)CNc2nccc3ncc(C(F)(F)F)cc23)C1]

Into a 10 mL round-bottom flask, was placed a solution of 5-chloro-3-(trifluoromethyl)-1,6-naphthyridine (as prepared in the previous step, 23.3 mg, 0.10 mmol, 1.00 equiv) in diglyme (3 mL), tert-butyl 3-(2-aminoacetamido)azetidine-1-carboxylate (prepared as described in Example 1, Step E) (27 mg, 0.12 mmol, 1.20 equiv) and triethylamine (30 mg, 0.30 mmol, 3.00 equiv). The reaction mixture was stirred overnight at 120° C. The resulting mixture was diluted with 20 mL of H₂O. The resulting solution was extracted with 3×20 mL of dichloromethane. The combined organic layers dried (Na₂SO₄) and concentrated under vacuum. The title compound was obtained as a gray solid.

Step G: N-(azetidin-3-yl)-2-(3-(trifluoromethyl)-1,6-naphthyridin-5-ylamino)acetamide (salt of TFA)

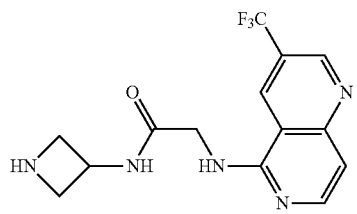 [SMILES: O=C(CNc1nccc2ncc(C(F)(F)F)cc12)NC1CNC1]

Into a 100 mL round-bottom flask, was placed a solution of tert-butyl 34243-(trifluoromethyl)-1,6-naphthyridin-5-ylamino)acetamido)azetidine-1-carboxylate (as prepared in the previous step, 20 mg, 0.05 mmol, 1.00 equiv) in dichloromethane (20 mL) and CF₃COOH (1 mL). The reaction mixture was stirred for 2 h at room temperature. The resulting mixture was concentrated under vacuum. The title compound was obtained as yellow oil.

Step H: N-(1-((1r,4r)-4-hydroxy-4-(thiazol-5-yl)cyclohexyl)azetidin-3-yl)-2-((3-(trifluoromethyl)-1,6-naphthyridin-5-yl)amino)acetamide and N-(1-((1s,4s)-4-hydroxy-4-(thiazol-5-yl)cyclohexyl)azetidin-3-yl)-2-((3-(trifluoromethyl)-1,6-naphthyridin-5-yl)amino)acetamide

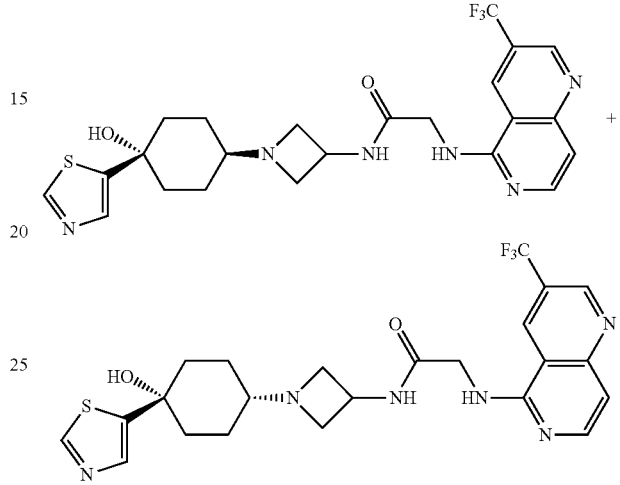

Into a 100 mL round-bottom flask, was placed a solution of N-(azetidin-3-yl)-2-(3-(trifluoromethyl)-1,6-naphthyridin-5-ylamino)acetamide (as prepared in the previous step, 325 mg, 1.00 mmol, 1.00 equiv) in dichloromethane (5 mL), 4-hydroxy-4-(thiazol-5-yl)cyclohexanone (prepared as described in Example 26, step C) (197 mg, 1.00 mmol, 1.00 equiv), NaBH(OAc)₃ (636 mg, 3.00 mmol, 3.00 equiv) and triethylamine (303 mg, 3.00 mmol, 3.00 equiv). The reaction mixture was stirred overnight at room temperature, and then the mixture was concentrated under vacuum. The resulting crude product (500 mg) was purified by Prep-HPLC with the following conditions (1#-PreP-HPLC-005(Waters)): Column, Atlantis T35 μm, 19×150 mm HPrepC-014(T) 186003698 011238204113 05; mobile phase, Phase A:water with 50 mL NH₄CO₃ Phase B: Gradient; Detector, UV 254 nm. The title compounds were isolated as light yellow solids.

For N-(1-((1r,4r)-4-hydroxy-4-(thiazol-5-yl)cyclohexyl)azetidin-3-yl)-2-(3-(trifluoromethyl)-1,6-naphthyridin-5-yl)amino)acetamide:

LC-MS (ES, m/z) 507 [M+H]⁺

¹H-NMR (300 MHz, CD₃OD) δ 9.159(d, J=1.8 Hz, 1H), 9.062-9.068(m, 1H), 8.902(s, 1H), 8.224(d, J=6 Hz, 1H), 7.822(s, 1H), 7.175-7.197(m, 1H), 4.445-4.492(m, 1H), 4.215(s, 2H), 3.611-3.663(m, 2H), 2.962-3.012(m, 2H), 2.330(s, 1H), 2.181-2.253(m, 2H), 1.721-1.886(m, 4H), 1.306-1.351(m, 2H).

For N-(1-((1s,4s)-4-hydroxy-4-(thiazol-5-yl)cyclohexyl)azetidin-3-yl)-2-((3-(trifluoromethyl)-1,6-naphthyridin-5-yl)amino)acetamide:

LC-MS (ES, m/z) 507 [M+1]⁺

¹H-NMR (300 MHz, CD3OD) δ 9.1615(d, J=2.1 Hz, 1H), 9.0745(d, J=0.9 Hz, 1H), 8.860(s, 1H), 8.233(d, J=6 Hz, 1H), 7.730(s, 1H), 7.191(d, J=6 Hz, 1H), 4.478-4.525(m, 1H), 4.226(s, 2H), 3.664-3.716(m, 2H), 3.078-3.102(m, 2H), 1.518-1.609(m, 2H), 2.231(m, 1H), 2.035(d, J=12.6 Hz, 2H), 1.763-1.802(m, 2H), 1.680-1.713(m, 2H).

Example 147

N-(1-((1r,4r)-4-hydroxy-4-(thiazol-5-yl)cyclohexyl) azetidin-3-yl)-2-((6-(trifluoromethyl)cinnolin-4-yl) amino)acetamide Step A: 1-(2-amino-5-iodophenyl)ethanone

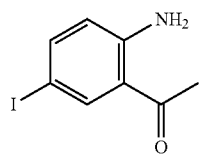

Into a 250 mL round-bottom flask, was placed a solution of 1-(2-aminophenyl)ethanone (11 g, 81.48 mmol, 1.00 equiv) in 1N HCl (300 mL). This was followed by the addition of a solution of ICl (14.5 g, 89.51 mmol, 1.10 equiv) in 2N HCl (50 mL) dropwise with stirring at 0° C. The reaction mixture was stirred for 2 h at room temperature in a water/ice bath. The solid were collected by filtration and then washed with 200 mL of ethyl acetate: MeOH (10:1). The title compound was obtained as a brown solid.

Step B: 6-iodocinnolin-4-ol

Into a 250 mL round-bottom flask, was placed a solution of 1-(2-amino-5-iodophenyl)ethanone (as prepared in the previous step, 6.5 g, 24.90 mmol, 1.00 equiv) in tetrahydrofuran (150 mL) and 1N HCl (49 mL, 2.00 equiv) and NaNO$_2$ (2.3 g, 27.06 mmol, 1.10 equiv). The reaction mixture was stirred for 1 h at 0° C., and then was heated to reflux for 2 h. after cooled to room temperature, the solid were collected by filtration and washed with ice water. The title compound was obtained as a brown solid.

Step C: 4-(benzyloxy)-6-iodocinnoline

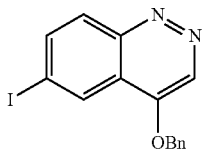 [SMILES: Ic1ccc2nncc(OCc3ccccc3)c2c1]

Into a 250 mL round-bottom flask, was placed a solution of 6-iodocinnolin-4-ol (as prepared in the previous step, 6.5 g, 23.90 mmol, 1.00 equiv) in N,N-dimethylformamide (120 mL), 1-(bromomethyl)benzene (4.4 g, 25.88 mmol, 1.10 equiv) and Cs$_2$CO$_3$ (5.47 g, 16.78 mmol, 0.70 equiv). The reaction mixture was stirred for 3 h at 60° C. in an oil bath. The reaction was then quenched by the addition of 50 mL of water. The resulting solution was extracted with 3×100 ml, of ethyl acetate, and the combined organic layers washed with 2×100 mL of sodium chloride, dried (Na$_2$SO$_4$), and concentrated under vacuum. The title compound was obtained as a yellow solid.

Step D: 4-(benzyloxy)-6-(trifluoromethyl)cinnoline

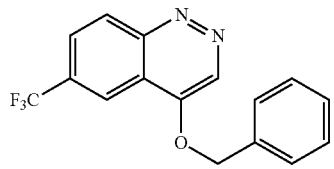 [SMILES: FC(F)(F)c1ccc2nncc(OCc3ccccc3)c2c1]

Into a 500 mL 3-necked round-bottom flask purged and maintained with an inert atmosphere of nitrogen, was placed CuI (6.4 g, 33.68 mmol, 1.20 equiv), a solution of KF (1.97 g, 33.97 mmol, 1.20 equiv) in 1-methylpyrrolidin-2-one (250 mL), TMS-CF$_3$ (4.828 g, 34.00 mmol, 1.20 equiv) and 4-(benzyloxy)-6-iodocinnoline (as prepared in the previous step, 10.2 g, 28.18 mmol, 1.00 equiv). The reaction mixture was stirred for 24 h at 50° C. in an oil bath. The reaction was then quenched by the addition of 30 mL of ammonia and 300 mL H$_2$O. The resulting solution was extracted with 3×300 mL of ether, and the combined ether portions was washed with 2×200 mL of brine, dried (Na$_2$SO$_4$), and concentrated under vacuum. The title compound was obtained as a brown solid.

Step E: 6-(trifluoromethyl)cinnolin-4-ol

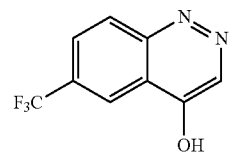 [SMILES: Oc1cnnc2ccc(C(F)(F)F)cc12]

Into a 250 mL round-bottom flask, was placed a solution of 4-(benzyloxy)-6-(trifluoromethyl)cinnoline (as prepared in the previous step, 18.1 g, 59.54 mmol, 1.00 equiv) in methanol/ethyl acetate (80/40 mL) and 10% Pd/C (1.8 g). Hydrogen was introduced into the above mixture. Under H$_2$ atmosphere, the reaction mixture was stirred overnight at 50° C. in an oil bath. The solids were filtered out. The filtrate was concentrated under vacuum. The crude product was purified by Flash-Prep-HPLC with the following conditions (IntelFlash-1): Column, silica gel; mobile phase, H$_2$O:CH$_3$CN=100% increasing to H$_2$O:CH$_3$CN=60% within 50 min; Detector, UV 254 nm. 5 g product was obtained. The title compound was obtained as a white solid.

LC-MS (ES, m/z) 215 [M+H]$^+$ $^1$H-NMR (300 MHz, DMSO) δ 13.790 (s, 1H), 8.287(s, 1H), 8.068-8.104(m, 1H), 7.883(s, 1H), 7.783(d, J=9 Hz, 1H).

Step F: 4-chloro-6-(trifluoromethyl)cinnoline

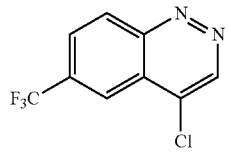 [SMILES: FC(F)(F)c1ccc2nncc(Cl)c2c1]

Into a 100 mL round-bottom flask, was placed a solution of 6-(trifluoromethyl)cinnolin-4-ol (as prepared in the previous step, 1.8 g, 8.41 mmol, 1.00 equiv) in acetonitrile (30 mL) and phosphoryl trichloride (12.78 g, 84.08 mmol, 10.00 equiv). The reaction mixture was stirred for 2 h at 100° C. in an oil bath. The resulting mixture was concentrated under vacuum. The residue was purified by chromatography over a silica gel column with ethyl acetate/petroleum ether (1:20-1:10). The title compound was obtained as a yellow solid.

Step G: tert-butyl 2-(6-(trifluoromethyl)cinnolin-4-ylamino)acetate

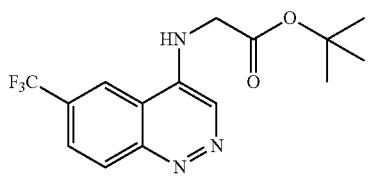 [SMILES: CC(C)(C)OC(=O)CNc1cnnc2ccc(C(F)(F)F)cc12]

Into a 8 mL vial, was placed a solution of 4-chloro-6-(trifluoromethyl)cinnoline (as prepared in the previous step, 260 mg, 1.12 mmol, 1.00 equiv) in 2-methoxyethyl ether (2 mL), tert-butyl 2-aminoacetate (187 mg, 1.12 mmol, 1.10 equiv) and triethylamine (339 mg, 3.36 mmol, 3.00 equiv). The reaction mixture was stirred overnight at 100° C. in an oil bath. The reaction was then quenched by the addition of 4 mL of water. The resulting solution was extracted with 3×10 mL of ethyl acetate, and the combined organic layers washed with 2×10 mL of brine, dried (Na$_2$SO$_4$), and concentrated under vacuum. The title compound was obtained as a yellow solid.

LC-MS (ES, m/z) 328 [M+H]$^+$

Step H: 2-(6-(trifluoromethyl)cinnolin-4-ylamino)acetic acid

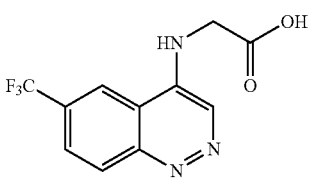 [SMILES: O=C(O)CNc1cnnc2ccc(C(F)(F)F)cc12]

Into a 100 mL round-bottom flask, was placed a solution of tert-butyl 2-(6-(trifluoromethyl)cinnolin-4-ylamino)acetate (as prepared in the previous step, 200 mg, 0.61 mmol, 1.00 equiv) in dichloromethane (5 mL) and CF$_3$COOH (0.2 mL). The reaction mixture was stirred overnight at room temperature, and then was concentrated under vacuum. The title compound was obtained as a yellow solid.

Step I: N-(1-((1r,4r)-4-hydroxy-4-(thiazol-5-yl)cyclohexyl)azetidin-3-yl)-2-((6-(trifluoromethyl)cinnolin-4-yl)amino)acetamide

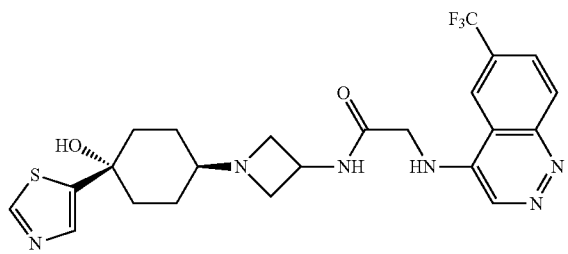 [SMILES: O=C(CNc1cnnc2ccc(C(F)(F)F)cc12)NC1CN([C@H]2CC[C@@](O)(c3cncs3)CC2)C1]

Into a 8 mL round-bottom flask, was placed a solution of 2-(6-(trifluoromethyl)cinnolin-4-ylamino)acetic acid (as prepared in the previous step, 70 mg, 0.26 mmol, 1.00 equiv) in dichloromethane (2 mL), EDC (65 mg, 0.34 mmol, 1.10 equiv), HOBt (38 mg, 0.28 mmol, 1.10 equiv), triethylamine (78 mg, 0.77 mmol, 3.00 equiv) and 1-(3-aminocyclobutyl)-4-(thiazol-5-yl)piperidin-4-ol (as prepared in Example 162, Step F) (65 mg, 0.26 mmol). The reaction mixture was stirred overnight at 40° C. in an oil bath. The resulting mixture was concentrated under vacuum. The crude product (200 mg) was purified by Prep-HPLC with the following conditions (1#-Waters 2767-5): Column, SunFire Prep C18, 5 μm, 19×100 mm; mobile phase, Water and CH$_3$CN; Phase A:water with 0.05% TFA Phase B: CH$_3$CN Gradient; Detector. 16 mg product was obtained. The title compound was obtained as a light yellow solid.

LC-MS (ES, m/z) 507 [M+H]$^+$ $^1$H-NMR (300 MHz, CD3OD) δ 8.912(s, 1H), 8.690(s, 1H), 8.609(s, 1H), 8.300-8.330(d, J=9 Hz, 1H), 8.023-8.058 (m, 1H), 7.839(s, 1H), 4.586(s, 1H), 4.481-4.528(m, 1H), 4.240(s, 2H), 3.749-3.799(m, 2H), 3.199(m, 2H), 2.508(s, 1H), 2.213-2.274(m, 2H), 1.755-1.944(m, 4H), 1.304-1.387 (m, 2H).

Examples 148 and 149

N-(1-((1r,4r)-4-hydroxy-4-(thiazol-5-yl)cyclohexyl)azetidin-3-yl)-2-((7-(trifluoromethyl)phthalazin-1-yl)amino)acetamide and N-(1-((1s,4s)-4-hydroxy-4-(thiazol-5-yl)cyclohexyl)azetidin-3-yl)-2-((7-(trifluoromethyl)phthalazin-1-yl)amino)acetamide

Step A: 6-nitroisobenzofuran-1(3H)-one

Into a 2000 mL 3-necked round-bottom flask, was placed a solution of isobenzofuran-1(3H)-one (130 g, 970.15 mmol, 1.00 equiv) in sulfuric acid (200 mL). This was followed by the addition of a solution of potassium nitrate (196 g, 1.94 mol, 1.39 equiv) in sulfuric acid (600 mL) dropwise with stirring at 0° C. The reaction mixture was stirred overnight at room temperature. The solid was collected by filtration and washed with 5×800 mL of H₂O. This resulted in 136 g (crude) of 6-nitroisobenzofuran-1(3H)-one as a white solid.

Step B: 6-aminoisobenzofuran-1(3H)-one

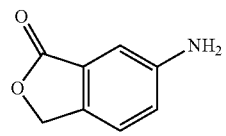 [SMILES: Nc1ccc2c(c1)C(=O)OC2]

Into a 2000 mL 3-necked round-bottom flask, was placed a solution of 6-nitroisobenzofuran-1(3H)-one (prepared as described in the previous step, 136 g, 759.78 mmol, 1.00 equiv) in water (50 mL), Fe (126.4 g), ethyl acetate (500 mL), acetic acid (180 mL). The reaction mixture was stirred for 2 h at 60° C. in an oil bath. The resulting mixture was added sodium bicarbonate 500 mL. The resulting solution was extracted with 5×500 mL of ethyl acetate. The combined organic layer was washed with 500 mL of brine, dried (Na₂SO₄), and concentrated under vacuum. The title compound was obtained as a yellow solid.

LC-MS (ES, m/z) 150 [M+H]⁺

Step C: 6-iodoisobenzofuran-1(3H)-one

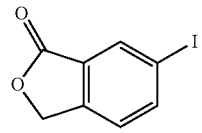 [SMILES: O=C1OCc2ccc(I)cc21]

Into a 2000 mL 3-necked round-bottom flask, was placed a solution of 6-aminoisobenzofuran-1(3H)-one (prepared as described in the previous step, 56 g, 375.84 mmol, 1.00 equiv) in H₂O/HCl (600 mL), a solution of NaNO₂ (31.1 g, 450.72 mmol, 1.70 equiv) in water (200 mL) dropwised at 0 degrees, a solution of KI (124.8 g, 751.81 mmol, 2.00 equiv) and CuI (17.85 g, 93.95 mmol, 0.20 equiv) in water (200 mL) was added at below 20 degree. The reaction mixture was stirred for 5 h at room temperature. The resulting mixture diluted 200 mL H₂O. The resulting solution was extracted with 3×500 mL of ethyl acetate. The combined organic layer was washed with 500 mL of brine, dried (Na₂SO₄), and concentrated under vacuum. The residue was purified by chromatography over a silica gel column with dichloromethane/petroleum ether (50:1-5:1). The title compound was obtained as a white solid.

LC-MS (ES, m/z) 261 [M+H]⁺

Step D: 6-(trifluoromethyl)isobenzofuran-1(3H)-one

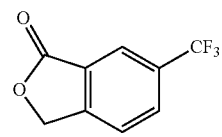 [SMILES: O=C1OCc2ccc(C(F)(F)F)cc21]

Into a 250 mL 3-necked round-bottom flask purged and maintained with an inert atmosphere of nitrogen, was placed copper(I) iodide (30 g, 157.89 mmol, 2.00 equiv), a solution of methyl 2,2-difluoro-2-(fluorosulfonyl)acetate (30 g, 144.23 mmol, 2.00 equiv) in N,N-dimethylformamide (30 mL) and 6-iodoisobenzofuran-1(3H)-one (prepared as described in the previous step, 20 g, 76.92 mmol, 1.00 equiv). The reaction mixture was stirred overnight at 100° C. in an oil bath. The reaction progress was monitored by GCMS. The reaction was then quenched by the addition of 15 mL of ammonia. The resulting solution was extracted with 3×50 mL of ethyl acetate. The combined organic layer was washed with 50 mL of brine, dried (Na₂SO₄), and concentrated under vacuum. The title compound was obtained as a yellow solid.

LC-MS (ES, m/z) 203 [M+H]⁺

Step E: 3-bromo-6-(trifluoromethyl)isobenzofuran-1(3H)-one

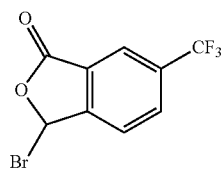

Into a 50 mL round-bottom flask, was placed a solution of 6-(trifluoromethyl)isobenzofuran-1(3H)-one (prepared as described in the previous step, 5.5 g, 27.23 mmol, 1.00 equiv) in CCl₄ (10 mL), NBS (5.8 g, 32.58 mmol, 1.20 equiv) and AIBN (0.45 g, 0.10 equiv). The reaction mixture was stirred for 3 h at 65° C. in an oil bath. The resulting mixture was concentrated under vacuum. The residue was dissolved in 100 mL of ethyl acetate, washed with 60 mL of brine, dried (Na₂SO₄), and concentrated under vacuum. The title compound was obtained as a yellow oil.

LC-MS (ES, m/z) 281 [M+H]⁺

Step F: 1-bromo-7-(trifluoromethyl)phthalazine

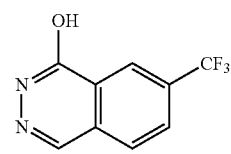 [SMILES: Oc1nncc2ccc(C(F)(F)F)cc12]

Into a 250 mL round-bottom flask, was placed a solution of 3-bromo-6-(trifluoromethyl)isobenzofuran-1(3H)-one (prepared as described in the previous step, 8.5 g, 30.36 mmol, 1.00 equiv) in ethanol (30 mL) and N₂H₄.H₂O (6 g, 111.11 mmol, 3.00 equiv). The reaction mixture was stirred overnight at 60° C. in an oil bath. The resulting mixture was concentrated under vacuum. The residue was purified by chromatography over a silica gel column with H₂O/CH₃CN (1-bromo-7-(trifluoromethyl)phthalazine). This resulted in 1.2 g (18%) of 1-bromo-7-(trifluoromethyl)phthalazine as a white solid.

LC-MS (ES, m/z) 215 [M+H]⁺

Step G: 1-chloro-7-(trifluoromethyl)phthalazine

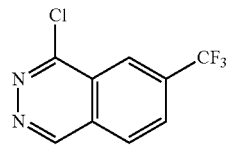 [SMILES: FC(F)(F)c1ccc2cnnc(Cl)c2c1]

Into a 50 mL round-bottom flask, was placed 7-(trifluoromethyl)phthalazin-1-ol (prepared as described in the previous step, 1.6 g, 7.48 mmol, 1.00 equiv) and POCl$_3$ (12 mL). The reaction mixture was stirred for 2 h at 100° C. in an oil bath. The resulting mixture was concentrated under vacuum. The residue was dissolved in 50 mL of dichloromethane, washed with 3×5 mL of H$_2$O, dried (Na2SO4), and concentrated under vacuum. The residue was purified by chromatography over a silica gel column with CH$_3$CN/H$_2$O (10:4). The title compound was obtained as a yellow solid.
LC-MS (ES, m/z) 233 [M+H]$^+$

Step H: tert-butyl 3-(2-(6-(trifluoromethyl)phthalazin-5-ylamino)acetamido)azetidine-1-carboxylate

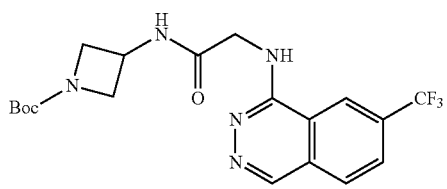 [SMILES: CC(C)(C)OC(=O)N1CC(NC(=O)CNc2nncc3ccc(C(F)(F)F)cc23)C1]

Into a 50 mL round-bottom flask, was placed a solution of 1-chloro-7-(trifluoromethyl)phthalazine (prepared as described in the previous step, 1.5 g, 6.47 mmol, 1.00 equiv) in 2-methoxyethyl ether (10 mL), tert-butyl 3-(2-aminoacetamido)azetidine-1-carboxylate (prepared as described in Example 1, Step E) (1.5 g, 6.55 mmol, 1.22 equiv) and triethylamine (1.95 g, 19.31 mmol, 2.99 equiv). The reaction mixture was stirred overnight at 100° C. in an oil bath. The reaction progress was monitored by LCMS. The resulting mixture was concentrated under vacuum. The residue was purified by chromatography over a silica gel column with CH$_3$CN:H$_2$O (3:1). The title compound was obtained as a white solid.
LC-MS (ES, m/z) 415 [M+H]$^+$

Step I: N-(azetidin-3-yl)-2-(7-(trifluoromethyl)phthalazin-1-ylamino)acetamide

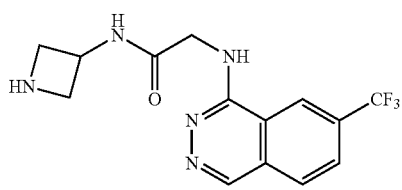 [SMILES: O=C(CNc1nncc2ccc(C(F)(F)F)cc12)NC1CNC1]

Into a 25 mL round-bottom flask, was placed a solution of tert-butyl 3-(2-(7-(trifluoromethyl)phthalazin-1-ylamino)acetamido)azetidine-1-carboxylate (prepared as described in the previous step, 160 mg, 0.38 mmol, 1.00 equiv) in dichloromethane (1 mL). This was followed by the addition of trifluoroacetic acid (0.8 mL). The reaction mixture was stirred for 2 h at 0° C. The resulting mixture was concentrated under vacuum. The title compound was obtained as a yellow oil.
LC-MS (ES, m/z) 325 [M+H]$^+$

Step J. N-(1-((1r,4r)-4-hydroxy-4-(thiazol-5-yl)cyclohexyl)azetidin-3-yl)-2-((7-(trifluoromethyl)phthalazin-1-yl)amino)acetamide and N-(1-((1s,4s)-4-hydroxy-4-(thiazol-5-yl)cyclohexyl)azetidin-3-yl)-2-((7-(trifluoromethyl)phthalazin-1-yl)amino)acetamide

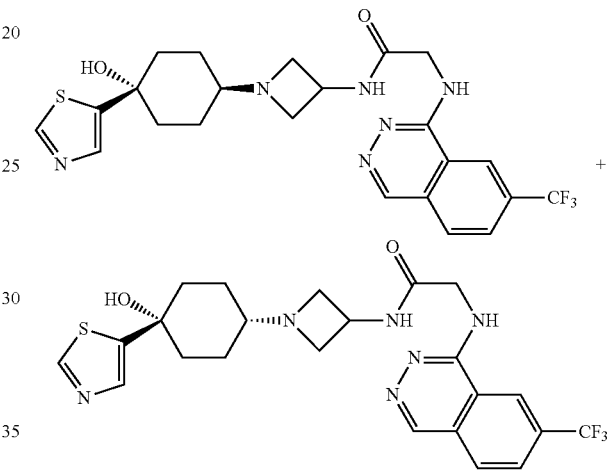

Into a 8 mL vial, was placed N-(azetidin-3-yl)-2-[[7-(trifluoromethyl)phthalazin-1-yl]amino]acetamide (prepared as described in the previous step, 150 mg, 0.46 mmol, 1.00 equiv) dichloromethane (5 mL), 4-hydroxy-4-(1,3-thiazol-5-yl)cyclohexan-1-one (prepared as described in example 26, Step C) (110 mg, 0.56 mmol, 1.21 equiv) and NaB(OAc)$_3$ (391 mg). The reaction mixture was stirred overnight at room temperature. The resulting mixture was concentrated under vacuum. The crude product was purified by Flash-Prep-HPLC with the following conditions (IntelFlash-1): Column, silica gel; mobile phase, TFA/CH$_3$CN=10 increasing to TFA/CH$_3$CN=70 within 12 min; Detector, UV 254 nm. The title compounds were isolated as white solids.

For N-(1-((1r,4r)-4-hydroxy-4-(thiazol-5-yl)cyclohexyl)azetidin-3-yl)-2-((7-(trifluoromethyl)phthalazin-1-yl)amino)acetamide:
LC-MS (ES, m/z) 507 [M+H]$^+$
$^1$H-NMR (300 MHz, CD$_3$OD) 1.279-1.353(2H, m), 1.726-1.889(4H, m), 2.185-2.269(2H, m), 2.231-2.344(1H, m), 2.970-3.021(2H, m), 3.612-3.664(2H, m), 4.275(2H,s), 4.449-4.496(1H, m), 4.596(1H,$), 7.824(1H,$), 8.135-8.198 (2H, m), 8.693(1H,$), 8.909(1H,$), 9.019(1H,$).

For N-(1-((1s,4s)-4-hydroxy-4-(thiazol-5-yl)cyclohexyl)azetidin-3-yl)-2-((7-(trifluoromethyl)phthalazin-1-yl)amino)acetamide:
LC-MS (ES, m/z) 507 [M+H]$^+$
$^1$H-NMR (300 MHz, CD$_3$OD) δ 9.028(s, 1H), 8.861(s, 1H), 8.703(s, 1H), 8.169-8.173(m, 2H), 7.736(s, 1H), 4.286

(s, 2H), 4.506(m, 1H), 3.669-3.721(m, 2H), 3.060-3.112(m, 2H), 2.040(d, J=12.6 Hz, 1H), 1.822(d, J=3.3 Hz, 2H), 1.552-1.686(m, 4H), 1.525(m, 2H).

Examples 150 and 151

N-(1-((1R,4s)-4-((S)-1-hydroxypropyl)cyclohexyl) azetidin-3-yl)-2-((3-(trifluoromethyl)-1,6-naphthyridin-5-yl)amino)acetamide and N-(1-((1S,4r)-44(S)-1-hydroxypropyl)cyclohexyl) azetidin-3-yl)-2-((3-(trifluoromethyl)-1,6-naphthyridin-5-yl)amino)acetamide

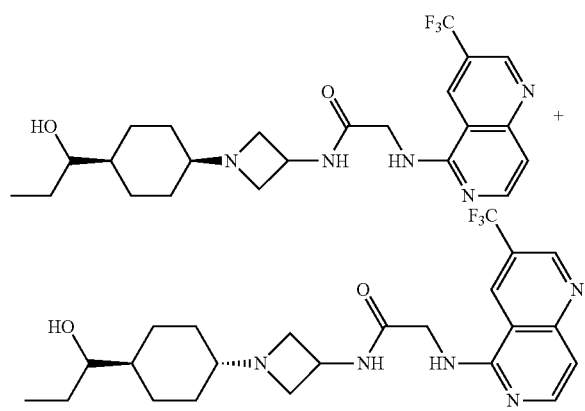

Into a 100 ml, round-bottom flask, was placed a solution of N-(azetidin-3-yl)-2-(3-(trifluoromethyl)-1,6-naphthyridin-5-ylamino)acetamide (prepared as described in example 146, Step G) (325 mg, 1.00 mmol, 1.00 equiv) in dichloromethane (5 mL), 4-(1-hydroxypropyl)cyclohexanone (as prepared in Example 25, Step B) (170 mg, 1.09 mmol), NaBH(OAc)$_3$ (636 mg, 3.00 mmol, 3.00 equiv) and triethylamine (303 mg, 3.00 mmol, 3.00 equiv). The reaction mixture was stirred overnight at room temperature. The resulting mixture was concentrated under vacuum. The crude product (500 mg) was purified by Prep-HPLC with the following conditions (1#-PreP-HPLC-005(Waters)): Column, Atlantis T35 μm, 19×150 mm HPrepC-014(T) 186003698 011238204113 05; mobile phase, Phase A: water with 50 mL NH$_4$CO$_3$ Phase B: CH$_3$CN Gradient; Detector, UV 254 nm. The title compounds were isolated as white solids.

For N-(1-((1R,4s)-4-((S)-1-hydroxypropyl)cyclohexyl) azetidin-3-yl)-2-((3-(trifluoromethyl)-1,6-naphthyridin-5-yl)amino)acetamide:

LC-MS (ES, m/z) 466 [M+H]$^+$ $^1$H-NMR (300 MHz, CD$_3$OD) δ9.045(s, 1H), 8.955(s, 1H), 8.115(d, J=4.8 Hz, 1H), 7.077(d, J=4.8 Hz, 1H), 4.360-4.394(m, 1H), 4.107(s, 2H), 3.562(s, 2H), 2.232(s, 1H), 1.177-1.492(m, 12H), 0.842-0.860(m, 3H).

For N-(1-41S,4r)-4-((S)-1-hydroxypropyl)cyclohexyl) azetidin-3-yl)-2-((3-(trifluoromethyl)-1,6-naphthyridin-5-yl)amino)acetamide:

LC-MS (ES, m/z) 466 [M+H]$^+$ $^1$H-NMR (300 MHz, CD$_3$OD) δ9.1595(d, J=0.6 Hz, 1H), 9.064-9.071(m, 1H), 8.226(d, J=6 Hz, 1H), 7.178-7.201(m, 1H), 4.479-4.526(m, 1H), 4.220(s, 2H), 3.73-3.76(m, 2H), 3.115-3.201(m, 3H), 2.147(m, 1H), 1.849-1.952(m, 3H), 1.864-1.878(m, 1H), 1.356-1.525(m, 4H), 1.062-1.164(m, 6H).

Example 152

N-(1-(4-(1-hydroxypropyl)cyclohexyl)azetidin-3-yl)-2-(6-(trifluoromethyl)cinnolin-4-ylamino)acetamide Step A: tert-butyl 3-(2-(6-(trifluoromethyl)cinnolin-4-ylamino) acetamido) azetidine-1-carboxylate

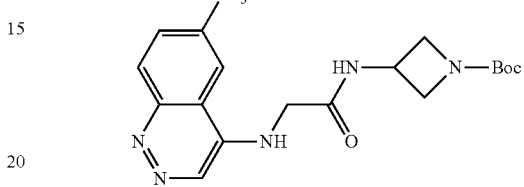

Into a 100-mL round-bottom flask, was placed a solution of 4-chloro-6-(trifluoromethyl)cinnoline (prepared as described in Example 147, Step F) (700 mg, 3.00 mmol) in 2-methoxyethyl ether (10 ml), tert-butyl 3-(2-aminoacetamido)azetidine-1-carboxylate (687 mg, 3.00 mmol) from example 1, step E and triethylamine (909 mg, 9.00 mmol). The reaction mixture was stirred overnight at 120° C. The resulting mixture was concentrated under vacuum. The residue was purified by chromatography over a silica gel column with CH$_3$CN:H$_2$O (0-40%) to give the title compound as a white solid.

Step B: N-(azetidin-3-yl)-2-(6-(trifluoromethyl)cinnolin-4-ylamino) acetamide

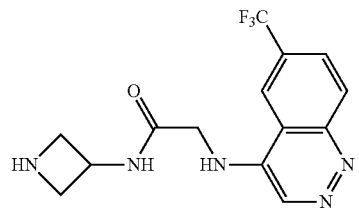 [SMILES: O=C(CNc1cnnc2ccc(C(F)(F)F)cc12)NC1CNC1]

Into a 50-mL round-bottom flask, was placed a solution of tert-butyl 3-(2-(6-(trifluoromethyl) cinnolin-4-ylamino) acetamido) azetidine-1-carboxylate (140 mg, 0.33 mmol,) in dichloromethane (10 ml) and CF$_3$COOH (1 ml). The reaction mixture was stirred for 2 h at room temperature. The resulting mixture was concentrated under vacuum to give the title compound as yellow oil.

Step C: Synthesis of N-(1-(4-(1-hydroxypropyl)cyclohexyl)azetidin-3-yl)-2-(6-(trifluoromethyl)cinnolin-4-ylamino)acetamide

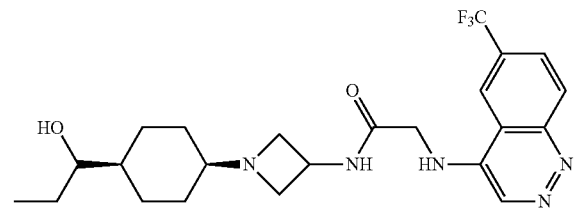 [SMILES: CCC(O)[C@H]1CC[C@@H](N2CC(NC(=O)CNc3cnnc4ccc(C(F)(F)F)cc34)C2)CC1]

Into a 100 mL round-bottom flask, was placed a solution of N-(azetidin-3-yl)-2-(6-(trifluoromethyl)cinnolin-4-ylamino) acetamide (as prepared in the previous step, 450 mg, 1.38 mmol, 1.00 equiv) in dichloromethane (30 mL), 4-(1-hydroxypropyl)cyclohexanone (as described in Example 25, Step B) (216 mg, 1.38 mmol, 1.00 equiv), NaBH(OAc)$_3$ (877 mg, 4.14 mmol, 3.00 equiv) and triethylamine (418 mg, 4.14 mmol, 3.00 equiv). The reaction mixture was stirred overnight at room temperature. The resulting mixture was concentrated under vacuum. The crude product (500 mg) was purified by Prep-HPLC with the following conditions (1#-Waters 2767-5): Column, SunFire Prep C18, 5 μm, 19×100 mm; mobile phase, Water and CH$_3$CN (30% CH$_3$CN up to 40% in 13 min, up to 100% in 0.1 min, hold 100% in 2 min, down to 30% in 0.1 min, hold 30% in 1.4 min); Detector, UV 220&254 nm. The title compound was obtained as a light yellow solid.

LC-MS (ES, m/z) 466 [M+H]$^+$ $^1$H-NMR (300 MHz CDCl$_3$) δ 8.691 (s, 1H), 8.601(s, 1H), 8.302-8.332(d, J=9 Hz, 1H), 8.026-8.056(d, J=9 Hz, 1H), 4.476-4.522(m, 1H), 4.232(s, 2H), 3.635-3.684(m, 2H), 2.937-2.984(m, 2H), 2.301(s, 1H), 1.287-1.656(m, 11H), 0.940-0.989(m, 3H).

Examples 153 and 154

N-(1-((1R,4s)-4-((S)-1-hydroxypropyl)cyclohexyl) azetidin-3-yl)-2-((7-(trifluoromethyl)phthalazin-1-yl) amino)acetamide and N-(1-((1R,4r)-44(R)-1-hydroxypropyl)cyclohexyl) azetidin-3-yl)-2-((7-(trifluoromethyl)phthalazin-1-yl) amino)acetamide tions (IntelFlash-1): Column, silica gel; mobile phase, TFA/CH$_3$CN=10 increasing to TFA/CH$_3$CN=100 within 9 min; Detector, UV 254 nm. The compound N-(1-((1R,4s)-4-((S)-1-hydroxypropyl)cyclohexyl)azetidin-3-yl)-247-(trifluoromethyl)phthalazin-1-yl)amino)acetamide was isolated as a light yellow solid, and N-(1-((1R,4r)-4-((R)-1-hydroxypropyl)cyclohexyl)azetidin-3-yl)-247-(trifluoromethyl)phthalazin-1-yl)amino)acetamide was isolated as a white solid.

For N-(1-((1R,4s)-4-((S)-1-hydroxypropyl)cyclohexyl) azetidin-3-yl)-2-((7-(trifluoromethyl)phthalazin-1-yl) amino)acetamide:

LC-MS (ES, m/z) 466 [M+H]$^+$ $^1$H-NMR (CD$_3$OD, ppm) 0.930-0.980 (3H, m), 1.373-1.508(11H, m), 2.300(1H, m), 2.962(2H, m), 3.336(1H, m), 3.644(2H, m), 4.277(2H, s), 4.489(1H, m), 8.164(2H, d), 8.697(1H, s), 9.021(1H, s).

For N-(1-((1R,4r)-4-((R)-1-hydroxypropyl)cyclohexyl) azetidin-3-yl)-2-((7-(trifluoromethyl)phthalazin-1-yl) amino)acetamide:

LC-MS (ES, m/z) 466 [M+H]$^+$ $^1$H-NMR (CD$_3$OD, 300 MHz) δ9.021(s, 1H), 8.697(s, 1H), 8.164(2H, J=1.5 Hz,d), 4.489(m, 1H), 4.277(s, 2H), 3.644(m, 2H), 3.336(m, 1H), 2.962(m, 2H), 2.300(m, 1H), 1.373-1.508(m, 11H), 0.930-0.980 (m, 3H).

Example 155 and 156

N-(1-((1R,4s)-4-((S)-1-hydroxy-2-methylpropyl) cyclohexyl)azetidin-3-yl)-2-((3-(trifluoromethyl)-1, 6-naphthyridin-5-yl)amino)acetamide and N-(1-((1R,4r)-4-((R)-1-hydroxy-2-methylpropyl) cyclohexyl)azetidin-3-yl)-2-((3-(trifluoromethyl)-1, 6-naphthyridin-5-yl)amino)acetamide

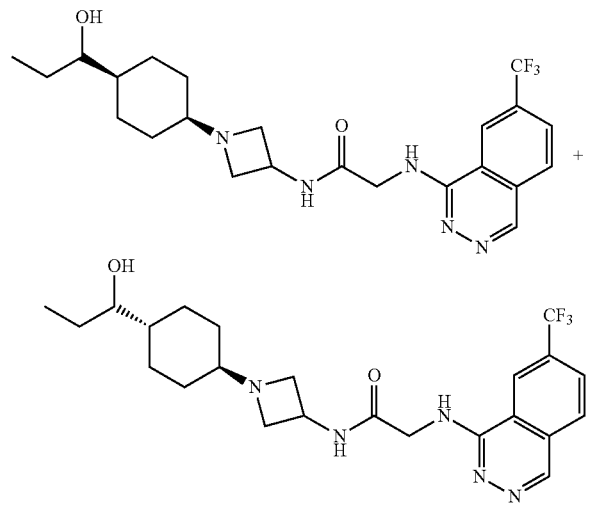

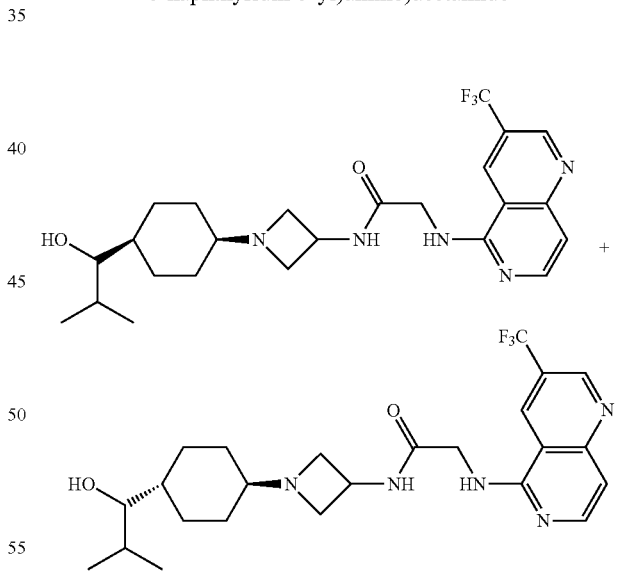

Into a 25 mL round-bottom flask, was placed N-(azetidin-3-yl)-2-[[7-(trifluoromethyl)phthalazin-1-yl]amino]acetamide (as prepared in Example 148, Step I) (100 mg, 0.31 mmol, 1.00 equiv), dichloromethane (5 mL), 4-(1-hydroxypropyl)cyclohexan-1-one (as described in Example 25, Step B) (67 mg, 0.43 mmol, 1.40 equiv), sodium triacetoxyborohydride (261 mg) and TEA (73 mg). The reaction mixture was stirred overnight at room temperature. The resulting mixture was concentrated under vacuum. The crude product (120 mg) was purified by Flash-Prep-HPLC with the following condi- Into a 10 mL round-bottom flask, was placed a solution of N-(azetidin-3-yl)-2-(3-(trifluoromethyl)-1,6-naphthyridin-5-ylamino)acetamide (as prepared in Example 146, Step G) (325 mg, 1.00 mmol, 1.00 equiv) in dichloromethane (5 mL), 4-(1-hydroxy-2-methylpropyl)cyclohexanone (as prepared in Example 7, Step B) (170 mg, 1.00 mmol), NaBH(OAc)$_3$ (636 mg, 3.00 mmol, 3.00 equiv) and triethylamine (303 mg, 3.00 mmol, 3.00 equiv). The reaction mixture was stirred overnight at room temperature. The resulting mixture was concentrated under vacuum. The crude product was purified by Prep-HPLC with the following conditions (1#-Waters 2767-5): Column, SunFire Prep C18, 5um, 19×100 mm; mobile phase, Water and CH$_3$CN (30% CH$_3$CN up to 40% in 13 min, up to 100% in 0.1 min, hold 100% in 2 min, down to 30% in 0.1 min, hold 30% in 1.4 min); Detector, UV 220& 254 nm. The compound N-(1-((1R,4s)-4-((S)-1-hydroxy-2-methylpropyl)cyclohexyl)azetidin-3-yl)-2-(3-(trifluoromethyl)-1,6-naphthyridin-5-ylamino)acetamide was isolated as a light yellow solid, and N-(1-((1R,4r)-4-((R)-1-hydroxy-2-methylpropyl)cyclohexyl)azetidin-3-yl)-2-(3-(trifluoromethyl)-1,6-naphthyridin-5-ylamino)acetamide was isolated as a green solid.

For N-(1-((1R,4s)-4-((S)-1-hydroxy-2-methylpropyl)cyclohexyl)azetidin-3-yl)-2-((3-(trifluoromethyl)-1,6-naphthyridin-5-yl)amino)acetamide:

LC-MS (ES, m/z) 480 [M+H]$^+$ $^1$H-NMR (300 MHz, CD$_3$OH) δ 9.157-9.162(d, J=1.5 Hz, 1H), 9.071(s, 1H), 8.228(d, J=6 Hz, 1H), 7.19(d, J=6 Hz, 1H), 4.467-4.490(m, 1H), 4.219(s, 2H), 3.640-3.688(m, 2H), 3.208-3.230(m, 1H), 2.996(s, 2H), 2.324(s, 1H), 1.767-1.790 (m, 1H), 1.337-1.548(m, 9H), 0.949(d, J=6.6 Hz, 3H), 0.844 (d, J=6.6 Hz, 3H).

For N-(1-((1R,4s)-4-((S)-1-hydroxy-2-methylpropyl)cyclohexyl)azetidin-3-yl)-2-((3-(trifluoromethyl)-1,6-naphthyridin-5-yl)amino) acetamide:

LC-MS (ES, m/z) 480 [M+H]$^+$ $^1$H-NMR (300 MHz, CD30H) δ 9.166(1H, s), 9.073(1H, s), 8.234(d, J=4.2 Hz, 1H), 7.199(d, J=4.8 Hz, 1H), 4.474-4.509(m, 1H), 4.221(s, 2H), 3.667-3.930(m, 2H), 2.947-3.154(m, 3H), 1.611-2.065(m, 6H), 1.368(s, 1H), 1.153-1.185(m, 4H), 1.068(s, 6H).

Examples 157 and 158

N-(1-((1R,4s)-4-((S)-1-hydroxy-2-methylpropyl) cyclohexyl)azetidin-3-yl)-2-((6-(trifluoromethyl) cinnolin-4-yl)amino)acetamide and N-(1-((1R,4r)-4-((R)-1-hydroxy-2-methylpropyl) cyclohexyl)azetidin-3-yl)-2-((6-(trifluoromethyl) cinnolin-4-yl)amino)acetamide mL), 4-(1-hydroxy-2-methylpropyl)cyclohexanone (as prepared in Example 7, Step B) (54 mg, 0.32 mmol, 1.00 equiv), NaBH(OAc)$_3$ (135 mg, 0.64 mmol, 3.00 equiv) and triethylamine (97 mg, 0.96 mmol, 2.08 equiv). The reaction mixture was stirred overnight at room temperature. The resulting mixture was concentrated under vacuum. The crude product (500 mg) was purified by Prep-HPLC with the following conditions (1#-Waters 2767-5): Column, SunFire Prep C18, 5 μm, 19×100 mm; mobile phase, Water and CH$_3$CN (30% CH$_3$CN up to 40% in 13 min, up to 100% in 0.1 min, hold 100% in 2 min, down to 30% in 0.1 min, hold 30% in 1.4 min); Detector, UV 220&254 nm. The title compounds were isolated as light yellow solids.

For N-(1-((1R,4s)-4-((S)-1-hydroxy-2-methylpropyl)cyclohexyl)azetidin-3-yl)-2-((6-(trifluoromethyl)cinnolin-4-yl)amino)acetamide:

LC-MS (ES, m/z) 480 [M+H]$^+$ $^1$H-NMR (300 MHz, CD$_3$OH) δ 8.684(s, 1H), 8.602(s, 1H), 8.310(d, J=9 Hz, 1H), 8.030(d, J=12.6 Hz, 1H), 4.456-4.591(m, 2H), 4.234(s, 2H), 3.721-3.746(m, 2H), 3.11-3.207 (m, 3H), 2.439(s, 1H), 1.311-1.815(m, 11H), 0.847-0.963(m, 6H).

For N-(1-((1R,4r)-4-((R)-1-hydroxy-2-methylpropyl)cyclohexyl)azetidin-3-yl)-2-((6-(trifluoromethyl)cinnolin-4-yl)amino)acetamide:

LC-MS (ES, m/z) 480 [M+H]$^+$ $^1$H-NMR (300 MHz, CD$_3$OH) 68.693(s, 1H), 8.608(s, 1H), 8.319(d, J=9 Hz, 1H), 8.025-8.061(m, 1H), 4.501-4.549 (m, 1H), 4.238(s, 2H), 3.773-3.802(m, 2H), 3.195-3.336(m, 2H), 2.948-2.987(m, 1H), 2.201-2.215(m, 1H), 1.172-1.952 (m, 11H), 1.006-1.096(m, 6H).

Examples 159 and 160

N-(1-((1R,4s)-4-((S)-1-hydroxy-2-methylpropyl) cyclohexyl)azetidin-3-yl)-2-((7-(trifluoromethyl) phthalazin-1-yl)amino)acetamide and N-(1-((1S,4r)-44(S)-1-hydroxy-2-methylpropyl)cyclohexyl)azetidin-3-yl)-2-((7-(trifluoromethyl)phthalazin-1-yl)amino)acetamide

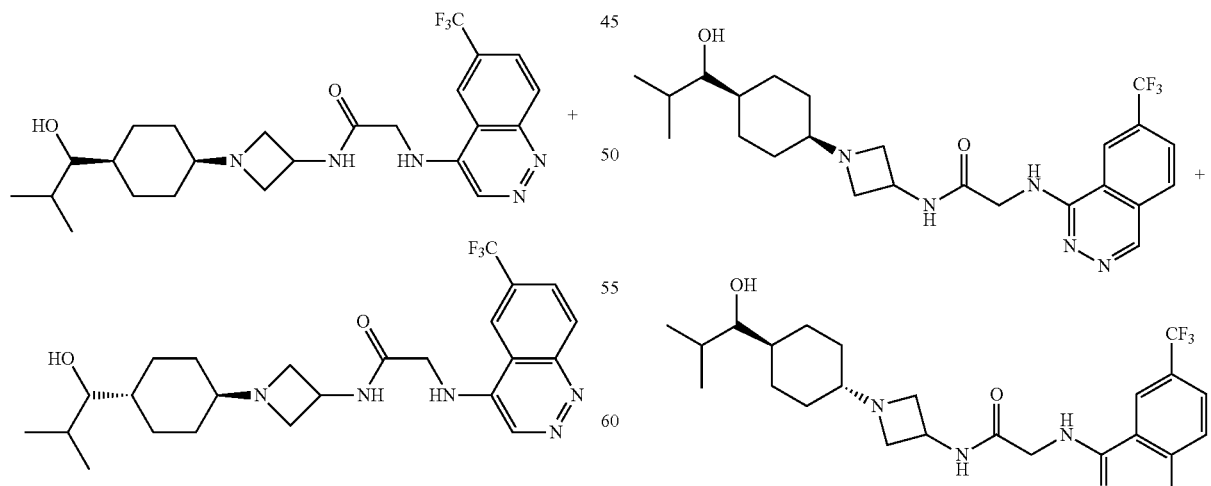

Into a 100 mL round-bottom flask, was placed a solution of N-(azetidin-3-yl)-2-(6-(trifluoromethyl)cinnolin-4-ylamino) acetamide (prepared as described in Example 152, Step B) (150 mg, 0.46 mmol, 1.00 equiv) in dichloromethane (20

Into a 8 mL vial, was placed N-(azetidin-3-yl)-2-[[7-(trifluoromethyl)phthalazin-1-yl]amino]acetamide (as prepared in Example 148, Step I) (150 mg, 0.46 mmol, 1.00 equiv), dichloromethane (5 mL), 4-(1-hydroxy-2-methylpropyl)cyclohexan-1-one (as prepared in Example 7, Step B) (100 mg, 0.59 mmol, 1.27 equiv, 98.2%), sodium triacetoxyborohydride (391 mg, 1.84 mmol, 4.00 equiv) and triethylamine (140 mg, 1.38 mmol, 3.00 equiv). The reaction mixture was stirred overnight at room temperature. The resulting mixture was quenched with 1 mL H$_2$O and concentrated under vacuum. The crude product (120 mg) was purified by Flash-Prep-HPLC with the following conditions (IntelFlash-1): Column, silica gel; mobile phase, TFA/CH$_3$CN=10 increasing to TFA/CH$_3$CN=70 within 12 min; Detector, UV 254 nm. The title compounds were isolated as white solids.

For N-(1-(((1R,4s)-4-((S)-1-hydroxy-2-methylpropyl)cyclohexyl)azetidin-3-yl)-2-((7-(trifluoromethyl)phthalazin-1-yl)amino)acetamide:

LC-MS (ES, m/z) 480 [M+H]$^+$ $^1$H-NMR (300 MHz, CD$_3$OD) 0.843-0.857 (3H, m), 0.939-0.962 (3H, m), 1.339 (1H, m), 1.434-1.6124 (9H, m), 1.781-1.816 (1H, m), 2.309 (1H, m), 2.982 (2H, s), 3.196-3.234 (1H, m), 3.634-3.658 (2H, m), 4.278 (2H, s), 4.469-4.869 (1H, m), 8.168-8.173 (2H, d), 8.700 (1H, s), 9.024 (1H, s).

For N-(1-((1S,4r)-4-((S)-1-hydroxy-2-methylpropyl)cyclohexyl)azetidin-3-yl)-2-((7-(trifluoromethyl)phthalazin-1-yl)amino)acetamide:

LC-MS (ES, m/z) 480 [M+H]$^+$ $^1$H-NMR (300 MHz, CD$_3$OD) δ 9.025 (s, 1H), 8.698 (s, 1H), 8.173 (s, 2H), 4.475-4.523 (m, 1H), 4.277 (s, 2H), 3.660-3.719 (m, 2H), 3.059-3.096 (m, 2H), 2.939-2.978 (m, 1H), 1.150-2.077 (m, 1H), 0.920-1.077 (m, 3H), 0.889-0.911 (m, 3H).

Examples 161 and 162

N-((1s,3s)-3-(4-hydroxy-4-(thiazol-5-yl)piperidin-1-yl)cyclobutyl)-2-((6-(trifluoromethyl)quinazolin-4-yl)amino)acetamide and N-((1r,3R)-3-(4-hydroxy-4-(thiazol-5-yl)piperidin-1-yl)cyclobutyl)-2-((6-(trifluoromethyl)quinazolin-4-yl)amino)acetamide Step A: 3-aminocyclobutanone

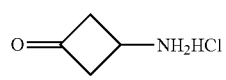

Into a 250 mL round-bottom flask, was placed a solution of 3-oxocyclobutanecarboxylic acid (4.28 g, 37.54 mmol, 1.00 equiv) in toluene (40 mL) and thionyl chloride (12 g). The resulting solution was stirred overnight at room temperature. This was followed by the addition of a solution of NaN$_3$ (4.6 g, 70.77 mmol, 1.98 equiv) in water (40 mL) dropwise with stirring at 0° C. in 1 min. The reaction mixture was stirred for 3 hours at 70° C. The resulting solution was diluted with 100 mL of DCM, was washed with 3×50 mL of sodium bicarbonate/H$_2$O, and was concentrated under vacuum. This resulted in 800 mg (25%) of 3-aminocyclobutanone as yellow oil.

Step B: tert-butyl 3-oxocyclobutylcarbamate

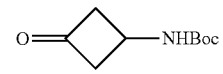

Into a 50 mL round-bottom flask, was placed a solution of 3-aminocyclobutanone (as prepared in the previous step) (250 mg, 2.94 mmol, 1.00 equiv) in N,N-dimethylformamide (15 mL), triethylamine (351 mg, 3.48 mmol) and (Boc)$_2$O (697 mg, 3.20 mmol, 1.09 equiv). The reaction mixture was stirred for 5 h at room temperature. The reaction was then quenched by the addition of 10 mL of H$_2$O. The resulting solution was extracted with 3×20 mL of ethyl acetate. The combined organic layers was washed with 3×10 mL brine, dried over sodium sulfate, and concentrated under vacuum. The title compound was obtained as a yellow solid.

Step C: benzyl 4-(2-(tert-butyldimethylsilyl) thiazol-5-yl)-4-hydroxypiperidine-1-carboxylate

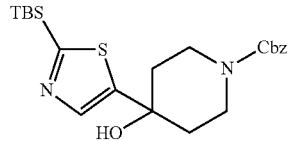

Into a 100 mL 3-necked round-bottom flask, was placed a solution of 2-(tert-butyldimethylsilyl) thiazole (1.58 g, 7.94 mmol, 1.00 equiv) in tetrahydrofuran (40 mL). This was followed by the addition of n-BuLi (3.7 mL, 1.20 equiv) dropwise with stirring at −78° C. in 1 hr. After half-hour, the benzyl 4-oxopiperidine-1-carboxylate (1.85 g, 7.94 mmol, 1.00 equiv) was added dropwise with stirring at −78° C. in 0.5 hr. The reaction mixture was stirred for 2 h at −78° C. in a liquid nitrogen bath. The reaction was then quenched by the addition of 50 mL of water. The resulting solution was extracted with 3×100 mL of ethyl acetate, and the combined organic layers washed with 2×100 mL of brine, dried (Na$_2$SO$_4$), and concentrated under vacuum. The residue was purified by chromatography over a silica gel column with ethyl acetate/petroleum ether (1:20-1:1). This resulted in 2 g (58%) of benzyl 4-(2-(tert-butyldimethylsilyl)thiazol-5-yl)-4-hydroxypiperidine-1-carboxylate as yellow oil.

Step D: 4-(2-(tert-butyldimethylsilyl) thiazol-5-yl) piperidin-4-ol

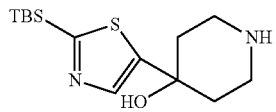

Into a 100 mL round-bottom flask, was placed a solution of benzyl 4-(2-(tert-butyldimethylsilyl)thiazol-5-yl)-4-hydroxypiperidine-1-carboxylate (as prepared in the previous step) (3 g, 6.94 mmol, 1.00 equiv) in methanol (20 mL) and Palladium carbon (0.3 g). Hydrogen was introduced into the above mixture. Under H₂ atmosphere, the resulting solution was stirred overnight at 50° C. in an oil bath. The solids were filtered out. The resulting mixture was concentrated under vacuum. The title compound was obtained as a white solid.

Step E: tert-butyl 3-(4-(2-(tert-butyldimethylsilyl) thiazol-5-yl)-4-hydroxypiperidin-1-yl) cyclobutylcarbamate

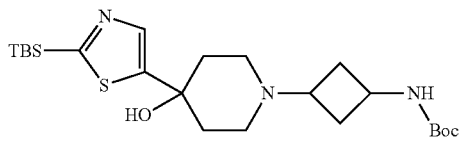

Into a 8 mL vial, was placed a solution of 4-(2-(tert-butyldimethylsilyl) thiazol-5-yl) piperidin-4-ol (as prepared in the previous step) (80 mg, 0.27 mmol, 1.00 equiv) in dichloromethane (1 mL), tert-butyl 3-oxocyclobutylcarbamate (as prepared in Step B, 128.8 mg, 0.70 mmol, 1.00 equiv) and NaBH(OAc)₃ (273 mg, 1.29 mmol, 3.00 equiv). The reaction mixture was stirred for 2 h at room temperature. The reaction was then quenched by the addition of 4 mL of H₂O. The resulting solution was extracted with 3×5 mL of DCM. The combined organic layers washed with 2×5 mL of brine, dried (Na₂SO₄), and concentrated under vacuum. The title compound was obtained as a yellow oil.

Step F: 1-(3-aminocyclobutyl)-4-(thiazol-5-yl) piperidin-4-ol

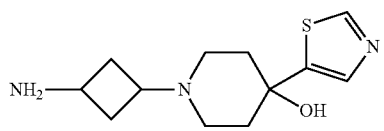 [SMILES: NC1CC(N2CCC(O)(c3cncs3)CC2)C1]

Into a 100 mL round-bottom flask, was placed a solution of tert-butyl 3-(4-(2-(tert-butyldimethylsilyl) thiazol-5-yl)-4-hydroxypiperidin-1-yl)cyclobutylcarbamate (as prepared in the previous step) (950 mg, 2.03 mmol, 1.00 equiv) in dichloromethane (10 mL) and CF₃COOH (2 mL). The reaction mixture was stirred for 3 h at room temperature. The resulting mixture was concentrated under vacuum. The title compound was obtained as a yellow oil.

Step G: tert-butyl 2-(3-(4-hydroxy-4-(thiazol-5-yl) piperidin-1-yl)cyclobutylamino)-2-oxoethylcarbamate

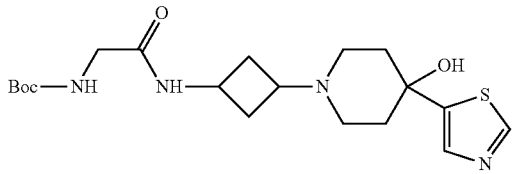 [SMILES: CC(C)(C)OC(=O)NCC(=O)NC1CC(N2CCC(O)(c3cncs3)CC2)C1]

Into a 50 mL round-bottom flask, was placed a solution of 2-(tert-butoxycarbonyl)acetic acid (899 mg, 5.14 mmol, 1.00 equiv) in dichloromethane (20 mL), EDC.HCl (1 g, 5.21 mmol, 1.10 equiv), HOBt (756 mg, 5.60 mmol, 1.10 equiv), triethylamine (1.5 g, 14.85 mmol, 3.00 equiv) and 1-(3-aminocyclobutyl)-4-(thiazol-5-yl)piperidin-4-ol (as prepared in the previous step) (1.3 g, 5.14 mmol, 1.00 equiv). The reaction mixture was stirred overnight at room temperature. The resulting mixture was concentrated under vacuum. The residue purified by chromatography over a silica gel column with EtOAc/petroleum ether (1:1-1:10). The title compound was obtained as a white solid.

Step H: 2-amino-N-(3-(4-hydroxy-4-(thiazol-5-yl) piperidin-1-yl)cyclobutyl)

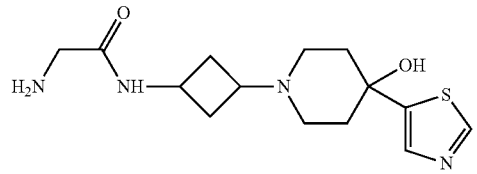 [SMILES: NCC(=O)NC1CC(N2CCC(O)(c3cncs3)CC2)C1]

Into a 100 mL round-bottom flask, was placed a solution of tert-butyl 2-(3-(4-hydroxy-4-(thiazol-5-yl)piperidin-1-yl)cyclobutylamino)-2-oxoethylcarbamate (1.48 g, 3.6 mmol) in dichloromethane (20 mL) and CF₃COOH (4 mL). The reaction mixture was stirred for 3 h at room temperature. The resulting mixture was concentrated under vacuum. The title compound was obtained as a yellow oil.

Step I: N-((1s,3s)-3-(4-hydroxy-4-(thiazol-5-yl)piperidin-1-yl)cyclobu 1)-2-((6-(trifluoromethyl) quinazolin-4-yl)amino)acetamide and N-((1r,3r)-3-(4-hydroxy-4-(thiazol-5-yl)piperidin-1-yl)cyclobu 1)-2-((6-(trifluoromethyl)quinazolin-4-yl) amino)acetamide

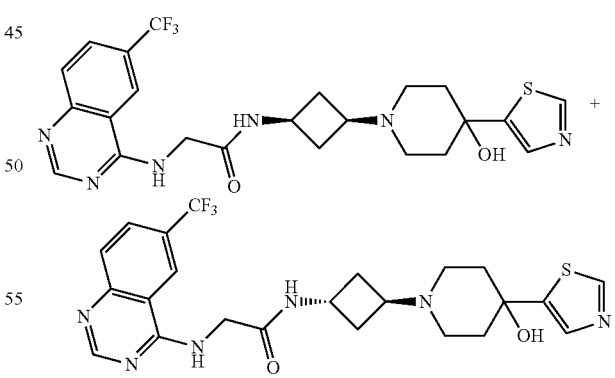

Into a 25 mL vial, was placed a solution of 2-amino-N-(3-(4-hydroxy-4-(thiazol-5-yl)piperidin-1-yl)cyclobutyl)acetamide (prepared as described in the previous step, 394 mg, 1.27 mmol, 1.00 equiv) in 2-methoxyethyl ether (10 mL), 4-chloro-6-(trifluoromethyl)quinazoline (294 mg, 1.27 mmol, 1.00 equiv) and triethylamine (385 mg, 3.81 mmol, 3.00 equiv). The reaction mixture was stirred for 2.5 h at 120° C. The resulting mixture was concentrated under vacuum.

The crude product (500 mg) was purified by Prep-HPLC with the following conditions (1#-Waters 2767-5): Column, SunFire Prep C18, 5 μm, 19×100 mm; mobile phase, Water and CH₃CN (30% CH₃CN up to 40% in 13 min, up to 100% in 0.1 min, hold 100% in 2 min, down to 30% in 0.1 min, hold 30% in 1.4 min); Detector, UV 220&254 nm. The title compounds were isolated as yellow solids.

For N-((1s,3s)-3-(4-hydroxy-4-(thiazol-5-yl)piperidin-1-yl)cyclobutyl)-2-((6-(trifluoromethyl)quinazolin-4-yl)amino)acetamide:

LC-MS 507 [M+H]⁺

¹H-NMR (300 MHz, CD₃OH) δ 8.693(s, 1H), 8.581(s, 1H), 8.030-8.066(m, 1H), 7.8985(d, J=8.7 Hz, 1H), 7.789(s, 1H), 4.281-4.322(m, 3H), 3.043-3.139(m, 1H), 2.752-2.851 (m, 2H), 2.340-2.435(m, 4H), 1.988-2.230(m, 6H).

For N-((1r,3R)-3-(4-hydroxy-4-(thiazol-5-yl)piperidin-1-yl)cyclobutyl)-2-((6-(trifluoromethyl)quinazolin-4-yl)amino)acetamide:

LC-MS (ES, m/z) 507 [M+H]⁺

¹H-NMR (300 MHz, CD₃OD) δ 8.639(s, 1H), 8.643(s, 1H), 8.578(s, 1H), 8.033-8.068(1H, s), 7.9005(d, J=8.7 Hz, 1H), 7.781-7.783(d, J=0.6 Hz, 1H), 4.281(s, 2H), 4.072-4.122(m, 1H), 2.428-2.769(m, 7H), 1.832-2.149(m, 6H).

Examples 163 and 164

2-((2-cyano-6-(trifluoromethyl)quinolin-4-yl)amino)-N-((1s,3s)-3-(4-hydroxy-4-(thiazol-5-yl)piperidin-1-yl)cyclobutyl)acetamide and 2-((2-cyano-6-(trifluoromethyl)quinolin-4-yl)amino)-N-((1r,3R)-3-(4-hydroxy-4-(thiazol-5-yl)piperidin-1-yl)cyclobutyl)acetamide Step A: tert-butyl 2-(2-cyano-6-(trifluoromethyl)quinolin-4-ylamino) acetate

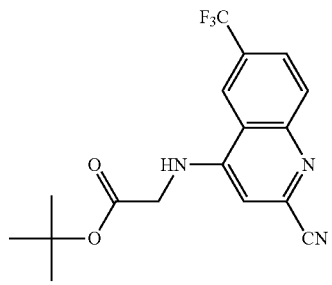 [SMILES: CC(C)(C)OC(=O)CNc1cc(C#N)nc2ccc(C(F)(F)F)cc12]

Into a 25 mL vial, was placed a solution of 4-hydroxy-6-(trifluoromethyl) quinoline-2-carbonitrile (238 mg, 1.00 mmol, 1.00 equiv) in dioxane (2 mL), PyBrOP (217 mg, 0.47 mmol, 1.10 equiv), triethylamine (354 mg, 3.50 mmol, 2.50 equiv) and tert-butyl 2-aminoacetate hydrochloride (217 mg, 1.30 mmol, 1.30 equiv). The reaction mixture was stirred overnight at room temperature. The reaction was then quenched by the addition of 25 mL of water. The resulting solution was extracted with 3×10 mL of ethyl acetate. The combined organic layers dried over anhydrous sodium sulfate and concentrated under vacuum. The residue purified by chromatography over a silica gel column with EtOAc/petroleum ether (1:1-1:10). The title compound was obtained as a white solid.

Step B: 2-(2-cyano-6-(trifluoromethyl)quinolin-4-ylamino)acetic acid

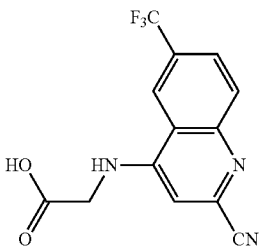 [SMILES: N#Cc1cc(NCC(=O)O)c2cc(C(F)(F)F)ccc2n1]

Into a 25 mL vial, was placed a solution of tert-butyl 2-(2-cyano-6-(trifluoromethyl)quinolin-4-ylamino)acetate (as prepared in the previous step, 80 mg, 0.23 mmol, 1.00 equiv) in dichloromethane (10 mL) and CF₃COOH (2 mL). The reaction mixture was stirred overnight at room temperature. The resulting mixture was concentrated under vacuum. The title compound was obtained as a white solid Step C: 2-((2-cyano-6-(trifluoromethyl)quinolin-4-yl)amino)-N-((1s,3s)-3-(4-hydroxy-4-(thiazol-5-yl)piperidin-1-yl)cyclobutyl)acetamide and 2-((2-cyano-6-(trifluoromethyl)quinolin-4-yl)amino)-N-Vr,3O-3-(4-hydroxy-4-(thiazol-5-yl)piperidin-1-yl)cyclobutyl)acetamide

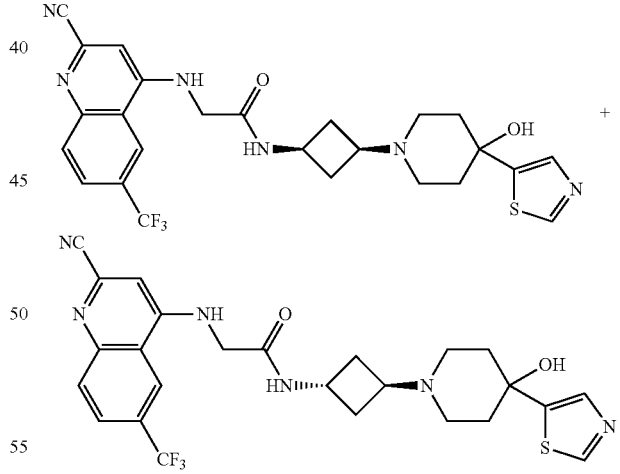

Into a 50 mL round-bottom flask, was placed a solution of 2-(2-cyano-6-(trifluoromethyl)quinolin-4-ylamino)acetic acid (as prepared in the previous step, 29 mg, 0.11 mmol, 1.00 equiv) in dichloromethane (2 mL), EDC (23 mg, 0.12 mmol, 1.12 equiv), HOBt (16.2 mg, 0.12 mmol, 1.12 equiv), triethylamine (30.5 mg, 0.30 mmol, 2.82 equiv) and 1-(3-aminocyclobutyl)-4-(thiazol-5-yl)piperidin-4-ol (as prepared in Example 162, Step F) (25 mg, 0.10 mmol, 1.00 equiv). The reaction mixture was stirred for 3 h at room temperature. The resulting mixture was concentrated under vacuum. The crude product (50 mg) was purified by Prep-HPLC with the following conditions (1#-Waters 2767-5): Column, SunFire Prep C18, 5um, 19×100 mm; mobile phase, Water and CH$_3$CN (30% CH$_3$CN up to 40% in 13 min, up to 100% in 0.1 min, hold 100% in 2 min, down to 30% in 0.1 min, hold 30% in 1.4 min); Detector, UV 220&254 nm. The title compounds were obtained as yellow solids.

For 2-((2-cyano-6-(trifluoromethyl)quinolin-4-yl)amino)-N-((1s,3s)-3-(4-hydroxy-4-(thiazol-5-yl)piperidin-1-yl)cyclobutyl)acetamide:

LC-MS (ES, m/z) 531 [M+H]$^+$ $^1$H-NMR (300 MHz, CD$_3$OD) δ 8.916(s, 1H), 8.657(s, 1H), 7.958-8.061(m, 2H), 7.791(s, 1H), 6.834(s, 1H), 4.097-4.146(m, 3H), 2.751-2.837(m, 3H), 2.508-2.653(m, 4H), 1.915-2.161(m, 6H).

For 2-((2-cyano-6-(trifluoromethyl)quinolin-4-yl)amino)-N-((1r,3r)-3-(4-hydroxy-4-(thiazol-5-yl)piperidin-1-yl)cyclobutyl)acetamide:

LC-MS (ES, m/z) 531 [M+H]$^{+1}$H-NMR (300 MHz, CD$_3$OD) δ 8.916(s, 1H), 8.657(s, 1H), 7.958-8.061(m, 2H), 7.791(s, 1H), 6.834(s, 1H), 4.097-4.146(m, 3H), 2.751-2.837(m, 3H), 2.508-2.653(m, 4H), 1.915-2.161(m, 6H).

Examples 165 and 166

N-(1-((1r,4r)-4-hydroxy-4-(thiazol-5-yl)cyclohexyl)azetidin-3-yl)-2-((7-(trifluoromethyl)isoquinolin-1-yl)amino)acetamide and N-(1-((1s,4s)-4-hydroxy-4-(thiazol-5-yl)cyclohexyl)azetidin-3-yl)-2-((7-(trifluoromethybisoquinolin-1-yl)amino)acetamide Step A: 7-bromo-1-chloroisoquinoline

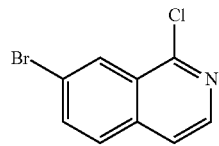 [SMILES: Clc1nccc2ccc(Br)cc12]

Into a 50 mL round-bottom flask, was placed a solution of 7-bromoisoquinolin-1-ol (1.0 g, 4.46 mmol, 1.00 equiv) in POCl$_3$ (5 mL). The reaction mixture was stirred for 60 min at 80° C. in an oil bath. The resulting mixture was concentrated under vacuum. The residue was dissolved in 20 mL of DCM, washed with 3×10 mL of water, dried over anhydrous sodium sulfate, and concentrated under vacuum. The title compound was obtained as a light yellow solid.

LC-MS (ES, m/z) 243[M+H]$^+$.

Step B: 1-chloro-7-iodoisoquinoline

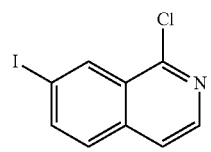 [SMILES: Clc1nccc2ccc(I)cc12]

Into a 50 mL round-bottom flask, was placed 7-bromo-1-chloroisoquinoline (as prepared in the previous step, 520 mg, 2.15 mmol, 1.00 equiv) and tetrahydrofuran (10 mL). This was followed by the addition of n-BuLi (0.85 mL, 1.25 equiv) dropwise with stirring at −78° C. in 2 min. The resulting solution was allowed to react, with stirring, for an additional 40 min at −80° C. To this was added a solution of I$_2$ (541 mg, 2.14 mmol, 1.25 equiv) in tetrahydrofuran (3 mL) dropwise with stirring at −78° C. in 1 min. The reaction mixture was allowed to react, with stirring, overnight at 25° C. The reaction was then quenched by the addition of 1 mL of water.

The residue was diluted with 40 mL of DCM, washed with 3×15 mL of water, dried over anhydrous sodium sulfate, and concentrated under vacuum. The residue was purified by chromatography over a silica gel column with ethyl acetate/hexane (1:50). The title compound was obtained as a yellow solid.

LC-MS (ES, m/z) 290[M+H]$^+$.

Step C: 1-chloro-7-(trifluoromethyl)isoquinoline

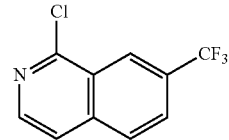 [SMILES: FC(F)(F)c1ccc2ccnc(Cl)c2c1]

Into a 8 mL sealed tube, was placed potassium fluoride (300 mg, 5.17 mmol, 6.00 equiv, 100%), copper(I) iodide (900 mg, 4.66 mmol, 5.50 equiv, 100%), trimethyl(trifluoromethyl)silane (720 mg, 5.07 mmol, 5.00 equiv, 100%), NMP (3 mL, 100%) and a solution of 1-chloro-7-iodoisoquinoline (as prepared in the previous step, 250 mg, 0.86 mmol, 1.00 equiv, 100%) in NMP (1 mL). The reaction mixture was stirred for 12 h at 120° C. in an oil bath. The resulting mixture was diluted with 20 mL of ethyl acetate, washed with 3×10 mL of saturated solution of KI, dried over anhydrous sodium sulfate, and concentrated under vacuum. The residue was purified by chromatography over a silica gel column with ethyl acetate:petroleum ether (1:50). The title compound was obtained as a yellow solid.

LC-MS (ES, m/z) 232[M+H]$^+$.

Step D: tert-butyl 3-(2-(7-(trifluoromethyl)isoquinolin-1-ylamino)acetamido)azetidine-1-carboxylate

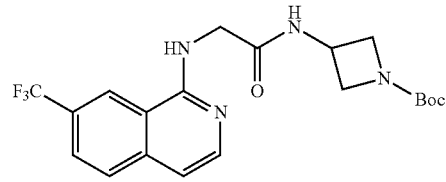 [SMILES: CC(C)(C)OC(=O)N1CC(NC(=O)CNc2nccc3ccc(C(F)(F)F)cc23)C1]

Into a 8 mL sealed tube, was placed 1-chloro-7-(trifluoromethyl)isoquinoline (as prepared in the previous step, 433 mg, 1.87 mmol, 1.00 equiv), tert-butyl 3-(2-aminoacetamido)azetidine-1-carboxylate (prepared as described in Example 1, Step E) (460 mg, 2.01 mmol, 1.18 equiv), Pd(OAc)$_2$ (15 mg, 0.07 mmol, 0.05 equiv), Cs$_2$CO$_3$ (1500 mg, 4.60 mmol, 1.77 equiv), BINAP (30 mg, 0.05 mmol, 0.04 equiv) and toluene (2 mL). The reaction mixture was stirred for 12 h at 100° C. in an oil bath. The solids were filtered off. The resulting mixture was concentrated under vacuum. The residue was purified by chromatography over a silica gel column with ethyl acetate: retroleum ether (1:3). The title compound was obtained as an off white solid.

LC-MS (ES, m/z) 425[M+H]+.

Step E: N-(azetidin-3-yl)-2-(7-(trifluoromethyl)isoquinolin-1-ylamino)acetamide

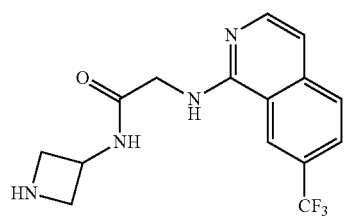 [SMILES: O=C(CNc1nccc2ccc(C(F)(F)F)cc12)NC1CNC1]

Into a 25 mL round-bottom flask, was placed a solution of tert-butyl 34247-(trifluoromethyl)isoquinolin-1-ylamino)acetamido)azetidine-1-carboxylate (as prepared in the previous step, 100 mg, 0.24 mmol, 1.00 equiv) in dichloromethane (5 mL). This was followed by the addition of trifluoroacetic acid (0.5 mL) at 0° C. in 5 min. The reaction mixture was stirred for 6 hr at 0° C. The resulting mixture was concentrated under vacuum. The title compound was obtained as a white solid.

LC-MS (ES, m/z) 325[M+H]

Step F: N-(1-((1r,4r)-4-hydroxy-4-(thiazol-5-yl)cyclohexyl)azetidin-3-yl)-2-((7-(trifluoromethyl)isoquinolin-1-yl)amino)acetamide and N-(1-((1s,4s)-4-hydroxy-4-(thiazol-5-yl)cyclohexyl)azetidin-3-yl)-2-((7-(trifluoromethyl)isoquinolin-1-yl)amino)acetamide

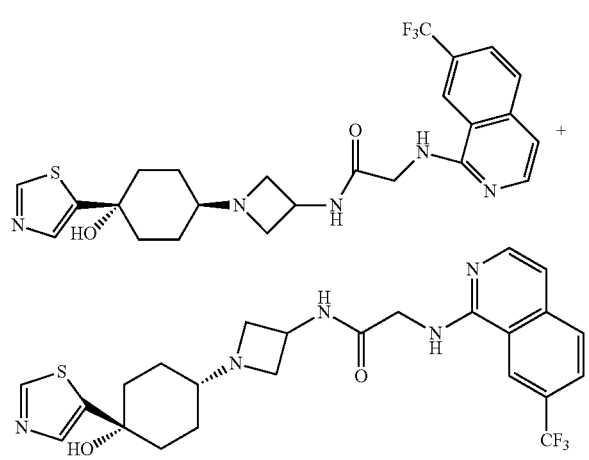

Into a 25 mL round-bottom flask, was placed a solution of 2-[[7-(pentafluoroethyl)isoquinolin-1-yl]amino]acetamide (as prepared in the previous step, 70 mg, 0.22 mmol, 1.00 equiv) in dichloromethane (5 mL), 4-hydroxy-4-(1,3-thiazol-5-yl)cyclohexan-1-one (prepared as described in Example 26, Step C) (80 mg, 0.41 mmol, 1.85 equiv), TEA (105 mg, 1.04 mmol, 4.73 equiv) and sodium triacetoxyborohydride (210 mg, 0.99 mmol, 4.52 equiv). The reaction mixture was stirred for 120 min at 25° C. The resulting mixture was concentrated under vacuum. The crude product (0.1 g) was purified by Prep-HPLC with the following conditions (1#waters 2761-1): Column, Sunfire PrepCl$_8$, 5 µM,19×100 mm; mobile phase, water in 0.05% NH$_4$HCO$_3$ and CH$_3$CN (30% CH$_3$CN up to 73% in 8 min, up to 100% in 2 min, down to 30% in 2 min); Detector, 254/220 nm. The title compounds were obtained as white solids.

For N-(1-((1r,4r)-4-hydroxy-4-(thiazol-5-yl)cyclohexyl)azetidin-3-yl)-2-((7-(trifluoromethyl)isoquinolin-1-yl)amino)acetamide:

LC-MS (ES, m/z) 506[M+H]+.

$^1$H-NMR (300 MHz, CD$_3$OD) δ 8.90(s, 1H), 8.60(s, 1H), 7.99(d, J=6.0 Hz, 1H), 7.80-7.95(m, 3H), 7.08(d, J=6.0 Hz, 1H), 4.40-4.56(m, 1H), 4.20(s, 2H), 3.63(t, J=7.2 Hz, 2H), 2.99(t, J=7.2 Hz, 2H), 2.30-2.38(m, 1H), 2.15-2.29(m, 2H), 1.70-1.90(m, 4H), 1.24-1.40(m, 2H).

For N-(1-((1s,4s)-4-hydroxy-4-(thiazol-5-yl)cyclohexyl)azetidin-3-yl)-2-((7-(trifluoromethyl)isoquinolin-1-yl)amino)acetamide:

LC-MS (ES, m/z) 506[M+H]+.

$^1$H-NMR (300 MHz, CD$_3$OD) δ 8.861(s, 1H), 8.61(s, 1H), 8.10(d, J=5.7 Hz, 1H), 7.90-7.87(m, 2H), 7.73(s, 1H), 7.09(s, J=5.7 Hz, 1H), 4.51(t, J=7.2 Hz, 1H), 4.21(s, 2H), 3.69(t, J=6.6 Hz, 2H,), 3.00-3.14(m, 2H), 2.16-2.29(s, 1H), 1.97-2.08(m, 2H), 1.76-1.88(m, 2H), 1.63-1.75 (m, 2H), 1.45-1.61 (m, 2H).

Examples 167 and 168

N-(1-((1R,4s)-4-(1-hydroxypropyl)cyclohexyl)azetidin-3-yl)-2-((7-(trifluoromethybisoquinolin-1-yl)amino)acetamide and N-(1-((1S,4r)-4-(1-hydroxypropyl)cyclohexyl)azetidin-3-yl)(-2-(7-(trifluoromethybisoquinolin-1-yl)amino)acetamide

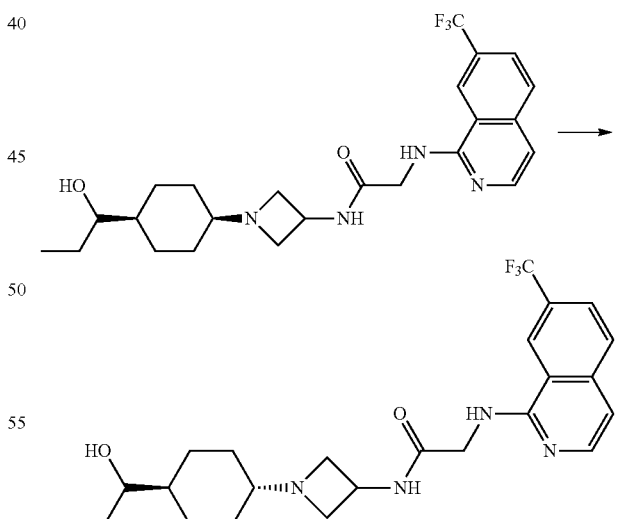

Into a 8 mL sealed tube, was placed a solution of 4-(1-hydroxypropyl)cyclohexan-1-one (as prepared in Example 25, Step B) (70 mg, 0.45 mmol, 1.00 equiv) in dichloromethane (2 mL), N-(azetidin-3-yl)-2-[[7-(trifluoromethyl)isoquinolin-1-yl]amino]acetamide (as prepared in Example 166, Step E) (50 mg, 0.15 mmol, 0.34 equiv), TEA (0.1 mL) and sodium triacetoxyborohydride (150 mg, 0.71 mmol, 1.58 equiv). The reaction mixture was stirred for 12 h at 25° C. The reaction was then quenched by the addition of 10 mL of water. The resulting mixture was extracted with 3×10 mL of dichloromethane. The combined organic layer was washed with 10 mL of brine, dried (Na$_2$SO$_4$), and concentrated under vacuum. The crude product (0.1 g) was purified by Prep-HPLC with the following conditions (1#waters 2761-1): Column, Sunfire PrepCl$_8$, 5 μM, 19×100 mm; mobile phase, water in 0.05% NH$_4$HCO$_3$ and CH$_3$CN (30% CH$_3$CN up to 47% in 14 min, up to 100% in 2 min, down to 30% in 2 min); Detector, 254/220 nm. 0.01 g product was obtained. The compound N-(1-((1s,4s)-4-(1-hydroxypropyl)cyclohexyl)azetidin-3-yl)-2-(7-(trifluoromethyl)isoquinolin-1-yl)amino)acetamide was isolated as an off-white solid, and N-(1-((1r,4r)-4-(1-hydroxypropyl)cyclohexyl)azetidin-3-yl)-247-(trifluoromethyl)isoquinolin-1-yl)amino)acetamide was isolated as a light yellow solid.

For N-(1-((1R,4s)-4-(1-hydroxypropyl)cyclohexyl)azetidin-3-yl)-2-((7-(trifluoromethyl)isoquinolin-1-yl)amino)acetamide:

LC-MS (ES, m/z) 465[M+H]$^+$.

$^1$H-NMR (300 MHz, CDCl$_3$) δ 8.25(s, 1H), 8.08(d, J=5.7 Hz, 1H), 7.79(m, 2H), 7.45-7.63(b, 1H), 7.03(d, J=6.0 Hz, 1H), 6.35(s, 1H), 4.53-4.70(m, 1H), 4.27-4.35(m, 2H), 3.71-3.80(m, 2H), 3.30-3.60(m, 2H), 2.66(s, 1H), 1.30-1.92(m, 12H), 0.90-1.01(m, 3H).

For N-(1-((1R,4s)-4-(1-hydroxypropyl)cyclohexyl)azetidin-3-yl)-2-((7-(trifluoromethyl)isoquinolin-1-yl)amino)acetamide:

LC-MS (ES, m/z) 465[M+H]$^+$ $^1$H-NMR (300 MHz, CDCl$_3$) δ 8.60(s, 1H), 7.99(d, J=6.0 Hz, 1H,), 7.82-7.95(m, 2H), 7.08(d, J=6.0 Hz, 1H), 4.47-4.57(m, 1H), 4.20(s, 2H), 3.79-3.90(m, 2H), 3.16-3.25(m, 1H), 2.25-2.36(m, 1H), 181-1.98(m, 3H), 1.65-1.76(m, 1H), 1.45-1.60(m, 1H), 1.32-1.43(m, 1H), 1.20-1.31(m, 1H), 0.90-1.10(m, 7H).

Example 169

N-(1-((1R,4s)-4-(1-hydroxy-2-methylpropyl)cyclohexyl)azetidin-3-yl)-2-((7-(trifluoromethybisoquinolin-1-yl)amino)acetamide

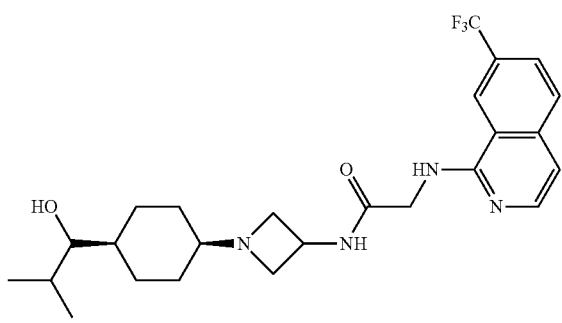 [SMILES: CC(C)C(O)[C@H]1CC[C@@H](N2CC(NC(=O)CNc3nccc4ccc(C(F)(F)F)cc34)C2)CC1]

Into a 8 mL round-bottom flask, was placed a solution of N-(azetidin-3-yl)-2-(7-(trifluoromethyl)isoquinolin-1-ylamino)acetamide (as prepared in Example 166, Step E) (120 mg, 0.37 mmol, 1.00 equiv) in dichloromethane (2 mL), 4-(1-hydroxy-2-methylpropyl) cyclohexanone (as described in Example 7, Step B) (115 mg, 0.74 mmol, 1.99 equiv), NaBH(OAc)$_3$ (360 mg, 1.70 mmol, 4.58 equiv) and TEA (180 mg, 1.78 mmol, 4.81 equiv). The reaction mixture was stirred for 12 h at 25° C. The reaction was then quenched by the addition of 10 mL of water. The resulting solution was extracted with 3×10 mL of dichloromethane. The combined organic layer was washed with 20 mL of brine, dried (Na$_2$SO$_4$), and concentrated under vacuum. The crude product (0.2 g) was purified by Prep-HPLC with the following conditions (Waters 2767-1): Column, SunFire Prep C18, 5 μm, 19×100 mm; mobile phase, water in 0.05% NH$_4$HCO$_3$ and CH$_3$CN (30% CH$_3$CN up to 73% in 8 min, up to 100% in 2 min, down to 30% in 2 min); Detector, UV 254 nm. The title compound was obtained as a white solid.

LC-MS (ES, m/z) 479[M+1]$^+$,502[M+Na]$^+$ $^1$H-NMR (300 MHz, CD$_3$OD) δ 8.61(s, 1H), 7.99(d, J=5.7 Hz, 1H), 7.82-7.96(m, 2H), 7.08(d, J=5.7 Hz, 1H), 4.862-4.875(m, 2H), 4.45-4.55(m, 1H), 4.20(s, 2H), 3.60-3.70(m, 2H), 3.04-3.10(m, 1H), 2.79-2.97(m, 2H), 2.29(s, 1H), 1.70-1.80(s, 1H), 1.30-1.65(m, 10H), 0.95(d, J=12.0 Hz, 3H), 0.85(d, J=12.0 Hz, 3H).

Example 170

N-(1-((1R,4s)-4-(1-hydroxypropyl)cyclohexyl)azetidin-3-yl)-2-((7-(perfluoroethybisoquinolin-1-yl)amino)acetamide Step A: 1-chloro-7-(pentafluoroethyl)isoquinoline

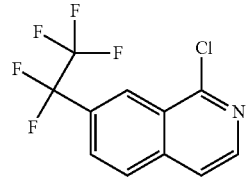 [SMILES: FC(F)(F)C(F)(F)c1ccc2ccnc(Cl)c2c1]

Into a 8 mL sealed tube, was placed CuI (900 mg, 4.73 mmol, 5.47 equiv), KF (0.3 g), trimethyl(trifluoromethyl)silane (720 mg, 5.06 mmol, 5.86 equiv) and NMP (4 mL), 1-chloro-7-iodoisoquinoline (250 mg, 0.86 mmol, 1.00 equiv, 30%). The reaction mixture was stirred for 12 h at 120° C. The resulting solution was diluted with 20 mL of ethyl acetate, washed with 3×5 mL of sat. KI solution, dried (Na$_2$SO$_4$), and concentrated under vacuum. The residue was applied onto a silica gel column with ethyl acetate/hexane (1:10). This resulted in 0.142 g (50%) of 1-chloro-7-(trifluoromethyl)isoquinoline as a yellow solid and 0.142 g (18%) of 1-chloro-7-(pentafluoroethyl)isoquinoline as a yellow solid.

Step B: tert-butyl 3-(2-[[7-(pentafluoroethyl)isoquinolin-1-yl]amino]acetamido)azetidine-1-carboxylate

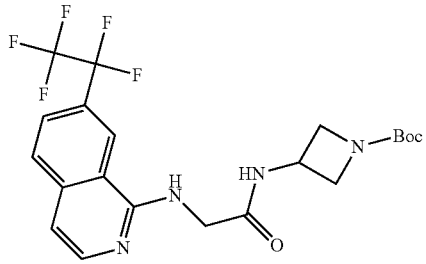 [SMILES: CC(C)(C)OC(=O)N1CC(NC(=O)CNc2nccc3ccc(C(F)(F)C(F)(F)F)cc23)C1]

Into a 8 mL sealed tube, was placed 1-chloro-7-(pentafluoroethyl)isoquinoline (as prepared in the previous step, 282 mg, 1.00 mmol, 1.00 equiv), tert-butyl 3-(2-aminoacetamido)azetidine-1-carboxylate (prepared as described in Example 1, Step E) (250 mg, 1.09 mmol, 1.09 equiv), $Cs_2CO_3$ (1.0 g, 3.07 mmol, 3.06 equiv), BINAP (24 mg, 0.04 mmol, 0.04 equiv), $Pd(OAc)_2$ (10 mg, 0.04 mmol, 0.04 equiv) and tol (2 mL). The reaction mixture was stirred overnight at 120° C. The resulting mixture was concentrated under vacuum. The residue was purified by chromatography over a silica gel column with dichloromethane/methanol (10:1). This resulted in 0.12 g (25%) of tert-butyl 3-(2-[[7-(pentafluoroethyl)isoquinolin-1-yl]amino]acetamido)azetidine-1-carboxylate as a brown solid.

Step C: N-(azetidin-3-yl)-2-[[7-(pentalluoroethyl)isoquinolin-1-yl]amino]acetamide

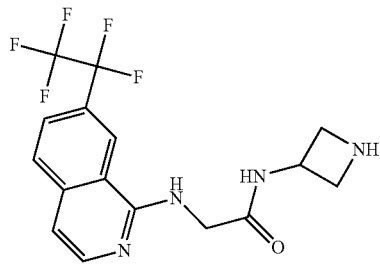 [SMILES: O=C(CNc1nccc2ccc(C(F)(F)C(F)(F)F)cc12)NC1CNC1]

Into a 8 mL sealed tube, was placed a solution of tert-butyl 3-(2-[[7-(pentafluoroethyl)isoquinolin-1-yl]amino]acetamido)azetidine-1-carboxylate (as prepared in the previous step, 100 mg, 0.21 mmol, 1.00 equiv) in dichloromethane (5 mL), TFA (0.5 g). The resulting solution was stirred for 5 h at 0° C. The resulting mixture was concentrated under vacuum. The residue was washed with 3×5 mL of ether. This resulted in 0.12 g (crude) of N-(azetidin-3-yl)-2-[[7-(pentafluoroethyl)isoquinolin-1-yl]amino]acetamide as a white solid.

Step D: N-(1-((1R,4s)-4-(1-hydroxypropyl)cyclohexyl)azetidin-3-yl)-2-((7-(perfluoroethyl)isoquinolin-1-yl)amino)acetamide

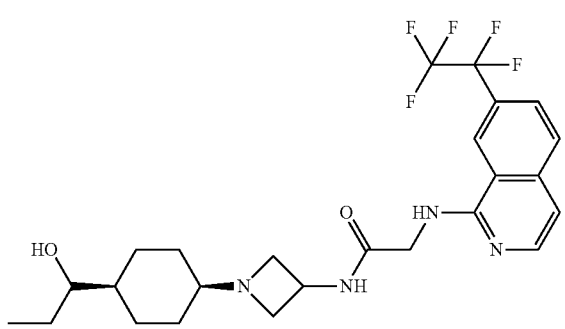 [SMILES: CCC(O)[C@H]1CC[C@@H](N2CC(NC(=O)CNc3nccc4ccc(C(F)(F)C(F)(F)F)cc34)C2)CC1]

Into a 8 mL sealed-tube, was placed a solution of N-(azetidin-3-yl)-2-[[7-(pentafluoroethyl)isoquinolin-1-yl]amino]acetamide (as prepared in the previous step, 100 mg, 0.27 mmol, 1.00 equiv) in dichloromethane (3 mL), 4-(1-hydroxypropyl)cyclohexan-1-one (as described in Example 25, Step B) (75 mg, 0.48 mmol, 1.80 equiv), TEA (150 mg, 1.48 mmol, 5.55 equiv) and sodium triacetoxyborohydride (300 mg, 1.42 mmol, 5.30 equiv). The reaction mixture was stirred for 2 hr at 25° C. The reaction was then quenched by the addition of 10 mL of water. The resulting solution was extracted with 2×10 mL of dichloromethane. The combined organic layer was washed with 10 mL of brine, dried ($Na_2SO_4$), and concentrated under vacuum. The crude product (0.1 g) was purified by Prep-HPLC with the following conditions (1#waters 2761-1): Column, Sunfire PrepCl$_8$, 5 μm, 19×100 mm; mobile phase, water in 0.05% $NH_4HCO_3$ and $CH_3CN$ (30% $CH_3CN$ up to 73% in 8 min, up to 100% in 2 min, down to 30% in 2 min); Detector, 254/220 nm. The title compound was obtained as a white solid.

LC-MS (ES, m/z) 515[M+H]$^+$.

$^1$H-NMR (300 MHz, CD$_3$OD) δ 8.58(s, 1H), 8.00(d, J=6.0 Hz, 1H,), 7.92(d, J=8.7 Hz, 1H), 7.82(d, J=8.7 Hz, 1H), 7.08(d, J=5.7 Hz, 1H), 4.45-4.55(m, 1H), 4.19(s, 2H), 3.60-3.70(m, 2H), 2.90-3.10(m, 2H), 2.30(s, 1H), 1.20-1.70(m, 12H), 0.90-1.00(m, 3H).

Example 171

In Vitro Biological Data

Compounds of the invention were subjected to various representative biological tests. The results of these tests are intended to illustrate the invention in a non-limiting fashion. MCP-1 Receptor Binding Assay in THP-1 Cells Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% $CO_2$ atmosphere at 37° C. The cell density was maintained between 0.5×10$^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 1 lists IC$_{50}$ values for inhibition of MCP-1 binding to CCR2 obtained for test compounds of the invention. Where an IC$_{50}$ value was not obtained for a particular compound, the percent inhibition is provided at a test concentration of 25 μM.

TABLE 1

| Inhibition of MCP-1 Binding IC$_{50}$ | |
|---|---|
| Example | MCP1B (μM) |
| 1 | 0.004 |
| 2 | 0.005 |
| 3 | 0.022 |
| (+) 4 | 0.024 |
| (−) 4 | 0.008 |
| 5 | 0.014 |
| (+) 6 | 0.025 |
| (−) 6 | 0.008 |
| 7 | 0.009 |

TABLE 1-continued

Inhibition of MCP-1 Binding IC$_{50}$

| Example | MCP1B (µM) |
|---|---|
| (+) 8 | 0.044 |
| (−) 8 | 0.010 |
| 9 | 0.009 |
| 10 | 0.009 |
| 11 | 0.012 |
| 12 | 0.021 |
| 13 | 0.010 |
| 14 | 0.015 |
| 15 | 0.049 |
| 16 | 0.035 |
| 17 | 0.058 |
| 18 | 0.010 |
| 19 | 0.016 |
| 20 | 0.058 |
| 21 | 0.172 |
| 22 | 0.064 |
| 23 | 0.714 |
| 24 | 0.028 |
| 25 | 0.099 |
| 26 | 0.072 |
| 27 | 0.017 |
| 28 | 0.023 |
| 29 | 0.033 |
| 30 | 0.209 |
| 31 | 0.300 |
| 32 | 0.690 |
| 33 | 0.140 |
| 34 | 0.073 |
| 35 | 0.270 |
| 36 | 0.075 |
| 37 | 0.235 |
| 38 | 0.160 |
| 39 | 0.231 |
| 40 | 0.078 |
| 41 | 0.670 |
| 42 | 0.210 |
| 43 | 0.510 |
| 44 | 0.520 |
| 45 | 0.390 |
| 46 | 0.810 |
| 47 | 0.160 |
| 48 | 0.300 |
| 49 | 0.950 |
| 50 | 0.810 |
| 51 | 0.037 |
| 52 | 0.064 |
| 53 | 0.350 |
| 54 | 0.720 |
| 55 | 0.015 |
| 56 | 0.550 |
| 57 | 0.280 |
| 58 | 0.091 |
| 59 | 0.130 |
| 60 | 0.040 |
| 61 | 0.023 |
| 62 | 0.009 |
| 63 | 0.039 |
| 64 | 0.830 |
| 65 | 0.005 |
| 66 | 0.005 |
| 67 | 0.006 |
| 68 | 0.006 |
| 69 | 0.007 |
| 70 | 0.009 |
| 71 | 0.017 |
| 72 | 0.021 |
| 73 | 0.055 |
| 74 | 0.130 |
| 75 | 0.011 |
| 76 | 0.019 |
| 77 | 0.056 |
| 78 | 0.015 |
| 79 | 0.027 |
| 80 | 0.022 |
| 81 | 0.022 |
| 82 | 0.050 |
| 83 | 0.010 |
| 84 | 0.013 |
| 85 | 0.040 |
| 86 | 0.025 |
| 87 | 0.039 |
| 88 | 0.007 |
| 89 | 0.008 |
| 90 | 0.013 |
| 91 | 0.016 |
| 92 | 0.016 |
| 93 | 0.021 |
| 94 | 0.024 |
| 95 | 0.028 |
| 96 | 0.075 |
| 97 | 0.089 |
| 98 | 0.753 |
| 99 | 0.019 |
| 100 | 0.028 |
| 101 | 0.063 |
| 102 | 0.880 |
| 103 | 0.530 |
| 104 | 0.644 |
| 105 | 0.014 |
| 106 | 0.013 |
| 107 | 0.015 |
| 108 | 0.019 |
| 109 | 0.058 |
| 110 | 0.068 |
| 111 | 0.037 |
| 112 | 0.081 |
| 113 | 0.120 |
| 114 | 0.280 |
| 115 | 0.340 |
| 116 | 0.240 |
| 117 | 0.100 |
| 118 | 0.085 |
| 119 | 0.082 |
| 120 | 0.083 |
| 121 | 0.098 |
| 122 | 0.120 |
| 123 | 0.130 |
| 124 | 0.210 |
| 125 | 0.220 |
| 126 | 0.091 |
| 127 | 0.200 |
| 128 | 0.360 |
| 129 | 0.390 |
| 130 | 1.000 |
| 131 | 0.300 |
| 132 | 0.190 |
| 133 | 0.200 |
| 134 | 0.072 |
| 135 | 2.98 |
| 136 | 0.04 |
| 137 | 5.04 |
| 138 | 1.9 |
| 139 | 1.45 |
| 140 | 3.00 |
| 141 | 0.25 |
| 142 | 1.23 |
| 143 | 13.84 |
| 144 | 0.64 |
| 145 | >25 |
| 146 | 0.38 |
| 147 | 0.0092 |
| 148 | 0.02 |
| 149 | >25 |
| 150 | 0.43 |
| 151 | >25 |
| 152 | 0.53 |
| 153 | 0.015 |
| 154 | 6.08 |
| 155 | >25 |
| 156 | 0.43 |

TABLE 1-continued

Inhibition of MCP-1 Binding $IC_{50}$

| Example | MCP1B ($\mu M$) |
|---------|-----------------|
| 157 | 0.53 |
| 158 | 2.56 |
| 159 | 8.29 |
| 160 | 0.022 |
| 161 | >25 |
| 162 | 1.22 |
| 163 | 2.6 |
| 164 | >25 |
| 165 | 0.02 |
| 166 | >25 |
| 167 | 0.044 |
| 168 | >25 |
| 169 | 0.035 |
| 170 | 0.072 |

Example 172

Animals

Mouse CCR2 knock-out/human CCR2 knock-in mice are generated using targeted 129Sv/Evbrd embryonic stem cell clones injected into C57BL/6 mice. Expression of the hCCR2 transcript is confirmed by quantitative reverse transcription-polymerase chain reaction performed on spleen and blood total RNA from homozygous hCCR2 knock-in mice. Back-crossing into C57BL/6 genetic background continued to the eighth generation. Transgenic mice are housed in a specific-pathogen-free, temperature-controlled facility that maintained a 12-hour light/12-hour dark cycle. Mice have free access to water and food. Experimental procedures are carried out in accordance with institutional standards for animal care and are approved by the institute's animal care and use committee.

Example 173

Murine In vivo Cell Migration Assay

Animals are orally dosed with vehicle or CCR2 antagonists at 3, 10 and 30 mg/kg bid. Animals undergo anesthesia and laparotomy. A distal loop of small bowel (5 cm in length) is gently eventrated onto moist sterile gauze. Synthetic human MCP-1 (1 mg/100 ml sterile PBS) or PBS alone is administered drop-wise onto the serosa of the eventrated loop. A suture knot is placed into the mesentery to mark the terminus of the treated area. Twenty-four hours later, the animal is sacrificed and the segment of bowel plus the adjacent region is removed. The tissue is opened along the mesenteric border, pinned flat and the mucosa removed. The remaining muscle layer is fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals.

Example 174

Thiolycollate-Induced Peritonitis in Mice

Animals are orally dosed with vehicle or CCR2 antagonists at 3, 10, 30 and 100 mg/kg bid). One hour later, the animals are intraperiponeally injected with sterile thioglycollate (25 mL/kg, ip, Sigma) for induction of peritonitis. Animals are orally treated twice daily with vehicle or CCR2 antagonists. At 72-hour time point, perinoteal cavities are lavaged with 10 mL of sterile saline. Total cell counts in the peritoneal lavage fluid are performed using a microscope and cell differentiation was performed using cytospin analysis after Giemsa staining (Hema Tek 2000). Percent inhibition of the thiogly-collate-induced peritonitis is calculated by comparing the change in number of leukocytes of CCR2 antagonist treated mice to the vehicle-treated mice.

Example 175

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 µg of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchoalveolar lavage (BAL) is performed using 1.4 mL of ice-cold PBS containing 3 mM EDTA. Total cell counts in the BAL lavage fluid are performed using a microscope and cell differentiation was performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 176

High-fat Diet Induced Obesity and Insulin Resistance in Mice

Obesity is induced by a high-fat diet that derived approximately 60% calories from lipids (D-12492; Research Diets Inc.) in animals for 10-24 weeks at age of 7 weeks. Prior to age 7 weeks, animals are fed a standard pellet diet, in which 5% of calories are provided as fat. Obese animals are randomized by body weight and fat mass. The obese animals are orally treated with vehicle or CCR2 antagonists at 3, 10 and 30 mg/kg, po bid. Body weight and food intake and fasting blood glucose levels are monitored. Body mass is determined by a NMR analyzer (Burker MiniSpec). Insulin tolerance test is carried out in animals that fasted for 3 hours. After an intraperitoneal bolus injection of recombinant human insulin (1.5 U/kg), blood glucose concentrations are measured using a Glucometer before and 15, 30, 45, 60, 90 and 120 minutes after injection. Glucose tolerance tests are performed after an overnight (17-hour) fast. Blood glucose concentrations are measured before and after 15, 30, 60, 90, 120 minutes after an oral dose of glucose dissolved in water (1 g/kg). Energy expenditure analysis is monitored by a complete laboratory animal monitor system. After 40 days treatment with vehicle or $CCR^2$ antagonists, the animals are sacrificed by $CO_2$ asphyxiation. Percent of weight loss is calculated by comparing the body weight changes of the compound-treated mice with the vehicle-treated mice.

Example 177

Mouse Model of Allergic Asthma

Animals are sensitized by intraperitoneal injection of 10 µg chicken egg albumin (OVA) absorbed to 1 mg Imject® in 100

μL phosphate-buffered saline (PBS) on days 0 and 5. Control animals receive PBS ip. OVA-immunized animals are challenged by inhalation of 0.5% OVA aerosol for 10 minutes by an ultrasonic nebulizer on days 12, 16 and 20. Control animals are challenged with PBS in similar fashion. The OVA-sensitized animals receive vehicle (0.5% Methocel) or $CCR^2$ antagonists orally at 3, 10, 30 mg/kg twice daily from days 9-20 and once daily on day 21, 2 hours before sacrifice. Dexamethason (5 mg/kg) and Montelukast (1 mg/kg) are given orally once a day. On day 21, 2 hours post the last dose of $CCR^2$ compounds, bronchial reactivity to aerosolized methacholine is measured using a Buxco whole body plethysmograpgh. On day 21, the animals are sacrificed. Bronchoalveolar lavage fluid is collected (1 mL) and total cells counted. The numbers of eosinophils, lymphocytes, monocytes and neutrophils are determined using cytospin analysis after Giemsa staining (Hema Tek 2000). Percent inhibition of total BAL leukocyte count (and eosinophil count) is calculated by comparing the compound-treated mice with vehicle-treated mice. Compounds are deemed efficacious if the inhibition reaches 30%.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula I

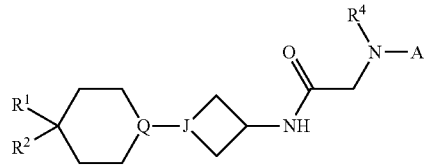

Formula I wherein:

A is

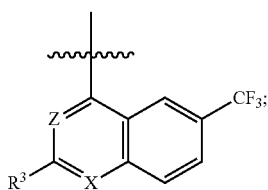

X is N;
Z is CH;
J is N or CH;
Q is C-$R^5$, provided that J is N, or Q is N, provided that J is CH;
$R^1$ is H, phenyl, heteroaryl, $CF_3$, —CH=$CH_2$, $CO_2C_{(1-4)}$ alkyl, NHBOC, NHC$_{(1-4)}$alkyl, N(C$_{(1-4)}$alkyl) $CO_2CH_2Ph$, $NR_bC(O)R_{bb}$, $NR_bSO_2R_{bb}$, $C(O)N(CH_3)$ $OCH_3$, $C(O)NR_bC_{(1-4)}$alkyl, $C(O)NHCH_2Ph(OCH_3)_2$, —C(OH)(CH$_2$CH=$CH_2$)$_2$, 3,6-dihydropyran-2-yl, 2,5-dihydrofuran-2-yl, tetrahydropyranyl, cyclopentenyl, cyclopentanyl, cyclohexenyl, cyclohexanyl, tetrahydrofuran-2-yl, cycloheptanyl,

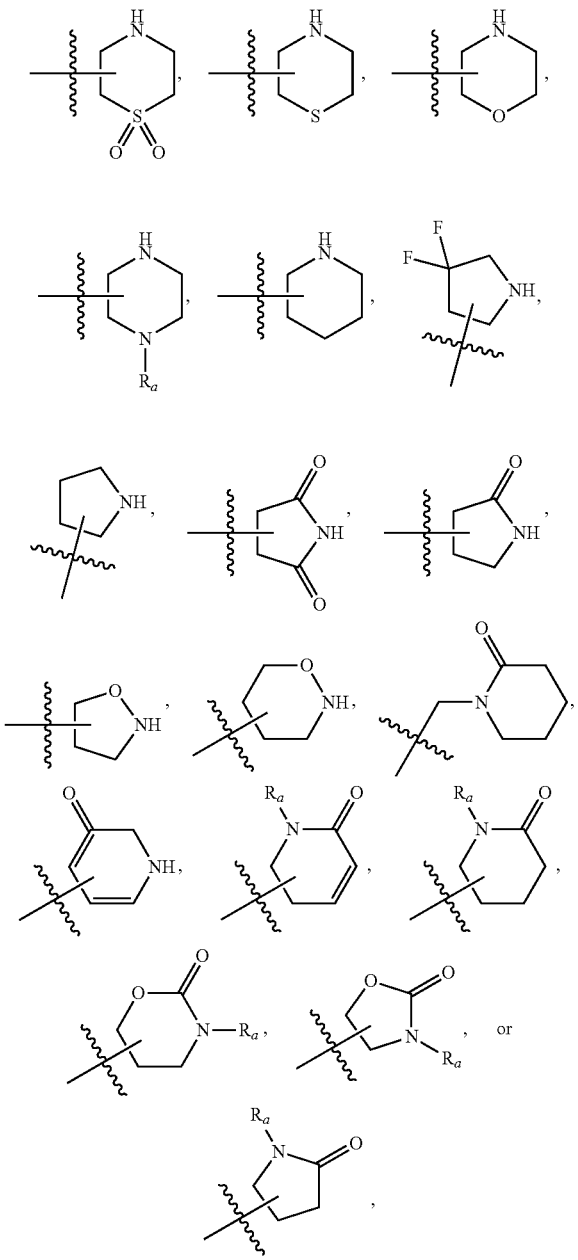

or unsubstituted or substituted $C_{(1-6)}$alkyl wherein said alkyl may be substituted with up to two substituents wherein one substituent is selected from the group consisting of OH, $C_{(2-4)}$alkenyl, $C_{(3-6)}$cycloalkyl, $NH_2$, NHBOC, N(C$_{(1-4)}$alkyl)$_2$, $NHSO_2R_b$, $NR_bC(O)R_{bb}$, $NHCO_2R_b$, $NHCONR_bR_{bb}$, $OC_{(1-2)}$alkyl, $OC(O)C_{(1-4)}$alkyl, $OC(O)NR_bR_{bb}$, $CO_2C_{(1-4)}$alkyl, $C(O)NR_bR_{bb}$, $C_{(2)}$alkylnyl, thiazolyl, oxazolyl, furyl, $CF_3$, $CF_2CF_2CF_3$, $CH_2NHCOC_{(1-3)}$alkyl, $N_3$, $SCH_3$, S(O) $CH_3$, $SO_2CH_3$ and —CN, and the second substituent on the $C_{(1-6)}$alkyl is OH, and wherein said phenyl or heteroaryl is optionally substituted with one substituent selected from the group consisting of: OH, —CN, $CH_2OH$, $OC_{(1-4)}$alkyl, $NH_2$, $NHC_{(1-4)}$alkyl, $OC_{(1-4)}$ alkyl, $C(O)C_{(1-4)}$alkyl, $CO_2C_{(1-4)}$alkyl, $C(O)NHC_{(1-4)}$ alkyl, $CO_2NHC_{(1-4)}$alkyl, $SC_{(1-4)}$alkyl, $SOC_{(1-4)}$alkyl, SO$_2$C$_{(1-4)}$alkyl, SO$_2$NHC$_{(1-4)}$alkyl, NHSO$_2$C$_{(1-4)}$alkyl, NHCO$_2$C$_{(1-4)}$alkyl, NHC(O)C$_{(1-4)}$alkyl, NO$_2$, and C$_{(1-4)}$alkyl;

R$^2$ is H, or OH;

or R$^1$ and R$^2$ may together form a carbonyl;

R$^3$ is H, C$_{(1-4)}$alkyl, —CN, CHF$_2$, or CF$_3$;

R$^4$ is H or CH$_3$;

R$^5$ is H or deuterium;

R$_a$ is H, or CH$_3$;

R$_b$ is H, C$_{(1-4)}$alkyl, or CF$_3$;

R$_{bb}$ is H, C$_{(1-4)}$alkyl, or CF$_3$;

and pharmaceutically acceptable salts thereof.

2. A compound of claim 1 wherein:

A is

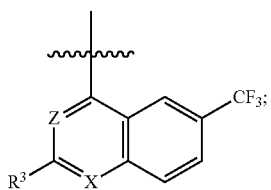

J is N;

Q is C-R$^5$;

and pharmaceutically acceptable salts thereof.

3. A compound of claim 2 wherein:

R$^1$ is pyridyl, pyrimidyl, pyrazyl, pyranyl, furyl, isoxazolyl, oxazolyl, phenyl, thiazolyl, isothiazolyl, CF$_3$, —CH═CH$_2$, CO$_2$C$_{(1-4)}$alkyl, NHBOC, N(C$_{(1-4)}$alkyl) CO$_2$CH$_2$Ph, NR$_b$C(O)R$_{bb}$, C(O)N(CH$_3$)OCH$_3$, C(O)NHC$_{(1-4)}$alkyl, C(O)NHCH$_2$Ph(OCH$_3$)$_2$, —C(OH)(CH$_2$CH═CH$_2$)$_2$, 3,6-dihydropyran-2-yl, 2,5-dihydrofuran-2-yl, tetrahydropyranyl, cyclopentenyl, cyclopentanyl, cyclohexenyl, tetrahydrofuran-2-yl, cycloheptanyl,

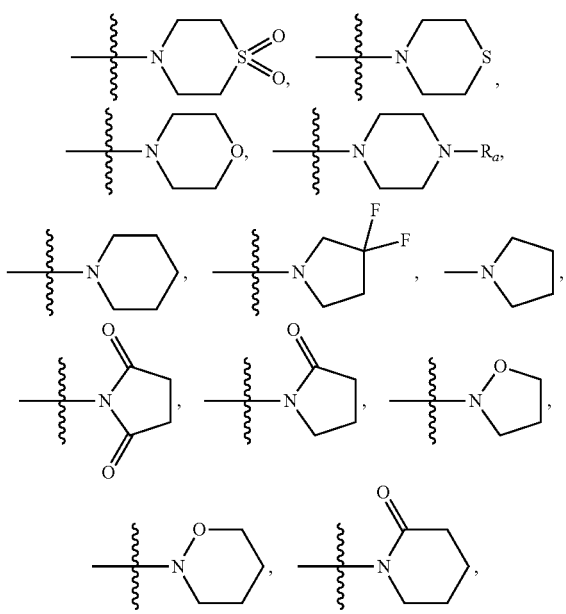

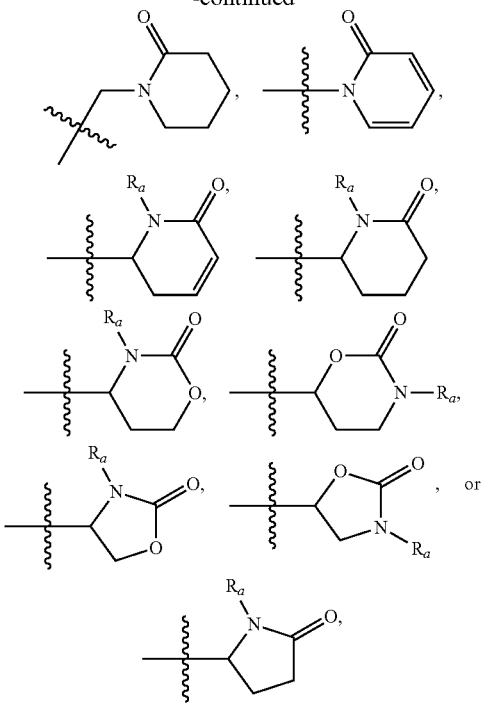

or unsubstituted or substituted C$_{(1-6)}$alkyl wherein said alkyl may be substituted with up to two substituents wherein one substituent is selected from the group consisting of OH, C$_{(3-6)}$cycloalkyl, C$_{(2-4)}$alkenyl, NHBOC, N(C$_{(1-4)}$alkyl)$_2$, NHSO$_2$R$_b$, NR$_b$C(O)R$_{bb}$, NHCO$_2$R$_b$, NHCONR$_b$R$_{bb}$, OC$_{(1-2)}$alkyl, OC(O)C$_{(1-4)}$alkyl, OC(O)NR$_b$R$_{bb}$, CO$_2$C$_{(1-4)}$alkyl, C(O)NR$_b$R$_{bb}$, C$_{(2)}$alkylnyl, thiazolyl, oxazolyl, CF$_3$, CF$_2$CF$_2$CF$_3$, CH$_2$NHCOC$_{(1-3)}$alkyl, N$_3$, SCH$_3$ and S(O)CH$_3$, and the second substituent on the C$_{(1-6)}$alkyl is OH, and wherein said pyridyl, pyrimidyl, pyrazyl, pyranyl, furyl, isoxazolyl, oxazolyl, phenyl, or thiazolyl is optionally substituted with one substituent selected from the group consisting of: OH, —CN, CH$_2$OH, OC$_{(1-4)}$alkyl, NH$_2$, NHC$_{(1-4)}$alkyl, OC$_{(1-4)}$alkyl, C(O)C$_{(1-4)}$alkyl, CO$_2$C$_{(1-4)}$alkyl, C(O)NHC$_{(1-4)}$alkyl, CO$_2$NHC$_{(1-4)}$alkyl, SC$_{(1-4)}$alkyl, SOC$_{(1-4)}$ alkyl, SO$_2$C$_{(1-4)}$alkyl, SO$_2$NHC$_{(1-4)}$alkyl, NHSO$_2$C$_{(1-4)}$ alkyl, NHCO$_2$C$_{(1-4)}$alkyl, NHC(O)C$_{(1-4)}$ alkyl, and C$_{(1-4)}$alkyl;

and pharmaceutically acceptable salts thereof.

4. A compound of claim 3 wherein:

R$^1$ is pyridyl, pyrimidyl, pyrazyl, oxazolyl, phenyl, thiazolyl, isothiazolyl, CF$_3$, —CH═CH$_2$, CO$_2$C$_{(1-4)}$alkyl, NHBOC, N(C$_{(1-4)}$alkyl)CO$_2$CH$_2$Ph, NR$_b$C(O)R$_{bb}$, C(O)N(CH$_3$)OCH$_3$, C(O)NHC$_{(1-4)}$alkyl, C(O)NHCH$_2$Ph(OCH$_3$)$_2$, —C(OH)(CH$_2$CH═CH$_2$)$_2$, 3,6-dihydropyran-2-yl, 2,5-dihydrofuran-2-yl, tetrahydropyranyl, cyclopentenyl, cyclopentanyl, cyclohexenyl, tetrahydrofuran-2-yl, cycloheptanyl,

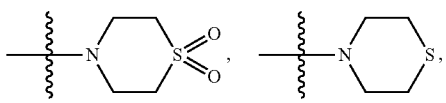

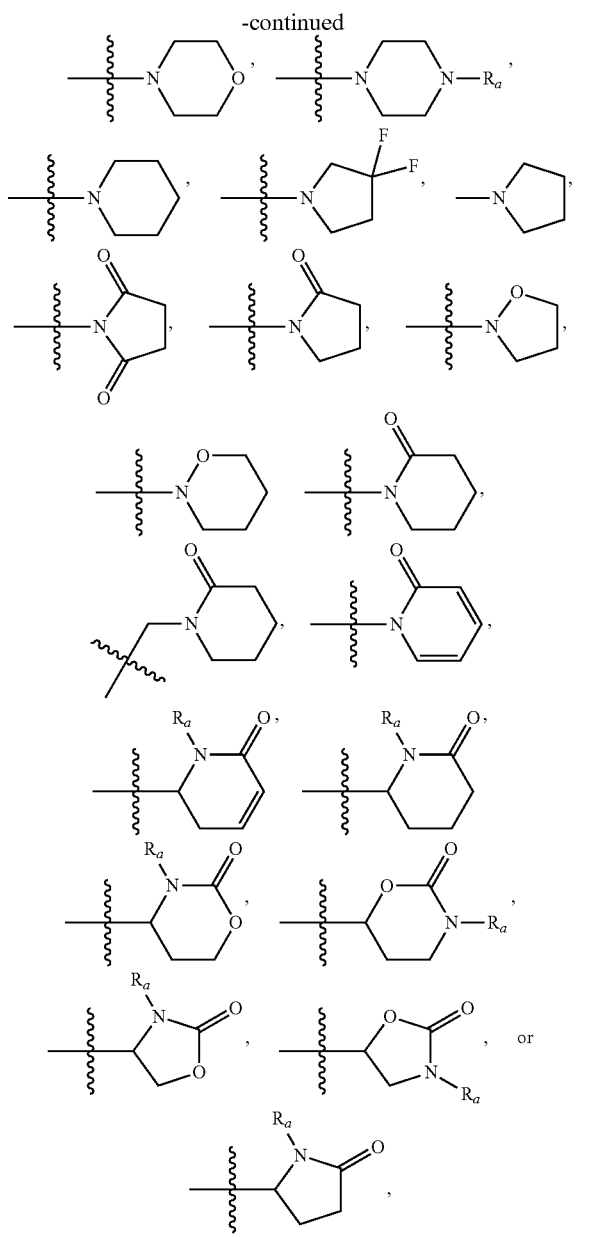

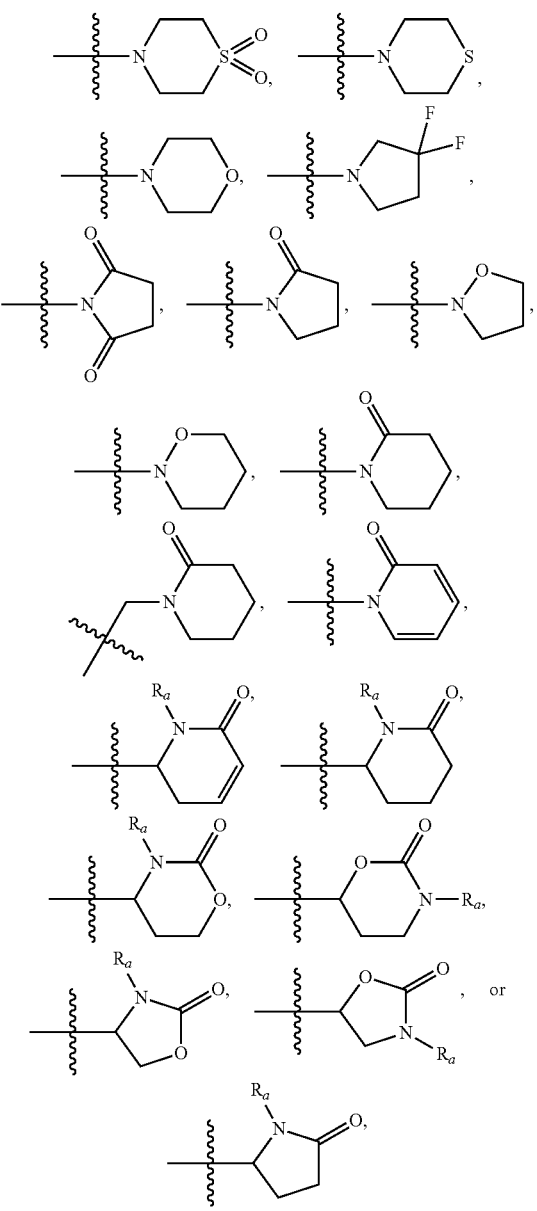

or unsubstituted or substituted $C_{(1-6)}$alkyl wherein said alkyl may be substituted with up to two substituents wherein one substituent is selected from the group consisting of OH, $C_{(3-6)}$cycloalkyl, $C_{(2-4)}$alkenyl, NHBOC, N($C_{(1-4)}$alkyl)$_2$, NHSO$_2$R$_b$, NR$_b$C(O)R$_{bb}$NHCO$_2$R$_b$, NHCONR$_b$R$_{bb}$, OC$_{(1-2)}$alkyl, OC(O)C$_{(1-4)}$alkyl, OC(O)NR$_b$R$_{bb}$, CO$_2$C$_{(1-4)}$alkyl, C(O)NR$_b$R$_{bb}$, C$_{(2)}$alkylnyl, thiazolyl, oxazolyl, CF$_3$, CF$_2$CF$_2$CF$_3$, CH$_2$NHCOC$_{(1-3)}$alkyl, N$_3$, SCH$_3$, S(O)CH$_3$ and SO$_2$CH$_3$, and the second substituent on the $C_{(1-6)}$alkyl is OH, and wherein said pyridyl, pyrimidyl, pyrazyl, oxazolyl, phenyl, or thiazolyl is optionally substituted with one substituent selected from the group consisting of: OH, —CN, CH$_2$OH, OC$_{(1-4)}$alkyl, NH$_2$, NHC$_{(1-4)}$alkyl, OC$_{(1-4)}$alkyl, C(O)C$_{(1-4)}$alkyl, CO$_2$C$_{(1-4)}$alkyl, C(O)NHC$_{(1-4)}$alkyl, CO$_2$NHC$_{(1-4)}$alkyl, SC$_{(1-4)}$alkyl, SOC$_{(1-4)}$alkyl, SO$_2$C$_{(1-4)}$alkyl, SO$_2$NHC$_{(1-4)}$alkyl, NHSO$_2$C$_{(1-4)}$alkyl, NHCO$_2$C$_{(1-4)}$alkyl, NHC(O)C$_{(1-4)}$alkyl, and C$_{(1-4)}$alkyl;

and pharmaceutically acceptable salts thereof.

5. A compound of claim 4 wherein:

R$^1$ is pyridyl, phenyl, thiazolyl, isothiazolyl, CF$_3$, —CH═CH$_2$, CO$_2$C$_{(1-4)}$alkyl, NHBOC, N(C$_{(1-3)}$alkyl)CO$_2$CH$_2$Ph, NR$_b$C(O)R$_{bb}$, C(O)N(CH$_3$)OCH$_3$, C(O)NHC$_{(1-4)}$alkyl, C(O)NHCH$_2$Ph(OCH$_3$)$_2$, —C(OH)(CH$_2$CH═CH$_2$)$_2$, 3,6-dihydropyran-2-yl, 2,5-dihydrofuran-2-yl, tetrahydropyranyl, cyclopentenyl, cyclopentanyl, tetrahydrofuran-2-yl, cycloheptanyl, or unsubstituted or substituted $C_{(1-6)}$alkyl wherein said alkyl may be substituted with up to two substituents wherein one substituent is selected from the group consisting of OH, $C_{(3-5)}$cycloalkyl, $C_{(2)}$alkenyl, NHBOC, N($C_{(1-4)}$alkyl)$_2$, NHSO$_2$R$_b$, NR$_b$C(O)R$_{bb}$, NHCO$_2$R$_b$, NHCONR$_b$R$_{bb}$, OC$_{(1-2)}$alkyl, OC(O)C$_{(1-4)}$alkyl, OC(O)NR$_b$R$_{bb}$, CO$_2$C$_{(1-4)}$alkyl, C(O)NR$_b$R$_{bb}$, C$_{(2)}$alkylnyl, cyclopentyl, thiazolyl, oxazolyl, CF$_3$, CF$_2$CF$_2$CF$_3$, CH$_2$NHCOC$_{(1-3)}$alkyl, N$_3$, SCH$_3$ and S(O)CH$_3$, and the second substituent on the $C_{(1-6)}$alkyl is OH, and wherein said phenyl, pyridyl or thiazolyl is optionally substituted with one substituent selected from the group consisting of: OH, —CN, $CH_2OH$, $OCH_3$, $NH_2$, $NHCH_3$, and $C_{(1-4)}$alkyl;

and pharmaceutically acceptable salts thereof.

6. A compound of claim 5 wherein:

$R^1$ is H, pyridyl, phenyl, thiazolyl, isothiazolyl, $CF_3$, —CH=$CH_2$, $CO_2CH_2CH_3$, NHBOC, $N(C_{(1-3)}$alkyl)$CO_2CH_2Ph$, $NR_bC(O)R_{bb}$, $C(O)N(CH_3)OCH_3$, $C(O)NHCH_2CH_3$, $C(O)NHCH_2Ph(OCH_3)_2$, —C(OH)$(CH_2CH=CH_2)_2$, 3,6-dihydropyran-2-yl, 2,5-dihydrofuran-2-yl, tetrahydropyranyl, cyclopentenyl, cyclopentanyl, tetrahydrofuran-2-yl, cycloheptanyl,

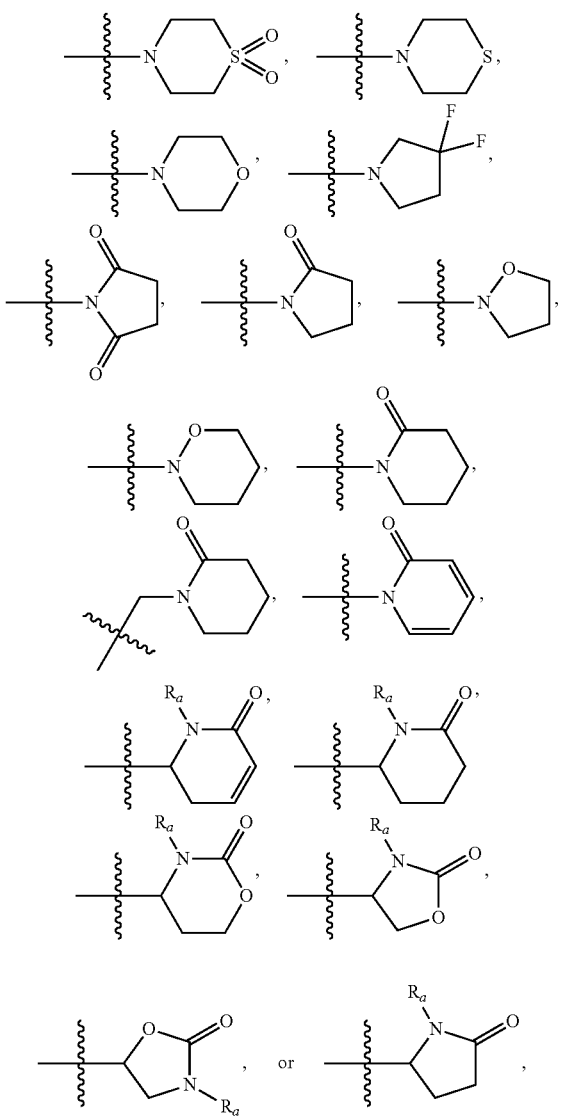

or unsubstituted or substituted $C_{(1-5)}$alkyl wherein said alkyl may be substituted with up to two substituents wherein one substituent is selected from the group consisting of: OH, cyclopropyl, cyclopentyl, $C_{(2)}$alkenyl, NHBOC, $N(CH_3)_2$, $NHSO_2R_b$, $NR_bC(O)R_{bb}$, $NHCO_2R_b$, $NHCONR_bR_{bb}$, $OC_{(1-2)}$alkyl, $OC(O)CH_3$, $OC(O)N(CH_3)_2$, $CO_2CH_2CH_3$, $C(O)N(CH_3)_2$, $C_{(2)}$alkylnyl, cyclopentyl, thiazolyl, $CF_3$, $CF_2CF_2CF_3$, $CH_2NHCOC_{(1-3)}$alkyl, $N_3$, $SCH_3$ and $S(O)CH_3$, and the second substituent on the $C_{(1-5)}$alkyl is OH, and wherein said phenyl is optionally substituted with one substituent selected from the group consisting of: OH, —CN, and $CH_2OH$;

wherein said pyridyl is optionally substituted with one substituent selected from the group consisting of:

$OCH_3$, OH, $NH_2$, $NHCH_3$, and $CH_3$; wherein said thiazolyl is optionally substituted with one substituent selected from the group consisting of isopropyl, and methyl;

$R^3$ is H, $CH_3$, —CN, $CH(CH_3)_2$, or $CF_3$;

and pharmaceutically acceptable salts thereof.

7. A compound selected from

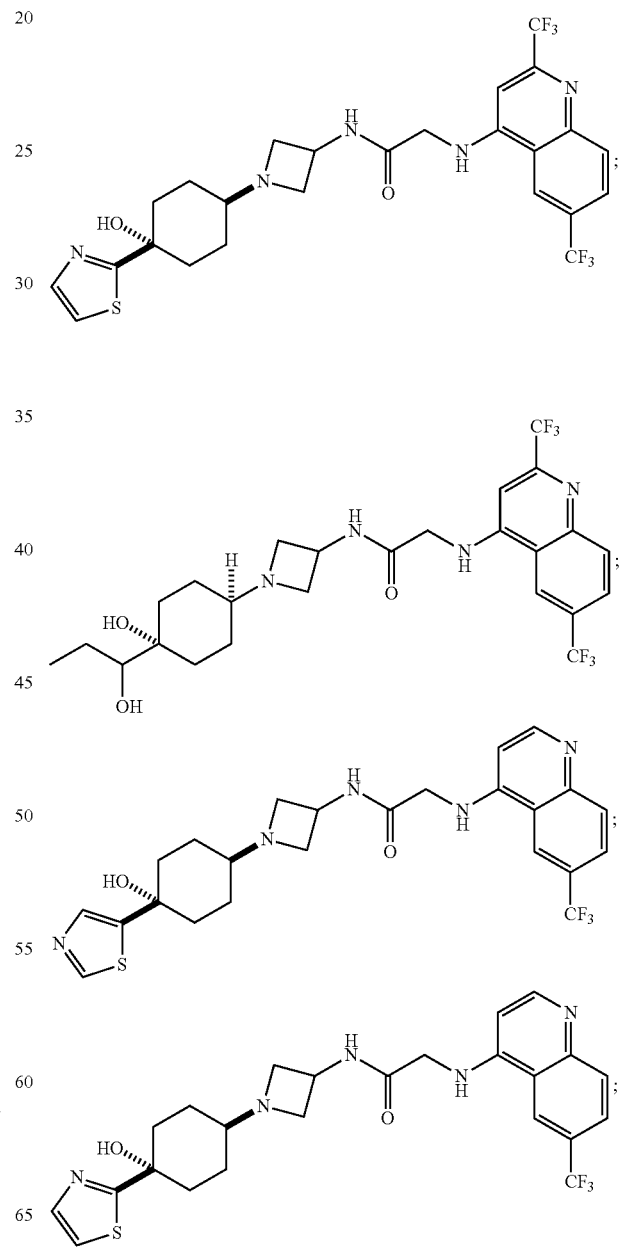

-continued

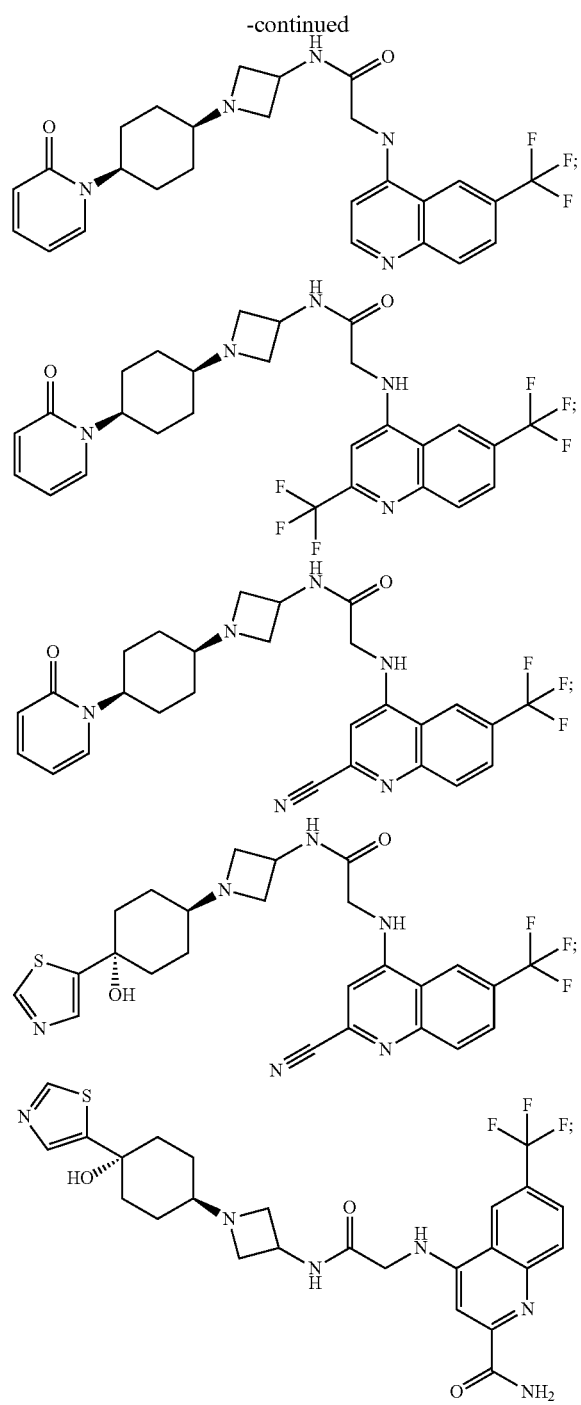

-continued

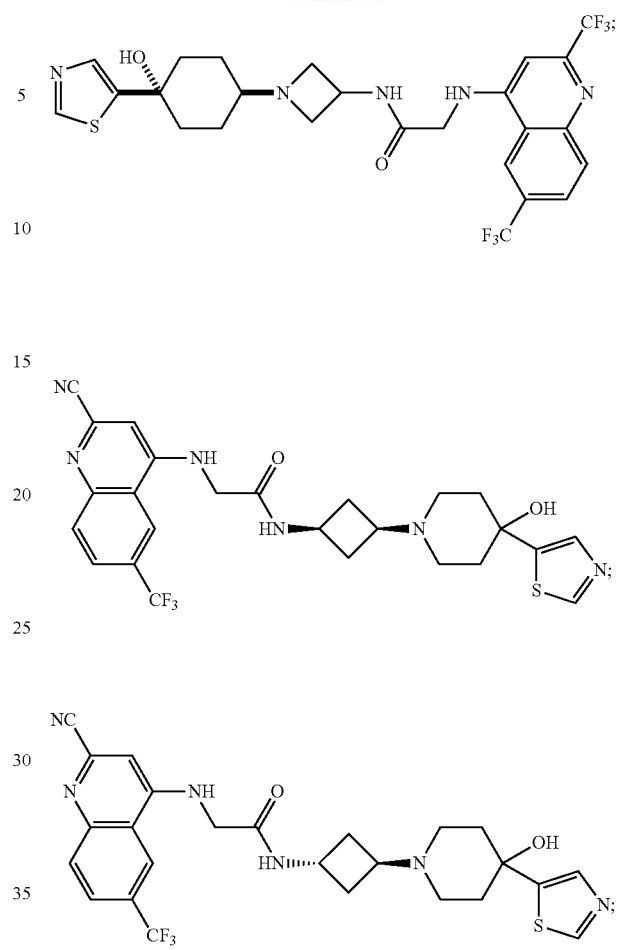

and pharmaceutically acceptable salts thereof.

8. A pharmaceutical composition, comprising a compound of claim 1 and a pharmaceutically acceptable carrier.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

11. A method of treating a disorder selected from the group consisting of type II diabetes, obesity and asthma comprising administering to a subject in need thereof a therapeutically effective amount of a compound of claim 1.

* * * * *

UNITED STATES PATENT AND TRADEMARK OFFICE
CERTIFICATE OF CORRECTION

PATENT NO. : 9,062,048 B2  
APPLICATION NO. : 13/947340  
DATED : June 23, 2015  
INVENTOR(S) : James C. Lanter et al.

Page 1 of 1

It is certified that error appears in the above-identified patent and that said Letters Patent is hereby corrected as shown below:

In the Claims:

COL. 238, line 35, delete first chemical structure, and substitute therefor:

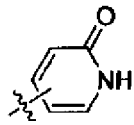

Signed and Sealed this  
Twenty-third Day of August, 2016

Michelle K. Lee  
*Director of the United States Patent and Trademark Office*